US007960612B2

(12) United States Patent
Zhang et al.

(10) Patent No.: US 7,960,612 B2
(45) Date of Patent: Jun. 14, 2011

(54) PLANT QUALITY WITH VARIOUS PROMOTERS

(75) Inventors: James Z. Zhang, Palo Alto, CA (US); Frederick D. Hempel, Hayward, CA (US); Luc J. Adam, Hayward, CA (US); Joseph M. Palys, Davis, CA (US); T. Lynne Reuber, San Mateo, CA (US); Oliver J. Ratcliffe, Oakland, CA (US); Robert A. Creelman, Castro Valley, CA (US); Raymond R. Samaha, Soquel, CA (US); Pierre E. Broun, St Cyr sur Loire (FR)

(73) Assignees: Mendel Biotechnology, Inc., Hayward, CA (US); Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/169,527

(22) Filed: Jul. 8, 2008

(65) Prior Publication Data

US 2009/0049566 A1 Feb. 19, 2009

Related U.S. Application Data

(60) Continuation-in-part of application No. 10/286,264, filed on Nov. 1, 2002, now abandoned, which is a division of application No. 09/533,030, filed on Mar. 22, 2000, now abandoned, said application No.12/169,527 is a continuation-in-part of application No. 11/479,226, filed on Jun. 30, 2006, now Pat. No. 7,858,848, and a continuation-in-part of application No. 10/675,852, filed on Sep. 30, 2003, which is a continuation-in-part of application No. 09/713,994, filed on Nov. 16, 2000, now abandoned, said application No. 12/169,527 is a continuation-in-part of application No. 10/669,824, filed on Sep. 23, 2003, which is a continuation-in-part of application No. 09/823,676, filed on Mar. 30, 2001, now Pat. No. 6,717,034, said application No. 12/169,527 is a continuation-in-part of application No. 11/725,235, filed on Mar. 16, 2007, now Pat. No. 7,601,893, which is a division of application No. 10/225,068, filed on Aug. 9, 2002, now Pat. No. 7,193,129, and a continuation-in-part of application No. 10/171,468, filed on Jun. 14, 2002, now abandoned, and a continuation-in-part of application No. 09/837,944, filed on Apr. 18, 2001, now abandoned, said application No. 12/169,527 is a continuation-in-part of application No. 11/728,567, filed on Mar. 26, 2007, now Pat. No. 7,635,860, which is a division of application No. 10/225,066, filed on Aug. 9, 2002, now Pat. No. 7,238,860, and a continuation-in-part of application No. 09/837,944, filed on Apr. 18, 2001, now abandoned, and a continuation-in-part of application No. 10/171,468, filed on Jun. 14, 2002, now abandoned, said application No. 12/169,527 is a continuation-in-part of application No. 11/375,241, filed on Mar. 13, 2006, now Pat. No. 7,598,429, and a continuation-in-part of application No. 10/225,067, filed on Aug. 9, 2002, now Pat. No. 7,135,616, and a continuation-in-part of application No. 10/171,468, filed on Jun. 14, 2002, now abandoned, and a continuation-in-part of application No. 09/837,944, filed on Apr. 18, 2001, now abandoned, said application No. 12/169,527 is a continuation-in-part of application No. 11/069,255, filed on Feb. 28, 2005, which is a continuation of application No. 10/112,887, filed on Mar. 18, 2002, now abandoned, said application No. 12/169,527 is a continuation of application No. 10/374,780, filed on Feb. 25, 2003, now Pat. No. 7,511,190, which is a continuation-in-part of application No. 09/934,455, filed on Aug. 22, 2001, now abandoned, and a continuation-in-part of application No. 09/837,944, filed on Apr. 18, 2001, now abandoned, which is a continuation-in-part of application No. 09/713,994, filed on Nov. 16, 2000, now abandoned, said application No. 10/374,780 is a continuation-in-part of application No. 10/225,068, filed on Aug. 9, 2002, now Pat. No. 7,193,129, and a continuation-in-part of application No. 10/171,468, filed on Jun. 14, 2002, now abandoned, and a continuation-in-part of (Continued)

(51) Int. Cl.
*A01H 5/00* (2006.01)
*A01H 5/10* (2006.01)
*C12N 5/14* (2006.01)

(52) U.S. Cl. ...................... 800/298; 800/317.4; 800/295; 435/419

(58) Field of Classification Search ........................ None
See application file for complete search history.

(56) References Cited

U.S. PATENT DOCUMENTS 6,121,513 A 9/2000 Zhang et al.

(Continued)

FOREIGN PATENT DOCUMENTS

EP 1033405 A2 * 6/2000

OTHER PUBLICATIONS

Abbaraju et al. (GenBank Accession No. AF079503.1, Published Aug. 4, 1998).*

(Continued)

*Primary Examiner* — Vinod Kumar
(74) *Attorney, Agent, or Firm* — Cooley LLP

(57) ABSTRACT

The invention relates to plant transcription factor polypeptides, polynucleotides that encode them, homologs from a variety of plant species, and methods of using the polynucleotides and polypeptides to produce transgenic plants having advantageous properties, including increased soluble solids, lycopene, and improved plant volume or yield, as compared to wild-type or control plants. The invention also pertains to expression systems that may be used to regulate these transcription factor polynucleotides, providing constitutive, transient, inducible and tissue-specific regulation.

12 Claims, 3 Drawing Sheets

Figure 1:
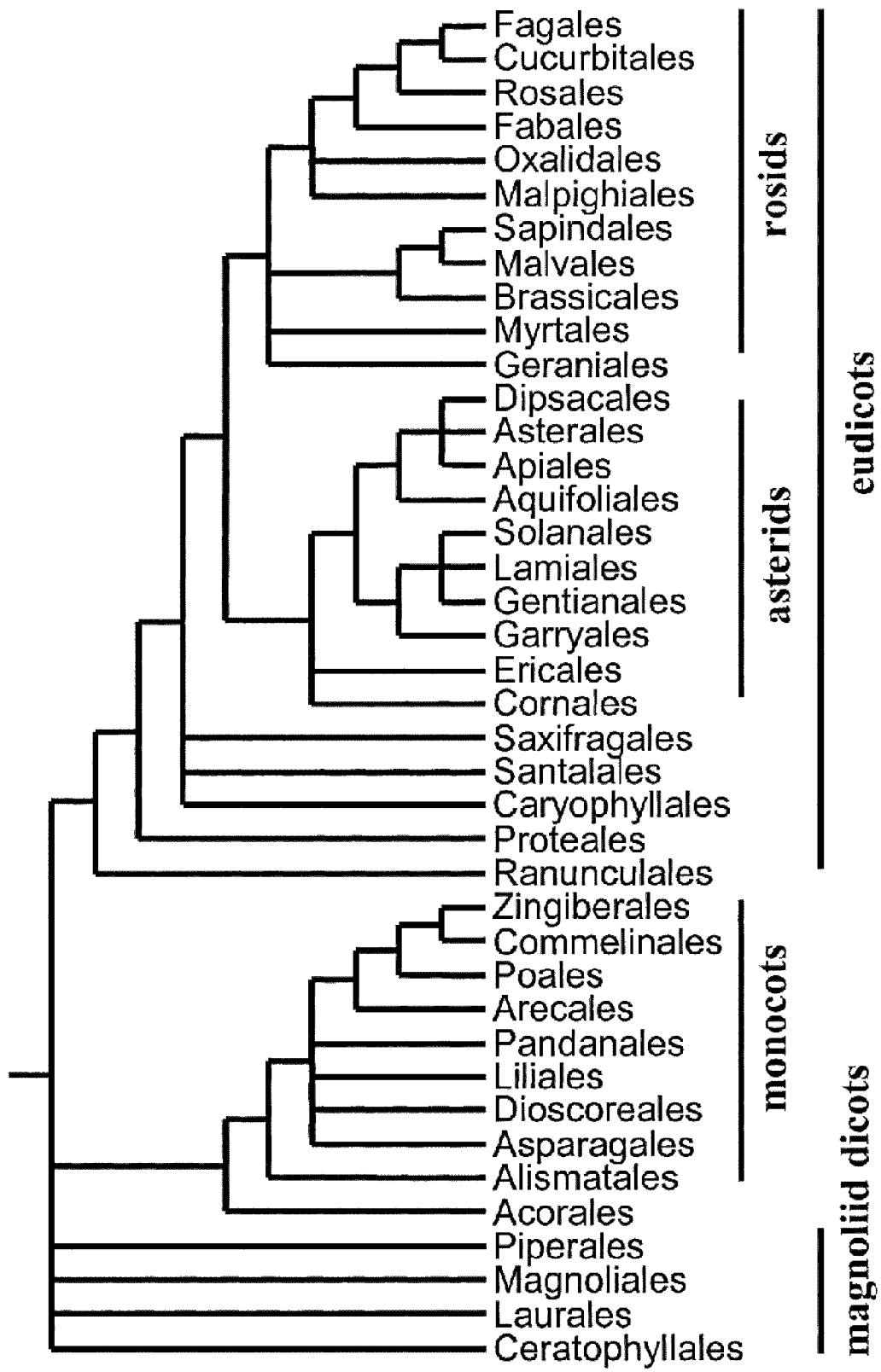

Related U.S. Application Data 60) application No. 09/837,944, filed on Apr. 18, 2001, now abandoned, said application No. 10/374,780 is a continuation-in-part of application No. 10/225,066, filed on Aug. 9, 2002, now Pat. No. 7,238,860, said application No. 10/225,066 is a continuation-in-part of application No. 10/171,468, filed on Jun. 14, 2002, now abandoned, and a continuation-in-part of application No. 09/837,944, filed on Apr. 18, 2001, now abandoned, said application No. 10/374,780 is a continuation-in-part of application No. 10/225,067, filed on Aug. 9, 2002, now Pat. No. 7,135,616, and a continuation-in-part of application No. 10/171,468, filed on Jun. 14, 2002, now abandoned, and a continuation-in-part of application No. 09/837,944, filed on Apr. 18, 2001, now abandoned, application No. 12/169,529, which is a continuation-in-part of application No. 10/546,266, filed as application No. PCT/US2004/05654 on Feb. 25, 2004, now Pat. No. 7,659,446, application No. 12/169,527, which is a continuation-in-part of application No. 11/986,992, filed on Nov. 26, 2007, which is a division of application No. 10/412,699, filed on Apr. 10, 2003, now Pat. No. 7,345,217, which is a continuation-in-part of application No. 10/295,403, filed on Nov. 15, 2002, now abandoned, which is a division of application No. 09/394,519, filed on Sep. 13, 1999, now abandoned, said application No. 10/412,699 is a continuation-in-part of application No. 09/489,376, filed on Jan. 21, 2000, now abandoned, said application No. 10/412,699 is a continuation-in-part of application No. 10/302,267, filed on Nov. 22, 2002, now Pat. No. 7,223,904, which is a division of application No. 09/506,720, filed on Feb. 17, 2000, now abandoned, said application No. 10/412,699 is a continuation-in-part of application No. 10/278,173, filed on Oct. 21, 2002, now abandoned, which is a division of application No. 09/533,392, filed on Mar. 22, 2000, now abandoned, said application No. 10/412,699 is a continuation-in-part of application No. 09/533,029, filed on Mar. 22, 2000, now Pat. No. 6,664,446, said application No. 10/412,699 is a continuation-in-part of application No. 10/278,536, filed on Oct. 22, 2002, now abandoned, which is a division of application No. 09/532,591, filed on Mar. 22, 2000, now abandoned, said application No. 10/412,699 is a continuation-in-part of application No. 09/713,994, filed on Nov. 16, 2000, now abandoned, said application No. 10/412,699 and a continuation-in-part of application No. 09/934,455, filed on Aug. 22, 2001, now abandoned, and a continuation-in-part of application No. 09/837,944, filed on Apr. 18, 2001, now abandoned, is a continuation-in-part of application No. 09/819,142, filed on Mar. 27, 2001, now abandoned, which is a continuation-in-part of application No. 09/713,994, filed on Nov. 16, 2000, now abandoned, said application No. 10/412,699 is a continuation-in-part of application No. 10/225,068, filed on Aug. 9, 2002, now Pat. No. 7,193,129, said application No. 10/225,068 and a continuation-in-part of application No. 10/171,468, filed on Jun. 14, 2002, now abandoned, is a continuation-in-part of application No. 09/837,944, filed on Apr. 18, 2001, now abandoned, said application No. 10/412,699 is a continuation-in-part of application No. 10/225,066, filed on Aug. 9, 2002, now Pat. No. 7,238,860, and a continuation-in-part of application No. 10/171,468, filed on Jun. 14, 2002, now abandoned, and a continuation-in-part of application No. 09/837,944, filed on Apr. 18, 2001, now abandoned, said application No. 10/412,699 is a continuation-in-part of application No. 10/225,067, filed on Aug. 9, 2002, now Pat. No. 7,135,616, and a continuation-in-part of application No. 10/171,468, filed on Jun. 14, 2002, now abandoned, and a continuation-in-part of application No. 09/837,944, filed on Apr. 18, 2001, now abandoned, said application No. 10/412,699 is a continuation-in-part of application No. 10/374,780, filed on Feb. 25, 2003, now Pat. No. 7,511,190, application No. 12/169,527, which is a continuation-in-part of application No. 10/559,441, filed as application No. PCT/US2004/17768 on Jun. 4, 2004, now abandoned, application No. 12/169,527, which is a continuation-in-part of application No. 11/642,814, filed on Dec. 20, 2006, now Pat. No. 7,825,296, which is a division of application No. 10/666,642, filed on Sep. 18, 2003, now Pat. No. 7,196,245, application No. 12/169,527, which is a continuation-in-part of application No. 10/714,887, filed on Nov. 13, 2003, and a continuation-in-part of application No. 10/666,642, filed on Sep. 18, 2003, now Pat. No. 7,196,245, which is a continuation-in-part of application No. 10/456,882, filed on Jun. 6, 2003, now abandoned, application No. 12/169,527, which is a continuation-in-part of application No. 11/435,388, filed on May 15, 2006, now Pat. No. 7,663,025, which is a continuation-in-part of application No. PCT/US2004/37584, filed on Nov. 12, 2004, application No. 12/169,527, which is a continuation-in-part of application No. 11/632,390, filed as application No. PCT/US2005/25010 on Jul. 14, 2005, now abandoned, application No. 12/169,527, which is a continuation-in-part of application No. 12/064,961, filed as application No. PCT/US2006/34615 on Aug. 31, 2006, application No. 12/169,527, which is a continuation-in-part of application No. 10/903,236, filed on Jul. 30, 2004, and a continuation-in-part of application No. 10/666,642, filed on Sep. 18, 2003, now Pat. No. 7,196,245, which is a continuation-in-part of application No. 10/456,882, filed on Jun. 6, 2003, now abandoned, application No. 12/169,527, which is a continuation-in-part of application No. 11/699,973, filed on Jan. 29, 2007, now abandoned, which is a continuation-in-part of application No. PCT/US2005/27151, filed on Jul. 29, 2005, application No. 12/169,527, which is a continuation-in-part of application No. 10/870,198, filed on Jun. 16, 2004, now Pat. No. 7,897,843, said application No. 10/870,198 is a continuation-in-part of application No. 10/669,824, filed on Sep. 23, 2003, which is a continuation-in-part of application No. 09/823,676, filed on Mar. 30, 2001, now Pat. No. 6,717,034, application No. 12/169,527, which is a continuation-in-part of application No. 10/838,616, filed on May 4, 2004, and a continuation-in-part of application No. 10/685,922, filed on Oct. 14, 2003, now abandoned, application No. 12/169,527, which is a continuation-in-part of application No.

PCT/US2007/17321, filed on Aug. 3, 2007, application No. 12/169,527, which is a continuation-in-part of application No. 11/705,903, filed on Feb. 12, 2007, now Pat. No. 7,868,229, which is a continuation-in-part of application No. PCT/US2006/34615, filed on Aug. 31, 2006, application No. 12/169,527, which is a continuation-in-part of application No. 11/821,448, filed on Jun. 22, 2007, now Pat. No. 7,692,067, application No. 12/169,527, which is a continuation-in-part of application No. PCT/US2007/09124, filed on Apr. 12, 2007, application No. 12/169,527, which is a continuation-in-part of application No. 11/981,667, filed on Mar. 7, 2008, and a continuation-in-part of application No. 11/981,576, filed on Oct. 30, 2007, now Pat. No. 7,888,558.

(60) Provisional application No. 60/791,663, filed on Apr. 12, 2006, provisional application No. 60/817,886, filed on Jun. 29, 2006, provisional application No. 60/713,952, filed on Aug. 31, 2005, provisional application No. 60/836,243, filed on Aug. 7, 2006, provisional application No. 60/565,948, filed on Apr. 26, 2004, provisional application No. 60/588,405, filed on Jul. 14, 2004, provisional application No. 60/542,928, filed on Feb. 5, 2004, provisional application No. 60/527,658, filed on Dec. 5, 2003, provisional application No. 60/465,809, filed on Apr. 24, 2003, provisional application No. 60/434,166, filed on Dec. 17, 2002, provisional application No. 60/411,837, filed on Sep. 18, 2002, provisional application No. 60/162,656, filed on Nov. 1, 1999, provisional application No. 60/161,143, filed on Oct. 22, 1999, provisional application No. 60/144,153, filed on Jul. 15, 1999, provisional application No. 60/135,134, filed on May 20, 1999, provisional application No. 60/129,450, filed on Apr. 15, 1999, provisional application No. 60/124,278, filed on Mar. 11, 1999, provisional application No. 60/121,037, filed on Feb. 22, 1999, provisional application No. 60/120,880, filed on Feb. 18, 1999, provisional application No. 60/116,841, filed on Jan. 22, 1999, provisional application No. 60/113,409, filed on Dec. 22, 1998, provisional application No. 60/108,734, filed on Nov. 17, 1998, provisional application No. 60/103,312, filed on Oct. 6, 1998, provisional application No. 60/101,349, filed on Sep. 22, 1998, provisional application No. 60/713,952, filed on Aug. 31, 2005, provisional application No. 60/338,692, filed on Dec. 11, 2001, provisional application No. 60/336,049, filed on Nov. 19, 2001, provisional application No. 60/310,847, filed on Aug. 9, 2001, provisional application No. 60/227,439, filed on Aug. 22, 2000, provisional application No. 60/197,899, filed on Apr. 17, 2000, provisional application No. 60/166,228, filed on Nov. 17, 1999, provisional application No. 60/125,814, filed on Mar. 23, 1999, provisional application No. 60/961,403, filed on Jul. 20, 2007.

(56) References Cited

U.S. PATENT DOCUMENTS

| | | |
|---|---|---|
| 6,946,586 B1 | 9/2005 | Fromm et al. |
| 2002/0142281 A1 | 10/2002 | Broun et al. |
| 2003/0018993 A1 | 1/2003 | Gutterson et al. |
| 2003/0041356 A1 | 2/2003 | Reuber et al. |
| 2003/0046723 A1 | 3/2003 | Heard et al. |
| 2003/0061637 A1 | 3/2003 | Jiang et al. |
| 2003/0093837 A1 | 5/2003 | Keddie et al. |
| 2003/0101481 A1 | 5/2003 | Zhang et al. |
| 2003/0121070 A1 | 6/2003 | Adam et al. |
| 2003/0131386 A1 | 7/2003 | Samaha et al. |
| 2003/0167537 A1 | 9/2003 | Jiang et al. |
| 2003/0188330 A1 | 10/2003 | Heard et al. |
| 2003/0217383 A1 | 11/2003 | Reuber et al. |
| 2003/0226173 A1 | 12/2003 | Ratcliffe et al. |
| 2003/0229915 A1 | 12/2003 | Heard et al. |
| 2004/0019925 A1 | 1/2004 | Heard et al. |
| 2004/0019927 A1 | 1/2004 | Sherman et al. |
| 2004/0045049 A1 | 3/2004 | Zhang et al. |
| 2004/0098764 A1 | 5/2004 | Heard et al. |
| 2004/0128712 A1 | 7/2004 | Jiang et al. |
| 2005/0086718 A1 | 4/2005 | Heard et al. |
| 2005/0097638 A1 | 5/2005 | Jiang et al. |
| 2005/0155117 A1 | 7/2005 | Century et al. |
| 2005/0172364 A1 | 8/2005 | Heard |
| 2006/0008874 A1 | 1/2006 | Creelman et al. |
| 2006/0015972 A1 | 1/2006 | Heard et al. |
| 2006/0162018 A1 | 7/2006 | Gutterson et al. |
| 2006/0195944 A1 | 8/2006 | Heard et al. |
| 2006/0242738 A1 | 10/2006 | Sherman et al. |
| 2006/0272060 A1 | 11/2006 | Heard et al. |
| 2007/0022495 A1* | 1/2007 | Reuber et al. ............... 800/279 |
| 2007/0033671 A1 | 2/2007 | Jiang et al. |
| 2007/0061911 A9* | 3/2007 | Zhang et al. ............... 800/278 |
| 2007/0101454 A1 | 5/2007 | Jiang et al. |
| 2007/0186308 A1 | 8/2007 | Reuber et al. |
| 2007/0199107 A1 | 8/2007 | Ratcliffe et al. |
| 2007/0209086 A1 | 9/2007 | Ratcliffe et al. |
| 2007/0226839 A1 | 9/2007 | Gutterson et al. |
| 2008/0010703 A1 | 1/2008 | Creelman et al. |
| 2008/0155706 A1 | 6/2008 | Riechmann et al. |
| 2008/0163397 A1 | 7/2008 | Ratcliffe et al. |
| 2008/0229448 A1 | 9/2008 | Libby et al. |
| 2008/0301836 A1 | 12/2008 | Century et al. |
| 2008/0301840 A1 | 12/2008 | Gutterson et al. |
| 2008/0301841 A1 | 12/2008 | Ratcliffe et al. |
| 2008/0313756 A1 | 12/2008 | Zhang et al. |
| 2009/0044297 A1* | 2/2009 | Andersen et al. ............ 800/289 |
| 2009/0049566 A1 | 2/2009 | Zhang et al. |
| 2009/0138981 A1* | 5/2009 | Repetti et al. ............... 800/263 |
| 2009/0151015 A1 | 6/2009 | Adam et al. |
| 2009/0192305 A1 | 7/2009 | Riechmann et al. |
| 2009/0205063 A1 | 8/2009 | Zhang et al. |
| 2009/0265807 A1* | 10/2009 | Kumimoto et al. .......... 800/279 |
| 2009/0265813 A1 | 10/2009 | Gutterson et al. |
| 2009/0276912 A1* | 11/2009 | Sherman et al. ............ 800/264 |

OTHER PUBLICATIONS

Valvekens et al. (PNAS, 85:5536-5540, 1998).*
Yanagisawa et al. (Plant Journal, 17:209-214, 1999).*
U.S. Appl. No. 12/526,042, filed Feb. 7, 2008, Repetti, Peter P. et al., Entire document.
U.S. Appl. No. 12/338,024, filed Dec. 18, 2008, Sherman, Bradley et al., Entire document.
U.S. Appl. No. 11/986,992, filed Nov. 26, 2007, Kumimoto, R. et al., entire document.
U.S. Appl. No. 09/394,519, filed Sep. 13, 1999, Zhang, J. et al., Entire document.
U.S. Appl. No. 12/573,311, filed Oct. 5, 2009, Heard, J. et al., Entire document.
U.S. Appl. No. 12/577,662, filed Oct. 12, 2009, Reuber, T. et al., Entire document.
U.S. Appl. No. 12/557,449, filed Sep. 10, 2009, Repetti, P. et al., Entire document.
U.S. Appl. No. 09/627,348, filed Jul. 28, 2000, Thomashow, Michael et al., Entire document.
U.S. Appl. No. 09/489,376, filed Jan. 21, 2000, Heard, J. et al., Entire document.
U.S. Appl. No. 09/489,230, filed Jan. 21, 2000, Broun, P. et al., Entire document.

U.S. Appl. No. 09/506,720, filed Feb. 17, 2000, Keddie, James et al., Entire document.
U.S. Appl. No. 09/533,030, filed Mar. 22, 2000, Keddie, James et al., Entire document.
U.S. Appl. No. 09/533,392, filed Mar. 22, 2000, Jiang, C-Z. et al., Entire document.
U.S. Appl. No. 09/532,591, filed Mar. 22, 2000, Samaha, R. et al., Entire document.
U.S. Appl. No. 09/533,648, filed Mar. 22, 2000, Riechmann, Jose Luis et al., Entire document.
U.S. Appl. No. 10/290,627, filed Nov. 7, 2002, Riechmann, Jose Luis et al., Entire document.
U.S. Appl. No. 09/713,994, filed Nov. 16, 2000, Keddie, James et al., Entire document.
U.S. Appl. No. 09/837,944, filed Apr. 18, 2001, Creelman, Robert et al., Entire document.
U.S. Appl. No. 09/594,214, filed Jun. 14, 2000, Jones, J. et al., Entire document.
U.S. Appl. No. 10/456,882, filed Jun. 6, 2003, Riechmann, Jose Luis et al., Entire document.
U.S. Appl. No. 10/171,468, filed Jun. 14, 2002, Creelman, Robert et al., Entire document.
U.S. Appl. No. 12/376,569, filed Aug. 3, 2007, Creelman, Robert et al., Entire document.
Yanagisawa S (1995) A novel DNA-binding domain that may form a single zinc finger motif Nuc Ac Res 23(17) 3403-3410.
Yanagisawa S (2000) Dof1 and Dof2 transcription factors are associated with expression of multiple genes involved in carbon metabolism Plant J 21(3) 281-288.
Oliver DJ, Raman R (1995) Glycine decarboxylase: protein chemistry and molecular biology of the major protein in leaf mitochondria. Bioenerg Biomembr 27(4):407-14.
Esaka,M., et al.—NCBI acc. No. D45066 (gi: 853689) (Jun. 8, 1995); "Pumpkin mRNA for Ascorbate oxidase promoter-binding protein"; source: Cucurbita maxima (winter squash); Title: (Unpublished (1995)).
Sasaki,T., et al.—NCBI acc. No. AP001383 (gi: 7242897) (Mar. 14, 2000); "Oryza sativa genomic DNA, chromosome 1, clone:P0453A06"; source: Oryza sativa; Title: "Oryza sativa nipponbare(GA3) genomic DNA, chromosome 1, PAC clone:P0453A06" (Published Only in DataBase (2000) In press).
Torrez-Jerez,I., et al.—NCBI acc. No. BF634026 (gi: 11898184) (Dec. 19, 2000); "NF072C11DT1F1085 Drought Medicago truncatula cDNA clone NF072C11DT 5', mRNA sequence"; source: Medicago truncatula (barrel medic); Title: "Expressed Sequence Tags from the Samuel Roberts Noble Foundation Medicago truncatula drought library" (Unpublished (2000)).
Alcala,J., et al.—NCBI acc. No. AW029804 (gi: 5888560) (Sep. 15, 1999); "EST273059 tomato callus, TAMU Solanum lycopersicum cDNA clone cLEC11E11 similar to H-protein promoter binding factor, putative, mRNA sequence"; source: Solanum lycopersicum (Lycopersicon esculentum); Title: "Generation of ESTs from tomato callus tissue" (Unpublished (1999)).
Shoemaker,R., et al.—NCBI acc. No. BG155371 (gi: 12689026) (Feb. 6, 2001); "sab42f05.y1 Gm-c1026 Glycine max cDNA clone Genome Systems Clone ID: Gm-c1026-4473 5' similar to TR:Q39540 Q39540 Ascorbate Oxidase Promoter-Binding Protein, mRNA sequence"; source: Glycine max (soybean); Title: "Public Soybean EST Project" (Unpublished (1999)).
Crookshanks,M., et al.—NCBI acc. No. BI406921 (gi: 15186335) (Aug. 14, 2001); "183H02 Mature tuber lambda ZAP Solanum tuberosum cDNA, mRNA sequence"; source: Solanum tuberosum (potato); Title: "The potato transcriptome: analysis of 6077 expressed sequence tags" (FEBS Lett 506 (2), 123-126 (2001)).
Sato,K., et al.—NCBI acc. No. AV835191 (gi: 14527280) (Jun. 22, 2001); "AV835191 K. Sato unpublished cDNA library: Hordeum vulgare subsp. spontaneum top three leaves adult, heading stage Hordeum vulgare subsp. spontaneum cDNA clone bah26m21, mRNA sequence"; source: Hordeum vulgare subsp. spontaneum; Title: "Barley EST sequencing project in NIG and Okayama Univ" (Unpublished (2001)).
Cordonnier-Pratt,M.-M., et al.—NCBI acc. No. AW671875 (gi: 7535776) (Apr. 11, 2000); "LG1__352__H02.b1__A002 Light Grown 1 (LG1) Sorghum bicolor cDNA, mRNA sequence"; source: Sorghum bicolor (sorghum); Title: "An EST database from Sorghum: light-grown seedlings" (Unpublished (2000)).
Cloutier,S., et al.—NCBI acc. No. BG910120 (gi: 14317796) (Jun. 5, 2001); "TaLr1145G11R TaLr1 Triticum aestivum cDNA clone TaLr1145G11 5', mRNA sequence"; source: Triticum aestivum (bread wheat); Title: "Wheat functional genomics—Thatcher Lr1 cDNA library" (Unpublished (2001)).
Anderson,O.A., et al.—NCBI acc. No. BE421651 (gi: 9419494) (Jul. 24, 2000); "HWM012cD.05r ITEC HWM Barley Leaf Library Hordeum vulgare subsp. vulgare cDNA clone HWM012cD.05, mRNA sequence"; source: Hordeum vulgare subsp. vulgare (domesticated barley); Title: "International Triticeae EST Cooperative (ITEC): Production of Expressed Sequence Tags for Species of the Triticeae" (Unpublished (2000)).
Sasaki,T., et al.—NCBI acc. No. BAA88190 (gi: 6539573) (Dec. 8, 1999); "Similar to H-protein promoter binding factor-2a (AF079503) [Oryza sativa]"; source: Oryza sativa; Title: "Oryza sativa nipponbare(GA3) genomic DNA, chromosome 1, PAC clone:P0038F12" (Published Only in DataBase.
Yamamoto,K., et al. NCBI acc. No. AU056531 (gi: 4715414) (Apr. 29, 1999); "AU056531 Oryza sativa mature leaf Nipponbare Oryza sativa Japonica Group cDNA clone S20663__1A, mRNA sequence"; source: Oryza sativa Japonica Group; Title: "Rice cDNA from mature leaf" (Unpublished (1999)).
Esaka,M., et al.—NCBI acc. No. BAA08094.1 (gi: GI:1669341) (Jun. 8, 1995); "AOBP=Ascorbate oxidase promoter-binding protein"; source: Cucurbita maxima (winter squash); Title: (Unpublished (1995)).
Sasaki,T., et al.—NCBI acc. No. BAA92506 (gi: 7242908) (Mar. 14, 2000); "ESTs C23582(S11122),AU056531(S20663) correspond to a region of the predicted gene.; Similar to AOBP (D45066) [Oryza sativa]"; source: Oryza sativa; Title: "Oryza sativa nipponbare(GA3) genomic DNA, chromosome 1, PAC clone:P0453A06" (Published Only in DataBase (2000) In press).
Vicente-Carbajosa,J., et al.—NCBI acc. No. AAB70119 (gi: 2393775) (Sep. 16, 1997); "prolamin box binding factor [Zea mays]"; source: Zea mays; Title: "A maize zinc-finger protein binds the prolamin box in zein gene promoters and interacts with the basic leucine zipper transcriptional activator Opaque2" (Proc. Natl. Acad. Sci. U.S.A. 94 (14), 7685-7690 (1997)).
Yu,H., et al.—NCBI acc. No. AAC79873 (gi: 3929325) (Nov. 30, 1998); "putative DNA-binding protein [Dendrobium grex Madame Thong-In]"; source: Dendrobium grex Madame Thong-In; Title: "Characterization of genes differentially expressed during orchid floral transiton" (Unpublished).
Mena,M., et al.—NCBI acc. No. (gi: 3777436) (Oct. 21, 1998); "DNA binding protein [Hordeum vulgare]"; source: Hordeum vulgare; Title: "An endosperm-specific DOF protein from barley, highly conserved in wheat, binds to and activates transcription from the prolamin-box of a native B-hordein promoter in barley endosperm" (Plant J. 16, 53-62 (1998)).
Mena,M., et al.—NCBI acc. No. (gi: 3790264) (Oct. 26, 1998); "PBF protein [Triticum aestivum]"; source: Triticum aestivum; Title: "An endosperm-specific DOF protein from barley, highly conserved in wheat, binds to and activates transcription from the prolamin-box of a native B-hordein promoter in barley endosperm" (Plant J. 16, 53-62 (1998)).
Plesch,G., et al.—NCBI acc. No. CAB89831 (gi: 7688355) (May 3, 2000); "Dof zinc finger protein [Solanum tuberosum]"; source: Solanum tuberosum; Title: "Involvement of TAAAG elements suggests a role of Dof transcriptions factors in guard cell-specific gene expression" (Unpublished).
Seki,H., et al.—NCBI acc. No. BAA85655 (gi: 6092016) (Oct. 21, 1999); "elicitor-responsive Dof protein ERDP [Pisum sativum]"; source: Pisum sativum; Title: "Molecular cloning and characterization of a novel elicitor-responsive DNA-binding protein with Dof domain" (Unpublished (1999)).
Baumann,K., et al.—NCBI acc. No. (gi: 3341468) (Jul. 25, 1998); The Dof zinc finger protein NtBBF1 is involved in tissue-specific and auxin-regulated expression of the rolB oncogene in plants.
NCBI acc. No. (gi: 1247386) (Apr. 2, 1996); , et al. "PRP2"; source: Nicotiana alata (Persian tobacco); Title.
Imaizumi et al. 2005 Science 309: 293-297.
U.S. Appl. No. 09/474,435, filed Dec. 28, 1999.

* cited by examiner

PLANT QUALITY WITH VARIOUS PROMOTERS

RELATIONSHIP TO COPENDING APPLICATIONS

This application claims the benefit of Application No. 60/961,403, filed Jul. 20, 2007. This application is a continuation-in-part of application Ser. No. 10/286,264, filed Nov. 1, 2002 (pending), which is a divisional of application Ser. No. 09/533,030, filed Mar. 22, 2000 (abandoned), which claims the benefit of Application No. 60/125,814, filed Mar. 23, 1999. This application is a continuation-in-part of application Ser. No. 10/675,852, filed Sep. 30, 2003 (pending). This application is a continuation-in-part of application Ser. No. 11/479,226, filed Jun. 30, 2006 (pending), which is a continuation-in-part of application Ser. No. 09/713,994, filed Nov. 16, 2000 (abandoned), which claims the benefit of Application No. 60/166,228, filed Nov. 17, 1999, which also claims the benefit of Application No. 60/197,899, filed Apr. 17, 2000, which also claims the benefit of Application No. 60/227,439, filed Aug. 22, 2000. This application is a continuation-in-part of application Ser. No. 10/669,824, filed Sep. 23, 2003, which is a continuation-in-part of, 09/823,676, filed Mar. 30, 2001 (issued as U.S. Pat. No. 6,717,034). This application is a continuation-in-part of application Ser. No. 11/725,235, filed Mar. 16, 2007, which is a divisional of application Ser. No. 10/225,068, filed Aug. 9, 2002 (issued as U.S. Pat. No. 7,193,129), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001; application Ser. No. 10/225,068 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). This application is a continuation-in-part of application Ser. No. 11/728,567, filed Mar. 26, 2007, which is a divisional of application Ser. No. 10/225,066, filed Aug. 9, 2002 (issued as U.S. Pat. No. 7,238,860), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001. Application Ser. No. 10/225,066 is also a continuation-in-part of application Ser. No. 09/837,944, filed Apr. 18, 2001 (abandoned), and is a continuation-in-part of application Ser. No. 10/171,468, filed Jun. 14, 2002 (abandoned). This application is a continuation-in-part of application Ser. No. 11/375,241, filed Mar. 16, 2006 (pending), which claims the benefit of Application No. 60/713,952, filed Aug. 31, 2005. Application Ser. No. 11/375, 241 is also a continuation-in-part of application Ser. No. 10/225,067, filed Aug. 9, 2002 (issued as U.S. Pat. No. 7,135, 616), which claims the benefit of Application No. 60/310, 847, filed Aug. 9, 2001, which also claims the benefit of Application No. 60/336,049, filed Nov. 19, 2001, and also claims the benefit of Application No. 60/338,692, filed Dec. 11, 2001. Application Ser. No. 10/225,067 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). This application is a continuation-in-part of application Ser. No. 11/069,255, filed Feb. 28, 2005 (pending), which is a continuation-in-part of application Ser. No. 10/112,887, filed Mar. 18, 2002 (abandoned). This application is a continuation-in-part of application Ser. No. 10/374,780, filed Feb. 25, 2003 (pending), which is a continuation-in-part of Application No. 09/934,455, filed Aug. 22, 2001 (abandoned), which is a continuation-in-part of application Ser. Nos. 09/713,994, Nov. 16, 2000 (abandoned), which is also a continuation-in-part of application Ser. No. 09/837,944, filed Apr. 18, 2001 (abandoned), which also claims priority to Application No. 60/227,439, filed Aug. 22, 2000. Application Ser. No. 10/374, 780 is also a continuation-in-part of application Ser. No. 10/225,068, filed Aug. 9, 2002 (issued as U.S. Pat. No. 7,193, 129), which claims the benefit of Application No. 60/310, 847, filed Aug. 9, 2001, and also claims the benefit of Application No. 60/336,049, filed Nov. 19, 2001, and also claims the benefit of Application No. 60/338,692, filed Dec. 11, 2001. Application Ser. No. 10/225,068 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). Application Ser. No. 10/374,780 is also a continuation-in-part of application Ser. No. 10/225,066, filed Aug. 9, 2002 (issued as U.S. Pat. No. 7,238,860), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; application Ser. No. 10/225, 066 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). Application Ser. No. 10/374,780 is also a continuation-in-part of application Ser. No. 10/225, 067, filed Aug. 9, 2002 (issued as U.S. Pat. No. 7,135,616), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001; application Ser. No. 10/225,067 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). This application is a continuation-in-part of application Ser. No. 10/546,266, filed Aug. 19, 2005 (pending), which is a '371 National Stage filing of International Application No. PCT/US2004005654, filed Feb. 25, 2004 (converted), which is a continuation-in-part of application Ser. No. 10/374,780, filed Feb. 25, 2003 (pending), and is also a continuation-in-part of application Ser. No. 10/675,852, filed Sep. 30, 2003 (pending). This application is also a continuation-in-part of application Ser. No. 11/986,992, filed Nov. 26, 2007, which is a division of application Ser. No. 10/412,699, filed Apr. 10, 2003 (issued as U.S. Pat. No. 7,345,217), which is a continuation-in-part of application Ser. No. 10/295,403, filed Nov. 15, 2002 (abandoned), which is a divisional of application Ser. No. 09/394, 519, filed Sep. 13, 1999 (abandoned), which claims the benefit of Application No. 60/101,349, filed Sep. 22, 1998, which also claims the benefit of Application No. 60/103,312, filed Oct. 6, 1998, which also claims the benefit of Application No. 60/108,734, filed Nov. 17, 1998, which also claims the benefit of Application No. 60/113,409, filed Dec. 22, 1998. Application Ser. No. 10/412,699 is also a continuation-in-part of application Ser. No. 09/489,376, filed Jan. 21, 2000 (abandoned), which claimed priority to Application No. 60/116, 841, filed Jan. 22, 1999. Application Ser. No. 10/412,699 is also a continuation-in-part of application Ser. No. 10/302, 267, filed Nov. 22, 2002 (issued as U.S. Pat. No. 7,223,904), which is a divisional of application Ser. No. 09/506,720, filed Feb. 17, 2000 (abandoned), which claims the benefit of Application No. 60/120,880, filed Feb. 18, 1999, which also claims the benefit of Application No. 60/121,037, filed Feb. 22, 1999, which also claims the benefit of Application No.

60/124,278, filed Mar. 11, 1999, which also claims the benefit of Application No. 60/129,450, filed Apr. 15, 1999, which also claims the benefit of Application No. 60/135,134, filed May 20, 1999, which also claims the benefit of Application No. 60/144,153, filed Jul. 15, 1999, which also claims the benefit of Application No. 60/161,143, filed Oct. 22, 1999, which also claims the benefit of Application No. 60/162,656, filed Nov. 1, 1999. Application Ser. No. 10/412,699 is also a continuation-in-part of application Ser. No. 10/278,173, filed Oct. 21, 2002 (abandoned), which is a divisional of application Ser. No. 09/533,392, filed Mar. 22, 2000 (abandoned), which claims the benefit of Application No. 60/125,814, filed Mar. 23, 1999. Application Ser. No. 10/412,699 is also a continuation-in-part of application Ser. No. 09/533,029, filed Mar. 22, 2000 (issued as U.S. Pat. No. 6,664,446), which claims the benefit of Application No. 60/125,814, filed Mar. 23, 1999. Application Ser. No. 10/412,699 is also a continuation-in-part of application Ser. No. 10/278,536, filed Oct. 22, 2002 (abandoned), which is a divisional of application Ser. No. 09/532,591, filed Mar. 22, 2000 (abandoned), which claims priority to Application No. 60/125,814, filed Mar. 23, 1999. Application Ser. No. 10/412,699 is also a continuation-in-part of application Ser. No. 09/713,994, filed Nov. 16, 2000 (abandoned), which claims the benefit of Application No. 60/166,228, filed Nov. 17, 1999, which also claims the benefit of Application No. 60/197,899, filed Apr. 17, 2000, which also claims the benefit of Application No. 60/227,439, filed Aug. 22, 2000. Application Ser. No. 10/412,699 is also a continuation-in-part of application Ser. No. 09/819,142, filed Mar. 27, 2001. Application Ser. No. 10/412,699 is also a continuation-in-part of application Ser. No. 09/934,455, filed Aug. 22, 2001 (abandoned), which is a continuation-in-part of application Ser. No. 09/713,994, filed Nov. 16, 2000 (abandoned), which is also a continuation-in-part of application Ser. No. 09/837,944, filed Apr. 18, 2001 (abandoned), which also claim the benefit of Application No. 60/227,439, filed Aug. 22, 2000. Application Ser. No. 10/412,699 is also a continuation-in-part of application Ser. No. 10/225,068, filed Aug. 9, 2002 (issued as U.S. Pat. No. 7,193,129), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,068 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). Application Ser. No. 10/412,699 is also a continuation-in-part of application Ser. No. 10/225,066, filed Aug. 9, 2002 (issued as U.S. Pat. No. 7,238,860), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,066 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). Application Ser. No. 10/412,699 is also a continuation-in-part of application Ser. No. 10/225,067, filed Aug. 9, 2002 (issued as U.S. Pat. No. 7,135,616), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,067 is also a continuation-in-part of application Ser. No. 09/837,944, filed Apr. 18, 2001 (abandoned), and is also a continuation-in-part of application Ser. No. 10/171,468, filed Jun. 14, 2002 (abandoned). Application Ser. No. 10/412,699 is also a continuation-in-part of application Ser. No. 10/374,780, filed Feb. 25, 2003 (pending). This application is a continuation-in-part of application Ser. No. 10/559,441, filed Dec. 2, 2005 (pending), which is a '371 National Stage filing of International Application No. PCT/US2004/017768, filed Jun. 4, 2004 (converted), which is a continuation-in-part of application Ser. No. 10/456,882, filed Jun. 6, 2003 (abandoned). This application is a continuation-in-part of application Ser. No. 11/642,814, filed Dec. 20, 2006, which is a divisional of application Ser. No. 10/666,642, filed Sep. 18, 2003 (issued as U.S. Pat. No. 7,196,245), which claims the benefit of Application No. 60/411,837, filed Sep. 18, 2002, and also claims the benefit of Application No. 60/434,166, filed Dec. 17, 2002, and also claims the benefit of Application No. 60/465,809, filed Apr. 24, 2003. This application is a continuation-in-part of application Ser. No. 10/714,887, filed Nov. 13, 2003 (pending), which is a continuation-in-part of application Ser. No. 10/456,882, filed Jun. 6, 2003 (abandoned); and application Ser. No. 10/714,887 is also a continuation-in-part of application Ser. No. 10/666,642, filed Sep. 18, 2003 (issued as U.S. Pat. No. 7,196,245), which claims the benefit of Application No. 60/411,837, filed Sep. 18, 2002, which also claims the benefit of Application No. 60/434,166, filed Dec. 17, 2002, which also claims the benefit of Application No. 60/465,809, filed Apr. 24, 2003. This application is a continuation-in-part of application Ser. No. 11/435,388, filed May 15, 2006 (pending), which is a continuation-in-part of International Application No. PCT/US04/37584, filed Nov. 12, 2004 (converted), which is a continuation-in-part of application Ser. No. 10/714,887, filed Nov. 13, 2003, and also claims the benefit of Application No. 60/527,658, filed Dec. 5, 2003, and also claims the benefit of Application No. 60/542,928, filed Feb. 5, 2004. This application is a continuation-in-part of application Ser. No. 11/632,390, filed Jan. 11, 2007, which is a '371 National Stage filing of International Application No. PCT/US2005/025010, filed Jul. 14, 2005 (converted), which claims the benefit of Application No. 60/588,405, filed Jul. 14, 2004. This application is a continuation-in-part of application Ser. No. 12/064,961, filed Feb. 26, 2008 (pending), which is a continuation-in-part of PCT application PCT/US06/34615, filed Aug. 31, 2006 (expired), which claims the benefit of Application No. 60/713,952, filed Aug. 31, 2005 (pending). This application is a continuation-in-part of International Application no. PCT/US2006/34615, filed Aug. 31, 2006, which claims the benefit of Application No. 60/713,952, filed Aug. 31, 2005. This application is a continuation-in-part of application Ser. No. 10/903,236, filed Jul. 30, 2004 (pending), which is a continuation-in-part of application Ser. No. 10/456,882, filed Jun. 6, 2003 (abandoned), and is also a continuation-in-part of application Ser. No. 10/666,642, filed Sep. 18, 2003 (issued as U.S. Pat. No. 7,196,245), which claims the benefit of Application No. 60/411,837, filed Sep. 18, 2002, and also claims the benefit of Application No. 60/465,809, filed Apr. 24, 2003. This application is a continuation-in-part of application Ser. No. 11/699,973, filed Jan. 29, 2007, which is a continuation-in-part of International Application No. PCT/US2005-027151, filed Jul. 29, 2005 (converted), which is a continuation-in-part of application Ser. No. 10/903,236, filed Jul. 30, 2004 (pending). This application is a continuation-in-part of application Ser. No. 10/870,198, filed Jun. 16, 2004 (pending), which claims the benefit of Application No. 60/565,948, filed Apr. 26, 2004, which also claims the benefit of Application No. 60/527,658, filed Dec. 5, 2003, which also claims the benefit of Application No. 60/542,928, filed Feb. 5, 2005; and, Application No. 10/870, 198 is also a continuation-in-part of application Ser. No. 10/669,824, filed Sep. 23, 2003 (pending), which is a continuation-in-part of application Ser. No. 09/823,676, filed Mar. 30, 2001 (issued as U.S. Pat. No. 6,717,034). This application is a continuation-in-part of application Ser. No. 10/838,616, filed May 4, 2004 (pending), which claims the benefit of Application No. 60/565,948, filed Apr. 26, 2004, and is a continuation-in-part of application Ser. No. 10/685,922, filed Oct. 14, 2003 (abandoned). This application is a continuation-in-part of International Application No. PCT/US2007/17321, filed Aug. 7, 2006 (pending), which claims the benefit of Application No. 60/836,243, filed Aug. 7, 2006. This application is a continuation-in-part of application Ser. No. 11/705,903, filed Feb. 12, 2007 (pending), which is a continuation-in-part of International Application No. PCT/US2006/34615, filed Aug. 31, 2006 (converted), which claims the benefit of Application No. 60/713,952, filed Aug. 31, 2005. This application is a continuation-in-part of application Ser. No. 11/821,448, filed Jun. 22, 2007 (pending), which claims priority to Application No. 60/817,886, filed Jun. 29, 2006. This application is a continuation-in-part of application Ser. No. 11/981,667, filed Oct. 31, 2007 (pending). This application is also a continuation-in-part of application Ser. No. 11/981,576 filed Oct. 31, 2007 (pending). This application is a continuation-in-part of International Application No. PCT/US2007/09124, filed Apr. 12, 2007 (pending), which claims priority to Application No. 60/791,663, filed Apr. 12, 2006. The contents of all applications herein are incorporated by reference in their entirety.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION

The present invention relates to compositions and methods for transforming plants for the purpose of improving plant traits, including yield and fruit quality.

BACKGROUND OF THE INVENTION

Biotechnological improvement of plants. Biotechnology approaches involving the expression of single transgenes in crops have resulted in the successful commercial introduction of new plant traits, including herbicide (e.g., glyphosate) resistance, insect resistance (expression of *Bacillus thuringiensis* toxins) and virus resistance (overexpression of viral coat proteins). Plant genomics may also be used to achieve control over polygenic traits. Some traits that may be improved, resulting in better yield and crop quality, include:

Increased lycopene levels. Lycopene is a pigment responsible for color of fruits (e.g., the red color of tomatoes). Consumers tend to prefer fruit products with good color, and often specifically buy fruit and fruit products based on lycopene levels.

Lycopene and other carotenoids are also valuable antioxidants. Lycopene is the subject of an increasing number of medical studies that demonstrate its efficacy in preventing certain cancers—including prostate, lung, stomach and breast cancers. Potential impacts also include ultraviolet protection and coronary heard disease prevention.

Increased soluble solids. Increased soluble solids are highly valuable to fruit processors for the production of various products. Grapes, for example, are harvested when soluble solids have reached an appropriate level, and the quality of wine produced from grapes is to a large extent dependent on soluble solid content. Increased soluble solids are also important in the production of tomato paste, sauces and ketchup. Increasing soluble solids in tomatoes increases the value of processed tomato products and decreases processing costs. Savings come from reduced processing time and less energy consumption due to shortened cooking times needed to achieve desired soluble solids levels. A one percent increase in tomato soluble solids may be worth $100 to $200 million to the tomato processing industry.

Fruit Weight. Increased fruit weight, such as the weight of tomato fruit, may directly impact yield when the fruit is the primary crop product. This is true for tomato plants, used as a model system in the present studies, and, generally, other fruit crops.

Control of cellular processes in plants with transcription factors. Strategies for manipulating traits by altering a plant cell's transcription factor content can result in plants and crops with new and/or improved commercially valuable properties. For example, manipulation of the levels of selected transcription factors may result in increased expression of economically useful proteins or biomolecules in plants or improvement in other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits, including traits that improve a plant's survival, yield and product quality.

SUMMARY OF THE INVENTION

The present invention relates to compositions and methods for modifying the genotype of a plant for the purpose of imparting desirable characteristics, including, but not limited to, yield and/or quality-related traits, and these characteristics may pertain to the fruit of the plant. The method steps include transforming a host plant cell with a DNA construct (such as an expression vector or a plasmid). The DNA construct comprises a polynucleotide that encodes a polypeptide that may regulate transcription. The polynucleotide is homologous to a polynucleotide of the invention provided in the Sequence Listing or Tables 7 or 8.

Once the host plant cell is transformed with the DNA construct, a plant may be regenerated from the transformed host plant cell to produce a plant having the desired yield or quality characteristic. Examples of yield and quality characteristics that may be improved by these method steps include increased fungal disease resistance, increased fruit weight, increased fruit number, increased lycopene, increased soluble solids, reduced fruit softening, increased plant vigor, and increased plant size.

BRIEF DESCRIPTION OF THE SEQUENCE LISTING AND FIGURES

The Sequence Listing provides exemplary polynucleotide and polypeptide sequences of the invention. The traits associated with the use of the sequences are included in the Examples.

The copy of the Sequence Listing, being submitted electronically with this patent application, provided under 37

CFR §1.821-1.825, is a read-only memory computer-readable file in ASCII text format. The Sequence Listing is named "MMBI-0070-2CIP_ST25.txt" and is 16,074 kilobytes in size (measured in MS-WINDOWS). The Sequence Listing file was created on Jun. 20, 2008. The Sequence Listing is herein incorporated by reference in its entirety.

FIG. 1 shows a conservative estimate of phylogenetic relationships among the orders of flowering plants (modified from Angiosperm Phylogeny Group (1998)). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001).

Figure 2:
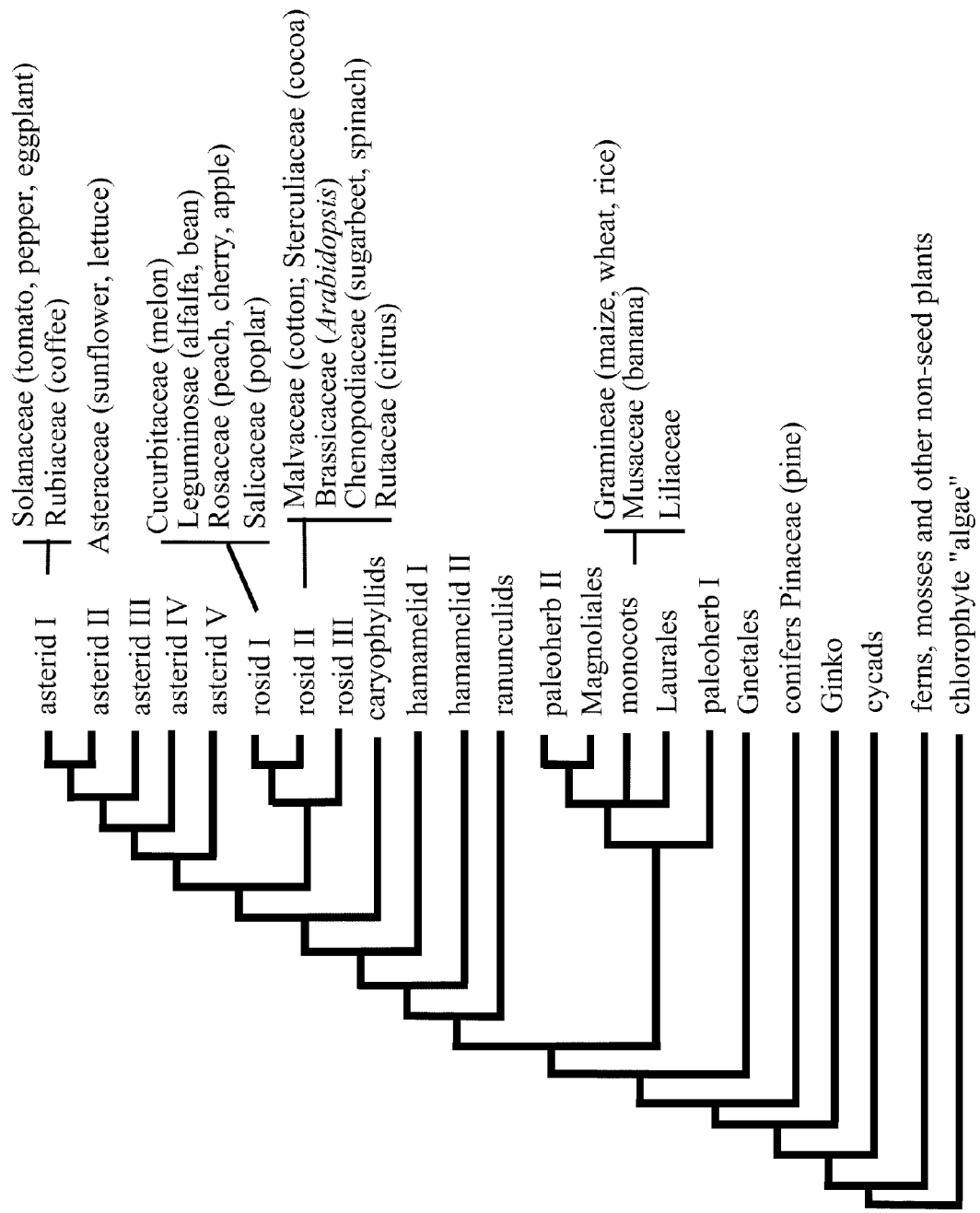

FIG. 2 shows a phylogenic dendogram depicting phylogenetic relationships of higher plant taxa, including clades containing tomato and *Arabidopsis*; adapted from Ku et al. (2000) and Chase et al. (1993).

Figure 3:
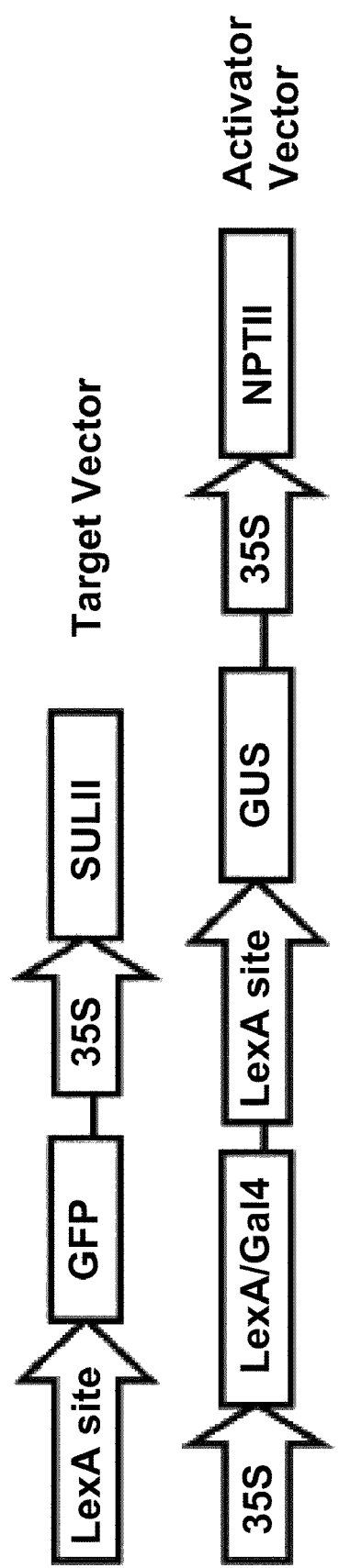

FIG. 3 is a schematic diagram of activator and target vectors used for transformation of tomato to achieve regulated expression of *Arabidopsis* transcription factors in tomato. The activator vector contained a promoter and a LexA-GAL4 or a-LacI-GAL4 transactivator (the transactivator comprises a LexA or LacI DNA binding domain fused to the GAL4 activation domain, and encodes a LexA-Gal4 or LacI-Gal4 transcriptional activator product), a GFP marker, and a neomycin phosphotransferase II (nptII) selectable marker. The target vector contains a transactivator binding site (opLexA) operably linked to a transgene encoding a polypeptide of interest (for example, a transcription factor of the invention), and a sulfonamide selectable marker (in this case, sulII; which encodes the dihydropteroate synthase enzyme for sulfonamide-resistance) necessary for the selection and identification of transformed plants. Binding of the transcriptional activator product encoded by the activator vector to the transactivator binding sites of the target vector initiates transcription of the transgenes of interest.

DESCRIPTION OF THE INVENTION

In an important aspect, the present invention relates to combinations of gene promoters and polynucleotides for modifying phenotypes of plants, including those associated with improved plant or fruit yield, or improved fruit quality. Throughout this disclosure, various information sources are referred to and/or are specifically incorporated. The information sources include scientific journal articles, patent documents, textbooks, and World Wide Web browser-active and inactive page addresses, for example. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a," "an," and "the" include plural reference unless the context clearly dictates otherwise. Thus, for example, a reference to "a plant" includes a plurality of such plants.

DEFINITIONS

"Polynucleotide" is a nucleic acid molecule comprising a plurality of polymerized nucleotides, e.g., at least about 15 consecutive polymerized nucleotides, optionally at least about 30 consecutive nucleotides, or at least about 50 consecutive nucleotides. A polynucleotide may be a nucleic acid, oligonucleotide, nucleotide, or any fragment thereof of a length listed above. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a polymerase chain reaction (PCR) product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as splicing and folding to obtain a functional protein or polypeptide. A gene may be isolated, partially isolated, or be found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and which may be used to determine the limits of the genetically active unit (Rieger et al. (1976)). A gene generally includes regions preceding ("leaders"; upstream) and following ("trailers"; downstream) of the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of the hybridization and amplification reactions. "Fully complementary" refers to the case where bonding occurs between every base pair and its complement in a pair of sequences, notwithstanding gaps that may occur in an alignment due to additional bases in one of the aligned sequences.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985), Sambrook et al. (1989), and by Hames and Higgins (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, transcription factors having 60% identity, or more preferably greater than about 70% identity, most preferably 72% or greater identity with disclosed transcription factors.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

"Ectopic expression" or "altered expression" in reference to a polynucleotide indicates that the pattern of expression in, e.g., a transgenic plant or plant tissue, is different from the expression pattern in a wild-type or control plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong promoter (e.g., the cauliflower mosaic virus 35S transcription initiation region). Overexpression may also under the control of an inducible or tissue specific promoter. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention generally possess at least one conserved domain characteristic of a particular transcription factor family. Examples of such conserved domains of the sequences of the invention may be found in Table 7. The transcription factors of the invention may also comprise an amino acid subsequence that forms a transcription activation domain that regulates expression of one or more abiotic stress tolerance genes in a plant when the transcription factor binds to the regulating region.

"Protein" refers to an amino acid sequence, oligopeptide, peptide, polypeptide or portions thereof whether naturally occurring or synthetic.

A "polypeptide" is an amino acid sequence comprising a plurality of consecutive polymerized amino acid residues e.g., at least about 15 consecutive polymerized amino acid residues, optionally at least about 30 consecutive polymerized amino acid residues, at least about 50 consecutive polymerized amino acid residues. In many instances, a polypeptide comprises a polymerized amino acid residue sequence that is a transcription factor or a domain or portion or fragment thereof. Additionally, the polypeptide may comprise 1) a localization domain, 2) an activation domain, 3) a repression domain, 4) an oligomerization domain, or 5) a DNA-binding domain, or the like. The polypeptide optionally comprises modified amino acid residues, naturally occurring amino acid residues not encoded by a codon, non-naturally occurring amino acid residues.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence. Additionally, the terms "homology" and "homologous sequence(s)" may refer to one or more polypeptide sequences that are modified by chemical or enzymatic means. The homologous sequence may be a sequence modified by lipids, sugars, peptides, organic or inorganic compounds, by the use of modified amino acids or the like. Protein modification techniques are illustrated in Ausubel et al. (1998).

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

With regard to polypeptides, the terms "substantial identity" or "substantially identical" may refer to sequences of sufficient similarity and structure to the transcription factors in the Sequence Listing to produce similar function when expressed, overexpressed, or knocked-out in a plant; in the present invention, this function is improved yield and/or fruit quality. Polypeptide sequences that are at least about 55% identical to the instant polypeptide sequences are considered to have "substantial identity" with the latter. Sequences having lesser degrees of identity but comparable biological activity are considered to be equivalents. The structure required to maintain proper functionality is related to the tertiary structure of the polypeptide. There are discreet domains and motifs within a transcription factor that must be present within the polypeptide to confer function and specificity. These specific structures are required so that interactive sequences will be properly oriented to retain the desired activity. "Substantial identity" may thus also be used with regard to subsequences, for example, motifs that are of sufficient structure and similarity, being at least about 55% identical to similar motifs in other related sequences. Thus, related polypeptides within the G1421 clade have the physical characteristics of substantial identity along their full length and within their AP2-related domains. These polypeptides also share functional characteristics, as the polypeptides within this clade bind to a transcription-regulating region of DNA and improve yield and/or fruit quality in a plant when the polypeptides are overexpressed.

"Alignment" refers to a number of nucleotide or amino acid residue sequences aligned by lengthwise comparison so that components in common (i.e., nucleotide bases or amino acid residues) may be visually and readily identified. The fraction or percentage of components in common is related to the homology or identity between the sequences. Alignments may be used to identify conserved domains and relatedness within these domains. An alignment may suitably be determined by means of computer programs known in the art, such as MacVector (1999) (Accelrys, Inc., San Diego, Calif.).

A "conserved domain" or "conserved region" as used herein refers to a region in heterologous polynucleotide or polypeptide sequences where there is substantial identity between the distinct sequences. bZIPT2-related domains are examples of conserved domains. With respect to polynucleotides encoding presently disclosed transcription factors, a conserved domain is encoded by a sequence preferably at least 10 base pairs (bp) in length. A conserved domain, with respect to presently disclosed polypeptides refers to a domain within a transcription factor family that exhibits a higher degree of sequence homology or substantial identity, such as at least 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid residue sequence identity to a sequence of consecutive amino acid residues such as SEQ ID NOs 2365-4175. As one of ordinary skill in the art recognizes, conserved domains may be identified as regions or domains of identity to a specific consensus sequence. Thus, by using alignment methods well known in the art, the conserved domains of the plant transcription factors of the invention (e.g., bZIPT2, MYB-related, CCAAT-box binding, AP2, and AT-hook family transcription factors) may be determined. An alignment of any of the polypeptides of the invention with another polypeptide allows one of skill in the art to identify conserved domains for any of the polypeptides listed or referred to in this disclosure.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

The term "variant", as used herein, may refer to polynucleotides or polypeptides that differ from the presently disclosed polynucleotides or polypeptides, respectively, in sequence from each other, and as set forth below.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. This, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, for example, replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an conserved domain of a transcription factor. Exemplary fragments also include fragments that comprise a conserved domain of a transcription factor. Exemplary fragments include fragments that comprise a conserved domain of a transcription factor, for example, amino acids: 84-146 of G1421, SEQ ID NO: 180, or 59-150 of G1437, SEQ ID NO: 186, or 9-111 of G663, SEQ ID NO: 1192, or 52-143 of G1957, SEQ ID NO: 446, which comprise, are comprised within, or approximate, the AP2 DNA binding domain, the QLQ/WRC protein interaction/putative DNA binding domains, the SANT/Myb DNA binding domain, or the B3 DNA binding domain of these polypeptides, respectively.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as three amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001); FIG. 2, adapted from Ku et al. (2000); and see also Tudge (2000).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as osmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

DETAILED DESCRIPTION

Generally, the polypeptides encoded by the present polynucleotide sequences are involved in cell differentiation, proliferation, and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to improved yield and/or fruit quality. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, for example, mutation reactions, PCR reactions, or the like; as substrates for cloning for example, including digestion or ligation reactions; and for identifying exogenous or endogenous modulators of the transcription factors. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, for example, genomic DNA or RNA, a transcript (such as an mRNA), a cDNA, a PCR product, a cloned DNA, a synthetic DNA or RNA, or the like. The polynucleotide can comprise a sequence in either sense or antisense orientations. Expression of genes that encode transcription factors and other regulatory proteins that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) and Peng et al. (1999). In addition, many others have demonstrated that an *Arabidopsis* transcription factor expressed in an exogenous plant species elicits the same or very similar phenotypic response (see, for example, Fu et al. (2001); Nandi et al. (2000); Coupland (1995); and Weigel and Nilsson (1995)).

In another example, Mandel et al. (1992b) and Suzuki et al. (2001) teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992b); Suzuki et al. (2001)).

Other examples include Müller et al. (2001); Kim et al. (2001); Kyozuka and Shimamoto (2002); Boss and Thomas (2002); He et al. (2000); and Robson et al. (2001).

In yet another example, Gilmour et al. (1998) teach an *Arabidopsis* AP2 transcription factor, CBF1, which, when overexpressed in transgenic plants, increases plant freezing tolerance. Jaglo et al. (2001) further identified sequences in *Brassica napus* that encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues which bracket the AP2/EREBP DNA binding domains of the proteins and distinguish them from other members of the AP2/EREBP protein family (Jaglo et al. (2001).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (for example, by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000); Borevitz et al. (2000)). Further, global transcript profiles have been used successfully as diagnostic tools for specific cellular states (for example, cancerous vs. non-cancerous; Bhattacharjee et al. (2001); Xu et al. (2001)). Consequently, it is evident to one skilled in the art that similarity of transcript profile upon overexpression of different transcription factors would indicate similarity of transcription factor function.

Polypeptides and Polynucleotides of the Invention

The present invention provides, among other things, transcription factors, and transcription factor homolog polypeptides, and isolated or recombinant polynucleotides encoding the polypeptides, or novel sequence variant polypeptides or polynucleotides encoding novel variants of transcription factors derived from the specific sequences provided here.

The polynucleotides of the invention can be or were ectopically expressed in overexpressor plant cells and the changes in the expression levels of a number of genes, polynucleotides, and/or proteins of the plant cells observed. Therefore, the polynucleotides and polypeptides can be employed to change expression levels of a genes, polynucleotides, and/or proteins of plants. These polypeptides and polynucleotides may be employed to modify a plant's characteristics, particularly improvement of yield and/or fruit quality. The polynucleotides of the invention can be or were ectopically expressed in overexpressor or knockout plants and the changes in the characteristic(s) or trait(s) of the plants observed. Therefore, the polynucleotides and polypeptides can be employed to improve the characteristics of plants. The polypeptide sequences of the sequence listing, including *Ara*- bidopsis sequences, such as those in Table 7, conferred improved characteristics when these polypeptides were overexpressed in tomato plants. These polynucleotides have been shown to confer increased lycopene levels and/or increased soluble solids, which impacts fruit quality, and/or increased fruit weight, which positively impacts fruit yield. Paralogs and orthologs of these sequences, listed herein, are expected to function in a similar manner by increasing these positive effects on fruit quality and/or yield.

The invention also encompasses sequences that are complementary to the polynucleotides of the invention. The polynucleotides are also useful for screening libraries of molecules or compounds for specific binding and for creating transgenic plants having improved yield and/or fruit quality. Altering the expression levels of equivalogs of these sequences, including paralogs and orthologs in the Sequence Listing, and other orthologs that are structurally and sequentially similar to the former orthologs, has been shown and is expected to confer similar phenotypes, including improved biomass, yield and/or fruit quality in plants.

In some cases, exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full-length cDNA was then recovered by a routine end-to-end PCR using primers specific to the isolated 5' and 3' ends. Exemplary sequences are provided in the Sequence Listing.

The invention also entails an agronomic composition comprising a polynucleotide of the invention in conjunction with a suitable carrier and a method for altering a plant's trait using the composition.

Examples of specific polynucleotide and polypeptides of the invention, and equivalog sequences, along with descriptions of the gene families that comprise these polynucleotides and polypeptides, are provided in Table 7, in the Sequence Listing, and in the description provided below.

Homologous Sequences

Sequences homologous, i.e., that share significant sequence identity or similarity, to those provided in the Sequence Listing, derived from *Arabidopsis thaliana* or from other plants of choice, are also an aspect of the invention. Homologous sequences can be derived from any plant including monocots and dicots and in particular agriculturally important plant species, including but not limited to, grasses such as *Miscanthus*, switchgrass, and sugarcane-*Miscanthus* crosses, and crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), the latter being related to corn (maize).

Homologous sequences can comprise orthologous or paralogous sequences, described below. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

Orthologs and Paralogs

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994); Higgins et al. (1996)). Groups of similar genes can also be identified with pair-wise BLAST analysis (Feng and Doolittle (1987)). For example, a clade of very similar MADS domain transcription factors from *Arabidopsis* all share a common function in flowering time (Ratcliffe et al. (2001)), and a group of very similar AP2 domain transcription factors from *Arabidopsis* are involved in tolerance of plants to freezing (Gilmour et al. (1998)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001))

Transcription factor genes and other regulatory sequences are conserved across diverse eukaryotic species lines (Goodrich et al. (1993); Lin et al. (1991); Sadowski et al. (1988)). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994); Higgins et al. (1996)) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

As described by Eisen (1998), evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen (1998)). In fact, many specific examples exist in which gene function has been shown to correlate well with gene phylogeny (Eisen (1998)). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen (1998)).

By using a phylogenetic analysis, one skilled in the art would recognize that the ability to deduce similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from eudicots and monocots can confer greater tolerance to drought-related stress as compared to control plants;

(iii) Myb-related *Arabidopsis* G682 (found in U.S. Pat. Nos. 7,223,904 and 7,193,129) and numerous phylogenetically-related sequences from eudicots and monocots can confer greater tolerance to heat, drought-related stress, cold, and salt as compared to control plants;

(iv) WRKY family *Arabidopsis* G1274 (found in U.S. Pat. No. 7,196,245) and numerous closely-related sequences from eudicots and monocots have been shown to confer increased water deprivation tolerance, and (v) AT-hook family soy sequence G3456 (found in US patent publication 20040128712A1) and numerous phylogenetically-related sequences from eudicots and monocots, increased biomass compared to control plants when these sequences are overexpressed in plants.

The polypeptides sequences belong to distinct clades of polypeptides that include members from diverse species. In each case, most or all of the clade member sequences derived from both eudicots and monocots have been shown to confer increased yield or tolerance to one or more abiotic stresses when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

A method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow (2002), have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

At the polypeptide level, the sequences of the invention will typically share at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid sequence identity, and have similar functions with the polypeptides listed in Table 7 when these sequences are overexpressed in plants.

Of particular interest is the structure of a transcription factor in the region of its conserved domain(s). Structural analyses may be performed by comparing the structure of the known transcription factor around its conserved domain with those of orthologs and paralogs. Analysis of a number of polypeptides within a transcription factor group or clade, including the functionally or sequentially similar polypeptides provided in the Sequence Listing, may also provide an understanding of structural elements required to regulate transcription within a given family. Polypeptides that are phylogenetically related to the polypeptides of Table 7 may also have conserved domains that share at least 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid sequence identity, and have similar functions in that the polypeptides of the invention may, when overexpressed in plants, confer at least one regulatory activity and altered trait selected from the group consisting of greater brix, greater fruit weight, greater lycopene, greater biomass, more chlorosis, darker green fruit, darker green leaves, deeper red fruit, larger flowers, larger leaflets, larger leaflets, larger and lighter green leaves, rugulose leaves, more anthocyanin, more trichomes, paler white fruit at the green fruit stage, thicker stems, very high vigor, and waxier leaves, as compared to a control plant.

At the nucleotide level, the sequences of the invention will typically share at least about 30% or 40% nucleotide sequence identity, preferably at least about 50%, 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%, sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Methods for Determining Sequence Relationships

A variety of methods for determining sequence relationships can be used, including manual alignment and computer assisted sequence alignment and analysis. This later approach is a preferred approach in the present invention, due to the increased throughput afforded by computer assisted methods. As noted below, a variety of computer programs for performing sequence alignment are available, or can be produced by one of skill.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., manually, using the algorithm provided above, or by the Jotun Hein method (see, for example, Hein (1990)). Identity between sequences can also be determined by other methods known in the art, e.g., by varying hybridization conditions (see US Patent Application No. 20010010913).

One example algorithm that is suitable for determining percent sequence identity and sequence similarity is the BLAST algorithm, which is described in Altschul et al. (1990). Software for performing BLAST analyses is publicly available, e.g., through the National Library of Medicine's National Center for Biotechnology Information (ncbi.nlm-.nih; see at world wide web (www) National Institutes of Health US government (gov) website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1993); Altschul et al. (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1992)). Unless otherwise indicated, "sequence identity" here refers to the % sequence identity generated from a tblastx using the NCBI version of the algorithm at the default settings using gapped alignments with the filter "off" (see, for example, NIH NLM NCBI website at ncbi.nlm.nih).

In addition to calculating percent sequence identity, the BLAST algorithm also performs a statistical analysis of the similarity between two sequences (see, e.g. Karlin and Altschul (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

Sequence alignment program, include, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PHYTOSEQ sequence database (Incyte Genomics, Wilmington, Del.) can be searched.

Alignment of sequences for comparison can be conducted by the local homology algorithm of Smith and Waterman (1981), by the homology alignment algorithm of Needleman and Wunsch (1970, by the search for similarity method of Pearson and Lipman (1988), or by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel (2000).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In addition, one or more polynucleotide sequences or one or more polypeptides encoded by the polynucleotide sequences may be used to search against a BLOCKS (Bairoch et al. (1997)), PFAM, and other databases which contain previously identified and annotated motifs, sequences and gene functions. Methods that search for primary sequence patterns with secondary structure gap penalties (Smith et al. (1992)) as well as algorithms such as Basic Local Alignment Search Tool (BLAST; Altschul (1990); Altschul et al. (1993)), BLOCKS (Henikoff and Henikoff (1991)), Hidden Markov Models (HMM; Eddy (1996); Sonnhammer et al. (1997)), and the like, can be used to manipulate and analyze polynucleotide and polypeptide sequences encoded by polynucleotides. These databases, algorithms and other methods are well known in the art and are described in Ausubel et al. (1997), and in Meyers (1995).

Furthermore, methods using manual alignment of sequences similar or homologous to one or more polynucleotide sequences or one or more polypeptides encoded by the polynucleotide sequences may be used to identify regions of similarity and B-box zinc finger domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Table 7 and the Sequence Listing. In addition to the sequences in Table 7 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al. (1989); Berger and Kimmel (1987); and Anderson and Young (1985)).

Encompassed by the invention are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987); and Kimmel (1987)). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989); Berger and Kimmel (1987) pp. 467-469; and Anderson and Young (1985).

Hybridization experiments are generally conducted in a buffer of pH between 6.8 to 7.4, although the rate of hybridization is nearly independent of pH at ionic strengths likely to be used in the hybridization buffer (Anderson and Young (1985)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements that encode the present transcription factors include, for example:

6×SSC and 1% SDS at 65° C.;
50% formamide, 4×SSC at 42° C.; or
0.5×SSC to 2.0×SSC, 0.1% SDS at 50° C. to 65° C.; or
0.1×SSC to 2×SSC, 0.1% SDS at 50° C.-65° C.;
with a first wash step of, for example, 10 minutes at about 42° C. with about 20% (v/v) formamide in 0.1×SSC, and with, for example, a subsequent wash step with 0.2×SSC and 0.1% SDS at 65° C. for 10, 20 or 30 minutes. An example of a polynucleotide sequence of the invention would thus include a polynucleotide sequence that hybridizes to the complement of any of SEQ ID NO: 2n−1, where n=1 to 1317, or SEQ ID NO: 4176-4823, or SEQ ID NO: 4839 to 10667 under these stringent conditions. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Wash procedures will generally employ at least two final wash steps. Additional variations on these conditions will be readily apparent to those skilled in the art (see, for example, U.S. patent application No. 20010010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 min in duration, or about 0.1×SSC, 0.1% SDS at 65° C. and washing twice for 10, 20 or 30 min. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a calorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the complements of the listed polynucleotide sequences, for example, to SEQ ID NO: 2n−1, where n=1 to 1317 or SEQ ID NO: 4176-4823, or SEQ ID NO: 4839-10667, and fragments thereof under various conditions of stringency (see, e.g., Wahl and Berger (1987); Kimmel (1987)). Estimates of homology are provided by either DNA-DNA or DNA-RNA hybridization under conditions of stringency as is well understood by those skilled in the art (Hames and Higgins (1985). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

Identifying Polynucleotides or Nucleic Acids with Expression Libraries

In addition to hybridization methods, transcription factor homolog polypeptides can be obtained by screening an expression library using antibodies specific for one or more transcription factors. With the provision herein of the disclosed transcription factor, and transcription factor homolog nucleic acid sequences, the encoded polypeptide(s) can be expressed and purified in a heterologous expression system (e.g., E. coli) and used to raise antibodies (monoclonal or polyclonal) specific for the polypeptide(s) in question. Antibodies can also be raised against synthetic peptides derived from transcription factor, or transcription factor homolog, amino acid sequences. Methods of raising antibodies are well known in the art and are described in Harlow and Lane (1988). Such antibodies can then be used to screen an expression library produced from the plant from which it is desired to clone additional transcription factor homologs, using the methods described above. The selected cDNAs can be confirmed by sequencing and enzymatic activity.

Producing Polypeptides

The polynucleotides of the invention include sequences that encode transcription factors and transcription factor homolog polypeptides and sequences complementary thereto, as well as unique fragments of coding sequence, or sequence complementary thereto. Such polynucleotides can be, for example, DNA or RNA, the latter including mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homolog polypeptide, in isolation, in combination with additional coding sequences (e.g., a purification tag, a localization signal, as a fusion-protein, as a pre-protein, or the like), in combination with non-coding sequences (for example, introns or inteins, regulatory elements such as promoters, enhancers, terminators, and the like), and/or in a vector or host environment in which the polynucleotide encoding a transcription factor or transcription factor homolog polypeptide is an endogenous or exogenous gene.

A variety of methods exist for producing the polynucleotides of the invention. Procedures for identifying and isolating DNA clones are well known to those of skill in the art, and are described in, for example, Berger and Kimmel (1987); Sambrook et al. (1989) and Ausubel et al. (1998; supplemented through 2000).

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qβ-replicase amplification and other RNA polymerase mediated techniques (for example, NASBA), e.g., for the production of the homologous nucleic acids of the invention are found in Berger and Kimmel (1987), Sambrook (1989), and Ausubel (2000), as well as Mullis et al. (1990). Improved methods for cloning in vitro amplified nucleic acids are described in U.S. Pat. No. 5,426,039. Improved methods for amplifying large nucleic acids by PCR are summarized in Cheng et al. (1994) and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel (2000), Sambrook (1989) and Berger and Kimmel (1987).

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) and Matthes et al. (1984). According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Sequence Variations

It will readily be appreciated by those of skill in the art, that any of a variety of polynucleotide sequences are capable of encoding the transcription factors and transcription factor homolog polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the Sequence Listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms that may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that, for example, G1421, SEQ ID NO: 180, represents a single transcription factor; allelic variation and alternative splicing may be expected to occur. Allelic variants of SEQ ID NO: 179 can be cloned by probing cDNA or genomic libraries from different individual organisms according to standard procedures. Allelic variants of the DNA sequence shown in SEQ ID NO: 179, including those containing silent mutations and those in which mutations result in amino acid sequence changes, are within the scope of the present invention, as are proteins which are allelic variants of SEQ ID NO: 180. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

Thus, in addition to the sequences set forth in the Sequence Listing, the invention also encompasses related nucleic acid molecules that include allelic or splice variants of the sequences of the invention, for example, SEQ ID NO: 2n−1, where n=1 to 1317, and include sequences that are complementary to any of the above nucleotide sequences. Related nucleic acid molecules also include nucleotide sequences encoding a polypeptide comprising a substitution, modification, addition and/or deletion of one or more amino acid residues compared to the polypeptide sequences of the invention, for example, SEQ ID NO: 2n, where n=1 to 1317, or sequences comprising any of SEQ ID NOs: 2365-4175 or polypeptides encoded by any of SEQ ID NOs: 4839-10667. Such related polypeptides may comprise, for example, additions and/or deletions of one or more N-linked or O-linked glycosylation sites, or an addition and/or a deletion of one or more cysteine residues.

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acid residues in the encoded polypeptide, can be made without altering the function of the polypeptide, these conservative variants are, likewise, a feature of the invention.

For example, substitutions, deletions and insertions introduced into the sequences provided in the Sequence Listing, are also envisioned by the invention. Such sequence modifications can be engineered into a sequence by site-directed mutagenesis (Wu (1993) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 1 when it is desired to maintain the activity of the protein. Table 1 shows amino acids which can be substituted for an amino acid in a protein and which are typically regarded as conservative substitutions.

TABLE 1

Possible conservative amino acid substitutions

| Amino Acid Residue | Conservative substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

The sequences provided in the Sequence Listing or in Table 7 have a novel activity, being plant transcription sequences that may be used to regulate expression of proteins. Although all conservative amino acid substitutions (for example, one basic amino acid substituted for another basic amino acid) in the protein of the invention will not necessarily result in a protein that has transcriptional regulatory activity, it is expected that many of these conservative mutations would result in a protein having transcriptional regulatory activity. Most mutations, conservative or non-conservative, made to a protein of the invention, but outside of a domain critical to the activity of the protein (for example, conserved domains of SEQ ID NOs: 2365-4175) and outside of other domains essential for protein activity, will not affect the activity of the protein to any great extent.

Similar substitutions are those in which at least one residue in the amino acid sequence has been removed and a different residue inserted in its place. Substitutions that are less conservative can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well know to those of skill in the art. For example, Ausubel (2000), provides additional details on mutagenesis methods. Artificial forced evolution methods are described, for example, by Stemmer (1994a), Stemmer (1994b), and U.S. Pat. Nos. 5,811,238, 5,837,500, and 6,242,568. Methods for engineering synthetic transcription factors and other polypeptides are described, for example, by Zhang et al. (2000), Liu et al. (2001), and Isalan et al. (2001). Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel (2000). Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for Saccharomyces cerevisiae and mammals are TAA and TGA, respectively. The preferred stop codon for monocotyledonous plants is TGA, whereas insects and E. coli prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP16 or GAL4 (Moore et al. (1998); Aoyama et al. (1995)), peptides derived from bacterial sequences (Ma and Ptashne (1987)) and synthetic peptides (Giniger and Ptashne (1987)).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homolog.

The transgenic plants of the present invention comprising recombinant polynucleotide sequences are generally derived from parental plants, which may themselves be non-transformed (or non-transgenic) plants. These transgenic plants may either have a transcription factor gene "knocked out" (for example, with a genomic insertion by homologous recombination, an antisense or ribozyme construct) or expressed to a normal or wild-type extent. However, overexpressing transgenic "progeny" plants will exhibit greater mRNA levels, wherein the mRNA encodes a transcription factor, that is, a DNA-binding protein that is capable of binding to a DNA regulatory sequence and inducing transcription, and preferably, expression of a plant trait gene, such as a gene that improves plant and/or fruit quality and/or yield. Preferably, the mRNA expression level will be at least three-fold greater than that of the parental plant, or more preferably at least ten-fold greater mRNA levels compared to said parental plant, and most preferably at least fifty-fold greater compared to said parental plant.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Protein Factors

A transcription factor provided by the present invention can also be used to identify additional endogenous or exogenous molecules that can affect a phenotype or trait of interest. Such molecules include endogenous molecules that are acted upon either at a transcriptional level by a transcription factor of the invention to modify a phenotype as desired. For example, the transcription factors can be employed to identify one or more downstream genes that are subject to a regulatory effect of the transcription factor. In one approach, a transcription factor or transcription factor homolog of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (such as binding sites on DNA sequences) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999)).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien et al. (1991) and is commercially available from Clontech (Palo Alto, Calif.). In such a system, plasmids are constructed that encode two hybrid proteins: one consists of the DNA-binding domain of a transcription activator protein fused to the transcription factor polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the transcription factor protein-protein interactions can be preformed.

Subsequences

Also contemplated are uses of polynucleotides, also referred to herein as oligonucleotides, typically having at least 12 bases, preferably at least 50 bases, which hybridize under stringent conditions to a polynucleotide sequence described above. The polynucleotides may be used as probes, primers, sense and antisense agents, and the like, according to methods as noted above.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologs of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook (1989), and Ausubel (2000).

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that activates transcription, e.g., by binding to a specific DNA promoter region an activation domain, or a domain for protein-protein interactions.

Vectors Promoters and Expression Systems

This section describes vectors, promoters, and expression systems that may be used with the present invention. Expression constructs that have been used to transform plants for testing in field trials are also described in Example III. The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger and Kimmel (1987), Sambrook (1989) and Ausubel (2000). Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) and Gelvin et al. (1990). Specific examples include those derived from a Ti plasmid of *Agrobacterium tumefaciens*, as well as those disclosed by Herrera-Estrella et al. (1983), Bevan (1984), and Klee (1985) for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) and corn (Gordon-Kamm (1990) can be produced. An immature embryo can also be a good target tissue for monocots for direct DNA delivery techniques by using the particle gun (Weeks et al. (1993); Vasil (1993a); Wan and Lemeaux (1994), and for *Agrobacterium*-mediated DNA transfer (Ishida et al. (1996)).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally—or developmentally—regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 KB of the start of translation, or within 1.5 KB of the start of translation, frequently within 1.0 KB of the start of translation, and sometimes within 0.5 KB of the start of translation.

The promoter sequences can be isolated according to methods known to one skilled in the art.

Examples of constitutive plant promoters which can be useful for expressing the transcription factor sequence include: the cauliflower mosaic virus (CaMV) 35S promoter, which confers constitutive, high-level expression in most plant tissues (see, e.g., Odell et al. (1985)); the nopaline synthase promoter (An et al. (1988)); and the octopine synthase promoter (Fromm et al. (1989)).

The transcription factors of the invention may be operably linked with a specific promoter that causes the transcription factor to be expressed in response to environmental, tissue-specific or temporal signals. A variety of plant gene promoters that regulate gene expression in response to environmental, hormonal, chemical, developmental signals, and in a tissue-active manner can be used for regulating the expression of a polypeptide sequence of the invention in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988)), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998)), flower-specific (Kaiser et al. (1995)), pollen (Baerson et al. (1994)), carpels (Ohl et al. (1990)), pollen and ovules (Baerson et al. (1993)), auxin-inducible promoters (such as that described in van der Kop et al. (1999) or Baumann et al. (1999)), cytokinin-inducible promoter (Guevara-Garcia (1998)), promoters responsive to gibberellin (Shi et al. (1998), Willmott et al. (1998)) and the like. Additional promoters are those that elicit expression in response to heat (Ainley et al. (1993)), light (e.g., the pea rbcS-3A promoter, Kuhlemeier et al. (1989)), and the maize rbcS promoter, Schaffner and Sheen (1991)); wounding (e.g., wun1, Siebertz et al. (1989)); pathogens (such as the PR-1 promoter described in Buchel et al. (1999) and the PDF1.2 promoter described in Manners et al. (1998), and chemicals such as methyl jasmonate or salicylic acid (Gatz (1997)). In addition, the timing of the expression can be controlled by using promoters such as those acting at senescence (Gan and Amasino (1995)); or late seed development (Odell et al. (1994)).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook (1989) and Ausubel (2000).

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al. (1985)), infection by viral vectors such as cauliflower mosaic virus (CaMV) (Hohn et al. (1982); U.S. Pat. No. 4,407,956), high velocity ballistic penetration by small particles with the nucleic acid either within the matrix of small beads or particles, or on the surface (Klein et al. (1987)), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984); Fraley et al. (1983)).

The cell can include a nucleic acid of the invention that encodes a polypeptide, wherein the cell expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Potential Applications of the Presently Disclosed Sequences that Improve Plant Yield and/or Fruit Yield or Quality The genes identified by the experiment presently disclosed represent potential regulators of plant yield and/or fruit yield or quality. As such, these sequences, or their functional equivalogs, orthologs or paralogs, can be introduced into plant species, including commercial plant species, in order to produce higher yield and/or quality, including higher fruit yield and/or quality.

Production of Transgenic Plants and Modification of Traits

The polynucleotides of the invention are favorably employed to produce transgenic plants with various traits, or characteristics, that have been modified in a desirable manner, e.g., to improve the fruit quality characteristics of a plant. For example, alteration of expression levels or patterns (e.g., spatial or temporal expression patterns) of one or more of the transcription factors (or transcription factor homologs) of the invention, as compared with the levels of the same protein found in a wild-type plant, can be used to modify a plant's traits. An illustrative example of trait modification, improved characteristics, by altering expression levels of a particular transcription factor is described further in the Examples and the Sequence Listing.

Homologous Genes Introduced into Transgenic Plants.

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Genes, Traits and Utilities that Affect Plant Characteristics

Plant transcription factors can modulate gene expression, and, in turn, be modulated by the environmental experience of a plant. Significant alterations in a plant's environment invariably result in a change in the plant's transcription factor gene expression pattern. Altered transcription factor expression patterns generally result in phenotypic changes in the plant. Transcription factor gene product(s) in transgenic plants then differ(s) in amounts or proportions from that found in wild-type or non-transformed plants, and those transcription factors likely represent polypeptides that are used to alter the response to the environmental change. By way of example, it is well accepted in the art that analytical methods based on altered expression patterns may be used to screen for phenotypic changes in a plant far more effectively than can be achieved using traditional methods.

Antisense and Co-Suppression

In addition to expression of the nucleic acids of the invention as gene replacement or plant phenotype modification nucleic acids, the nucleic acids are also useful for sense and anti-sense suppression of expression, e.g. to down-regulate expression of a nucleic acid of the invention, e.g. as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g. as set forth in Lichtenstein and Nellen (1997). Antisense regulation is also described in Crowley et al. (1985); Rosenberg et al. (1985); Preiss et al. (1985); Melton (1985); Izant and Weintraub (1985); and Kim and Wold (1985). Additional methods for antisense regulation are known in the art. Antisense regulation has been used to reduce or inhibit expression of plant genes in, for example in European Patent Publication No. 271988. Antisense RNA may be used to reduce gene expression to produce a visible or biochemical phenotypic change in a plant (Smith et al. (1988); Smith et al. (1990)). In general, sense or anti-sense sequences are introduced into a cell, where they are optionally amplified, e.g. by transcription. Such sequences include both simple oligonucleotide sequences and catalytic sequences such as ribozymes.

For example, a reduction or elimination of expression (i.e., a "knock-out") of a transcription factor or transcription factor homolog polypeptide in a transgenic plant, e.g., to modify a plant trait, can be obtained by introducing an antisense construct corresponding to the polypeptide of interest as a cDNA. For antisense suppression, the transcription factor or homolog cDNA is arranged in reverse orientation (with respect to the coding sequence) relative to the promoter sequence in the expression vector. The introduced sequence need not be the full-length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using RNA interference, or RNAi. RNAi is a post-transcriptional, targeted gene-silencing technique that uses double-stranded RNA (dsRNA) to incite degradation of messenger RNA (mRNA) containing the same sequence as the dsRNA (Constans (2002)). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore (2001). RNAi has been used for gene function determination in a manner similar to antisense oligonucleotides (Constans (2002)). Expression vectors that continually express siRNAs in transiently and stably transfected have been engineered to express small hairpin RNAs (shRNAs), which get processed in vivo into siRNAs-like molecules capable of carrying out gene-specific silencing (Brummelkamp et al. (2002), and Paddison, et al. (2002)). Post-transcriptional gene silencing by double-stranded RNA is discussed in further detail by Hammond et al. (2001), Fire et al. (1998) and Timmons and Fire (1998). Vectors in which RNA encoded by a transcription factor or transcription factor homolog cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999)). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homolog gene. Plants containing a single transgene insertion event at the desired gene can be crossed to generate homozygous plants for the mutation. Such methods are well known to those of skill in the art (see for example Koncz et al. (1992a, 1992b)).

Alternatively, a plant phenotype can be altered by eliminating an endogenous gene, such as a transcription factor or transcription factor homolog, e.g., by homologous recombination (Kempin et al. (1997)).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, such as, for example, by ectopically expressing a gene by T-DNA activation tagging (Ichikawa et al. (1997); Kakimoto et al. (1996)). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (see, e.g., PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984); Shimamoto et al. (1989); Fromm et al. (1990); and Vasil et al. (1990).

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified using methods well known in the art that are specifically directed to improved fruit or yield characteristics. Methods that may be used are provided in Examples II through VI. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Methods for Increasing Plant Yield or Quality by Modifying Transcription Factor Expression The present invention includes compositions and methods for increasing the yield and quality of a plant or its products, including those derived from a crop plant. These methods incorporate steps described in the Examples listed below, and may be achieved by inserting a nucleic acid sequence of the invention into the genome of a plant cell: (i) a promoter that functions in the cell; and (ii) a nucleic acid sequence that is substantially identical to any of SEQ ID NO: 2n−1, where n=1 to 1317, or SEQ ID NO: 4839-10667, where the promoter is operably linked to the nucleic acid sequence. A transformed plant may then be generated from the cell. One may either obtain transformed seeds from that plant or its progeny, or propagate the transformed plant asexually. Alternatively, the transformed plant may be grown and harvested for plant products directly.

The methods encompassed by the invention may be extended to propagation techniques used to generate plants. For example, a target plant is transformed with a polynucleotide encoding provided in the Sequence Listing, or a polynucleotide encoding a polypeptide that is an equivalog of one of the polypeptides provided in the Sequence Listing, and that has an improved trait relative to a control plant such as one or more traits provided in Table 7, and the transformed target plant may be "selfed" (i.e., self-pollinated) or crossed with another plant to produce transgenic seed. A progeny plant may be grown from this seed, thus generating a transformed progeny plant with the improved trait as compared to the control plant.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a transcription factor that is associated with a particular first trait may also be associated with at least one other, unrelated and inherent second trait which was not predicted by the first trait.

Example I

Isolation and Cloning of Full-Length Plant Transcription Factor cDNAs

Putative transcription factor sequences (genomic or ESTs) related to known transcription factors were identified in the *Arabidopsis thaliana* GenBank database using the tblastn sequence analysis program using default parameters and a P-value cutoff threshold of B4 or B5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 600 C) and labeled with $^{32}$P dCTP using the High Prime DNA Labeling Kit (Roche Diagnostics Corp., Indianapolis, Ind.). Purified radiolabelled probes were added to filters immersed in Church hybridization medium (0.5 M NaPO$_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the MARATHON cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the MARATHON Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Strategy to Produce a Tomato Population Expressing all Transcription Factors Driven by Various Promoters Ten promoters were chosen to control the expression of transcription factors in tomato for the purpose of evaluating complex traits in fruit development. All ten are expressed in fruit tissues, although the temporal and spatial expression patterns in the fruit vary (Table 2). All of the promoters have been characterized in tomato using a LexA-GAL4 two-component activation system. The PID (Plasmid IDentifier) and PID SEQ ID NOs used in the field study to drive expression of the sequences of the invention are listed in the second column.

TABLE 2

Promoters, promoter constructs and expression patterns used in the field study

| Promoter | PID and SEQ ID NO: of promoter construct | General expression patterns | References |
|---|---|---|---|
| CaMV35S ("35S") | P6506 SEQ ID NO: 4837 | Constitutive, high levels of expression in all throughout the plant and fruit | Odell et al (1985) |
| SHOOT MERISTEMLESS (STM) | P5318 SEQ ID NO: 4832 | Expressed in meristematic tissues, including apical meristems, cambium. Low levels of expression also in some differentiating tissues. In fruit, most strongly expressed in vascular tissues and endosperm. | Long and Barton (1998) Long and Barton (2000) |
| ASYMMETRIC LEAVES 1 (AS1) | P5319 SEQ ID NO: 4833 | Expressed predominately in differentiating tissues. In fruit, most strongly expressed in vascular tissues and in endosperm. | Byrne et al (2000) Ori et al. (2000) |
| LIPID TRANSFER PROTEIN 1 (LTP1) | P5287 SEQ ID NO: 4825 | In vegetative tissues, expression predominately in epidermis. Low levels of expression also evident in vascular tissue. In fruit, expression is strongest in the pith-like columella/placental tissue. | Thoma et al. (1994) |
| RIBULOSE-1,5-BISPHOSPHATE CARBOXYLASE, SMALL SUBUNIT 3 (RbcS3) | P5284 SEQ ID NO: 4824 | Expression predominately in highly photosynthetic vegetative tissues. Fruit expression predominately in the pericarp. | Wanner and Gruissem (1991) |
| ROOT SYSTEM INDUCIBLE 1 (RSI-1) | P5310 SEQ ID NO: 4830 | Expression generally limited to roots. Also expressed in the vascular tissues of the fruit. | Taylor and Scheuring (1994) |
| APETALA 1 (AP1) | P5326 SEQ ID NO: 4835 | Light expression in leaves increases with maturation. Highest expression in flower primordia and flower organs. In fruits, predominately in pith-like columella/placental tissue. | Mandel et al. (1992a) Hempel et al. (1997) |
| POLYGALACTURONASE (PG) | P5297 SEQ ID NO: 4828 | High expression throughout the fruit, comparable to 35S. Strongest late in fruit development. | Nicholass et al. (1995) Montgomery et al. (1993) |
| PHYTOENE DESATURASE (PD) | P5303 SEQ ID NO: 4829 | Moderate expression in fruit tissues. | Corona et al. (1996) |
| CRUCIFERIN 1 (Cru) | P5324 SEQ ID NO: 4834 | Expressed at low levels in fruit vascular tissue and columella, endosperm expression. | Breen and Crouch (1992) Sjodahl et al. (1995) |

Transgenic tomato lines expressing all *Arabidopsis* transcription factors driven by ten tissue and/or developmentally regulated promoters relied on the use of a two-component system similar to that developed by Guyer et al. (1998) that uses the DNA binding domain of the yeast GAL4 transcriptional activator fused to the activation domains of the maize C1 or the herpes simplex virus VP16 transcriptional activators, respectively. Modifications used either the *E. coli* lactose repressor DNA binding domain (LacI) or the *E. coli* LexA DNA binding domain fused to the GAL4 activation domain. The LexA-based system was the most reliable in activating tissue-specific GFP expression in tomato and was used to generate the tomato population. A diagram of the test transformation vectors is shown in FIG. 3. *Arabidopsis* transcription factor genes replaced the GFP gene in the target vector. As shown in Table 7, various promoters were used in the activator plasmid. Both families of vectors were used to transform tomato to yield one set of transgenic lines harboring different target vector constructs of transcription factor genes and a second population harboring the activator vector constructs of promoter-LexA/GAL4 fusions. Transgenic plants harboring the activator vector construct of promoter-LexA/GAL4 fusions were screened to identify plants with appropriate and high level expression of GUS. In addition, five of each of the transgenic plants harboring the target vector constructs of transcription factor genes were grown and crossed with a 35S activator line. F1 progeny were assayed to ensure that the transgene was capable of being activated by the LexA/GAL4 activator protein. The best plants constitutively expressing transcription factors were selected for subsequent crossing to the ten transgenic activator lines. Several of these initial lines have been evaluated and preliminary results of seedling traits indicate that similar phenotypes observed in *Arabidopsis* were also observed in tomato when the same transcription factor was constitutively overexpressed. Thus, each parental line harboring either a promoter-LexA/GAL4 activator or an activatible *Arabidopsis* transcription factors gene were pre-selected based on a functional assessment. These parental lines were used in sexual crosses to generate F1 (hemizygous for the activator and target genes) lines representing the complete set of *Arabidopsis* transcription factors under the regulation of the promoter. The transgenic tomato population was grown field conditions for evaluation.

Example III

Test Constructs

The Two-Component Multiplication System vectors have an activator vector and a target vector. The LexA version of these is shown in FIG. 3. The LacI versions are identical except that LacI replaces LexA portions. Both LacI and LexA DNA binding regions were tested in otherwise identical vectors. These regions were made from portions of the test vectors described above, using standard cloning methods. They were cloned into a binary vector that had been previously tested in tomato transformations. These vectors were then introduced into *Arabidopsis* and tomato plants to verify their functionality. The LexA-based system was determined to be the most reliable in activating tissue-specific GFP expression in tomato and was used to generate the tomato population.

A useful feature of the PTF Tool Kit vectors described in FIG. 3 is the use of two different resistance markers, one in the activator vector and another in the target vector. This greatly facilitates identifying the activator and target plant transcription factor genes in plants following crosses. The presence of both the activator and target in the same plant can be confirmed by resistance to both markers. Additionally, plants homozygous for one or both genes can be identified by scoring the segregation ratios of resistant progeny. These resistance markers are useful for making the technology easier to use for the breeder.

Another useful feature of the PTF Tool Kit activator vector described in FIG. 3 is the use of a target GFP construct to characterize the expression pattern of each of the 10 activator promoters. The Activator vector contains a construct consisting of multiple copies of the LexA (or LacI) binding sites and a TATA box upstream of the gene encoding the green fluorescence protein (GFP). This GFP reporter construct verifies that the activator gene is functional and that the promoter has the desired expression pattern before extensive plant crossing and characterizations proceed. The GFP reporter gene is also useful in plants derived from crossing the activator and target parents because it provides an easy method to detect the pattern of expression of expressed plant transcription factor genes.

Example IV

Tomato Transformation and Sulfonamide Selection

After the activator and target vectors were constructed, the vectors were used to transform *Agrobacterium tumefaciens* cells. Since the target vector comprised a polypeptide or interest (in the example given in FIG. 3, the polypeptide of interest was green fluorescent protein; other polypeptides of interest may include transcription factor polypeptides of the invention), it was expected that plants containing both vectors would be conferred with improved and useful traits. Methods for generating transformed plants with expression vectors are well known in the art; this Example also describes a novel method for transforming tomato plants with a sulfonamide selection marker. In this Example, tomato cotyledon explants were transformed with *Agrobacterium* cultures comprising target vectors having a sulfonamide selection marker.

Seed sterilization. T63 seeds were surface sterilized in a sterilization solution of 20% bleach (containing 6% sodium hypochlorite) for 20 minutes with constant stirring. Two drops of Tween 20 were added to the sterilization solution as a wetting agent. Seeds were rinsed five times with sterile distilled water, blotted dry with sterile filter paper and transferred to Sigma P4928 phytacons (25 seeds per phytacon) containing 84 ml of MSO medium (the formula for MS medium may be found in Murashige and Skoog (1962); MSO is supplemented as indicated in Table 3).

Seed germination and explanting. Phytacons were placed in a growth room at 24° C. with a 16 hour photoperiod. Seedlings were grown for seven days.

Explanting plates were prepared by placing a 9 cm Whatman No. 2 filter paper onto a plate of 100 mm×25 mm Petri dish containing 25 ml of R1F medium. Tomato seedlings were cut and placed into a 100 mm×25 mm Petri dish containing a 9 cm Whatman No. 2 filter paper and 3 ml of distilled water. Explants were prepared by cutting cotyledons into three pieces. The two proximal pieces were transferred onto the explanting plate, and the distal section was discarded. One hundred twenty explants were placed on each plate. A control plate was also prepared that was not subjected to the *Agrobacterium* transformation procedure. Explants were kept in the dark at 24° C. for 24 hours.

*Agrobacterium* culture preparation and cocultivation. The stock of *Agrobacterium tumefaciens* cells for transformation were made as described by Nagel et al. (1990). *Agrobacterium* strain ABI was grown in 250 ml LB medium (Sigma)

overnight at 28° C. with shaking until an absorbance over 1 cm at 600 nm ($A_{600}$) of 0.5-1.0 was reached. Cells were harvested by centrifugation at 4,000×g for 15 minutes at 4° C. Cells were then resuspended in 250l chilled buffer (1 mM HEPES, pH adjusted to 7.0 with KOH). Cells were centrifuged again as described above and resuspended in 125 μL chilled buffer. Cells were then centrifuged and resuspended two more times in the same HEPES buffer as described above at a volume of 100 μL and 750 μL, respectively. Resuspended cells were then distributed into 40 μL aliquots, quickly frozen in liquid nitrogen, and stored at −80° C.

Agrobacterium cells were transformed with vectors prepared as described above following the protocol described by Nagel et al. (1990). For each DNA construct to be transformed, 50 to 100 ng DNA (generally resuspended in 10 mM Tris-HCl, 1 mM EDTA, pH 8.0) were mixed with 40 μL of Agrobacterium cells. The DNA/cell mixture was then transferred to a chilled cuvette with a 2 mm electrode gap and subject to a 2.5 kV charge dissipated at 25 RF and 200 RF using a Gene Pulser TI apparatus (Bio-Rad, Hercules, Calif.). After electroporation, cells were immediately resuspended in 1.0 ml LB and allowed to recover without antibiotic selection for 2 B 4 hours at 28° C. in a shaking incubator. After recovery, cells were plated onto selective medium of LB broth containing 100 μg/ml spectinomycin (Sigma) and incubated for 24-48 hours at 28° C. Single colonies were then picked and inoculated in fresh medium. The presence of the vector construct was verified by PCR amplification and sequence analysis.

Agrobacteria were cultured in two sequential overnight cultures. On day 1, the agrobacteria containing the target vectors having the sulfonamide selection vector (FIG. 3) were grown in 25 ml of liquid 523 medium (Moore et al. (1988)) plus 100 mg spectinomycin, 50 mg kanamycin, and 25 mg chloramphenicol per liter. On day 2, five ml of the first overnight suspension were added to 25 ml of AB medium to which is added 100 mg spectinomycin, 50 mg kanamycin, and 25 mg chloramphenicol per liter. Cultures were grown at 28° C. with constant shaking on a gyratory shaker. The second overnight suspension was centrifuged in a 38 ml sterile Oakridge tubes for 5 minutes at 8000 rpm in a Beckman JA20 rotor. The pellet was resuspended in 10 ml of MSO liquid medium containing 600 μm acetosyringone (for each 20 ml of MSO medium, 40 μl of 0.3 M stock acetosyringone were added). The Agrobacterium concentration was adjusted to an $A_{600}$ of 0.25.

Seven milliliters of this Agrobacterium suspension were added to each of explanting plates. After 20 minutes, the Agrobacterium suspension was aspirated and the explants were blotted dry three times with sterile filter paper. The plates were sealed with Parafilm® and incubated in the dark at 21° C. for 48 hours.

Regeneration. Cocultivated explants were transferred after 48 hours in the dark to 100 mm×25 mm Petri plates (20 explants per plate) containing 25 ml of R1SB10 medium (this medium and subsequently used media contained sulfadiazine, the sulfonamide antibiotic used to select transformants). Plates were kept in the dark for 72 hours and then placed in low light. After 14 days, the explants were transferred to fresh RZ1/2SB25 medium. After an additional 14 days, the regenerating tissues at the edge of the explants were excised away from the primary explants and were transferred onto fresh RZ1/2SB25 medium. After another 14 day interval, regenerating tissues were again transferred to fresh ROSB25 medium. After this period, the regenerating tissues were subsequently rotated between ROSB25 and RZ1/2SB25 media at two week intervals. The well defined shoots that appeared were excised and transferred to ROSB100 medium for rooting.

Shoot Analysis. Once shoots were rooted on ROSB100 medium, small leaf pieces from the rooted shoots were sampled and analyzed with a polymerase chain reaction procedure (PCR) for the presence of the SulA gene. The PCR-positive shoots (TO) were then grown to maturity in the greenhouses. Some TO plants were crossed to plants containing the CaMV 35S activator vector. The TO self pollinated seeds were saved for later crosses to different activator promoters.

TABLE 3

Media Compositions (amounts per liter)

|  | MSO | R1F | R1SB10 | RZ1/2SB25 | ROSB25 | ROSB100 |
|---|---|---|---|---|---|---|
| Gibco ® MS Salts | 4.3 g | 4.3 g | 4.3 g | 4.3 g | 4.3 g | 4.3 g |
| RO Vitamins (100X) | 10 ml |  |  | 5 ml | 10 ml | 10 ml |
| R1 Vitamins (100X) |  | 10 ml | 10 ml |  |  |  |
| RZ Vitamins (100X) |  |  |  | 5 ml |  |  |
| Glucose | 16.0 g | 16.0 g | 16.0 g | 16.0 g | 16.0 g | 16.0 g |
| Timentin ® |  |  | 100 mg |  |  |  |
| Carbenicillin |  |  |  | 350 mg | 350 mg | 350 mg |
| Noble Agar | 8 | 11.5 | 10.3 | 10.45 | 10.45 | 10.45 |
| MES |  |  | 0.6 g | 0.6 g | 0.6 g | 0.6 g |
| Sulfadiazine free acid (10 mg/ml stock) |  |  | 1 ml | 2.5 ml | 2.5 ml | 10 ml |
| pH | 5.7 | 5.7 | 5.7 | 5.7 | 5.7 | 5.7 |

TABLE 4

100x Vitamins (amounts per liter)

|  | RO | R1 | RZ |
|---|---|---|---|
| Nicotinic acid | 500 mg | 500 mg | 500 mg |
| Thiamine HCl | 50 mg | 50 mg | 50 mg |
| Pyridoxine HCl | 50 mg | 50 mg | 50 mg |
| Myo-inositol | 20 g | 20 g | 20 g |
| Glycine | 200 mg | 200 mg | 200 mg |
| Zeatin |  | 0.65 mg | 0.65 mg |
| IAA |  | 1.0 mg |  |
| pH | 5.7 | 5.7 | 5.7 |

TABLE 5

523 Medium (amounts per liter)

| | |
|---|---|
| Sucrose | 10 g |
| Casein Enzymatic Hydrolysate | 8 g |
| Yeast Extract | 4 g |
| $K_2HPO_4$ | 2 g |
| $MgSO_4 \cdot 7H_2O$ | 0.3 g |
| pH | 7.00 |

TABLE 6

AB Medium

| Part A | | Part B (10X stock) | |
|---|---|---|---|
| $K_2HPO_4$ | 3 g | $MgSO_4 \cdot 7H_2O$ | 3 g |
| $NaH_2PO_4$ | 1 g | $CaCl_2$ | 0.1 g |
| $NH_4Cl$ | 1 g | $FeSO_4 \cdot 7H_2O$ | 0.025 g |
| KCl | 0.15 g | Glucose | 50 g |
| pH | 7.00 | | 7.00 |
| Volume | 900 ml | | 1000 ml |

Prepared by autoclaving and mixing 900 ml Part A with 100 ml Part B.

Example V

Population Characterization and Measurements

After the crosses were made (to generate plants having both activator and target vectors), general characterization of the F1 population was performed in the field. General evaluation included photographs of seedling and adult plant morphology, photographs of leaf shape, open flower morphology and of mature green and ripe fruit. Vegetative plant size, a measure of plant biomass, was measured by ruler at approximately two months after transplant. Plant volume was obtained by the multiplication of the three dimensions. In addition, observations were made to determine fruit number per plant. Three red-ripe fruit were harvested from each individual plant when possible and were used for the lycopene and Brix assays. Two weeks later, six fruits per promoter:: gene grouping were harvested, with two fruits per plant harvested when possible. The fruits were pooled, weighed, and seeds collected.

Measurement of soluble solids. "Brix" measurement was used to determine the amount of sugar in solution. For example, 18 degree Brix sugar solution contains 18% sugar (w/w basis). Brix was measured using a refractometer (which measures refractive index). Brix measurements were performed by the follow protocol:

1. Three red ripe fruit were harvest from each plant sampled.
2. Each sample of three fruit was weighed together
3. The three fruit were then quartered and blended together at high speed in a blender for approximately four minutes, until a fine puree was produced.
4. Two 40 ml aliquots were decanted from the pureed sampled into 50 ml polypropylene tubes.
5. Samples were then kept frozen at −20° C. until analysis
6. For analysis samples were thawed in warm water.
7. Approximately 15 ml of thawed tomato puree was filtered and placed onto the reading surface of a digital refractometer, and the reading recorded.

Fruit lycopene measurements. Lycopene is a pigment responsible for color of fruits (e.g., the red color of tomatoes). It was measured by the following procedure:

1. Three red ripe fruit were harvest from each plant sampled.
2. Each sample of three fruit was weighed together
3. The three fruit were then quartered and blended together at high speed in a blender for approximately four minutes, until a fine puree was produced.
4. Two 40 ml aliquots were decanted from the pureed sampled into 50 ml polypropylene tubes.
5. Samples were frozen at −20° C. until further analysis was performed
6. Samples were thawed in warm water.
7. Lycopene level was measured using high performance liquid chromatography (HPLC).

Source/sink activities. Source/sink activities were determined by screening for lines in which *Arabidopsis* transcription factors were driven by the RbcS-3 (leaf mesophyll expression), LTP1 (epidermis and vascular expression) and the PD (early fruit development) promoters. These promoters target source processes localized in photosynthetically active cells (RbcS-3), sink processes localized in developing fruit (PD) or transport processes active in vascular tissues (LTP1) that link source and sink activities. Leaf punches were collected within one hour of sunrise, in the seventh week after transplant, and stored in ethanol. The leaves were then stained with iodine, and plants with notably high or low levels of starch were noted.

Fruit ripening regulation. Screening for traits associated with fruit ripening focused on transgenic tomato lines in which *Arabidopsis* transcription factors are driven by the PD (early fruit development) and PG (fruit ripening) promoters. These promoters target fruit regulatory processes that lead to fruit maturation or which trigger ripening or components of the ripening process. In order to identify lines expressing transcription factors that impact ripening, fruits at 1 cm stage, a developmental time 7-10 days post anthesis and shortly after fruit set were tagged. Tagging occurred over a single two-day period per field trial at a time when plants are in the early fruiting stage to ensure tagging of one to two fruits per plant, and four to six fruits per line. Tagged fruit at the "breaker" stage on any given inspection were marked with a second colored and dated tag. Later inspections included monitoring of breaker-tagged fruit to identify any that have reached the full red ripe stage. To assess the regulation of components of the ripening process, fruit at the mature green and red ripe stage have been harvested and fruit texture analyzed by force necessary to compress equator of the fruit by 2 mm.

Example VI

Screening CaMV 35S Activator Line Progeny with the Transcription Factor Target Lines to Identify Lines Expressing Plant Transcription Factors The plant transcription factor target plants that were initially prepared lacked an activator gene to facilitate later crosses to various activator promoter lines. In order to find transformants that were adequately expressed in the presence of an activator, the plant transcription factor plants were crossed to the CaMV 35S promoter activator line and screened for transcription factor expression by RT-PCR. The mRNA was reverse transcribed into cDNA and the amount of product was measured by quantitative PCR.

Because the parental lines were each heterozygous for the transgenes, T1 hybrid progeny were sprayed with chlorsulfuron and cyanamide to find the 25% of the progeny containing both the activator (chlorsulfuron resistant) and target (cyanamide resistant) transgenes. Segregation ratios were measured and lines with abnormal ratios were discarded. Too high a ratio indicated multiple inserts, while too low a ratio indicated a variety of possible problems. The ideal inserts produced 50% resistant progeny. Progeny containing both inserts appeared at 25% because they also required the other herbicidal markers from the Activator parental line (50%×50%).

These T1 hybrid progeny were then screened in a 96 well format for plant transcription factor gene expression by RT-PCR to ensure expression of the target plant transcription factor gene, as certain chromosomal positions can be silent or very poorly expressed or the gene can be disrupted during the integration process. The 96 well format was also used for cDNA synthesis and PCR. This procedure involves the use of one primer in the transcribed portion of the vector and a second gene-specific primer.

Because both the activator and target genes are dominant in their effects, phenotypes were observable in hybrid progeny containing both genes. These T1F1 plants were examined for visual phenotypes. However, more detailed analysis for increased color, high solids and disease resistance were also conducted once the best lines were identified and reproduced on a larger scale.

Example VII

Results of Overexpressing Specific Promoter::Transcription Factor Combinations in Tomato Plants Using the methods described in the above Examples, a number of *Arabidopsis* sequences were identified that resulted, when expressed in tomato plants, in greater brix, greater fruit weight, greater lycopene, greater biomass, more chlorosis, darker green fruit, darker green leaves, deeper red fruit, larger flowers, larger leaflets, larger leaflets, larger and lighter green leaves, rugulose leaves, more anthocyanin, more trichomes, paler white fruit at the green fruit stage, thicker stems, very high vigor, and/or waxier leaves, as compared to a control plant. Table 7 shows a number of polypeptides of the invention shown to improve fruit or yield characteristics. SEQ ID NOs and GID (Gene IDentifiers) are listed in Columns 1 and 2. The conserved domains in amino acid coordinates (beginning from the n-terminus of each polypeptide) of each polypeptide associates with particular Transcription Factor Family, and the Transcription Factor Families to which the polypeptide belongs, are listed in Columns 3 and 4, respectively. The PID (Plasmid IDentifier) and PID SEQ ID NOs are listed in Columns 5 and 6, respectively. The promoters used to drive expression of the polynucleotides encoding the polypeptides and the traits that were observed in tomato plants when each polypeptide sequence was overexpressed in tomato plants, relative to traits observed in control tomato plants, are listed in Column 7. Sequences listed below for the traits of increased lycopene, brix and fruit weight were in the top 5% of all tomato lycopene, brix and fruit weight measurements, respectively.

TABLE 7

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2 | 464 | AP2 (129-195, 221-288) | P5310 (root-expressed RSI1 prom.) | P8197 | 4657 | Inc. brix |
| G2 | 464 | AP2 (129-195, 221-288) | P5284 (leaf-expressed RbcS3 prom.) | P8197 | 4657 | Inc. lycopene |
| G2 | 464 | AP2 (129-195, 221-288) | P5310 (root-expressed RSI1 prom.) | P8197 | 4657 | Inc. lycopene |
| G3 | 944 | AP2 (28-95) | P5284 (leaf-expressed RbcS3 prom.) | P3375 | 4181 | Inc. lycopene |
| G3 | 944 | AP2 (28-95) | P5326 (floral meristem-expressed AP1 prom.) | P3375 | 4181 | Inc. lycopene |
| G4 | 1054 | AP2 (121-183) | P5326 (floral meristem-expressed AP1 prom.) | P7794 | 4619 | Inc. lycopene |
| G7 | 1210 | AP2 (58-125) | P5319 (emergent leaf primordia-expressed AS1 prom.) | P6439 | 4454 | Inc. fruit weight |
| G8 | 1256 | AP2 (151-217, 243-293) | P5297 (fruit tissue-expressed PG prom.) | P6038 | 4416 | Inc. brix |
| G8 | 1256 | AP2 (151-217, 243-293) | P5303 (fruit tissue-expressed PD prom.) | P6038 | 4416 | Inc. brix |
| G8 | 1256 | AP2 (151-217, 243-293) | P5318 (shoot apical meristem-expressed STM prom.) | P6038 | 4416 | Inc. brix |
| G15 | 230 | AP2 (281-357, 383-451) | P5284 (leaf-expressed RbcS3 prom.) | P9218 | 4812 | Inc. lycopene |
| G19 | 416 | AP2 (76-143) | P5297 (fruit tissue-expressed PG prom.) | P5056 | 4370 | Inc. brix |
| G19 | 416 | AP2 (76-143) | P5297 (fruit tissue-expressed PG prom.) | P5056 | 4370 | Inc. lycopene |
| G20 | 466 | AP2 (68-144) | P5284 (leaf-expressed RbcS3 prom.) | P9251 | 4816 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G20 | 466 | AP2 (68-144) | P5297 (fruit tissue-expressed PG prom.) | P9251 | 4816 | Inc. lycopene |
| G20 | 466 | AP2 (68-144) | P5284 (leaf-expressed RbcS3 prom.) | P9251 | 4816 | Inc. lycopene |
| G21 | 516 | AP2 (97-164) | P5324 (fruit vascular tissue-expressed Cru prom.) | P4364 | 4290 | Inc. lycopene |
| G22 | 570 | AP2 (88-152) | P5326 (floral meristem-expressed AP1 prom.) | P3376 | 4182 | Inc. brix |
| G22 | 570 | AP2 (88-152) | P5284 (leaf-expressed RbcS3 prom.) | P3376 | 4182 | Inc. lycopene |
| G22 | 570 | AP2 (88-152) | P5303 (fruit tissue-expressed PD prom.) | P3376 | 4182 | Inc. lycopene |
| G22 | 570 | AP2 (88-152) | P5326 (floral meristem-expressed AP1 prom.) | P3376 | 4182 | Inc. lycopene |
| G26 | 728 | AP2 (67-134) | P5297 (fruit tissue-expressed PG prom.) | P9131 | 4790 | Inc. lycopene |
| G28 | 828 | AP2 (145-208) | P5326 (floral meristem-expressed AP1 prom.) | P7826 | 4620 | Inc. lycopene |
| G28 | 828 | AP2 (145-208) | P5297 (fruit tissue-expressed PG prom.) | P7826 | 4620 | Inc. lycopene |
| G28 | 828 | AP2 (145-208) | P5287 (epidermal tissue-expressed LTP1 prom.) | P7826 | 4620 | Inc. lycopene |
| G29 | 884 | AP2 (134-197) | P5284 (leaf-expressed RbcS3 prom.) | P6441 | 4455 | Inc. brix |
| G30 | 946 | AP2 (16-80) | P5297 (fruit tissue-expressed PG prom.) | P3852 | 4223 | Inc. brix |
| G32 | 1002 | AP2 (17-84) | P6506 (constitutive CaMv 35S prom.) | P6849 | 4480 | Inc. brix |
| G32 | 1002 | AP2 (17-84) | P5324 (fruit vascular tissue-expressed Cru prom.) | P6849 | 4480 | Inc. fruit weight |
| G35 | 1022 | AP2 (NA) | P5326 (floral meristem-expressed AP1 prom.) | P5130 | 4383 | Inc. fruit weight |
| G35 | 1022 | AP2 (NA) | P5318 (shoot apical meristem-expressed STM prom.) | P5130 | 4383 | Inc. fruit weight |
| G36 | 1034 | AP2 (NA) | P5297 (fruit tissue-expressed PG prom.) | P6149 | 4426 | Inc. brix |
| G43 | 1072 | AP2 (104-172) | P5287 (epidermal tissue-expressed LTP1 prom.) | P9092 | 4778 | Inc. fruit weight |
| G43 | 1072 | AP2 (104-172) | P5326 (floral meristem-expressed AP1 prom.) | P9092 | 4778 | Inc. fruit weight |
| G47 | 1096 | AP2 (10-75) | P5318 (shoot apical meristem-expressed STM prom.) | P3853 | 4224 | Inc. lycopene |
| G137 | 154 | MADS (1-57) | P5297 (fruit tissue-expressed PG prom.) | P7474 | 4555 | Inc. brix |
| G137 | 154 | MADS (1-57) | P6506 (constitutive CaMv 35S prom.) | P7474 | 4555 | Inc. brix |
| G137 | 154 | MADS (1-57) | P5324 (fruit vascular tissue-expressed Cru prom.) | P7474 | 4555 | Inc. brix |
| G138 | 158 | MADS (1-57) | P5284 (leaf-expressed RbcS3 prom.) | P7475 | 4556 | Inc. brix |
| G139 | 166 | MADS (1-57) | P5319 (emergent leaf primordia-expressed AS1 prom.) | P7476 | 4557 | Inc. fruit weight |
| G140 | 172 | MADS (16-72) | P5318 (shoot apical meristem-expressed STM prom.) | P7771 | 4611 | Inc. fruit weight |
| G145 | 196 | MADS (1-57) | P5297 (fruit tissue-expressed PG prom.) | P8652 | 4730 | Inc. fruit weight |
| G146 | 202 | MADS (1-57) | P5318 (shoot apical meristem-expressed STM prom.) | P7477 | 4558 | Inc. lycopene |
| G148 | 216 | MADS (1-57) | P5326 (floral meristem-expressed AP1 prom.) | P8537 | 4695 | Inc. fruit weight |
| G154 | 254 | MADS (2-57) | P5326 (floral meristem-expressed AP1 prom.) | P9152 | 4799 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G156 | 270 | MADS (2-57) | P5326 (floral meristem-expressed AP1 prom.) | P3354 | 4176 | Inc. lycopene |
| G157 | 272 | MADS (2-57) | P6506 (constitutive CaMv 35S prom.) | P6885 | 4492 | Inc. brix |
| G159 | 274 | MADS (7-61) | P5287 (epidermal tissue-expressed LTP1 prom.) | P4955 | 4369 | Inc. lycopene |
| G165 | 292 | MADS (7-62) | P5284 (leaf-expressed RbcS3 prom.) | P7065 | 4510 | Inc. brix |
| G166 | 300 | MADS (2-56) | P5297 (fruit tissue-expressed PG prom.) | P7056 | 4507 | Inc. lycopene |
| G167 | 310 | MADS (2-57) | P5318 (shoot apical meristem-expressed STM prom.) | P6872 | 4487 | Inc. brix |
| G168 | 314 | MADS (1-57) | P5326 (floral meristem-expressed AP1 prom.) | P7059 | 4508 | Inc. fruit weight |
| G168 | 314 | MADS (1-57) | P5287 (epidermal tissue-expressed LTP1 prom.) | P7059 | 4508 | Inc. fruit weight |
| G179 | 356 | WRKY (65-121) | P6506 (constitutive CaMv 35S prom.) | P6892 | 4493 | Inc. lycopene |
| G179 | 356 | WRKY (65-121) | P5287 (epidermal tissue-expressed LTP1 prom.) | P6892 | 4493 | Inc. lycopene |
| G179 | 356 | WRKY (65-121) | P5297 (fruit tissue-expressed PG prom.) | P6892 | 4493 | Inc. lycopene |
| G189 | 410 | WRKY (240-297) | P5318 (shoot apical meristem-expressed STM prom.) | P3357 | 4177 | Inc. fruit weight |
| G190 | 418 | WRKY (110-169) | P5318 (shoot apical meristem-expressed STM prom.) | P5142 | 4384 | Inc. lycopene |
| G190 | 418 | WRKY (110-169) | P5326 (floral meristem-expressed AP1 prom.) | P5142 | 4384 | Inc. lycopene |
| G194 | 438 | WRKY (174-230) | P5318 (shoot apical meristem-expressed STM prom.) | P3582 | 4194 | Inc. lycopene |
| G194 | 438 | WRKY (174-230) | P5284 (leaf-expressed RbcS3 prom.) | P3582 | 4194 | Inc. lycopene |
| G194 | 438 | WRKY (174-230) | P5284 (leaf-expressed RbcS3 prom.) | P3582 | 4194 | Inc. brix |
| G204 | 482 | MYB-related (6-54) | P5318 (shoot apical meristem-expressed STM prom.) | P9076 | 4774 | Inc. brix |
| G204 | 482 | MYB-related (6-54) | P5287 (epidermal tissue-expressed LTP1 prom.) | P9076 | 4774 | Inc. brix |
| G206 | 490 | MYB-(R1)R2R3 (13-116) | P5287 (epidermal tissue-expressed LTP1 prom.) | P9137 | 4793 | Inc. brix |
| G206 | 490 | MYB-(R1)R2R3 (13-116) | P5326 (floral meristem-expressed AP1 prom.) | P9137 | 4793 | Inc. lycopene |
| G206 | 490 | MYB-(R1)R2R3 (13-116) | P5310 (root-expressed RSI1 prom.) | P9137 | 4793 | Inc. lycopene |
| G209 | 510 | MYB-related (36-82) | P5318 (shoot apical meristem-expressed STM prom.) | P3765 | 4213 | Inc. fruit weight |
| G210 | 518 | MYB-(R1)R2R3 (14-114) | P5297 (fruit tissue-expressed PG prom.) | P9123 | 4788 | Inc. fruit weight |
| G210 | 518 | MYB-(R1)R2R3 (14-114) | P5318 (shoot apical meristem-expressed STM prom.) | P9123 | 4788 | Inc. fruit weight |
| G210 | 518 | MYB-(R1)R2R3 (14-114) | P5287 (epidermal tissue-expressed LTP1 prom.) | P9123 | 4788 | Inc. fruit weight |
| G210 | 518 | MYB-(R1)R2R3 (14-114) | P5284 (leaf-expressed RbcS3 prom.) | P9123 | 4788 | Inc. fruit weight |
| G210 | 518 | MYB-(R1)R2R3 (14-114) | P5326 (floral meristem-expressed AP1 prom.) | P9123 | 4788 | Inc. fruit weight |
| G211 | 528 | MYB-(R1)R2R3 (24-137) | P5287 (epidermal tissue-expressed LTP1 prom.) | P4359 | 4288 | Inc. lycopene |
| G211 | 528 | MYB-(R1)R2R3 (24-137) | P5318 (shoot apical meristem-expressed STM prom.) | P4359 | 4288 | Inc. lycopene |
| G216 | 564 | MYB-(R1)R2R3 (49-151) | P5310 (root-expressed RSI1 prom.) | P9134 | 4791 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G217 | 566 | MYB-related (8-55) | P5287 (epidermal tissue-expressed LTP1 prom.) | P5842 | 4406 | Inc. lycopene |
| G219 | 568 | MYB-related (98-146) | P5303 (fruit tissue-expressed PD prom.) | P7082 | 4514 | Inc. brix |
| G219 | 568 | MYB-related (98-146) | P5318 (shoot apical meristem-expressed STM prom.) | P7082 | 4514 | Inc. brix |
| G219 | 568 | MYB-related (98-146) | P5284 (leaf-expressed RbcS3 prom.) | P7082 | 4514 | Inc. brix |
| G219 | 568 | MYB-related (98-146) | P5326 (floral meristem-expressed AP1 prom.) | P7082 | 4514 | Inc. brix |
| G222 | 576 | MYB-(R1)R2R3 (13-119) | P5310 (root-expressed RSI1 prom.) | P5839 | 4405 | Inc. lycopene |
| G225 | 588 | MYB-related (36-80) | P5310 (root-expressed RSI1 prom.) | P9125 | 4789 | Inc. brix |
| G225 | 588 | MYB-related (36-80) | P5326 (floral meristem-expressed AP1 prom.) | P9125 | 4789 | Inc. fruit weight |
| G227 | 596 | MYB-(R1)R2R3 (13-113) | P5297 (fruit tissue-expressed PG prom.) | P4021 | 4247 | Inc. brix |
| G229 | 598 | MYB-(R1)R2R3 (14-120) | P5284 (leaf-expressed RbcS3 prom.) | P7860 | 4627 | Inc. brix |
| G232 | 622 | MYB-(R1)R2R3 (14-115) | P5284 (leaf-expressed RbcS3 prom.) | P9119 | 4786 | Inc. brix |
| G236 | 632 | MYB-(R1)R2R3 (NA) | P5287 (epidermal tissue-expressed LTP1 prom.) | P5843 | 4407 | Inc. brix |
| G236 | 632 | MYB-(R1)R2R3 (NA) | P6506 (constitutive CaMv 35S prom.) | P5843 | 4407 | Inc. biomass |
| G236 | 632 | MYB-(R1)R2R3 (NA) | P5284 (leaf-expressed RbcS3 prom.) | P5843 | 4407 | Inc. biomass |
| G237 | 634 | MYB-(R1)R2R3 (11-113) | P5303 (fruit tissue-expressed PD prom.) | P4877 | 4361 | Inc. lycopene |
| G237 | 634 | MYB-(R1)R2R3 (11-113) | P5297 (fruit tissue-expressed PG prom.) | P4877 | 4361 | Inc. lycopene |
| G237 | 634 | MYB-(R1)R2R3 (11-113) | P5284 (leaf-expressed RbcS3 prom.) | P4877 | 4361 | Dark green leaves |
| G239 | 644 | MYB-(R1)R2R3 (21-125) | P5287 (epidermal tissue-expressed LTP1 prom.) | P5843 | 4407 | Inc. brix |
| G239 | 644 | MYB-(R1)R2R3 (21-125) | P5287 (epidermal tissue-expressed LTP1 prom.) | P5843 | 4407 | Inc. lycopene |
| G239 | 644 | MYB-(R1)R2R3 (21-125) | P5318 (shoot apical meristem-expressed STM prom.) | P5843 | 4407 | Inc. lycopene |
| G241 | 650 | MYB-(R1)R2R3 (14-114) | P5297 (fruit tissue-expressed PG prom.) | P9136 | 4792 | Inc. lycopene |
| G242 | 654 | MYB-(R1)R2R3 (6-106) | P5310 (root-expressed RSI1 prom.) | P9121 | 4787 | Inc. lycopene |
| G242 | 654 | MYB-(R1)R2R3 (6-106) | P5326 (floral meristem-expressed AP1 prom.) | P9121 | 4787 | Inc. fruit weight |
| G242 | 654 | MYB-(R1)R2R3 (6-106) | P5297 (fruit tissue-expressed PG prom.) | P9121 | 4787 | Inc. fruit weight |
| G242 | 654 | MYB-(R1)R2R3 (6-106) | P5284 (leaf-expressed RbcS3 prom.) | P9121 | 4787 | Inc. fruit weight |
| G242 | 654 | MYB-(R1)R2R3 (6-106) | P5287 (epidermal tissue-expressed LTP1 prom.) | P9121 | 4787 | Inc. fruit weight |
| G243 | 666 | MYB-(R1)R2R3 (12-128) | P5326 (floral meristem-expressed AP1 prom.) | P7459 | 4551 | Inc. brix |
| G245 | 670 | MYB-(R1)R2R3 (14-114) | P5284 (leaf-expressed RbcS3 prom.) | P7007 | 4500 | Inc. fruit weight |
| G246 | 678 | MYB-(R1)R2R3 (57-159) | P5297 (fruit tissue-expressed PG prom.) | P9046 | 4770 | Inc. lycopene |
| G255 | 696 | MYB-(R1)R2R3 (14-116) | P5318 (shoot apical meristem-expressed STM prom.) | P6841 | 4479 | Inc. fruit weight |
| G258 | 720 | MYB-(R1)R2R3 (24-124) | P5297 (fruit tissue-expressed PG prom.) | P4194 | 4267 | Inc. brix |
| G258 | 720 | MYB-(R1)R2R3 (24-124) | P5326 (floral meristem-expressed AP1 prom.) | P4194 | 4267 | Inc. fruit weight |
| G259 | 726 | HS (40-131) | P5287 (epidermal tissue-expressed LTP1 prom.) | P4172 | 4261 | Inc. lycopene |
| G261 | 734 | HS (15-106) | P5297 (fruit tissue-expressed PG prom.) | P5145 | 4385 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G262 | 738 | HS (52-143) | P5284 (leaf-expressed RbcS3 prom.) | P4759 | 4347 | Inc. lycopene |
| G264 | 746 | HS (23-114) | P5284 (leaf-expressed RbcS3 prom.) | P8948 | 4764 | Inc. fruit weight |
| G264 | 746 | HS (23-114) | P5318 (shoot apical meristem-expressed STM prom.) | P8948 | 4764 | Inc. fruit weight |
| G264 | 746 | HS (23-114) | P5287 (epidermal tissue-expressed LTP1 prom.) | P8948 | 4764 | Inc. fruit weight |
| G265 | 750 | HS (13-104) | P5297 (fruit tissue-expressed PG prom.) | P7086 | 4517 | Inc. brix |
| G268 | 762 | AKR (186-689) | P5287 (epidermal tissue-expressed LTP1 prom.) | P8695 | 4748 | Inc. fruit weight |
| G273 | 794 | AKR (93-610) | P5318 (shoot apical meristem-expressed STM prom.) | P6817 | 4474 | Inc. fruit weight |
| G274 | 798 | AKR (94-600) | P5287 (epidermal tissue-expressed LTP1 prom.) | P7087 | 4518 | Inc. fruit weight |
| G277 | 812 | AKR (28-173) | P5319 (emergent leaf primordia-expressed AS1 prom.) | P7162 | 4541 | Inc. fruit weight |
| G279 | 820 | HMG (31-103) | P5303 (fruit tissue-expressed PD prom.) | P7021 | 4502 | Inc. brix |
| G280 | 830 | AT-hook (97-104, 130-137-155-162, 185-192) | P5324 (fruit vascular tissue-expressed Cru prom.) | P6901 | 4497 | Inc. brix |
| G285 | 860 | MISC (NA) | P5297 (fruit tissue-expressed PG prom.) | P5248 | 4386 | Inc. brix |
| G286 | 866 | ENBP (206-252, 332-409, 588-786) | P5284 (leaf-expressed RbcS3 prom.) | P5249 | 4387 | Inc. brix |
| G286 | 866 | ENBP (206-252, 332-409, 588-786) | P5297 (fruit tissue-expressed PG prom.) | P5249 | 4387 | Inc. brix |
| G286 | 866 | ENBP (206-252, 332-409, 588-786) | P6506 (constitutive CaMv 35S prom.) | P5249 | 4387 | Inc. brix |
| G286 | 866 | ENBP (206-252, 332-409, 588-786) | P5319 (emergent leaf primordia-expressed AS1 prom.) | P5249 | 4387 | Inc. brix |
| G286 | 866 | ENBP (206-252, 332-409, 588-786) | P5326 (floral meristem-expressed AP1 prom.) | P5249 | 4387 | Inc. brix |
| G288 | 870 | MISC (309-361) | P5287 (epidermal tissue-expressed LTP1 prom.) | P6452 | 4458 | Inc. fruit weight |
| G288 | 870 | MISC (309-361) | P5284 (leaf-expressed RbcS3 prom.) | P6452 | 4458 | Inc. fruit weight |
| G290 | 886 | SWI/SNF (538-784, 919-958, 1086-1169) | P5284 (leaf-expressed RbcS3 prom.) | P4785 | 4360 | Inc. fruit weight |
| G290 | 886 | SWI/SNF (538-784, 919-958, 1086-1169) | P5287 (epidermal tissue-expressed LTP1 prom.) | P4785 | 4360 | Inc. fruit weight |
| G294 | 908 | MISC (NA) | P5297 (fruit tissue-expressed PG prom.) | P4560 | 4313 | Inc. brix |
| G295 | 910 | bZIP (287-354) | P5318 (shoot apical meristem-expressed STM prom.) | P4783 | 4359 | Inc. brix |
| G306 | 974 | SCR (370-435, 486-573, 576-649) | P5324 (fruit vascular tissue-expressed Cru prom.) | | | Inc. lycopene |
| G309 | 992 | SCR (223-288, 342-427, 431-505) | P5287 (epidermal tissue-expressed LTP1 prom.) | P9195 | 4811 | Inc. fruit weight |
| G321 | 1004 | RING/C3HC4 (NA) | P5297 (fruit tissue-expressed PG prom.) | | | Inc. fruit weight |
| G322 | 1006 | RING/C3HC4 (NA) | P5287 (epidermal tissue-expressed LTP1 prom.) | | | Inc. lycopene |
| G323 | 1008 | RING/C3HC4 (48-96) | P5297 (fruit tissue-expressed PG prom.) | P4201 | 4269 | Inc. brix |
| G323 | 1008 | RING/C3HC4 (48-96) | P5318 (shoot apical meristem-expressed STM prom.) | P4201 | 4269 | Inc. lycopene |
| G326 | 1010 | Z-CO-like (11-94, 354-400) | P5303 (fruit tissue-expressed PD prom.) | P5256 | 4388 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G326 | 1010 | Z-CO-like (11-94, 354-400) | P6506 (constitutive CaMv 35S prom.) | P5256 | 4388 | Inc. brix |
| G326 | 1010 | Z-CO-like (11-94, 354-400) | P5284 (leaf-expressed RbcS3 prom.) | P5256 | 4388 | Inc. brix |
| G328 | 1012 | Z-CO-like (12-78) | P5297 (fruit tissue-expressed PG prom.) | P3955 | 4227 | Inc. lycopene |
| G328 | 1012 | Z-CO-like (12-78) | P5326 (floral meristem-expressed AP1 prom.) | P3955 | 4227 | Inc. lycopene |
| G335 | 1014 | Z-Tall-1 (205-218) | P5287 (epidermal tissue-expressed LTP1 prom.) | P8167 | 4653 | Inc. brix |
| G335 | 1014 | Z-Tall-1 (205-218) | P5287 (epidermal tissue-expressed LTP1 prom.) | P8167 | 4653 | Inc. lycopene |
| G341 | 1016 | Z-C3H (254-374) | P5297 (fruit tissue-expressed PG prom.) | P8566 | 4703 | Inc. brix |
| G344 | 1018 | GATA/Zn (166-192) | P5287 (epidermal tissue-expressed LTP1 prom.) | P6181 | 4431 | Inc. brix |
| G344 | 1018 | GATA/Zn (166-192) | P5326 (floral meristem-expressed AP1 prom.) | P6181 | 4431 | Inc. brix |
| G345 | 1020 | GATA/Zn (NA) | P5287 (epidermal tissue-expressed LTP1 prom.) | P6819 | 4475 | Inc. brix |
| G350 | 1024 | Z-C2H2 (91-113, 150-170) | P5326 (floral meristem-expressed AP1 prom.) | P6197 | 4434 | Inc. brix |
| G351 | 1026 | Z-C2H2 (77-97, 118-140) | P5284 (leaf-expressed RbcS3 prom.) | P7773 | 4612 | Inc. lycopene |
| G351 | 1026 | Z-C2H2 (77-97, 118-140) | P5297 (fruit tissue-expressed PG prom.) | P7773 | 4612 | Inc. lycopene |
| G352 | 1028 | Z-C2H2 (99-119, 166-186) | P5284 (leaf-expressed RbcS3 prom.) | P4225 | 4276 | Inc. brix |
| G354 | 1030 | Z-C2H2 (42-62, 88-109) | P5297 (fruit tissue-expressed PG prom.) | P4535 | 4310 | Inc. brix |
| G354 | 1030 | Z-C2H2 (42-62, 88-109) | P5284 (leaf-expressed RbcS3 prom.) | P4535 | 4310 | Inc. brix |
| G354 | 1030 | Z-C2H2 (42-62, 88-109) | P5287 (epidermal tissue-expressed LTP1 prom.) | P4535 | 4310 | Inc. fruit weight |
| G357 | 1032 | Z-C2H2 (7-29) | P5326 (floral meristem-expressed AP1 prom.) | | | Inc. lycopene |
| G362 | 1036 | Z-C2H2 (62-82) | P5324 (fruit vascular tissue-expressed Cru prom.) | P6468 | 4464 | Inc. fruit weight |
| G363 | 1038 | Z-C2H2 (87-108) | P5287 (epidermal tissue-expressed LTP1 prom.) | | | Inc. lycopene |
| G365 | 1040 | Z-C2H2 (70-90) | P5303 (fruit tissue-expressed PD prom.) | P6820 | 4476 | Inc. brix |
| G368 | 1042 | Z-C2H2 (NA) | P5324 (fruit vascular tissue-expressed Cru prom.) | P5262 | 4389 | Inc. lycopene |
| G379 | 1044 | RING/C3HC4 (16-56) | P5318 (shoot apical meristem-expressed STM prom.) | P8225 | 4665 | Inc. fruit weight |
| G383 | 1046 | GATA/Zn (77-102) | P5318 (shoot apical meristem-expressed STM prom.) | P4352 | 4285 | Inc. lycopene |
| G383 | 1046 | GATA/Zn (77-102) | P5303 (fruit tissue-expressed PD prom.) | P4352 | 4285 | Inc. fruit weight |
| G385 | 1048 | HB (60-123) | P5287 (epidermal tissue-expressed LTP1 prom.) | P8937 | 4762 | Inc. fruit weight |
| G385 | 1048 | HB (60-123) | P5284 (leaf-expressed RbcS3 prom.) | P8937 | 4762 | Inc. fruit weight |
| G385 | 1048 | HB (60-123) | P5318 (shoot apical meristem-expressed STM prom.) | P8937 | 4762 | Inc. fruit weight |
| G392 | 1050 | HB (15-75) | P5318 (shoot apical meristem-expressed STM prom.) | P9145 | 4796 | Inc. fruit weight |
| G399 | 1052 | HB (126-186) | P5287 (epidermal tissue-expressed LTP1 prom.) | P5060 | 4371 | Inc. lycopene |
| G399 | 1052 | HB (126-186) | P5326 (floral meristem-expressed AP1 prom.) | P5060 | 4371 | Inc. lycopene |
| G406 | 1056 | HB (58-118) | P5326 (floral meristem-expressed AP1 prom.) | P4533 | 4309 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G409 | 1058 | HB (64-124) | P5318 (shoot apical meristem-expressed STM prom.) | P9141 | 4794 | Inc. fruit weight |
| G411 | 1060 | HB (NA) | P5319 (emergent leaf primordia-expressed AS1 prom.) | P9142 | 4795 | Inc. brix |
| G411 | 1060 | HB (NA) | P5310 (root-expressed RSI1 prom.) | P9142 | 4795 | Inc. brix |
| G411 | 1060 | HB (NA) | P5310 (root-expressed RSI1 prom.) | P9142 | 4795 | Inc. lycopene |
| G413 | 1062 | HB (37-97) | P5318 (shoot apical meristem-expressed STM prom.) | P8730 | 4754 | Inc. fruit weight |
| G413 | 1062 | HB (37-97) | P5326 (floral meristem-expressed AP1 prom.) | P8730 | 4754 | Inc. fruit weight |
| G413 | 1062 | HB (37-97) | P5297 (fruit tissue-expressed PG prom.) | P8730 | 4754 | Inc. fruit weight |
| G415 | 1064 | HB (550-610) | P5297 (fruit tissue-expressed PG prom.) | P6044 | 4418 | Inc. brix |
| G415 | 1064 | HB (550-610) | P5284 (leaf-expressed RbcS3 prom.) | P6044 | 4418 | Inc. brix |
| G421 | 1066 | HB (371-434) | P5297 (fruit tissue-expressed PG prom.) | P8206 | 4658 | Inc. lycopene |
| G426 | 1068 | HB (346-406) | P5326 (floral meristem-expressed AP1 prom.) | P6445 | 4456 | Inc. fruit weight |
| G428 | 1070 | HB (229-292) | P5297 (fruit tissue-expressed PG prom.) | P5061 | 4372 | Inc. brix |
| G432 | 1074 | HB (NA) | P5287 (epidermal tissue-expressed LTP1 prom.) | P3967 | 4230 | Inc. lycopene |
| G432 | 1074 | HB (NA) | P5318 (shoot apical meristem-expressed STM prom.) | P3967 | 4230 | Inc. fruit weight |
| G435 | 1076 | HB (4-67) | P5284 (leaf-expressed RbcS3 prom.) | P3771 | 4214 | Inc. lycopene |
| G440 | 1078 | AP2 (122-184) | P5303 (fruit tissue-expressed PD prom.) | P5265 | 4390 | Inc. brix |
| G443 | 1080 | IAA (NA) | P5297 (fruit tissue-expressed PG prom.) | P9079 | 4775 | Inc. brix |
| G443 | 1080 | IAA (NA) | P5297 (fruit tissue-expressed PG prom.) | P9079 | 4775 | Inc. lycopene |
| G443 | 1080 | IAA (NA) | P5310 (root-expressed RSI1 prom.) | P9079 | 4775 | Inc. lycopene |
| G449 | 1082 | IAA (NA) | P5326 (floral meristem-expressed AP1 prom.) | P5266 | 4391 | Inc. brix |
| G450 | 1084 | IAA (6-14, 78-89, 112-128, 180-217) | P5318 (shoot apical meristem-expressed STM prom.) | P4012 | 4244 | Inc. lycopene |
| G450 | 1084 | IAA (6-14, 78-89, 112-128, 180-217) | P5326 (floral meristem-expressed AP1 prom.) | P4012 | 4244 | Inc. lycopene |
| G451 | 1086 | IAA (12-20, 57-68, 76-92, 131-164) | P5297 (fruit tissue-expressed PG prom.) | P9081 | 4776 | Inc. brix |
| G452 | 1088 | IAA (NA) | P5287 (epidermal tissue-expressed LTP1 prom.) | P5065 | 4373 | Inc. brix |
| G463 | 1090 | IAA (14-23, 77-88, 130-146, 194-227) | P5318 (shoot apical meristem-expressed STM prom.) | P5067 | 4374 | Inc. lycopene |
| G463 | 1090 | IAA (14-23, 77-88, 130-146, 194-227) | P5284 (leaf-expressed RbcS3 prom.) | P5067 | 4374 | Inc. lycopene |
| G467 | 1092 | IAA (NA) | P5287 (epidermal tissue-expressed LTP1 prom.) | P7027 | 4503 | Inc. fruit weight |
| G468 | 1094 | IAA (86-102, 141-171) | P5297 (fruit tissue-expressed PG prom.) | P7537 | 4576 | Inc. brix |
| G468 | 1094 | IAA (86-102, 141-171) | P5297 (fruit tissue-expressed PG prom.) | P7537 | 4576 | Inc. lycopene |
| G481 | 1098 | CAAT (20-109) | P5324 (fruit vascular tissue-expressed Cru prom.) | P6812 | 4473 | Inc. fruit weight |
| G481 | 1098 | CAAT (20-109) | P5326 (floral meristem-expressed AP1 prom.) | P6812 | 4473 | Inc. fruit weight |
| G482 | 1100 | CAAT (26-115) | P5287 (epidermal tissue-expressed LTP1 prom.) | P5072 | 4375 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G485 | 1102 | CAAT (20-109) | P5318 (shoot apical meristem-expressed STM prom.) | P4190 | 4266 | Inc. fruit weight |
| G489 | 1104 | CAAT (68-164) | P5297 (fruit tissue-expressed PG prom.) | P3404 | 4183 | Inc. brix |
| G501 | 1106 | NAC (10-131) | P5318 (shoot apical meristem-expressed STM prom.) | P5272 | 4392 | Inc. brix |
| G501 | 1106 | NAC (10-131) | P5303 (fruit tissue-expressed PD prom.) | P5272 | 4392 | Inc. brix |
| G508 | 1108 | NAC (NA) | P5319 (emergent leaf primordia-expressed AS1 prom.) | P5274 | 4393 | Inc. brix |
| G508 | 1108 | NAC (NA) | P5303 (fruit tissue-expressed PD prom.) | P5274 | 4393 | Inc. brix |
| G513 | 1110 | NAC (16-161) | P5287 (epidermal tissue-expressed LTP1 prom.) | P5507 | 4394 | Inc. fruit weight |
| G519 | 1112 | NAC (10-131) | P5297 (fruit tissue-expressed PG prom.) | P9098 | 4779 | Inc. brix |
| G522 | 1114 | NAC (10-165) | P6506 (constitutive CaMv 35S prom.) | P4942 | 4366 | Inc. brix |
| G525 | 1116 | NAC (23-167) | P5287 (epidermal tissue-expressed LTP1 prom.) | P5076 | 4376 | Inc. fruit weight |
| G525 | 1116 | NAC (23-167) | P5318 (shoot apical meristem-expressed STM prom.) | P5076 | 4376 | Inc. fruit weight |
| G525 | 1116 | NAC (23-167) | P5326 (floral meristem-expressed AP1 prom.) | P5076 | 4376 | Inc. fruit weight |
| G527 | 1118 | NAC (NA) | P5326 (floral meristem-expressed AP1 prom.) | P6470 | 4465 | Inc. brix |
| G527 | 1118 | NAC (NA) | P5297 (fruit tissue-expressed PG prom.) | P6470 | 4465 | Inc. brix |
| G527 | 1118 | NAC (NA) | P5303 (fruit tissue-expressed PD prom.) | P6470 | 4465 | Inc. brix |
| G527 | 1118 | NAC (NA) | P6506 (constitutive CaMv 35S prom.) | P6470 | 4465 | Inc. brix |
| G529 | 1120 | GF14 (229-236) | P5303 (fruit tissue-expressed PD prom.) | P5513 | 4395 | Inc. brix |
| G530 | 1122 | GF14 (227-235) | P5284 (leaf-expressed RbcS3 prom.) | P4523 | 4307 | Inc. brix |
| G530 | 1122 | GF14 (227-235) | P5287 (epidermal tissue-expressed LTP1 prom.) | P4523 | 4307 | Inc. fruit weight |
| G531 | 1124 | GF14 (227-234) | P5326 (floral meristem-expressed AP1 prom.) | P7130 | 4530 | Inc. brix |
| G531 | 1124 | GF14 (227-234) | P5287 (epidermal tissue-expressed LTP1 prom.) | P7130 | 4530 | Inc. brix |
| G532 | 1126 | GF14 (NA) | P5297 (fruit tissue-expressed PG prom.) | P7131 | 4531 | Inc. brix |
| G547 | 1128 | Z-C2H2 (79-99, 164-184, 222-244) | P5326 (floral meristem-expressed AP1 prom.) | P8614 | 4716 | Inc. fruit weight |
| G553 | 1130 | bZIP (94-160) | P6506 (constitutive CaMv 35S prom.) | P3778 | 4215 | Inc. lycopene |
| G553 | 1130 | bZIP (94-160) | P5303 (fruit tissue-expressed PD prom.) | P3778 | 4215 | Inc. fruit weight |
| G556 | 1132 | bZIP (83-143) | P5287 (epidermal tissue-expressed LTP1 prom.) | P4162 | 4259 | Inc. fruit weight |
| G558 | 1134 | bZIP (45-105) | P5319 (emergent leaf primordia-expressed AS1 prom.) | P3573 | 4191 | Inc. lycopene |
| G558 | 1134 | bZIP (45-105) | P5318 (shoot apical meristem-expressed STM prom.) | P3573 | 4191 | Inc. lycopene |
| G559 | 1136 | bZIP (203-264) | P5326 (floral meristem-expressed AP1 prom.) | P3585 | 4195 | Inc. lycopene |
| G562 | 1138 | bZIP (253-315) | P5318 (shoot apical meristem-expressed STM prom.) | P6000 | 4412 | Inc. fruit weight |
| G563 | 1140 | bZIP (186-248) | P5318 (shoot apical meristem-expressed STM prom.) | P4896 | 4363 | Large leaflets |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G563 | 1140 | bZIP (186-248) | P5324 (fruit vascular tissue-expressed Cru prom.) | P4896 | 4363 | Large leaflets |
| G567 | 1142 | bZIP (210-270) | P5297 (fruit tissue-expressed PG prom.) | P4762 | 4348 | Inc. brix |
| G567 | 1142 | bZIP (210-270) | P5297 (fruit tissue-expressed PG prom.) | P4762 | 4348 | Inc. lycopene |
| G567 | 1142 | bZIP (210-270) | P5319 (emergent leaf primordia-expressed AS1 prom.) | P4762 | 4348 | Inc. lycopene |
| G568 | 1144 | bZIP (215-265) | P5297 (fruit tissue-expressed PG prom.) | P7120 | 4527 | Inc. brix |
| G577 | 1146 | BZIPT2 (1-53, 356-466) | P5326 (floral meristem-expressed AP1 prom.) | P4026 | 4250 | Inc. brix |
| G577 | 1146 | BZIPT2 (1-53, 356-466) | P5326 (floral meristem-expressed AP1 prom.) | P4026 | 4250 | Inc. lycopene |
| G579 | 1148 | bZIP (167-227) | P5287 (epidermal tissue-expressed LTP1 prom.) | P3981 | 4237 | Inc. lycopene |
| G579 | 1148 | bZIP (167-227) | P5287 (epidermal tissue-expressed LTP1 prom.) | P4025 | 4249 | Inc. lycopene |
| G580 | 1150 | bZIP (162-218) | P5318 (shoot apical meristem-expressed STM prom.) | P3657 | 4212 | Inc. brix |
| G580 | 1150 | bZIP (162-218) | P5318 (shoot apical meristem-expressed STM prom.) | P3657 | 4212 | Inc. lycopene |
| G580 | 1150 | bZIP (162-218) | P6506 (constitutive CaMv 35S prom.) | P3657 | 4212 | Inc. lycopene |
| G580 | 1150 | bZIP (162-218) | P5287 (epidermal tissue-expressed LTP1 prom.) | P6493 | 4469 | Inc. fruit weight |
| G588 | 1152 | HLH/MYC (313-370) | P5284 (leaf-expressed RbcS3 prom.) | P7856 | 4625 | Inc. fruit weight |
| G591 | 1154 | HLH/MYC (149-206) | P5318 (shoot apical meristem-expressed STM prom.) | P5085 | 4377 | Inc. fruit weight |
| G595 | 1156 | HLH/MYC (NA) | P5287 (epidermal tissue-expressed LTP1 prom.) | P9103 | 4780 | Inc. brix |
| G596 | 1158 | AT-hook (89-97, 98-244) | P5318 (shoot apical meristem-expressed STM prom.) | P7033 | 4504 | Inc. fruit weight |
| G598 | 1160 | DBP (205-263) | P5319 (emergent leaf primordia-expressed AS1 prom.) | P6001 | 4413 | Inc. brix |
| G598 | 1160 | DBP (205-263) | P5326 (floral meristem-expressed AP1 prom.) | P6001 | 4413 | Inc. lycopene |
| G599 | 1162 | DBP (187-219, 264-300) | P5303 (fruit tissue-expressed PD prom.) | P6417 | 4445 | Inc. brix |
| G599 | 1162 | DBP (187-219, 264-300) | P5326 (floral meristem-expressed AP1 prom.) | P6417 | 4445 | Inc. brix |
| G599 | 1162 | DBP (187-219, 264-300) | P5324 (fruit vascular tissue-expressed Cru prom.) | P6417 | 4445 | Inc. brix |
| G615 | 1164 | TEO (88-147) | P5284 (leaf-expressed RbcS3 prom.) | P7159 | 4540 | Inc. brix |
| G619 | 1166 | ARF (64-406) | P6506 (constitutive CaMv 35S prom.) | P5706 | 4403 | Inc. brix |
| G619 | 1166 | ARF (64-406) | P5326 (floral meristem-expressed AP1 prom.) | P5706 | 4403 | Inc. brix |
| G625 | 1168 | AP2 (52-119) | P5297 (fruit tissue-expressed PG prom.) | P6837 | 4478 | Inc. brix |
| G631 | 1170 | bZIP (212-282) | P5326 (floral meristem-expressed AP1 prom.) | P6460 | 4461 | Inc. lycopene |
| G634 | 1172 | TH (62-147, 189-245) | P5297 (fruit tissue-expressed PG prom.) | P7198 | 4545 | Inc. lycopene |
| G635 | 1174 | TH (239-323) | P5303 (fruit tissue-expressed PD prom.) | P3619 | 4203 | Inc. brix |
| G635 | 1174 | TH (239-323) | P5303 (fruit tissue-expressed PD prom.) | P3619 | 4203 | Inc. lycopene |
| G639 | 1176 | TH (304-389) | P5284 (leaf-expressed RbcS3 prom.) | P3641 | 4206 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G641 | 1178 | TH (23-102) | P5326 (floral meristem-expressed AP1 prom.) | P7134 | 4532 | Inc. fruit weight |
| G645 | 1180 | SCR (276-341, 392-479, 480-553) | P5297 (fruit tissue-expressed PG prom.) | P6053 | 4420 | Inc. brix |
| G645 | 1180 | SCR (276-341, 392-479, 480-553) | P5284 (leaf-expressed RbcS3 prom.) | P6053 | 4420 | Inc. lycopene |
| G649 | 1182 | RING/C3H2C3 (NA) | P5326 (floral meristem-expressed AP1 prom.) | P5091 | 4378 | Inc. brix |
| G653 | 1184 | Z-LIM (10-61, 109-160) | P5284 (leaf-expressed RbcS3 prom.) | P9248 | 4815 | Inc. lycopene |
| G655 | 1186 | MYB-(R1)R2R3 (44-206) | P5284 (leaf-expressed RbcS3 prom.) | P6430 | 4448 | Inc. lycopene |
| G655 | 1186 | MYB-(R1)R2R3 (44-206) | P5324 (fruit vascular tissue-expressed Cru prom.) | P6430 | 4448 | Inc. fruit weight |
| G658 | 1188 | MYB-(R1)R2R3 (2-105) | P5324 (fruit vascular tissue-expressed Cru prom.) | P6002 | 4414 | Inc. brix |
| G658 | 1188 | MYB-(R1)R2R3 (2-105) | P5284 (leaf-expressed RbcS3 prom.) | P6002 | 4414 | Inc. lycopene |
| G659 | 1190 | MYB-(R1)R2R3 (16-116) | P5326 (floral meristem-expressed AP1 prom.) | P6429 | 4447 | Inc. fruit weight |
| G663 | 1192 | MYB-(R1)R2R3 (9-111) | P6506 (constitutive CaMv 35S prom.) | P5094 | 4379 | Inc. fruit weight |
| G663 | 1192 | MYB-(R1)R2R3 (9-111) | P5303 (fruit tissue-expressed PD prom.) | P5094 | 4379 | Inc. fruit weight |
| G664 | 1194 | MYB-(R1)R2R3 (14-116) | P5287 (epidermal tissue-expressed LTP1 prom.) | P7015 | 4501 | Inc. lycopene |
| G665 | 1196 | MYB-related (91-139) | P5284 (leaf-expressed RbcS3 prom.) | P6430 | 4448 | Inc. lycopene |
| G666 | 1198 | MYB-(R1)R2R3 (14-116) | P5297 (fruit tissue-expressed PG prom.) | P6431 | 4449 | Inc. biomass |
| G674 | 1200 | MYB-(R1)R2R3 (20-120) | P5284 (leaf-expressed RbcS3 prom.) | P7123 | 4528 | Inc. lycopene |
| G675 | 1202 | MYB-(R1)R2R3 (13-116) | P5284 (leaf-expressed RbcS3 prom.) | P4019 | 4245 | Inc. lycopene |
| G675 | 1202 | MYB-(R1)R2R3 (13-116) | P5318 (shoot apical meristem-expressed STM prom.) | P4019 | 4245 | Inc. lycopene |
| G675 | 1202 | MYB-(R1)R2R3 (13-116) | P5319 (emergent leaf primordia-expressed AS1 prom.) | P4019 | 4245 | Inc. lycopene |
| G675 | 1202 | MYB-(R1)R2R3 (13-116) | P5326 (floral meristem-expressed AP1 prom.) | P4019 | 4245 | Inc. lycopene |
| G679 | 1204 | MYB-related (102-150) | P6506 (constitutive CaMv 35S prom.) | P6433 | 4450 | Inc. brix |
| G682 | 1206 | MYB-related (33-77) | P5287 (epidermal tissue-expressed LTP1 prom.) | P5099 | 4380 | Inc. lycopene |
| G699 | 1208 | HB (52-115) | P5287 (epidermal tissue-expressed LTP1 prom.) | P6494 | 4470 | Inc. fruit weight |
| G699 | 1208 | HB (52-115) | P5284 (leaf-expressed RbcS3 prom.) | P6494 | 4470 | Inc. fruit weight |
| G707 | 1212 | HB (109-169) | P5284 (leaf-expressed RbcS3 prom.) | P8734 | 4757 | Inc. brix |
| G707 | 1212 | HB (109-169) | P5287 (epidermal tissue-expressed LTP1 prom.) | P8734 | 4757 | Inc. brix |
| G714 | 1214 | CAAT (58-150) | P5284 (leaf-expressed RbcS3 prom.) | P7861 | 4628 | Inc. lycopene |
| G714 | 1214 | CAAT (58-150) | P5297 (fruit tissue-expressed PG prom.) | P7861 | 4628 | Inc. lycopene |
| G715 | 1216 | CAAT (53-149) | P5287 (epidermal tissue-expressed LTP1 prom.) | P8668 | 4736 | Inc. fruit weight |
| G720 | 1218 | GARP (301-349) | P5284 (leaf-expressed RbcS3 prom.) | P6076 | 4425 | Inc. lycopene |
| G720 | 1218 | GARP (301-349) | P5287 (epidermal tissue-expressed LTP1 prom.) | P6076 | 4425 | Inc. lycopene |
| G721 | 1220 | GARP (NA) | P5326 (floral meristem-expressed AP1 prom.) | P4888 | 4362 | Inc. brix |
| G722 | 1222 | GARP (188-236) | P5324 (fruit vascular tissue-expressed Cru prom.) | P6042 | 4417 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G724 | 1224 | GARP (86-134) | P5326 (floral meristem-expressed AP1 prom.) | P8493 | 4688 | Inc. brix |
| G724 | 1224 | GARP (86-134) | P5310 (root-expressed RSI1 prom.) | P8493 | 4688 | Inc. lycopene |
| G724 | 1224 | GARP (86-134) | P5287 (epidermal tissue-expressed LTP1 prom.) | P8493 | 4688 | Inc. lycopene |
| G724 | 1224 | GARP (86-134) | P5284 (leaf-expressed RbcS3 prom.) | P8493 | 4688 | Inc. fruit weight |
| G727 | 1226 | GARP (226-269) | P5287 (epidermal tissue-expressed LTP1 prom.) | P6406 | 4441 | Inc. fruit weight |
| G730 | 1228 | GARP (169-217) | P5287 (epidermal tissue-expressed LTP1 prom.) | P8528 | 4693 | Inc. lycopene |
| G732 | 1230 | bZIP (31-91) | P5318 (shoot apical meristem-expressed STM prom.) | P7084 | 4515 | Inc. fruit weight |
| G748 | 1232 | Z-Dof (112-140) | P5324 (fruit vascular tissue-expressed Cru prom.) | P3363 | 4178 | Inc. lycopene |
| G748 | 1232 | Z-Dof (112-140) | P6506 (constitutive CaMv 35S prom.) | P3363 | 4178 | Inc. lycopene |
| G748 | 1232 | Z-Dof (112-140) | P5318 (shoot apical meristem-expressed STM prom.) | P3363 | 4178 | Inc. fruit weight |
| G749 | 1234 | Z-C3H (125-177) | P5287 (epidermal tissue-expressed LTP1 prom.) | P5105 | 4381 | Inc. fruit weight |
| G751 | 1236 | Z-Dof (37-82) | P5284 (leaf-expressed RbcS3 prom.) | P6495 | 4471 | Inc. brix |
| G751 | 1236 | Z-Dof (37-82) | P5287 (epidermal tissue-expressed LTP1 prom.) | P6495 | 4471 | Inc. brix |
| G756 | 1238 | Z-C3H (199-319) | P5287 (epidermal tissue-expressed LTP1 prom.) | P7748 | 4603 | Inc. brix |
| G763 | 1240 | NAC (17-157) | P5318 (shoot apical meristem-expressed STM prom.) | P5541 | 4396 | Inc. brix |
| G763 | 1240 | NAC (17-157) | P5297 (fruit tissue-expressed PG prom.) | P5541 | 4396 | Inc. brix |
| G764 | 1242 | NAC (27-171) | P5297 (fruit tissue-expressed PG prom.) | P6496 | 4472 | Inc. brix |
| G764 | 1242 | NAC (27-171) | P5297 (fruit tissue-expressed PG prom.) | P6496 | 4472 | Inc. lycopene |
| G783 | 1244 | HLH/MYC (24-82) | P5319 (emergent leaf primordia-expressed AS1 prom.) | | | Inc. lycopene |
| G783 | 1244 | HLH/MYC (24-82) | P5318 (shoot apical meristem-expressed STM prom.) | | | Inc. fruit weight |
| G783 | 1244 | HLH/MYC (24-82) | P5287 (epidermal tissue-expressed LTP1 prom.) | | | Inc. fruit weight |
| G783 | 1244 | HLH/MYC (24-82) | P5297 (fruit tissue-expressed PG prom.) | | | Inc. fruit weight |
| G787 | 1246 | HLH/MYC (49-105) | P5297 (fruit tissue-expressed PG prom.) | P9254 | 4817 | Inc. brix |
| G787 | 1246 | HLH/MYC (49-105) | P5287 (epidermal tissue-expressed LTP1 prom.) | P9254 | 4817 | Inc. brix |
| G787 | 1246 | HLH/MYC (49-105) | P5326 (floral meristem-expressed AP1 prom.) | P9254 | 4817 | Inc. brix |
| G789 | 1248 | HLH/MYC (253-310) | P5324 (fruit vascular tissue-expressed Cru prom.) | P7068 | 4511 | Inc. brix |
| G790 | 1250 | HLH/MYC (NA) | P5284 (leaf-expressed RbcS3 prom.) | P4044 | 4254 | Inc. brix |
| G792 | 1252 | HLH/MYC (63-122) | P5318 (shoot apical meristem-expressed STM prom.) | P7110 | 4524 | Inc. brix |
| G792 | 1252 | HLH/MYC (63-122) | P5319 (emergent leaf primordia-expressed AS1 prom.) | P7110 | 4524 | Inc. brix |
| G793 | 1254 | HLH/MYC (147-204) | P5287 (epidermal tissue-expressed LTP1 prom.) | P5111 | 4382 | Inc. brix |
| G793 | 1254 | HLH/MYC (147-204) | P5287 (epidermal tissue-expressed LTP1 prom.) | P5111 | 4382 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G810 | 1258 | HS (23-114) | P5284 (leaf-expressed RbcS3 prom.) | P4763 | 4349 | Inc. brix |
| G811 | 1260 | HS (17-108) | P5326 (floral meristem-expressed AP1 prom.) | P8573 | 4704 | Inc. fruit weight |
| G811 | 1260 | HS (17-108) | P5287 (epidermal tissue-expressed LTP1 prom.) | P8573 | 4704 | Inc. fruit weight |
| G811 | 1260 | HS (17-108) | P5318 (shoot apical meristem-expressed STM prom.) | P8573 | 4704 | Inc. fruit weight |
| G812 | 1262 | HS (29-120) | P5284 (leaf-expressed RbcS3 prom.) | P3650 | 4209 | Inc. lycopene |
| G819 | 1264 | AKR (88-598) | P5284 (leaf-expressed RbcS3 prom.) | P8953 | 4765 | Inc. brix |
| G830 | 1266 | AKR (89-601) | P5324 (fruit vascular tissue-expressed Cru prom.) | P6165 | 4428 | Inc. brix |
| G843 | 1268 | MISC (60-119, 270-350) | P6506 (constitutive CaMv 35S prom.) | P4559 | 4312 | Inc. lycopene |
| G843 | 1268 | MISC (60-119, 270-350) | P5326 (floral meristem-expressed AP1 prom.) | P4559 | 4312 | Inc. lycopene |
| G865 | 1270 | AP2 (36-103) | P5297 (fruit tissue-expressed PG prom.) | P7088 | 4519 | Inc. brix |
| G865 | 1270 | AP2 (36-103) | P5318 (shoot apical meristem-expressed STM prom.) | P7088 | 4519 | Inc. brix |
| G865 | 1270 | AP2 (36-103) | P5319 (emergent leaf primordia-expressed AS1 prom.) | P7088 | 4519 | Inc. brix |
| G869 | 1272 | AP2 (110-165) | P5297 (fruit tissue-expressed PG prom.) | P9105 | 4781 | Inc. lycopene |
| G869 | 1272 | AP2 (110-165) | P5310 (root-expressed RSI1 prom.) | P9105 | 4781 | Inc. lycopene |
| G881 | 1274 | WRKY (176-233) | P5318 (shoot apical meristem-expressed STM prom.) | P5557 | 4397 | Inc. lycopene |
| G886 | 1276 | BZIPT2 (1-53, 542-652) | P5287 (epidermal tissue-expressed LTP1 prom.) | P6828 | 4477 | Inc. brix |
| G896 | 1278 | Z-LSDlike (18-39) | P5303 (fruit tissue-expressed PD prom.) | P7452 | 4548 | Inc. fruit weight |
| G896 | 1278 | Z-LSDlike (18-39) | P5284 (leaf-expressed RbcS3 prom.) | P7452 | 4548 | Inc. fruit weight |
| G896 | 1278 | Z-LSDlike (18-39) | P5297 (fruit tissue-expressed PG prom.) | P7452 | 4548 | Inc. fruit weight |
| G896 | 1278 | Z-LSDlike (18-39) | P5324 (fruit vascular tissue-expressed Cru prom.) | P7452 | 4548 | Inc. fruit weight |
| G896 | 1278 | Z-LSDlike (18-39) | P5287 (epidermal tissue-expressed LTP1 prom.) | P7452 | 4548 | Inc. fruit weight |
| G896 | 1278 | Z-LSDlike (18-39) | P5318 (shoot apical meristem-expressed STM prom.) | P7452 | 4548 | Inc. fruit weight |
| G897 | 1280 | Z-CO-like (8-39, 51-82) | P5318 (shoot apical meristem-expressed STM prom.) | P7085 | 4516 | Inc. lycopene |
| G902 | 1282 | Z-CO-like (NA) | P5319 (emergent leaf primordia-expressed AS1 prom.) | P9089 | 4777 | Inc. fruit weight |
| G902 | 1282 | Z-CO-like (NA) | P5324 (fruit vascular tissue-expressed Cru prom.) | P9089 | 4777 | Inc. fruit weight |
| G902 | 1282 | Z-CO-like (NA) | P5318 (shoot apical meristem-expressed STM prom.) | P9089 | 4777 | Inc. fruit weight |
| G904 | 1284 | RING/C3H2C3 (117-158) | P5318 (shoot apical meristem-expressed STM prom.) | P4748 | 4342 | Inc. lycopene |
| G905 | 1286 | RING/C3H2C3 (118-159) | P5318 (shoot apical meristem-expressed STM prom.) | P8548 | 4697 | Inc. brix |
| G910 | 1288 | Z-CO-like (14-37, 77-103) | P5297 (fruit tissue-expressed PG prom.) | P6867 | 4486 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G920 | 1290 | WRKY (152-211) | P5326 (floral meristem-expressed AP1 prom.) | P8941 | 4763 | Inc. lycopene |
| G921 | 1292 | WRKY (146-203) | P5287 (epidermal tissue-expressed LTP1 prom.) | P5826 | 4404 | Inc. lycopene |
| G927 | 1294 | CAAT (136-199) | P5284 (leaf-expressed RbcS3 prom.) | P6434 | 4451 | Inc. brix |
| G927 | 1294 | CAAT (136-199) | P5297 (fruit tissue-expressed PG prom.) | P6434 | 4451 | Inc. brix |
| G927 | 1294 | CAAT (136-199) | P5284 (leaf-expressed RbcS3 prom.) | P6434 | 4451 | Inc. lycopene |
| G927 | 1294 | CAAT (136-199) | P5297 (fruit tissue-expressed PG prom.) | P6434 | 4451 | Inc. lycopene |
| G929 | 1296 | CAAT (98-157) | P5324 (fruit vascular tissue-expressed Cru prom.) | P9107 | 4782 | Very high vigor |
| G934 | 1298 | ARF (NA) | P5326 (floral meristem-expressed AP1 prom.) | P8669 | 4737 | Inc. brix |
| G934 | 1298 | ARF (NA) | P5284 (leaf-expressed RbcS3 prom.) | P8669 | 4737 | Inc. lycopene |
| G936 | 1300 | GARP (59-107) | P5318 (shoot apical meristem-expressed STM prom.) | P7536 | 4575 | Inc. brix |
| G937 | 1302 | GARP (197-246) | P5324 (fruit vascular tissue-expressed Cru prom.) | P4527 | 4308 | Inc. fruit weight |
| G938 | 1304 | EIL (96-104) | P5310 (root-expressed RSI1 prom.) | | | Inc. lycopene |
| G939 | 1306 | EIL (97-106) | P5318 (shoot apical meristem-expressed STM prom.) | P3590 | 4196 | Inc. brix |
| G939 | 1306 | EIL (97-106) | P5318 (shoot apical meristem-expressed STM prom.) | P3590 | 4196 | Inc. lycopene |
| G941 | 1308 | EIL (95-103) | P5297 (fruit tissue-expressed PG prom.) | P5565 | 4398 | Inc. lycopene |
| G961 | 1310 | NAC (12-180) | P5326 (floral meristem-expressed AP1 prom.) | P8222 | 4663 | Inc. fruit weight |
| G961 | 1310 | NAC (12-180) | P5310 (root-expressed RSI1 prom.) | P8222 | 4663 | Inc. fruit weight |
| G962 | 1312 | NAC (53-175) | P5297 (fruit tissue-expressed PG prom.) | P6873 | 4488 | Inc. brix |
| G963 | 1314 | NAC (NA) | P5324 (fruit vascular tissue-expressed Cru prom.) | P4330 | 4279 | Inc. lycopene |
| G975 | 1316 | AP2 (4-71) | P5324 (fruit vascular tissue-expressed Cru prom.) | P3367 | 4179 | Inc. lycopene |
| G976 | 1318 | AP2 (87-153) | P5318 (shoot apical meristem-expressed STM prom.) | P3823 | 4216 | Inc. brix |
| G976 | 1318 | AP2 (87-153) | P5326 (floral meristem-expressed AP1 prom.) | P3823 | 4216 | Inc. brix |
| G976 | 1318 | AP2 (87-153) | P5287 (epidermal tissue-expressed LTP1 prom.) | P3823 | 4216 | Inc. brix |
| G979 | 1320 | AP2 (63-139, 165-233) | P5287 (epidermal tissue-expressed LTP1 prom.) | P3635 | 4205 | Inc. fruit weight |
| G988 | 1322 | SCR (150-217, 277-366, 371-444) | P5326 (floral meristem-expressed AP1 prom.) | P4204 | 4270 | Inc. brix |
| G991 | 1324 | IAA (7-14, 48-59, 82-115, 128-164) | P5297 (fruit tissue-expressed PG prom.) | P5703 | 4402 | Inc. lycopene |
| G993 | 1326 | AP2 (69-134, 191-290) | P5324 (fruit vascular tissue-expressed Cru prom.) | | | Deep red fruit |
| G997 | 1328 | MYB-related (9-59) | P5297 (fruit tissue-expressed PG prom.) | P7039 | 4505 | Inc. brix |
| G999 | 1330 | MYB-(R1)R2R3 (28-363) | P5297 (fruit tissue-expressed PG prom.) | P8150 | 4648 | Inc. lycopene |
| G1004 | 2 | AP2 (153-221) | P5297 (fruit tissue-expressed PG prom.) | P4764 | 4350 | Inc. fruit weight |
| G1006 | 4 | AP2 (113-177) | P5303 (fruit tissue-expressed PD prom.) | P7145 | 4533 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1006 | 4 | AP2 (113-177) | P5324 (fruit vascular tissue-expressed Cru prom.) | P7145 | 4533 | Inc. biomass |
| G1007 | 6 | AP2 (23-90) | P5326 (floral meristem-expressed AP1 prom.) | P4002 | 4243 | Inc. lycopene |
| G1008 | 8 | AP2 (96-163) | P5297 (fruit tissue-expressed PG prom.) | P7040 | 4506 | Inc. lycopene |
| G1014 | 10 | ABI3/VP-1 (90-172) | P5318 (shoot apical meristem-expressed STM prom.) | P9109 | 4783 | Inc. fruit weight |
| G1018 | 12 | ABI3/VP-1 (222-311) | P5318 (shoot apical meristem-expressed STM prom.) | P8584 | 4706 | Inc. fruit weight |
| G1021 | 14 | PMR (NA) | P5297 (fruit tissue-expressed PG prom.) | P4777 | 4356 | Inc. brix |
| G1021 | 14 | PMR (NA) | P5284 (leaf-expressed RbcS3 prom.) | P4777 | 4356 | Inc. lycopene |
| G1022 | 16 | WRKY (281-340) | P5318 (shoot apical meristem-expressed STM prom.) | P7865 | 4631 | Inc. fruit weight |
| G1033 | 18 | HMG (49-121) | P5326 (floral meristem-expressed AP1 prom.) | P7786 | 4615 | Inc. lycopene |
| G1048 | 20 | bZIP (138-190) | P5324 (fruit vascular tissue-expressed Cru prom.) | P6435 | 4452 | Inc. fruit weight |
| G1048 | 20 | bZIP (138-190) | P5326 (floral meristem-expressed AP1 prom.) | P6435 | 4452 | Inc. fruit weight |
| G1053 | 22 | bZIP (74-120) | P5318 (shoot apical meristem-expressed STM prom.) | P3599 | 4197 | Inc. lycopene |
| G1057 | 24 | bZIP (305-365) | P5284 (leaf-expressed RbcS3 prom.) | P6436 | 4453 | Inc. lycopene |
| G1062 | 26 | HLH/MYC (300-357) | P5303 (fruit tissue-expressed PD prom.) | P6854 | 4481 | Inc. brix |
| G1065 | 28 | DBP (101-210) | P5326 (floral meristem-expressed AP1 prom.) | P3579 | 4192 | Inc. fruit weight |
| G1067 | 30 | AT-hook (86-94, 95-246) | P5326 (floral meristem-expressed AP1 prom.) | P7832 | 4621 | Inc. brix |
| G1067 | 30 | AT-hook (86-94, 95-246) | P5326 (floral meristem-expressed AP1 prom.) | P7832 | 4621 | Inc. lycopene |
| G1067 | 30 | AT-hook (86-94, 95-246) | P5297 (fruit tissue-expressed PG prom.) | P7832 | 4621 | Inc. lycopene |
| G1072 | 32 | AT-hook (56-64, 123-238) | P5318 (shoot apical meristem-expressed STM prom.) | P6160 | 4427 | Inc. brix |
| G1076 | 34 | AT-hook (82-90, 91-233) | P5284 (leaf-expressed RbcS3 prom.) | P7092 | 4520 | Inc. lycopene |
| G1078 | 36 | BZIPT2 (1-53, 440-550) | P5284 (leaf-expressed RbcS3 prom.) | P3580 | 4193 | Inc. lycopene |
| G1080 | 38 | BZIPT2 (1-50) | P5297 (fruit tissue-expressed PG prom.) | P6453 | 4459 | Inc. brix |
| G1080 | 38 | BZIPT2 (1-50) | P5318 (shoot apical meristem-expressed STM prom.) | P6453 | 4459 | Inc. brix |
| G1080 | 38 | BZIPT2 (1-50) | P5287 (epidermal tissue-expressed LTP1 prom.) | P6453 | 4459 | Inc. lycopene |
| G1084 | 40 | BZIPT2 (1-53, 490-619) | P5318 (shoot apical meristem-expressed STM prom.) | P4779 | 4357 | Inc. lycopene |
| G1089 | 42 | BZIPT2 (425-500) | P5284 (leaf-expressed RbcS3 prom.) | P6421 | 4446 | Inc. brix |
| G1090 | 44 | AP2 (17-84) | P5318 (shoot apical meristem-expressed STM prom.) | P7093 | 4521 | Inc. brix |
| G1091 | 46 | WRKY (262-319) | P5318 (shoot apical meristem-expressed STM prom.) | | | Inc. fruit weight |
| G1091 | 46 | WRKY (262-319) | P5284 (leaf-expressed RbcS3 prom.) | | | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1098 | 48 | RING/C3H2C3 (10-29, 190-230, 255-262, 286-290) | P5326 (floral meristem-expressed AP1 prom.) | P8230 | 4667 | Inc. fruit weight |
| G1098 | 48 | RING/C3H2C3 (10-29, 190-230, 255-262, 286-290) | P5297 (fruit tissue-expressed PG prom.) | P8230 | 4667 | Inc. fruit weight |
| G1113 | 50 | RING/C3H2C3 (85-128) | P5310 (root-expressed RSI1 prom.) | P8232 | 4668 | Inc. lycopene |
| G1113 | 50 | RING/C3H2C3 (85-128) | P5297 (fruit tissue-expressed PG prom.) | P8232 | 4668 | Inc. fruit weight |
| G1127 | 52 | AT-hook (102-110, 155-162, 180-295) | P5297 (fruit tissue-expressed PG prom.) | P4185 | 4264 | Inc. fruit weight |
| G1131 | 54 | HLH/MYC (160-217) | P5297 (fruit tissue-expressed PG prom.) | P3950 | 4225 | Inc. lycopene |
| G1131 | 54 | HLH/MYC (160-217) | P5326 (floral meristem-expressed AP1 prom.) | P3950 | 4225 | Inc. fruit weight |
| G1133 | 56 | HLH/MYC (260-317) | P5319 (emergent leaf primordia-expressed AS1 prom.) | P7148 | 4534 | Inc. brix |
| G1134 | 58 | HLH/MYC (187-245) | P6506 (constitutive CaMv 35S prom.) | P7112 | 4525 | Inc. brix |
| G1136 | 60 | HLH/MYC (408-465) | P5287 (epidermal tissue-expressed LTP1 prom.) | P7769 | 4609 | Inc. fruit weight |
| G1137 | 62 | HLH/MYC (257-314) | P5297 (fruit tissue-expressed PG prom.) | P3410 | 4184 | Inc. brix |
| G1140 | 64 | MADS (2-57) | P5326 (floral meristem-expressed AP1 prom.) | P4765 | 4351 | Inc. brix |
| G1141 | 66 | AP2 (75-142) | P5284 (leaf-expressed RbcS3 prom.) | P7149 | 4535 | Inc. brix |
| G1141 | 66 | AP2 (75-142) | P5326 (floral meristem-expressed AP1 prom.) | P7149 | 4535 | Inc. brix |
| G1141 | 66 | AP2 (75-142) | P5319 (emergent leaf primordia-expressed AS1 prom.) | P7149 | 4535 | Inc. brix |
| G1141 | 66 | AP2 (75-142) | P5297 (fruit tissue-expressed PG prom.) | P7149 | 4535 | Inc. lycopene |
| G1141 | 66 | AP2 (75-142) | P5319 (emergent leaf primordia-expressed AS1 prom.) | P7149 | 4535 | Inc. lycopene |
| G1146 | 68 | PAZ (886-896) | P6506 (constitutive CaMv 35S prom.) | P7061 | 4509 | Inc. brix |
| G1146 | 68 | PAZ (886-896) | P5297 (fruit tissue-expressed PG prom.) | P7061 | 4509 | Inc. brix |
| G1148 | 70 | PAZ (770-807) | P5318 (shoot apical meristem-expressed STM prom.) | P8627 | 4723 | Inc. fruit weight |
| G1148 | 70 | PAZ (770-807) | P5326 (floral meristem-expressed AP1 prom.) | P8627 | 4723 | Inc. fruit weight |
| G1150 | 72 | PAZ (887-907) | P5287 (epidermal tissue-expressed LTP1 prom.) | | | Inc. lycopene |
| G1198 | 74 | bZIP (173-223) | P5287 (epidermal tissue-expressed LTP1 prom.) | P4766 | 4352 | Inc. fruit weight |
| G1211 | 76 | MISC (123-179) | P5297 (fruit tissue-expressed PG prom.) | P6173 | 4430 | Inc. brix |
| G1211 | 76 | MISC (123-179) | P5319 (emergent leaf primordia-expressed AS1 prom.) | P6173 | 4430 | Inc. brix |
| G1211 | 76 | MISC (123-179) | P5324 (fruit vascular tissue-expressed Cru prom.) | P6173 | 4430 | Inc. brix |
| G1216 | 78 | BPF-1 (293-373, 464-550) | P5297 (fruit tissue-expressed PG prom.) | P7850 | 4624 | Inc. fruit weight |
| G1226 | 80 | HLH/MYC (109-168) | P5284 (leaf-expressed RbcS3 prom.) | P3647 | 4208 | Inc. lycopene |
| G1228 | 82 | HLH/MYC (172-231) | P5326 (floral meristem-expressed AP1 prom.) | P3411 | 4185 | Inc. lycopene |
| G1228 | 82 | HLH/MYC (172-231) | P5297 (fruit tissue-expressed PG prom.) | P3411 | 4185 | Inc. lycopene |
| G1231 | 84 | Z-C4HC3 (201-249) | P5318 (shoot apical meristem-expressed STM prom.) | P7870 | 4634 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1233 | 86 | Z-C4HC3 (192-240) | P5318 (shoot apical meristem-expressed STM prom.) | P7152 | 4536 | Inc. lycopene |
| G1240 | 88 | MISC (NA) | P5318 (shoot apical meristem-expressed STM prom.) | P7153 | 4537 | Inc. brix |
| G1240 | 88 | MISC (NA) | P5297 (fruit tissue-expressed PG prom.) | P7153 | 4537 | Inc. brix |
| G1243 | 90 | SWI/SNF (185-377, 520-604, 842-891, 944-1005) | P5326 (floral meristem-expressed AP1 prom.) | P3998 | 4242 | Inc. fruit weight |
| G1246 | 92 | MYB-(R1)R2R3 (27-139) | P5303 (fruit tissue-expressed PD prom.) | P6062 | 4423 | Inc. fruit weight |
| G1247 | 94 | MYB-(R1)R2R3 (18-141) | P5318 (shoot apical meristem-expressed STM prom.) | P7737 | 4599 | Inc. lycopene |
| G1249 | 96 | CAAT (13-89) | P5318 (shoot apical meristem-expressed STM prom.) | P3993 | 4240 | Inc. brix |
| G1256 | 98 | Z-C2H2 (67-87, 143-163) | P5287 (epidermal tissue-expressed LTP1 prom.) | P8611 | 4715 | Inc. fruit weight |
| G1266 | 100 | AP2 (79-147) | P5303 (fruit tissue-expressed PD prom.) | P7154 | 4538 | Inc. brix |
| G1272 | 102 | PAZ (800-837) | P5297 (fruit tissue-expressed PG prom.) | P4181 | 4263 | Inc. lycopene |
| G1273 | 104 | WRKY (163-218, 347-403) | P5326 (floral meristem-expressed AP1 prom.) | P3994 | 4241 | Inc. lycopene |
| G1274 | 106 | WRKY (110-166) | P5297 (fruit tissue-expressed PG prom.) | P8239 | 4675 | Inc. brix |
| G1275 | 108 | WRKY (113-169) | P5287 (epidermal tissue-expressed LTP1 prom.) | P3412 | 4186 | Inc. lycopene |
| G1278 | 110 | bZIP (230-328) | P5284 (leaf-expressed RbcS3 prom.) | P4780 | 4358 | Inc. lycopene |
| G1293 | 112 | AKR (NA) | P5318 (shoot apical meristem-expressed STM prom.) | P9114 | 4784 | Inc. fruit weight |
| G1293 | 112 | AKR (NA) | P5297 (fruit tissue-expressed PG prom.) | P9114 | 4784 | Inc. fruit weight |
| G1293 | 112 | AKR (NA) | P6506 (constitutive CaMv 35S prom.) | P9114 | 4784 | More trichomes |
| G1297 | 114 | ENBP (77-124, 480-795) | P5297 (fruit tissue-expressed PG prom.) | P8552 | 4698 | Inc. fruit weight |
| G1303 | 116 | Z-C4HC3 (187-235) | P5284 (leaf-expressed RbcS3 prom.) | P7871 | 4635 | Inc. brix |
| G1303 | 116 | Z-C4HC3 (187-235) | P5318 (shoot apical meristem-expressed STM prom.) | P7871 | 4635 | Inc. brix |
| G1303 | 116 | Z-C4HC3 (187-235) | P5284 (leaf-expressed RbcS3 prom.) | P7871 | 4635 | Inc. lycopene |
| G1305 | 118 | MYB-(R1)R2R3 (15-118) | P5326 (floral meristem-expressed AP1 prom.) | P6207 | 4437 | Inc. brix |
| G1308 | 120 | MYB-(R1)R2R3 (1-128) | P5287 (epidermal tissue-expressed LTP1 prom.) | P3830 | 4217 | Inc. fruit weight |
| G1309 | 122 | MYB-(R1)R2R3 (13-115) | P5297 (fruit tissue-expressed PG prom.) | P3413 | 4187 | Inc. lycopene |
| G1309 | 122 | MYB-(R1)R2R3 (13-115) | P5287 (epidermal tissue-expressed LTP1 prom.) | P3413 | 4187 | Inc. fruit weight |
| G1313 | 124 | MYB-(R1)R2R3 (32-135) | P5297 (fruit tissue-expressed PG prom.) | P7462 | 4552 | Inc. lycopene |
| G1313 | 124 | MYB-(R1)R2R3 (32-135) | P5326 (floral meristem-expressed AP1 prom.) | P7462 | 4552 | Inc. fruit weight |
| G1315 | 126 | MYB-(R1)R2R3 (14-115) | P5326 (floral meristem-expressed AP1 prom.) | P3832 | 4218 | Inc. fruit weight |
| G1319 | 128 | MYB-(R1)R2R3 (14-114) | P5318 (shoot apical meristem-expressed STM prom.) | P4020 | 4246 | Inc. fruit weight |
| G1320 | 130 | MYB-(R1)R2R3 (5-108) | P5287 (epidermal tissue-expressed LTP1 prom.) | P3834 | 4219 | Inc. brix |
| G1324 | 132 | MYB-(R1)R2R3 (20-118) | P5297 (fruit tissue-expressed PG prom.) | P4914 | 4364 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1326 | 134 | MYB-(R1)R2R3 (18-121) | P5287 (epidermal tissue-expressed LTP1 prom.) | P3417 | 4188 | Inc. fruit weight |
| G1335 | 136 | Z-CLDSH (24-43, 131-144, 185-203) | P6506 (constitutive CaMv 35S prom.) | P5689 | 4399 | Inc. brix |
| G1335 | 136 | Z-CLDSH (24-43, 131-144, 185-203) | P5326 (floral meristem-expressed AP1 prom.) | P5689 | 4399 | Inc. brix |
| G1341 | 138 | BZIPT2 (1-34, 288-398) | P5287 (epidermal tissue-expressed LTP1 prom.) | P8628 | 4724 | Inc. lycopene |
| G1349 | 140 | Z-LSDlike (6-39) | P5287 (epidermal tissue-expressed LTP1 prom.) | P5692 | 4400 | Inc. brix |
| G1349 | 140 | Z-LSDlike (6-39) | P5319 (emergent leaf primordia-expressed AS1 prom.) | P5692 | 4400 | Inc. brix |
| G1349 | 140 | Z-LSDlike (6-39) | P5324 (fruit vascular tissue-expressed Cru prom.) | P5692 | 4400 | Inc. brix |
| G1349 | 140 | Z-LSDlike (6-39) | P5324 (fruit vascular tissue-expressed Cru prom.) | P5692 | 4400 | Inc. lycopene |
| G1352 | 142 | Z-C2H2 (108-129, 167-188) | P5310 (root-expressed RSI1 prom.) | P9257 | 4818 | Inc. lycopene |
| G1352 | 142 | Z-C2H2 (108-129, 167-188) | P5287 (epidermal tissue-expressed LTP1 prom.) | P9257 | 4818 | Inc. fruit weight |
| G1354 | 144 | NAC (7-157) | P5297 (fruit tissue-expressed PG prom.) | P3976 | 4235 | Inc. brix |
| G1354 | 144 | NAC (7-157) | P5326 (floral meristem-expressed AP1 prom.) | P3976 | 4235 | Inc. brix |
| G1354 | 144 | NAC (7-157) | P5318 (shoot apical meristem-expressed STM prom.) | P3976 | 4235 | Inc. brix |
| G1354 | 144 | NAC (7-157) | P5310 (root-expressed RSI1 prom.) | P3976 | 4235 | Inc. lycopene |
| G1355 | 146 | NAC (9-159) | P5287 (epidermal tissue-expressed LTP1 prom.) | P7864 | 4630 | Inc. fruit weight |
| G1361 | 148 | NAC (59-200) | P5297 (fruit tissue-expressed PG prom.) | P7770 | 4610 | Inc. brix |
| G1361 | 148 | NAC (59-200) | P5326 (floral meristem-expressed AP1 prom.) | P7770 | 4610 | Inc. brix |
| G1364 | 150 | CAAT (29-118) | P5287 (epidermal tissue-expressed LTP1 prom.) | P4357 | 4286 | Inc. fruit weight |
| G1367 | 152 | AT-hook (179-201, 262-285, 298-319, 335-357) | P5297 (fruit tissue-expressed PG prom.) | P7184 | 4544 | Inc. lycopene |
| G1379 | 156 | AP2 (18-85) | P5319 (emergent leaf primordia-expressed AS1 prom.) | P6858 | 4483 | Inc. brix |
| G1379 | 156 | AP2 (18-85) | P5318 (shoot apical meristem-expressed STM prom.) | P6858 | 4483 | Inc. brix |
| G1379 | 156 | AP2 (18-85) | P5326 (floral meristem-expressed AP1 prom.) | P6858 | 4483 | Inc. brix |
| G1379 | 156 | AP2 (18-85) | P5297 (fruit tissue-expressed PG prom.) | P6858 | 4483 | Inc. brix |
| G1382 | 160 | WRKY (210-266, 385-437) | P5326 (floral meristem-expressed AP1 prom.) | P9268 | 4821 | Inc. fruit weight |
| G1382 | 160 | WRKY (210-266, 385-437) | P5287 (epidermal tissue-expressed LTP1 prom.) | P9268 | 4821 | Inc. fruit weight |
| G1382 | 160 | WRKY (210-266, 385-437) | P5318 (shoot apical meristem-expressed STM prom.) | P9268 | 4821 | Inc. fruit weight |
| G1384 | 162 | AP2 (127-194) | P5297 (fruit tissue-expressed PG prom.) | P7479 | 4559 | Inc. brix |
| G1384 | 162 | AP2 (127-194) | P5284 (leaf-expressed RbcS3 prom.) | P7479 | 4559 | Inc. brix |
| G1389 | 164 | TEO (30-87) | P5318 (shoot apical meristem-expressed STM prom.) | P6866 | 4485 | Inc. brix |
| G1394 | 168 | S1FA (13-63) | P5287 (epidermal tissue-expressed LTP1 prom.) | P6857 | 4482 | Inc. brix |
| G1394 | 168 | S1FA (13-63) | P6506 (constitutive CaMv 35S prom.) | P6857 | 4482 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1395 | 170 | S1FA (1-72) | P5284 (leaf-expressed RbcS3 prom.) | P7157 | 4539 | Inc. fruit weight |
| G1403 | 174 | GF14 (16-61) | P5326 (floral meristem-expressed AP1 prom.) | | | Inc. lycopene |
| G1410 | 176 | HS (206-298) | P5287 (epidermal tissue-expressed LTP1 prom.) | P4771 | 4353 | Inc. fruit weight |
| G1419 | 178 | AP2 (69-137) | P6506 (constitutive CaMv 35S prom.) | P3616 | 4201 | Inc. lycopene |
| G1421 | 180 | AP2 (84-146) | P5326 (floral meristem-expressed AP1 prom.) | P3631 | 4204 | Inc. brix |
| G1421 | 180 | AP2 (84-146) | P5319 (emergent leaf primordia-expressed AS1 prom.) | P3631 | 4204 | Inc. brix |
| G1421 | 180 | AP2 (84-146) | P5287 (epidermal tissue-expressed LTP1 prom.) | P3631 | 4204 | Inc. brix |
| G1421 | 180 | AP2 (84-146) | P5297 (fruit tissue-expressed PG prom.) | P3631 | 4204 | Inc. brix |
| G1421 | 180 | AP2 (84-146) | P5318 (shoot apical meristem-expressed STM prom.) | P3631 | 4204 | Inc. brix |
| G1421 | 180 | AP2 (84-146) | P5287 (epidermal tissue-expressed LTP1 prom.) | P3631 | 4204 | Inc. lycopene |
| G1421 | 180 | AP2 (84-146) | P5324 (fruit vascular tissue-expressed Cru prom.) | P3631 | 4204 | Inc. lycopene |
| G1421 | 180 | AP2 (84-146) | P5303 (fruit tissue-expressed PD prom.) | P3631 | 4204 | Inc. lycopene |
| G1421 | 180 | AP2 (84-146) | P5284 (leaf-expressed RbcS3 prom.) | P3631 | 4204 | Inc. lycopene |
| G1421 | 180 | AP2 (84-146) | P5297 (fruit tissue-expressed PG prom.) | P3631 | 4204 | Inc. lycopene |
| G1421 | 180 | AP2 (84-146) | P5319 (emergent leaf primordia-expressed AS1 prom.) | P3631 | 4204 | Inc. lycopene |
| G1421 | 180 | AP2 (84-146) | P5318 (shoot apical meristem-expressed STM prom.) | P3631 | 4204 | Inc. lycopene |
| G1423 | 182 | MADS (6-62) | P6506 (constitutive CaMv 35S prom.) | P7511 | 4567 | Inc. brix |
| G1435 | 184 | GARP (146-194) | P5326 (floral meristem-expressed AP1 prom.) | P9116 | 4785 | Inc. fruit weight |
| G1437 | 186 | GRF-like (59-150) | P5303 (fruit tissue-expressed PD prom.) | P4918 | 4365 | Inc. fruit weight |
| G1437 | 186 | GRF-like (59-150) | P5287 (epidermal tissue-expressed LTP1 prom.) | P4918 | 4365 | Inc. fruit weight |
| G1437 | 186 | GRF-like (59-150) | P5297 (fruit tissue-expressed PG prom.) | P4918 | 4365 | Inc. fruit weight |
| G1438 | 188 | GRF-like (16-124) | P6506 (constitutive CaMv 35S prom.) | P3840 | 4220 | Larger leaflets |
| G1439 | 190 | GRF-like (133-239) | P5284 (leaf-expressed RbcS3 prom.) | P6019 | 4415 | Inc. lycopene |
| G1442 | 192 | GRF-like (111-223) | P6506 (constitutive CaMv 35S prom.) | P6050 | 4419 | Large light green leaves |
| G1442 | 192 | GRF-like (111-223) | P6506 (constitutive CaMv 35S prom.) | P6050 | 4419 | Rugulose leaves (small wrinkles) |
| G1443 | 194 | GRF-like (24-132) | P5284 (leaf-expressed RbcS3 prom.) | P3841 | 4221 | Inc. fruit weight |
| G1451 | 198 | ARF (22-357) | P5319 (emergent leaf primordia-expressed AS1 prom.) | P8610 | 4714 | Inc. fruit weight |
| G1451 | 198 | ARF (22-357) | P5318 (shoot apical meristem-expressed STM prom.) | P8610 | 4714 | Inc. fruit weight |
| G1451 | 198 | ARF (22-357) | P5287 (epidermal tissue-expressed LTP1 prom.) | P8610 | 4714 | Inc. fruit weight |
| G1456 | 200 | NAC (NA) | P5318 (shoot apical meristem-expressed STM prom.) | P3978 | 4236 | Inc. fruit weight |
| G1460 | 204 | NAC (NA) | P5284 (leaf-expressed RbcS3 prom.) | P4946 | 4367 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1462 | 206 | NAC (14-273) | P5326 (floral meristem-expressed AP1 prom.) | P4336 | 4280 | Inc. lycopene |
| G1469 | 208 | Z-C2H2 (11-31, 230-250, 276-296) | P5297 (fruit tissue-expressed PG prom.) | P8615 | 4717 | Inc. fruit weight |
| G1469 | 208 | Z-C2H2 (11-31, 230-250, 276-296) | P5318 (shoot apical meristem-expressed STM prom.) | P8615 | 4717 | Inc. fruit weight |
| G1469 | 208 | Z-C2H2 (11-31, 230-250, 276-296) | P5326 (floral meristem-expressed AP1 prom.) | P8615 | 4717 | Inc. fruit weight |
| G1469 | 208 | Z-C2H2 (11-31, 230-250, 276-296) | P5287 (epidermal tissue-expressed LTP1 prom.) | P8615 | 4717 | Inc. fruit weight |
| G1471 | 210 | Z-C2H2 (49-70) | P5297 (fruit tissue-expressed PG prom.) | P4375 | 4292 | Inc. fruit weight |
| G1471 | 210 | Z-C2H2 (49-70) | P5287 (epidermal tissue-expressed LTP1 prom.) | P4375 | 4292 | Inc. fruit weight |
| G1474 | 212 | Z-C2H2 (41-68) | P5319 (emergent leaf primordia-expressed AS1 prom.) | P7456 | 4549 | Inc. fruit weight |
| G1474 | 212 | Z-C2H2 (41-68) | P5324 (fruit vascular tissue-expressed Cru prom.) | P7456 | 4549 | Thick stems |
| G1478 | 214 | Z-CO-like (32-76) | P5318 (shoot apical meristem-expressed STM prom.) | P4378 | 4293 | Inc. brix |
| G1480 | 218 | Z-CO-like (50-73, 92-116) | P5326 (floral meristem-expressed AP1 prom.) | P5883 | 4408 | Inc. fruit weight |
| G1487 | 220 | GATA/Zn (251-276) | P5287 (epidermal tissue-expressed LTP1 prom.) | P9266 | 4819 | Inc. fruit weight |
| G1487 | 220 | GATA/Zn (251-276) | P5284 (leaf-expressed RbcS3 prom.) | P9266 | 4819 | Inc. fruit weight |
| G1487 | 220 | GATA/Zn (251-276) | P5318 (shoot apical meristem-expressed STM prom.) | P9266 | 4819 | Inc. fruit weight |
| G1488 | 222 | GATA/Zn (221-246) | P5287 (epidermal tissue-expressed LTP1 prom.) | P9267 | 4820 | Inc. fruit weight |
| G1488 | 222 | GATA/Zn (221-246) | P5297 (fruit tissue-expressed PG prom.) | P9267 | 4820 | Inc. fruit weight |
| G1488 | 222 | GATA/Zn (221-246) | P5284 (leaf-expressed RbcS3 prom.) | P9267 | 4820 | Inc. fruit weight |
| G1491 | 224 | GARP (50-100) | P5287 (epidermal tissue-expressed LTP1 prom.) | P4583 | 4317 | Inc. lycopene |
| G1494 | 226 | HLH/MYC (254-311) | P5284 (leaf-expressed RbcS3 prom.) | P4772 | 4354 | Inc. lycopene |
| G1498 | 228 | HLH/MYC (281-338) | P5284 (leaf-expressed RbcS3 prom.) | P3952 | 4226 | Inc. brix |
| G1498 | 228 | HLH/MYC (281-338) | P5326 (floral meristem-expressed AP1 prom.) | P3952 | 4226 | Inc. brix |
| G1505 | 232 | GATA/Zn (NA) | P5318 (shoot apical meristem-expressed STM prom.) | P4414 | 4303 | Inc. lycopene |
| G1506 | 234 | GATA/Zn (7-33) | P5287 (epidermal tissue-expressed LTP1 prom.) | P4024 | 4248 | Inc. fruit weight |
| G1506 | 234 | GATA/Zn (7-33) | P5297 (fruit tissue-expressed PG prom.) | P4024 | 4248 | Inc. fruit weight |
| G1510 | 236 | GATA/Zn (230-263) | P5297 (fruit tissue-expressed PG prom.) | P8244 | 4677 | Inc. lycopene |
| G1517 | 238 | RING/C3HC4 (312-349) | P5310 (root-expressed RSI1 prom.) | P9147 | 4798 | Inc. lycopene |
| G1518 | 240 | RING/C3HC4 (51-93, 126-209, 374-670) | P5287 (epidermal tissue-expressed LTP1 prom.) | P6449 | 4457 | Inc. brix |
| G1518 | 240 | RING/C3HC4 (51-93, 126-209, 374-670) | P5324 (fruit vascular tissue-expressed Cru prom.) | P6449 | 4457 | Inc. fruit weight |
| G1521 | 242 | RING/C3HC4 (39-80) | P5310 (root-expressed RSI1 prom.) | P3652 | 4211 | Inc. brix |
| G1521 | 242 | RING/C3HC4 (39-80) | P5310 (root-expressed RSI1 prom.) | P3652 | 4211 | Inc. lycopene |
| G1527 | 244 | RING/C3HC4 (129-166) | P5326 (floral meristem-expressed AP1 prom.) | P9146 | 4797 | Inc. fruit weight |
| G1530 | 246 | RING/C3H2C3 (102-144) | P5287 (epidermal tissue-expressed LTP1 prom.) | P8233 | 4669 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1530 | 246 | RING/C3H2C3 (102-144) | P5319 (emergent leaf primordia-expressed AS1 prom.) | P8233 | 4669 | Inc. fruit weight |
| G1530 | 246 | RING/C3H2C3 (102-144) | P5318 (shoot apical meristem-expressed STM prom.) | P8233 | 4669 | Inc. fruit weight |
| G1530 | 246 | RING/C3H2C3 (102-144) | P5297 (fruit tissue-expressed PG prom.) | P8233 | 4669 | Inc. fruit weight |
| G1531 | 248 | RING/C3HC4 (41-77) | P5284 (leaf-expressed RbcS3 prom.) | P6473 | 4466 | Inc. brix |
| G1531 | 248 | RING/C3HC4 (41-77) | P5324 (fruit vascular tissue-expressed Cru prom.) | P6473 | 4466 | Inc. brix |
| G1531 | 248 | RING/C3HC4 (41-77) | P5297 (fruit tissue-expressed PG prom.) | P6473 | 4466 | Inc. brix |
| G1535 | 250 | HB (109-169) | P5287 (epidermal tissue-expressed LTP1 prom.) | P8616 | 4718 | Inc. brix |
| G1538 | 252 | HB (66-126) | P5287 (epidermal tissue-expressed LTP1 prom.) | P3968 | 4231 | Inc. lycopene |
| G1540 | 256 | HB (35-98) | P5326 (floral meristem-expressed AP1 prom.) | P3423 | 4189 | Inc. fruit weight |
| G1540 | 256 | HB (35-98) | P5318 (shoot apical meristem-expressed STM prom.) | P3423 | 4189 | Inc. fruit weight |
| G1543 | 258 | HB (135-195) | P5284 (leaf-expressed RbcS3 prom.) | P3424 | 4190 | Inc. brix |
| G1543 | 258 | HB (135-195) | P5284 (leaf-expressed RbcS3 prom.) | P3424 | 4190 | Inc. lycopene |
| G1549 | 260 | HB (75-135) | P5287 (epidermal tissue-expressed LTP1 prom.) | P7720 | 4595 | Inc. fruit weight |
| G1550 | 262 | HB (NA) | P5319 (emergent leaf primordia-expressed AS1 prom.) | P3970 | 4232 | Inc. brix |
| G1551 | 264 | HB (99-160) | P5319 (emergent leaf primordia-expressed AS1 prom.) | P4575 | 4316 | Inc. lycopene |
| G1551 | 264 | HB (99-160) | P5284 (leaf-expressed RbcS3 prom.) | P4575 | 4316 | Inc. fruit weight |
| G1553 | 266 | ARF (20-351) | P5284 (leaf-expressed RbcS3 prom.) | P9057 | 4771 | Inc. fruit weight |
| G1553 | 266 | ARF (20-351) | P5326 (floral meristem-expressed AP1 prom.) | P9057 | 4771 | Inc. fruit weight |
| G1553 | 266 | ARF (20-351) | P5318 (shoot apical meristem-expressed STM prom.) | P9057 | 4771 | Inc. fruit weight |
| G1553 | 266 | ARF (20-351) | P5287 (epidermal tissue-expressed LTP1 prom.) | P9057 | 4771 | Inc. fruit weight |
| G1559 | 268 | TH (55-154) | P5287 (epidermal tissue-expressed LTP1 prom.) | P7788 | 4617 | Inc. brix |
| G1559 | 268 | TH (55-154) | P5297 (fruit tissue-expressed PG prom.) | P7788 | 4617 | Inc. lycopene |
| G1559 | 268 | TH (55-154) | P5287 (epidermal tissue-expressed LTP1 prom.) | P7788 | 4617 | Inc. lycopene |
| G1592 | 276 | HB (NA) | P5326 (floral meristem-expressed AP1 prom.) | P4153 | 4257 | Inc. fruit weight |
| G1592 | 276 | HB (NA) | P5318 (shoot apical meristem-expressed STM prom.) | P4153 | 4257 | Inc. fruit weight |
| G1634 | 278 | MYB-related (29-79, 131-179) | P5287 (epidermal tissue-expressed LTP1 prom.) | P7863 | 4629 | Inc. brix |
| G1635 | 280 | MYB-related (56-102) | P5318 (shoot apical meristem-expressed STM prom.) | P3606 | 4200 | Inc. lycopene |
| G1635 | 280 | MYB-related (56-102) | P5287 (epidermal tissue-expressed LTP1 prom.) | P3606 | 4200 | Inc. lycopene |
| G1637 | 282 | MYB-related (108-156) | P5318 (shoot apical meristem-expressed STM prom.) | P6168 | 4429 | Inc. brix |
| G1638 | 284 | MYB-related (27-77, 141-189) | P5297 (fruit tissue-expressed PG prom.) | P3843 | 4222 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1640 | 286 | MYB-(R1)R2R3 (14-115) | P5324 (fruit vascular tissue-expressed Cru prom.) | P3604 | 4199 | Inc. lycopene |
| G1642 | 288 | MYB-(R1)R2R3 (NA) | P5324 (fruit vascular tissue-expressed Cru prom.) | P6893 | 4494 | Inc. fruit weight |
| G1646 | 290 | CAAT (66-162) | P5297 (fruit tissue-expressed PG prom.) | P7118 | 4526 | Inc. fruit weight |
| G1656 | 294 | HLH/MYC (112-169) | P5326 (floral meristem-expressed AP1 prom.) | P4156 | 4258 | Inc. lycopene |
| G1657 | 296 | DBP (56-97, 149-268) | P5319 (emergent leaf primordia-expressed AS1 prom.) | P6184 | 4432 | Inc. fruit weight |
| G1659 | 298 | DBP (17-116) | P5319 (emergent leaf primordia-expressed AS1 prom.) | P4594 | 4320 | Inc. lycopene |
| G1659 | 298 | DBP (17-116) | P5318 (shoot apical meristem-expressed STM prom.) | P4594 | 4320 | Inc. lycopene |
| G1659 | 298 | DBP (17-116) | P5324 (fruit vascular tissue-expressed Cru prom.) | P4594 | 4320 | Inc. lycopene |
| G1660 | 302 | DBP (362-476) | P5297 (fruit tissue-expressed PG prom.) | | | Inc. fruit weight |
| G1660 | 302 | DBP (362-476) | P5284 (leaf-expressed RbcS3 prom.) | | | Inc. fruit weight |
| G1660 | 302 | DBP (362-476) | P5326 (floral meristem-expressed AP1 prom.) | | | Inc. fruit weight |
| G1665 | 304 | HLH/MYC (NA) | P5297 (fruit tissue-expressed PG prom.) | P4186 | 4265 | Inc. lycopene |
| G1666 | 306 | HLH/MYC (356-413) | P5318 (shoot apical meristem-expressed STM prom.) | P4595 | 4321 | Inc. fruit weight |
| G1666 | 306 | HLH/MYC (356-413) | P5284 (leaf-expressed RbcS3 prom.) | P4595 | 4321 | More anthocyanin |
| G1669 | 308 | Z-CO-like (NA) | P5287 (epidermal tissue-expressed LTP1 prom.) | P5702 | 4401 | Inc. brix |
| G1670 | 312 | NAC (15-198) | P5326 (floral meristem-expressed AP1 prom.) | P4340 | 4281 | Inc. fruit weight |
| G1730 | 316 | RING/C3H2C3 (103-144) | P5287 (epidermal tissue-expressed LTP1 prom.) | P8234 | 4670 | Inc. brix |
| G1730 | 316 | RING/C3H2C3 (103-144) | P5297 (fruit tissue-expressed PG prom.) | P8234 | 4670 | Inc. brix |
| G1730 | 316 | RING/C3H2C3 (103-144) | P5284 (leaf-expressed RbcS3 prom.) | P8234 | 4670 | Inc. lycopene |
| G1730 | 316 | RING/C3H2C3 (103-144) | P5287 (epidermal tissue-expressed LTP1 prom.) | P8234 | 4670 | Inc. lycopene |
| G1736 | 318 | RING/C3H2C3 (139-179) | P5297 (fruit tissue-expressed PG prom.) | P8235 | 4671 | Inc. lycopene |
| G1736 | 318 | RING/C3H2C3 (139-179) | P5284 (leaf-expressed RbcS3 prom.) | P8235 | 4671 | Inc. lycopene |
| G1750 | 320 | AP2 (115-177) | P5284 (leaf-expressed RbcS3 prom.) | P3963 | 4229 | Inc. brix |
| G1750 | 320 | AP2 (115-177) | P5287 (epidermal tissue-expressed LTP1 prom.) | P3963 | 4229 | Inc. brix |
| G1750 | 320 | AP2 (115-177) | P5319 (emergent leaf primordia-expressed AS1 prom.) | P3963 | 4229 | Inc. lycopene |
| G1750 | 320 | AP2 (115-177) | P5324 (fruit vascular tissue-expressed Cru prom.) | P3963 | 4229 | Inc. lycopene |
| G1751 | 322 | AP2 (133-200) | P5318 (shoot apical meristem-expressed STM prom.) | P4207 | 4272 | Inc. brix |
| G1751 | 322 | AP2 (133-200) | P5284 (leaf-expressed RbcS3 prom.) | P4207 | 4272 | Inc. lycopene |
| G1751 | 322 | AP2 (133-200) | P5297 (fruit tissue-expressed PG prom.) | P4207 | 4272 | Inc. leaf dissection |
| G1751 | 322 | AP2 (133-200) | P5297 (fruit tissue-expressed PG prom.) | P4207 | 4272 | Pale white fruit at green stage |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1752 | 324 | AP2 (83-151) | P5287 (epidermal tissue-expressed LTP1 prom.) | P4390 | 4295 | Inc. fruit weight |
| G1755 | 326 | AP2 (71-133) | P5303 (fruit tissue-expressed PD prom.) | P4407 | 4302 | Inc. lycopene |
| G1757 | 328 | WRKY (158-218) | P6506 (constitutive CaMv 35S prom.) | P6412 | 4442 | Inc. brix |
| G1757 | 328 | WRKY (158-218) | P5303 (fruit tissue-expressed PD prom.) | P6412 | 4442 | Inc. brix |
| G1757 | 328 | WRKY (158-218) | P5284 (leaf-expressed RbcS3 prom.) | P6412 | 4442 | Inc. brix |
| G1758 | 330 | WRKY (109-165) | P5318 (shoot apical meristem-expressed STM prom.) | P9153 | 4800 | Inc. fruit weight |
| G1758 | 330 | WRKY (109-165) | P5326 (floral meristem-expressed AP1 prom.) | P9153 | 4800 | Inc. fruit weight |
| G1758 | 330 | WRKY (109-165) | P5287 (epidermal tissue-expressed LTP1 prom.) | P9153 | 4800 | Inc. fruit weight |
| G1759 | 332 | MADS (2-57) | P5297 (fruit tissue-expressed PG prom.) | P4147 | 4256 | Inc. brix |
| G1760 | 334 | MADS (2-57) | P5318 (shoot apical meristem-expressed STM prom.) | P3371 | 4180 | Inc. fruit weight |
| G1763 | 336 | AP2 (140-207) | P5303 (fruit tissue-expressed PD prom.) | P7165 | 4542 | Inc. fruit weight |
| G1765 | 338 | NAC (20-140) | P5297 (fruit tissue-expressed PG prom.) | P4343 | 4283 | Inc. brix |
| G1767 | 340 | SCR (225-290, 355-450, 453-528) | P5326 (floral meristem-expressed AP1 prom.) | P4205 | 4271 | Inc. lycopene |
| G1772 | 342 | RING/C3HC4 (123-176) | P5310 (root-expressed RSI1 prom.) | P8224 | 4664 | Inc. fruit weight |
| G1774 | 344 | RING/C3HC4 (128-242) | P6506 (constitutive CaMv 35S prom.) | P6861 | 4484 | Inc. brix |
| G1775 | 346 | RING/C3HC4 (121-241) | P5318 (shoot apical meristem-expressed STM prom.) | P7869 | 4633 | Inc. brix |
| G1777 | 348 | RING/C3HC4 (124-247) | P5297 (fruit tissue-expressed PG prom.) | P6895 | 4495 | Inc. brix |
| G1781 | 350 | CAAT (35-124) | P5318 (shoot apical meristem-expressed STM prom.) | P4774 | 4355 | Inc. brix |
| G1781 | 350 | CAAT (35-124) | P5284 (leaf-expressed RbcS3 prom.) | P4774 | 4355 | Inc. fruit weight |
| G1786 | 352 | MYB-(R1)R2R3 (NA) | P5326 (floral meristem-expressed AP1 prom.) | P4037 | 4251 | Inc. fruit weight |
| G1786 | 352 | MYB-(R1)R2R3 (NA) | P5318 (shoot apical meristem-expressed STM prom.) | P4037 | 4251 | Inc. fruit weight |
| G1789 | 354 | MYB-related (12-62) | P5287 (epidermal tissue-expressed LTP1 prom.) | P4358 | 4287 | Inc. lycopene |
| G1797 | 358 | MADS (1-57) | P5284 (leaf-expressed RbcS3 prom.) | P8673 | 4738 | Inc. brix |
| G1797 | 358 | MADS (1-57) | P5284 (leaf-expressed RbcS3 prom.) | P8673 | 4738 | Inc. lycopene |
| G1800 | 360 | AP2 (25-92) | P5287 (epidermal tissue-expressed LTP1 prom.) | P4209 | 4273 | Inc. brix |
| G1800 | 360 | AP2 (25-92) | P5318 (shoot apical meristem-expressed STM prom.) | P4209 | 4273 | Inc. brix |
| G1800 | 360 | AP2 (25-92) | P5297 (fruit tissue-expressed PG prom.) | P4209 | 4273 | Inc. brix |
| G1804 | 362 | bZIP (357-407) | P5287 (epidermal tissue-expressed LTP1 prom.) | P6416 | 4444 | Inc. brix |
| G1806 | 364 | bZIP (165-225) | P5287 (epidermal tissue-expressed LTP1 prom.) | P6061 | 4422 | Inc. brix |
| G1807 | 366 | bZIP (249-297) | P6506 (constitutive CaMv 35S prom.) | P6415 | 4443 | Inc. brix |
| G1808 | 368 | bZIP (140-200) | P5318 (shoot apical meristem-expressed STM prom.) | P4601 | 4324 | Inc. brix |
| G1808 | 368 | bZIP (140-200) | P6506 (constitutive CaMv 35S prom.) | P4601 | 4324 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1809 | 370 | bZIP (23-35, 68-147) | P5287 (epidermal tissue-expressed LTP1 prom.) | P3982 | 4238 | Inc. lycopene |
| G1811 | 372 | ABI3/VP-1 (34-128) | P5284 (leaf-expressed RbcS3 prom.) | P5884 | 4409 | Inc. lycopene |
| G1812 | 374 | PCOMB (32-365) | P5297 (fruit tissue-expressed PG prom.) | P7789 | 4618 | Inc. fruit weight |
| G1812 | 374 | PCOMB (32-365) | P5303 (fruit tissue-expressed PD prom.) | P7789 | 4618 | Inc. fruit weight |
| G1812 | 374 | PCOMB (32-365) | P5326 (floral meristem-expressed AP1 prom.) | P7789 | 4618 | Inc. fruit weight |
| G1812 | 374 | PCOMB (32-365) | P5319 (emergent leaf primordia-expressed AS1 prom.) | P7789 | 4618 | Inc. fruit weight |
| G1819 | 376 | CAAT (52-148) | P5326 (floral meristem-expressed AP1 prom.) | P4039 | 4252 | Inc. brix |
| G1821 | 378 | CAAT (57-146) | P5297 (fruit tissue-expressed PG prom.) | P4040 | 4253 | Inc. lycopene |
| G1824 | 380 | GARP (158-205) | P5287 (epidermal tissue-expressed LTP1 prom.) | P7446 | 4546 | Inc. brix |
| G1824 | 380 | GARP (158-205) | P5297 (fruit tissue-expressed PG prom.) | P7446 | 4546 | Dark green fruit |
| G1836 | 382 | CAAT (24-110) | P5318 (shoot apical meristem-expressed STM prom.) | P3603 | 4198 | Inc. lycopene |
| G1836 | 382 | CAAT (24-110) | P5326 (floral meristem-expressed AP1 prom.) | P3603 | 4198 | Inc. lycopene |
| G1838 | 384 | AP2 (230-304, 330-400) | P5284 (leaf-expressed RbcS3 prom.) | P6474 | 4467 | Inc. brix |
| G1839 | 386 | AP2 (118-182) | P5297 (fruit tissue-expressed PG prom.) | P4166 | 4260 | Inc. lycopene |
| G1839 | 386 | AP2 (118-182) | P6506 (constitutive CaMv 35S prom.) | P4166 | 4260 | Inc. lycopene |
| G1842 | 388 | MADS (2-57) | P5287 (epidermal tissue-expressed LTP1 prom.) | P7845 | 4623 | Inc. brix |
| G1842 | 388 | MADS (2-57) | P5287 (epidermal tissue-expressed LTP1 prom.) | P7845 | 4623 | Inc. lycopene |
| G1843 | 390 | MADS (2-57) | P6506 (constitutive CaMv 35S prom.) | P4402 | 4300 | Inc. lycopene |
| G1844 | 392 | MADS (2-57) | P5318 (shoot apical meristem-expressed STM prom.) | P4403 | 4301 | Inc. brix |
| G1847 | 394 | WRKY (141-200) | P5326 (floral meristem-expressed AP1 prom.) | P8237 | 4673 | Inc. fruit weight |
| G1847 | 394 | WRKY (141-200) | P5284 (leaf-expressed RbcS3 prom.) | P8237 | 4673 | Inc. fruit weight |
| G1847 | 394 | WRKY (141-200) | P5318 (shoot apical meristem-expressed STM prom.) | P8237 | 4673 | Inc. fruit weight |
| G1850 | 396 | HS (59-150) | P5297 (fruit tissue-expressed PG prom.) | P7867 | 4632 | Inc. lycopene |
| G1850 | 396 | HS (59-150) | P5326 (floral meristem-expressed AP1 prom.) | P7867 | 4632 | Inc. fruit weight |
| G1855 | 398 | AKR (102-613) | P5284 (leaf-expressed RbcS3 prom.) | P5886 | 4411 | Inc. fruit weight |
| G1855 | 398 | AKR (102-613) | P5318 (shoot apical meristem-expressed STM prom.) | P5886 | 4411 | Inc. fruit weight |
| G1855 | 398 | AKR (102-613) | P5326 (floral meristem-expressed AP1 prom.) | P5886 | 4411 | Inc. fruit weight |
| G1863 | 400 | GRF-like (76-187) | P5297 (fruit tissue-expressed PG prom.) | P4179 | 4262 | Inc. lycopene |
| G1865 | 402 | GRF-like (45-162) | P5326 (floral meristem-expressed AP1 prom.) | P3645 | 4207 | Inc. lycopene |
| G1881 | 404 | Z-CO-like (5-28, 56-79) | P5284 (leaf-expressed RbcS3 prom.) | P6466 | 4463 | Inc. brix |
| G1881 | 404 | Z-CO-like (5-28, 56-79) | P6506 (constitutive CaMv 35S prom.) | P6466 | 4463 | Inc. lycopene |
| G1884 | 406 | Z-Dof (43-71) | P5287 (epidermal tissue-expressed LTP1 prom.) | P4563 | 4314 | Inc. lycopene |
| G1888 | 408 | Z-CO-like (2-33, 58-100) | P5297 (fruit tissue-expressed PG prom.) | P4219 | 4275 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1888 | 408 | Z-CO-like (2-33, 58-100) | P5326 (floral meristem-expressed AP1 prom.) | P4219 | 4275 | Inc. fruit weight |
| G1896 | 412 | Z-Dof (43-85) | P5326 (floral meristem-expressed AP1 prom.) | P4706 | 4331 | Inc. brix |
| G1896 | 412 | Z-Dof (43-85) | P5287 (epidermal tissue-expressed LTP1 prom.) | P4706 | 4331 | Inc. brix |
| G1896 | 412 | Z-Dof (43-85) | P5303 (fruit tissue-expressed PD prom.) | P4706 | 4331 | Inc. brix |
| G1896 | 412 | Z-Dof (43-85) | P5287 (epidermal tissue-expressed LTP1 prom.) | P4706 | 4331 | Inc. lycopene |
| G1896 | 412 | Z-Dof (43-85) | P5303 (fruit tissue-expressed PD prom.) | P4706 | 4331 | Inc. biomass |
| G1898 | 414 | Z-Dof (31-59) | P5297 (fruit tissue-expressed PG prom.) | P4226 | 4277 | Inc. brix |
| G1901 | 420 | Z-Dof (NA) | P5319 (emergent leaf primordia-expressed AS1 prom.) | P3972 | 4233 | Inc. lycopene |
| G1903 | 422 | Z-Dof (134-180) | P5287 (epidermal tissue-expressed LTP1 prom.) | P3617 | 4202 | Inc. lycopene |
| G1906 | 424 | Z-Dof (19-47) | P5284 (leaf-expressed RbcS3 prom.) | P3975 | 4234 | Inc. lycopene |
| G1917 | 426 | GATA/Zn (153-179) | P5318 (shoot apical meristem-expressed STM prom.) | P4952 | 4368 | Inc. lycopene |
| G1918 | 428 | RING/C3HC4 (26-164) | P5326 (floral meristem-expressed AP1 prom.) | P4367 | 4291 | Inc. fruit weight |
| G1923 | 430 | NAC (23-153) | P5326 (floral meristem-expressed AP1 prom.) | P9167 | 4803 | Inc. fruit weight |
| G1925 | 432 | NAC (6-150) | P5326 (floral meristem-expressed AP1 prom.) | P6209 | 4438 | Inc. brix |
| G1933 | 434 | WRKY (205-263, 344-404) | P5318 (shoot apical meristem-expressed STM prom.) | P7874 | 4637 | Inc. brix |
| G1933 | 434 | WRKY (205-263, 344-404) | P5297 (fruit tissue-expressed PG prom.) | P7874 | 4637 | Inc. brix |
| G1933 | 434 | WRKY (205-263, 344-404) | P5297 (fruit tissue-expressed PG prom.) | P7874 | 4637 | Inc. lycopene |
| G1936 | 436 | PCF (64-129) | P5297 (fruit tissue-expressed PG prom.) | P4214 | 4274 | Inc. brix |
| G1936 | 436 | PCF (64-129) | P5284 (leaf-expressed RbcS3 prom.) | P4214 | 4274 | Inc. lycopene |
| G1944 | 440 | AT-hook (89-97, 170-285) | P5326 (floral meristem-expressed AP1 prom.) | P4146 | 4255 | Inc. brix |
| G1947 | 442 | HS (19-110) | P5324 (fruit vascular tissue-expressed Cru prom.) | P4553 | 4311 | Inc. biomass* |
| G1950 | 444 | AKR (65-228) | P5318 (shoot apical meristem-expressed STM prom.) | P3651 | 4210 | Inc. lycopene |
| G1950 | 444 | AKR (65-228) | P5287 (epidermal tissue-expressed LTP1 prom.) | P3651 | 4210 | Inc. lycopene |
| G1950 | 444 | AKR (65-228) | P5303 (fruit tissue-expressed PD prom.) | P3651 | 4210 | Inc. lycopene |
| G1957 | 446 | ABI3/VP-1 (52-143) | P5318 (shoot apical meristem-expressed STM prom.) | P7451 | 4547 | Inc. brix |
| G1957 | 446 | ABI3/VP-1 (52-143) | P5297 (fruit tissue-expressed PG prom.) | P7451 | 4547 | Inc. brix |
| G1957 | 446 | ABI3/VP-1 (52-143) | P5319 (emergent leaf primordia-expressed AS1 prom.) | P7451 | 4547 | Inc. brix |
| G1957 | 446 | ABI3/VP-1 (52-143) | P5326 (floral meristem-expressed AP1 prom.) | P7451 | 4547 | Inc. brix |
| G1957 | 446 | ABI3/VP-1 (52-143) | P5303 (fruit tissue-expressed PD prom.) | P7451 | 4547 | Inc. brix |
| G1957 | 446 | ABI3/VP-1 (52-143) | P5324 (fruit vascular tissue-expressed Cru prom.) | P7451 | 4547 | Inc. brix |
| G1957 | 446 | ABI3/VP-1 (52-143) | P5303 (fruit tissue-expressed PD prom.) | P7451 | 4547 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G1957 | 446 | ABI3/VP-1 (52-143) | P5319 (emergent leaf primordia-expressed AS1 prom.) | P7451 | 4547 | Inc. lycopene |
| G1957 | 446 | ABI3/VP-1 (52-143) | P5324 (fruit vascular tissue-expressed Cru prom.) | P7451 | 4547 | Inc. lycopene |
| G1957 | 446 | ABI3/VP-1 (52-143) | P5326 (floral meristem-expressed AP1 prom.) | P7451 | 4547 | Inc. lycopene |
| G1957 | 446 | ABI3/VP-1 (52-143) | P5318 (shoot apical meristem-expressed STM prom.) | P7451 | 4547 | Inc. lycopene |
| G1957 | 446 | ABI3/VP-1 (52-143) | P5297 (fruit tissue-expressed PG prom.) | P7451 | 4547 | Inc. lycopene |
| G1957 | 446 | ABI3/VP-1 (52-143) | P5284 (leaf-expressed RbcS3 prom.) | P7451 | 4547 | Inc. lycopene |
| G1959 | 448 | GARP (46-97) | P5284 (leaf-expressed RbcS3 prom.) | P4584 | 4318 | Inc. fruit weight |
| G1965 | 450 | Z-Dof (27-55) | P5287 (epidermal tissue-expressed LTP1 prom.) | P3960 | 4228 | Inc. brix |
| G1965 | 450 | Z-Dof (27-55) | P5297 (fruit tissue-expressed PG prom.) | P3960 | 4228 | Inc. brix |
| G1965 | 450 | Z-Dof (27-55) | P5326 (floral meristem-expressed AP1 prom.) | P3960 | 4228 | Inc. brix |
| G1969 | 452 | Z-C2H2 (93-113, 129-152, 230-252) | P5284 (leaf-expressed RbcS3 prom.) | P7762 | 4607 | Inc. lycopene |
| G1969 | 452 | Z-C2H2 (93-113, 129-152, 230-252) | P5297 (fruit tissue-expressed PG prom.) | P7762 | 4607 | Inc. lycopene |
| G1969 | 452 | Z-C2H2 (93-113, 129-152, 230-252) | P5310 (root-expressed RSI1 prom.) | P7762 | 4607 | Inc. lycopene |
| G1969 | 452 | Z-C2H2 (93-113, 129-152, 230-252) | P5326 (floral meristem-expressed AP1 prom.) | P7762 | 4607 | Inc. fruit weight |
| G1969 | 452 | Z-C2H2 (93-113, 129-152, 230-252) | P5318 (shoot apical meristem-expressed STM prom.) | P7762 | 4607 | Inc. fruit weight |
| G1972 | 454 | Z-C2H2 (79-101, 132-152, 342-364, 411-433) | P5284 (leaf-expressed RbcS3 prom.) | P8504 | 4690 | Inc. brix |
| G1972 | 454 | Z-C2H2 (79-101, 132-152, 342-364, 411-433) | P5310 (root-expressed RSI1 prom.) | P8504 | 4690 | Inc. brix |
| G1972 | 454 | Z-C2H2 (79-101, 132-152, 342-364, 411-433) | P5310 (root-expressed RSI1 prom.) | P8504 | 4690 | Inc. lycopene |
| G1981 | 456 | Z-C3H (45-157) | P5318 (shoot apical meristem-expressed STM prom.) | P8492 | 4687 | Inc. fruit weight |
| G1981 | 456 | Z-C3H (45-157) | P5284 (leaf-expressed RbcS3 prom.) | P8492 | 4687 | Inc. fruit weight |
| G1987 | 458 | Z-C2H2 (103-123) | P5284 (leaf-expressed RbcS3 prom.) | | | Inc. lycopene |
| G1987 | 458 | Z-C2H2 (103-123) | P5318 (shoot apical meristem-expressed STM prom.) | | | Inc. fruit weight |
| G1990 | 460 | Z-C2H2 (184-204, 261-283) | P5310 (root-expressed RSI1 prom.) | P8692 | 4746 | Inc. lycopene |
| G1990 | 460 | Z-C2H2 (184-204, 261-283) | P5287 (epidermal tissue-expressed LTP1 prom.) | P8692 | 4746 | Inc. lycopene |
| G1990 | 460 | Z-C2H2 (184-204, 261-283) | P5297 (fruit tissue-expressed PG prom.) | P8692 | 4746 | Inc. lycopene |
| G1991 | 462 | Z-C2H2 (6-26, 175-195, 224-226) | P5284 (leaf-expressed RbcS3 prom.) | P8151 | 4649 | Inc. brix |
| G2005 | 468 | Z-Dof (29-71) | P5326 (floral meristem-expressed AP1 prom.) | P7557 | 4580 | Inc. brix |
| G2005 | 468 | Z-Dof (29-71) | P5318 (shoot apical meristem-expressed STM prom.) | P7557 | 4580 | Inc. brix |
| G2006 | 470 | MYB-(R1)R2R3 (NA) | P5284 (leaf-expressed RbcS3 prom.) | P6455 | 4460 | Inc. brix |
| G2007 | 472 | MYB-(R1)R2R3 (14-118) | P5310 (root-expressed RSI1 prom.) | P4400 | 4299 | Inc. lycopene |
| G2011 | 474 | HS (55-146) | P5326 (floral meristem-expressed AP1 prom.) | P6903 | 4498 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2011 | 474 | HS (55-146) | P5318 (shoot apical meristem-expressed STM prom.) | P6903 | 4498 | Inc. fruit weight |
| G2011 | 474 | HS (55-146) | P5319 (emergent leaf primordia-expressed AS1 prom.) | P6903 | 4498 | Inc. fruit weight |
| G2015 | 476 | AKR (131-454) | P5284 (leaf-expressed RbcS3 prom.) | P7465 | 4554 | Inc. brix |
| G2015 | 476 | AKR (131-454) | P5287 (epidermal tissue-expressed LTP1 prom.) | P7465 | 4554 | Inc. brix |
| G2018 | 478 | AKR (101-416) | P5287 (epidermal tissue-expressed LTP1 prom.) | P7582 | 4587 | Inc. lycopene |
| G2020 | 480 | AKR (122-486) | P5324 (fruit vascular tissue-expressed Cru prom.) | P7458 | 4550 | Inc. brix |
| G2020 | 480 | AKR (122-486) | P6506 (constitutive CaMv 35S prom.) | P7458 | 4550 | Inc. brix |
| G2020 | 480 | AKR (122-486) | P5287 (epidermal tissue-expressed LTP1 prom.) | P7458 | 4550 | Inc. brix |
| G2020 | 480 | AKR (122-486) | P5303 (fruit tissue-expressed PD prom.) | P7458 | 4550 | Inc. brix |
| G2020 | 480 | AKR (122-486) | P5297 (fruit tissue-expressed PG prom.) | P7458 | 4550 | Inc. lycopene |
| G2020 | 480 | AKR (122-486) | P5303 (fruit tissue-expressed PD prom.) | P7458 | 4550 | Inc. lycopene |
| G2020 | 480 | AKR (122-486) | P5303 (fruit tissue-expressed PD prom.) | P7458 | 4550 | Inc. fruit weight |
| G2053 | 484 | NAC (6-152) | P5297 (fruit tissue-expressed PG prom.) | P4738 | 4339 | Inc. brix |
| G2053 | 484 | NAC (6-152) | P5297 (fruit tissue-expressed PG prom.) | P4738 | 4339 | Inc. lycopene |
| G2057 | 486 | TEO (46-103) | P5297 (fruit tissue-expressed PG prom.) | P3983 | 4239 | Inc. fruit weight |
| G2059 | 488 | AP2 (184-251) | P5326 (floral meristem-expressed AP1 prom.) | P6463 | 4462 | Inc. brix |
| G2059 | 488 | AP2 (184-251) | P5297 (fruit tissue-expressed PG prom.) | P6463 | 4462 | Inc. brix |
| G2061 | 492 | MADS (1-57) | P5310 (root-expressed RSI1 prom.) | P7756 | 4605 | Inc. lycopene |
| G2062 | 494 | MADS (8-63) | P5287 (epidermal tissue-expressed LTP1 prom.) | P4392 | 4296 | Inc. fruit weight |
| G2063 | 496 | MADS (7-63) | P5284 (leaf-expressed RbcS3 prom.) | P7464 | 4553 | Inc. fruit weight |
| G2068 | 498 | bZIP (338-455) | P5310 (root-expressed RSI1 prom.) | P8586 | 4708 | Inc. lycopene |
| G2071 | 500 | bZIP (307-358) | P5310 (root-expressed RSI1 prom.) | | | Inc. lycopene |
| G2072 | 502 | bZIP (90-149) | P5319 (emergent leaf primordia-expressed AS1 prom.) | P4603 | 4325 | Inc. lycopene |
| G2084 | 504 | RING/C3HC4 (41-172) | P5319 (emergent leaf primordia-expressed AS1 prom.) | P6896 | 4496 | Inc. fruit weight |
| G2084 | 504 | RING/C3HC4 (41-172) | P5319 (emergent leaf primordia-expressed AS1 prom.) | P6896 | 4496 | Inc. biomass |
| G2085 | 506 | GATA/Zn (214-241) | P5326 (floral meristem-expressed AP1 prom.) | | | Inc. fruit weight |
| G2085 | 506 | GATA/Zn (214-241) | P5287 (epidermal tissue-expressed LTP1 prom.) | | | Inc. fruit weight |
| G2086 | 508 | RING/C3HC4 (83-131) | P5284 (leaf-expressed RbcS3 prom.) | P4348 | 4284 | Inc. lycopene |
| G2092 | 512 | RING/C3HC4 (176-208) | P5318 (shoot apical meristem-expressed STM prom.) | P8226 | 4666 | Inc. fruit weight |
| G2094 | 514 | GATA/Zn (43-68) | P5284 (leaf-expressed RbcS3 prom.) | P7074 | 4512 | Inc. fruit weight |
| G2105 | 520 | TH (100-153) | P5297 (fruit tissue-expressed PG prom.) | P6877 | 4490 | Inc. brix |
| G2107 | 522 | AP2 (27-94) | P5287 (epidermal tissue-expressed LIP1 prom.) | P7170 | 4543 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2108 | 524 | AP2 (18-85) | P5297 (fruit tissue-expressed PG prom.) | P4196 | 4268 | Inc. lycopene |
| G2108 | 524 | AP2 (18-85) | P5324 (fruit vascular tissue-expressed Cru prom.) | P4196 | 4268 | Inc. lycopene |
| G2109 | 526 | MADS (1-57) | P5284 (leaf-expressed RbcS3 prom.) | P7509 | 4566 | Inc. brix |
| G2109 | 526 | MADS (1-57) | P5326 (floral meristem-expressed AP1 prom.) | P7509 | 4566 | Inc. fruit weight |
| G2116 | 530 | bZIP (150-210) | P6506 (constitutive CaMv 35S prom.) | P4605 | 4326 | Inc. lycopene |
| G2116 | 530 | bZIP (150-210) | P5297 (fruit tissue-expressed PG prom.) | P4605 | 4326 | Inc. lycopene |
| G2117 | 532 | bZIP (46-106) | P5326 (floral meristem-expressed AP1 prom.) | P4606 | 4327 | Inc. brix |
| G2117 | 532 | bZIP (46-106) | P5326 (floral meristem-expressed AP1 prom.) | P4606 | 4327 | Inc. brix |
| G2117 | 532 | bZIP (46-106) | P5284 (leaf-expressed RbcS3 prom.) | P4606 | 4327 | Inc. fruit weight |
| G2121 | 534 | VAR (130-226) | P5303 (fruit tissue-expressed PD prom.) | P6199 | 4435 | Inc. brix |
| G2121 | 534 | VAR (130-226) | P5318 (shoot apical meristem-expressed STM prom.) | P6199 | 4435 | Inc. brix |
| G2129 | 536 | bZIP (71-140) | P5303 (fruit tissue-expressed PD prom.) | P7539 | 4577 | Inc. brix |
| G2130 | 538 | AP2 (101-169) | P5326 (floral meristem-expressed AP1 prom.) | P6056 | 4421 | Inc. fruit weight |
| G2130 | 538 | AP2 (101-169) | P5287 (epidermal tissue-expressed LTP1 prom.) | P6056 | 4421 | Inc. fruit weight |
| G2130 | 538 | AP2 (101-169) | P5297 (fruit tissue-expressed PG prom.) | P6056 | 4421 | Inc. fruit weight |
| G2130 | 538 | AP2 (101-169) | P5318 (shoot apical meristem-expressed STM prom.) | P6056 | 4421 | Inc. fruit weight |
| G2132 | 540 | AP2 (84-151) | P5297 (fruit tissue-expressed PG prom.) | P4229 | 4278 | Inc. lycopene |
| G2135 | 542 | AP2 (73-140) | P5287 (epidermal tissue-expressed LTP1 prom.) | P4363 | 4289 | Inc. brix |
| G2135 | 542 | AP2 (73-140) | P5287 (epidermal tissue-expressed LTP1 prom.) | P4363 | 4289 | Inc. fruit weight |
| G2139 | 544 | MADS (14-69) | P5287 (epidermal tissue-expressed LTP1 prom.) | P6884 | 4491 | Inc. lycopene |
| G2139 | 544 | MADS (14-69) | P5318 (shoot apical meristem-expressed STM prom.) | P6884 | 4491 | Inc. fruit weight |
| G2141 | 546 | HLH/MYC (306-364) | P5297 (fruit tissue-expressed PG prom.) | P4753 | 4344 | Inc. brix |
| G2141 | 546 | HLH/MYC (306-364) | P5297 (fruit tissue-expressed PG prom.) | P4753 | 4344 | Inc. lycopene |
| G2144 | 548 | HLH/MYC (207-265) | P5284 (leaf-expressed RbcS3 prom.) | P4597 | 4322 | Inc. brix |
| G2145 | 550 | HLH/MYC (170-227) | P5284 (leaf-expressed RbcS3 prom.) | P4754 | 4345 | Inc. lycopene |
| G2147 | 552 | HLH/MYC (163-220) | P5287 (epidermal tissue-expressed LTP1 prom.) | P4574 | 4315 | Inc. brix |
| G2147 | 552 | HLH/MYC (163-220) | P5287 (epidermal tissue-expressed LTP1 prom.) | P4574 | 4315 | Inc. lycopene |
| G2148 | 554 | HLH/MYC (135-192) | P5318 (shoot apical meristem-expressed STM prom.) | P7877 | 4638 | Inc. brix |
| G2148 | 554 | HLH/MYC (135-192) | P5318 (shoot apical meristem-expressed STM prom.) | P7877 | 4638 | Inc. lycopene |
| G2150 | 556 | HLH/MYC (194-252) | P6506 (constitutive CaMv 35S prom.) | P4598 | 4323 | Inc. lycopene |
| G2154 | 558 | AT-hook (105-113, 171-283) | P5324 (fruit vascular tissue-expressed Cru prom.) | P6196 | 4433 | Inc. brix |
| G2156 | 560 | AT-hook (72-80, 81-232) | P5297 (fruit tissue-expressed PG prom.) | P4418 | 4304 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2156 | 560 | AT-hook (72-80, 81-232) | P5319 (emergent leaf primordia-expressed AS1 prom.) | P4418 | 4304 | Inc. fruit weight |
| G2156 | 560 | AT-hook (72-80, 81-232) | P5303 (fruit tissue-expressed PD prom.) | P4418 | 4304 | Inc. fruit weight |
| G2157 | 562 | AT-hook (88-96, 97-240) | P5287 (epidermal tissue-expressed LTP1 prom.) | P4419 | 4305 | Inc. lycopene |
| G2213 | 572 | bZIP-NIN (156-205) | P5297 (fruit tissue-expressed PG prom.) | P7541 | 4578 | Inc. brix |
| G2215 | 574 | bZIP-NIN (150-246) | P5284 (leaf-expressed RbcS3 prom.) | P4608 | 4328 | Inc. brix |
| G2223 | 578 | RING/C3H2C3 (338-378) | P5318 (shoot apical meristem-expressed STM prom.) | P8256 | 4684 | Inc. fruit weight |
| G2226 | 580 | RING/C3H2C3 (103-144) | P5297 (fruit tissue-expressed PG prom.) | P8236 | 4672 | Inc. lycopene |
| G2237 | 582 | RING/C3H2C3 (127-168) | P5284 (leaf-expressed RbcS3 prom.) | P8247 | 4678 | Inc. lycopene |
| G2238 | 584 | RING/C3H2C3 (113-154) | P5284 (leaf-expressed RbcS3 prom.) | P8248 | 4679 | Inc. brix |
| G2238 | 584 | RING/C3H2C3 (113-154) | P5284 (leaf-expressed RbcS3 prom.) | P8248 | 4679 | Inc. lycopene |
| G2238 | 584 | RING/C3H2C3 (113-154) | P5310 (root-expressed RSI1 prom.) | P8248 | 4679 | Inc. lycopene |
| G2239 | 586 | RING/C3H2C3 (128-169) | P5287 (epidermal tissue-expressed LTP1 prom.) | P8588 | 4710 | Inc. fruit weight |
| G2251 | 590 | RING/C3H2C3 (89-132) | P5297 (fruit tissue-expressed PG prom.) | P8249 | 4680 | Inc. fruit weight |
| G2251 | 590 | RING/C3H2C3 (89-132) | P5326 (floral meristem-expressed AP1 prom.) | P8249 | 4680 | Inc. fruit weight |
| G2251 | 590 | RING/C3H2C3 (89-132) | P5318 (shoot apical meristem-expressed STM prom.) | P8249 | 4680 | Inc. fruit weight |
| G2251 | 590 | RING/C3H2C3 (89-132) | P5287 (epidermal tissue-expressed LTP1 prom.) | P8249 | 4680 | Inc. fruit weight |
| G2251 | 590 | RING/C3H2C3 (89-132) | P5284 (leaf-expressed RbcS3 prom.) | P8249 | 4680 | Inc. fruit weight |
| G2252 | 592 | RING/C3H2C3 (257-297) | P5310 (root-expressed RSI1 prom.) | P8250 | 4681 | Inc. fruit weight |
| G2269 | 594 | RING/C3H2C3 (136-177) | P5310 (root-expressed RSI1 prom.) | P8252 | 4682 | Inc. lycopene |
| G2269 | 594 | RING/C3H2C3 (136-177) | P5287 (epidermal tissue-expressed LTP1 prom.) | P8252 | 4682 | Inc. fruit weight |
| G2269 | 594 | RING/C3H2C3 (136-177) | P5297 (fruit tissue-expressed PG prom.) | P8252 | 4682 | Inc. fruit weight |
| G2269 | 594 | RING/C3H2C3 (136-177) | P5326 (floral meristem-expressed AP1 prom.) | P8252 | 4682 | Inc. fruit weight |
| G2269 | 594 | RING/C3H2C3 (136-177) | P5318 (shoot apical meristem-expressed STM prom.) | P8252 | 4682 | Inc. fruit weight |
| G2290 | 600 | WRKY (147-205) | P5297 (fruit tissue-expressed PG prom.) | P4742 | 4341 | Inc. brix |
| G2290 | 600 | WRKY (147-205) | P6506 (constitutive CaMv 35S prom.) | P4742 | 4341 | Chlorotic |
| G2291 | 602 | AP2 (113-180) | P5287 (epidermal tissue-expressed LTP1 prom.) | P7125 | 4529 | Inc. brix |
| G2291 | 602 | AP2 (113-180) | P5324 (fruit vascular tissue-expressed Cru prom.) | P7125 | 4529 | Inc. brix |
| G2291 | 602 | AP2 (113-180) | P5318 (shoot apical meristem-expressed STM prom.) | P7125 | 4529 | Inc. fruit weight |
| G2293 | 604 | WRKY (74-134) | P5324 (fruit vascular tissue-expressed Cru prom.) | P6213 | 4440 | Inc. fruit weight |
| G2295 | 606 | MADS (1-57) | P5284 (leaf-expressed RbcS3 prom.) | P7859 | 4626 | Inc. brix |
| G2296 | 608 | WRKY (85-145) | P5319 (emergent leaf primordia-expressed AS1 prom.) | P4741 | 4340 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
| --- | --- | --- | --- | --- | --- | --- |
| G2296 | 608 | WRKY (85-145) | P5324 (fruit vascular tissue-expressed Cru prom.) | P4741 | 4340 | Inc. brix |
| G2296 | 608 | WRKY (85-145) | P5284 (leaf-expressed RbcS3 prom.) | P4741 | 4340 | Inc. lycopene |
| G2299 | 610 | AP2 (48-115) | P5318 (shoot apical meristem-expressed STM prom.) | P6211 | 4439 | Inc. brix |
| G2304 | 612 | AKR (381-886) | P5287 (epidermal tissue-expressed LTP1 prom.) | P8209 | 4659 | Inc. fruit weight |
| G2313 | 614 | MYB-related (111-159) | P5297 (fruit tissue-expressed PG prom.) | P4382 | 4294 | Inc. brix |
| G2313 | 614 | MYB-related (111-159) | P5319 (emergent leaf primordia-expressed AS1 prom.) | P4382 | 4294 | Inc. lycopene |
| G2313 | 614 | MYB-related (111-159) | P5297 (fruit tissue-expressed PG prom.) | P4382 | 4294 | Inc. fruit weight |
| G2315 | 616 | PMR (4-60) | P5326 (floral meristem-expressed AP1 prom.) | P7723 | 4596 | Inc. lycopene |
| G2316 | 618 | PMR (96-282) | P5287 (epidermal tissue-expressed LTP1 prom.) | P7078 | 4513 | Inc. lycopene |
| G2318 | 620 | MYB-related (134-182) | P5318 (shoot apical meristem-expressed STM prom.) | P5885 | 4410 | Inc. brix |
| G2318 | 620 | MYB-related (134-182) | P5310 (root-expressed RSI1 prom.) | P5885 | 4410 | Inc. lycopene |
| G2334 | 624 | GRF-like (82-194) | P5310 (root-expressed RSI1 prom.) | P8694 | 4747 | Inc. lycopene |
| G2342 | 626 | MYB-(R1)R2R3 (75-179) | P5326 (floral meristem-expressed AP1 prom.) | P7872 | 4636 | Inc. fruit weight |
| G2343 | 628 | MYB-(R1)R2R3 (14-116) | P5297 (fruit tissue-expressed PG prom.) | P9162 | 4801 | Inc. fruit weight |
| G2344 | 630 | CAAT (100-159) | P5287 (epidermal tissue-expressed LTP1 prom.) | P6063 | 4424 | Inc. fruit weight |
| G2371 | 636 | ABI3/VP-1 (25-127) | P5326 (floral meristem-expressed AP1 prom.) | P8070 | 4639 | Inc. brix |
| G2371 | 636 | ABI3/VP-1 (25-127) | P5287 (epidermal tissue-expressed LTP1 prom.) | P8070 | 4639 | Inc. lycopene |
| G2373 | 638 | TH (290-350) | P5326 (floral meristem-expressed AP1 prom.) | P4609 | 4329 | Inc. lycopene |
| G2376 | 640 | TH (79-178, 336-408) | P5287 (epidermal tissue-expressed LTP1 prom.) | P4610 | 4330 | Inc. brix |
| G2376 | 640 | TH (79-178, 336-408) | P5287 (epidermal tissue-expressed LTP1 prom.) | P4610 | 4330 | Inc. lycopene |
| G2376 | 640 | TH (79-178, 336-408) | P5297 (fruit tissue-expressed PG prom.) | P4610 | 4330 | Inc. lycopene |
| G2376 | 640 | TH (79-178, 336-408) | P5318 (shoot apical meristem-expressed STM prom.) | P4610 | 4330 | Inc. lycopene |
| G2376 | 640 | TH (79-178, 336-408) | P5319 (emergent leaf primordia-expressed AS1 prom.) | P4610 | 4330 | Inc. lycopene |
| G2377 | 642 | TH (17-110, 153-237) | P5318 (shoot apical meristem-expressed STM prom.) | P7485 | 4560 | Inc. fruit weight |
| G2394 | 646 | RING/C3H2C3 (355-395) | P5310 (root-expressed RSI1 prom.) | P9030 | 4767 | Inc. lycopene |
| G2400 | 648 | RING/C3H2C3 (158-198) | P5287 (epidermal tissue-expressed LTP1 prom.) | P8255 | 4683 | Inc. fruit weight |
| G2417 | 652 | GARP (235-285) | P5287 (epidermal tissue-expressed LTP1 prom.) | P4394 | 4297 | Inc. lycopene |
| G2421 | 656 | MYB-(R1)R2R3 (9-110) | P5318 (shoot apical meristem-expressed STM prom.) | P7844 | 4622 | Inc. brix |
| G2421 | 656 | MYB-(R1)R2R3 (9-110) | P5318 (shoot apical meristem-expressed STM prom.) | P7844 | 4622 | Inc. lycopene |
| G2422 | 658 | MYB-(R1)R2R3 (9-110) | P5310 (root-expressed RSI1 prom.) | P9164 | 4802 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2422 | 658 | MYB-(R1)R2R3 (9-110) | P5318 (shoot apical meristem-expressed STM prom.) | P9164 | 4802 | Inc. fruit weight |
| G2425 | 660 | MYB-(R1)R2R3 (12-119) | P5284 (leaf-expressed RbcS3 prom.) | P4396 | 4298 | Inc. brix |
| G2426 | 662 | MYB-(R1)R2R3 (14-114) | P5297 (fruit tissue-expressed PG prom.) | P6478 | 4468 | Inc. brix |
| G2427 | 664 | MYB-(R1)R2R3 (90-244) | P5284 (leaf-expressed RbcS3 prom.) | P4724 | 4336 | Inc. brix |
| G2437 | 668 | GATA/Zn (223-250) | P5310 (root-expressed RSI1 prom.) | P9274 | 4823 | Inc. lycopene |
| G2437 | 668 | GATA/Zn (223-250) | P5326 (floral meristem-expressed AP1 prom.) | P9274 | 4823 | Inc. fruit weight |
| G2452 | 672 | MYB-related (28-79, 146-194) | P5297 (fruit tissue-expressed PG prom.) | P6206 | 4436 | Inc. brix |
| G2454 | 674 | YABBY (25-64, 136-183) | P5326 (floral meristem-expressed AP1 prom.) | P8594 | 4711 | Inc. fruit weight |
| G2457 | 676 | YABBY (21-59, 110-157) | P5318 (shoot apical meristem-expressed STM prom.) | P8560 | 4700 | Inc. fruit weight |
| G2457 | 676 | YABBY (21-59, 110-157) | P5284 (leaf-expressed RbcS3 prom.) | P8560 | 4700 | Inc. fruit weight |
| G2462 | 680 | E2F (126-350) | P5287 (epidermal tissue-expressed LTP1 prom.) | P7783 | 4613 | Inc. fruit weight |
| G2484 | 682 | Z-C4HC3 (202-250) | P5318 (shoot apical meristem-expressed STM prom.) | P7094 | 4522 | Inc. brix |
| G2484 | 682 | Z-C4HC3 (202-250) | P5319 (emergent leaf primordia-expressed AS1 prom.) | P7094 | 4522 | Inc. brix |
| G2499 | 684 | SWI/SNF (209-414, 618-701) | P5326 (floral meristem-expressed AP1 prom.) | P8561 | 4701 | Inc. fruit weight |
| G2505 | 686 | NAC (9-137) | P5284 (leaf-expressed RbcS3 prom.) | P4342 | 4282 | Inc. lycopene |
| G2510 | 688 | AP2 (42-109) | P5284 (leaf-expressed RbcS3 prom.) | P6906 | 4499 | Inc. brix |
| G2510 | 688 | AP2 (42-109) | P6506 (constitutive CaMv 35S prom.) | P6906 | 4499 | Waxy leaves |
| G2519 | 690 | HLH/MYC (1-54) | P6506 (constitutive CaMv 35S prom.) | P6875 | 4489 | Inc. brix |
| G2535 | 692 | NAC (11-114) | P5318 (shoot apical meristem-expressed STM prom.) | P4521 | 4306 | Inc. brix |
| G2546 | 694 | HB (349-413) | P5297 (fruit tissue-expressed PG prom.) | P4592 | 4319 | Inc. brix |
| G2550 | 698 | HB (345-408) | P5326 (floral meristem-expressed AP1 prom.) | P8728 | 4753 | Inc. fruit weight |
| G2552 | 700 | HLH/MYC (124-181) | P5319 (emergent leaf primordia-expressed AS1 prom.) | P4757 | 4346 | Inc. biomass |
| G2553 | 702 | HLH/MYC (538-598) | P5297 (fruit tissue-expressed PG prom.) | P7527 | 4573 | Inc. lycopene |
| G2554 | 704 | HLH/MYC (338-398) | P5326 (floral meristem-expressed AP1 prom.) | P7576 | 4586 | Inc. fruit weight |
| G2554 | 704 | HLH/MYC (338-398) | P5287 (epidermal tissue-expressed LTP1 prom.) | P7576 | 4586 | Inc. fruit weight |
| G2555 | 706 | HLH/MYC (184-242) | P5284 (leaf-expressed RbcS3 prom.) | P7103 | 4523 | Inc. lycopene |
| G2555 | 706 | HLH/MYC (184-242) | P5318 (shoot apical meristem-expressed STM prom.) | P7103 | 4523 | Inc. fruit weight |
| G2555 | 706 | HLH/MYC (184-242) | P6506 (constitutive CaMv 35S prom.) | P7103 | 4523 | Inc. biomass |
| G2556 | 708 | HLH/MYC (546-606) | P5310 (root-expressed RSI1 prom.) | P8720 | 4750 | Inc. brix |
| G2556 | 708 | HLH/MYC (546-606) | P5297 (fruit tissue-expressed PG prom.) | P8720 | 4750 | Inc. fruit weight |
| G2556 | 708 | HLH/MYC (546-606) | P5287 (epidermal tissue-expressed LTP1 prom.) | P8720 | 4750 | Inc. fruit weight |
| G2573 | 710 | AP2 (31-98) | P5284 (leaf-expressed RbcS3 prom.) | P4715 | 4332 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2573 | 710 | AP2 (31-98) | P5284 (leaf-expressed RbcS3 prom.) | P4715 | 4332 | Inc. lycopene |
| G2574 | 712 | WRKY (225-284) | P5310 (root-expressed RSI1 prom.) | P7507 | 4564 | Inc. brix |
| G2575 | 714 | WRKY (137-192) | P5326 (floral meristem-expressed AP1 prom.) | P8238 | 4674 | Inc. fruit weight |
| G2575 | 714 | WRKY (137-192) | P5318 (shoot apical meristem-expressed STM prom.) | P8238 | 4674 | Inc. fruit weight |
| G2575 | 714 | WRKY (137-192) | P5284 (leaf-expressed RbcS3 prom.) | P8238 | 4674 | Inc. fruit weight |
| G2577 | 716 | AP2 (208-281, 307-375) | P5310 (root-expressed RSI1 prom.) | P8647 | 4729 | Inc. brix |
| G2577 | 716 | AP2 (208-281, 307-375) | P5318 (shoot apical meristem-expressed STM prom.) | P8647 | 4729 | Inc. brix |
| G2579 | 718 | AP2 (52-119) | P5287 (epidermal tissue-expressed LTP1 prom.) | P9029 | 4766 | Inc. fruit weight |
| G2579 | 718 | AP2 (52-119) | P5326 (floral meristem-expressed AP1 prom.) | P9029 | 4766 | Inc. fruit weight |
| G2582 | 722 | MADS (1-57) | P5310 (root-expressed RSI1 prom.) | P9174 | 4804 | Inc. lycopene |
| G2582 | 722 | MADS (1-57) | P5326 (floral meristem-expressed AP1 prom.) | P9174 | 4804 | Inc. fruit weight |
| G2586 | 724 | WRKY (103-160) | P5310 (root-expressed RSI1 prom.) | P8722 | 4751 | Inc. lycopene |
| G2604 | 730 | Z-LSDlike (34-64, 73-103) | P6506 (constitutive CaMv 35S prom.) | P7700 | 4592 | Inc. fruit weight |
| G2604 | 730 | Z-LSDlike (34-64, 73-103) | P5303 (fruit tissue-expressed PD prom.) | P7700 | 4592 | Inc. fruit weight |
| G2606 | 732 | Z-C2H2 (120-140, 192-214) | P5287 (epidermal tissue-expressed LTP1 prom.) | P7753 | 4604 | Inc. lycopene |
| G2616 | 736 | HB (79-139) | P5326 (floral meristem-expressed AP1 prom.) | P8735 | 4758 | Inc. fruit weight |
| G2620 | 740 | TH (118-193) | P5297 (fruit tissue-expressed PG prom.) | P8643 | 4728 | Inc. brix |
| G2632 | 742 | CAAT (166-223) | P5284 (leaf-expressed RbcS3 prom.) | P8662 | 4734 | Inc. fruit weight |
| G2639 | 744 | SRS (114-167) | P5310 (root-expressed RSI1 prom.) | | | Inc. lycopene |
| G2639 | 744 | SRS (114-167) | P5318 (shoot apical meristem-expressed STM prom.) | | | Inc. fruit weight |
| G2639 | 744 | SRS (114-167) | P5284 (leaf-expressed RbcS3 prom.) | | | Inc. fruit weight |
| G2639 | 744 | SRS (114-167) | P5326 (floral meristem-expressed AP1 prom.) | | | Inc. fruit weight |
| G2639 | 744 | SRS (114-167) | P5287 (epidermal tissue-expressed LTP1 prom.) | | | Inc. fruit weight |
| G2640 | 748 | SRS (146-189) | P5310 (root-expressed RSI1 prom.) | P9243 | 4814 | Inc. lycopene |
| G2650 | 752 | TEO (34-91) | P5318 (shoot apical meristem-expressed STM prom.) | P8144 | 4647 | Inc. lycopene |
| G2650 | 752 | TEO (34-91) | P5297 (fruit tissue-expressed PG prom.) | P8144 | 4647 | Inc. lycopene |
| G2655 | 754 | HLH/MYC (119-178) | P6506 (constitutive CaMv 35S prom.) | P7531 | 4574 | Inc. brix |
| G2655 | 754 | HLH/MYC (119-178) | P5326 (floral meristem-expressed AP1 prom.) | P7531 | 4574 | Inc. fruit weight |
| G2656 | 756 | DBP (173-292) | P5284 (leaf-expressed RbcS3 prom.) | P9176 | 4805 | Inc. lycopene |
| G2656 | 756 | DBP (173-292) | P5310 (root-expressed RSI1 prom.) | P9176 | 4805 | Inc. lycopene |
| G2656 | 756 | DBP (173-292) | P5318 (shoot apical meristem-expressed STM prom.) | P9176 | 4805 | Inc. fruit weight |
| G2656 | 756 | DBP (173-292) | P5326 (floral meristem-expressed AP1 prom.) | P9176 | 4805 | Inc. fruit weight |
| G2661 | 758 | HLH/MYC (40-97) | P5287 (epidermal tissue-expressed LTP1 prom.) | P9177 | 4806 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2661 | 758 | HLH/MYC (40-97) | P5326 (floral meristem-expressed AP1 prom.) | P9177 | 4806 | Inc. fruit weight |
| G2674 | 760 | HB (56-116) | P5310 (root-expressed RSI1 prom.) | P9272 | 4822 | Inc. brix |
| G2674 | 760 | HB (56-116) | P5287 (epidermal tissue-expressed LTP1 prom.) | P9272 | 4822 | Inc. fruit weight |
| G2674 | 760 | HB (56-116) | P5318 (shoot apical meristem-expressed STM prom.) | P9272 | 4822 | Inc. fruit weight |
| G2674 | 760 | HB (56-116) | P5297 (fruit tissue-expressed PG prom.) | P9272 | 4822 | Inc. fruit weight |
| G2674 | 760 | HB (56-116) | P5284 (leaf-expressed RbcS3 prom.) | P9272 | 4822 | Inc. fruit weight |
| G2682 | 764 | CPP (67-181) | P5284 (leaf-expressed RbcS3 prom.) | P8241 | 4676 | Inc. lycopene |
| G2686 | 766 | WRKY (122-173) | P5287 (epidermal tissue-expressed LTP1 prom.) | P8080 | 4640 | Inc. brix |
| G2686 | 766 | WRKY (122-173) | P5284 (leaf-expressed RbcS3 prom.) | P8080 | 4640 | Inc. lycopene |
| G2688 | 768 | WRKY (67-124) | P5319 (emergent leaf primordia-expressed AS1 prom.) | P7508 | 4565 | Inc. brix |
| G2688 | 768 | WRKY (67-124) | P5297 (fruit tissue-expressed PG prom.) | P7508 | 4565 | Inc. brix |
| G2688 | 768 | WRKY (67-124) | P5287 (epidermal tissue-expressed LTP1 prom.) | P7508 | 4565 | Inc. brix |
| G2688 | 768 | WRKY (67-124) | P6506 (constitutive CaMv 35S prom.) | P7508 | 4565 | Inc. brix |
| G2696 | 770 | SCR (330-398, 545-621) | P5326 (floral meristem-expressed AP1 prom.) | P8161 | 4650 | Inc. fruit weight |
| G2697 | 772 | SCR (233-298, 361-449, 453-525) | P5318 (shoot apical meristem-expressed STM prom.) | P8636 | 4725 | Inc. brix |
| G2697 | 772 | SCR (233-298, 361-449, 453-525) | P5310 (root-expressed RSI1 prom.) | P8636 | 4725 | Inc. lycopene |
| G2699 | 774 | SCR (107-172, 243-333, 333-407) | P5287 (epidermal tissue-expressed LTP1 prom.) | P7759 | 4606 | Inc. brix |
| G2699 | 774 | SCR (107-172, 243-333, 333-407) | P5297 (fruit tissue-expressed PG prom.) | P7759 | 4606 | Inc. lycopene |
| G2699 | 774 | SCR (107-172, 243-333, 333-407) | P5284 (leaf-expressed RbcS3 prom.) | P7759 | 4606 | Inc. lycopene |
| G2704 | 776 | MYB-(R1)R2R3 (158-258) | P5310 (root-expressed RSI1 prom.) | P9039 | 4768 | Inc. lycopene |
| G2710 | 778 | HB (55-115) | P5310 (root-expressed RSI1 prom.) | P8513 | 4691 | Inc. brix |
| G2710 | 778 | HB (55-115) | P5318 (shoot apical meristem-expressed STM prom.) | P8513 | 4691 | Inc. lycopene |
| G2710 | 778 | HB (55-115) | P5287 (epidermal tissue-expressed LTP1 prom.) | P8513 | 4691 | Inc. lycopene |
| G2712 | 780 | HB (65-125) | P5318 (shoot apical meristem-expressed STM prom.) | P8163 | 4651 | Inc. fruit weight |
| G2715 | 782 | MYB-(R1)R2R3 (25-110) | P5326 (floral meristem-expressed AP1 prom.) | P4721 | 4333 | Inc. brix |
| G2719 | 784 | MYB-(R1)R2R3 (56-154) | P5287 (epidermal tissue-expressed LTP1 prom.) | P4723 | 4335 | Inc. brix |
| G2719 | 784 | MYB-(R1)R2R3 (56-154) | P5318 (shoot apical meristem-expressed STM prom.) | P4723 | 4335 | Inc. lycopene |
| G2719 | 784 | MYB-(R1)R2R3 (56-154) | P5287 (epidermal tissue-expressed LTP1 prom.) | P4723 | 4335 | Inc. lycopene |
| G2720 | 786 | MYB-(R1)R2R3 (10-114) | P5284 (leaf-expressed RbcS3 prom.) | P4722 | 4334 | Inc. brix |
| G2720 | 786 | MYB-(R1)R2R3 (10-114) | P5297 (fruit tissue-expressed PG prom.) | P4722 | 4334 | Inc. brix |
| G2721 | 788 | MYB-related (10-60) | P5324 (fruit vascular tissue-expressed Cru prom.) | P7734 | 4598 | Inc. biomass |
| G2723 | 790 | MYB-related (10-60) | P5287 (epidermal tissue-expressed LTP1 prom.) | P9190 | 4809 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2724 | 792 | MYB-(R1)R2R3 (7-113) | P5284 (leaf-expressed RbcS3 prom.) | P4727 | 4337 | Inc. lycopene |
| G2739 | 796 | SCR (243-309, 368-457, 466-541) | P5297 (fruit tissue-expressed PG prom.) | P8743 | 4761 | Inc. fruit weight |
| G2739 | 796 | SCR (243-309, 368-457, 466-541) | P5318 (shoot apical meristem-expressed STM prom.) | P8743 | 4761 | Inc. fruit weight |
| G2739 | 796 | SCR (243-309, 368-457, 466-541) | P5326 (floral meristem-expressed AP1 prom.) | P8743 | 4761 | Inc. fruit weight |
| G2739 | 796 | SCR (243-309, 368-457, 466-541) | P5284 (leaf-expressed RbcS3 prom.) | P8743 | 4761 | Inc. fruit weight |
| G2742 | 800 | GARP (28-76) | P5287 (epidermal tissue-expressed LTP1 prom.) | P8637 | 4726 | Inc. fruit weight |
| G2747 | 802 | ABI3/VP-1 (19-113) | P5287 (epidermal tissue-expressed LTP1 prom.) | P8127 | 4643 | Inc. brix |
| G2747 | 802 | ABI3/VP-1 (19-113) | P5326 (floral meristem-expressed AP1 prom.) | P8127 | 4643 | Inc. brix |
| G2747 | 802 | ABI3/VP-1 (19-113) | P5297 (fruit tissue-expressed PG prom.) | P8127 | 4643 | Inc. brix |
| G2747 | 802 | ABI3/VP-1 (19-113) | P5287 (epidermal tissue-expressed LTP1 prom.) | P8127 | 4643 | Inc. lycopene |
| G2748 | 804 | TEO (51-108) | P5303 (fruit tissue-expressed PD prom.) | P8126 | 4642 | Inc. brix |
| G2748 | 804 | TEO (51-108) | P5326 (floral meristem-expressed AP1 prom.) | P8126 | 4642 | Inc. lycopene |
| G2750 | 806 | AKR (231-719) | P5284 (leaf-expressed RbcS3 prom.) | P8215 | 4660 | Inc. lycopene |
| G2754 | 808 | SWI/SNF (198-393, 554-638) | P5318 (shoot apical meristem-expressed STM prom.) | P8655 | 4731 | Inc. fruit weight |
| G2766 | 810 | HLH/MYC (234-292) | P5310 (root-expressed RSI1 prom.) | P8606 | 4713 | Inc. lycopene |
| G2766 | 810 | HLH/MYC (234-292) | P6506 (constitutive CaMv 35S prom.) | P8606 | 4713 | Inc. fruit weight |
| G2774 | 814 | HLH/MYC (158-215) | P5284 (leaf-expressed RbcS3 prom.) | P8725 | 4752 | Inc. brix |
| G2779 | 816 | HLH/MYC (148-206) | P5297 (fruit tissue-expressed PG prom.) | P9060 | 4773 | Inc. brix |
| G2789 | 818 | AT-hook (59-67, 68-208) | P5287 (epidermal tissue-expressed LTP1 prom.) | P4750 | 4343 | Inc. fruit weight |
| G2790 | 822 | HLH/MYC (141-198) | P5287 (epidermal tissue-expressed LTP1 prom.) | P7497 | 4563 | Inc. brix |
| G2790 | 822 | HLH/MYC (141-198) | P5284 (leaf-expressed RbcS3 prom.) | P7497 | 4563 | Inc. lycopene |
| G2791 | 824 | HLH/MYC (102-159) | P5284 (leaf-expressed RbcS3 prom.) | P8133 | 4644 | Inc. brix |
| G2791 | 824 | HLH/MYC (102-159) | P5326 (floral meristem-expressed AP1 prom.) | P8133 | 4644 | Inc. brix |
| G2791 | 824 | HLH/MYC (102-159) | P5287 (epidermal tissue-expressed LTP1 prom.) | P8133 | 4644 | Inc. brix |
| G2791 | 824 | HLH/MYC (102-159) | P5284 (leaf-expressed RbcS3 prom.) | P8133 | 4644 | Inc. lycopene |
| G2791 | 824 | HLH/MYC (102-159) | P5326 (floral meristem-expressed AP1 prom.) | P8133 | 4644 | Inc. lycopene |
| G2792 | 826 | HLH/MYC (307-364) | P5326 (floral meristem-expressed AP1 prom.) | P8731 | 4755 | Inc. brix |
| G2800 | 832 | NAC (11-150) | P5297 (fruit tissue-expressed PG prom.) | P8536 | 4694 | Inc. brix |
| G2800 | 832 | NAC (11-150) | P5318 (shoot apical meristem-expressed STM prom.) | P8536 | 4694 | Inc. brix |
| G2802 | 834 | NAC (48-196) | P5287 (epidermal tissue-expressed LTP1 prom.) | P8660 | 4733 | Inc. fruit weight |
| G2803 | 836 | NAC (8-160) | P5318 (shoot apical meristem-expressed STM prom.) | P7594 | 4589 | Inc. fruit weight |
| G2803 | 836 | NAC (8-160) | P5287 (epidermal tissue-expressed LTP1 prom.) | P7594 | 4589 | Inc. fruit weight |
| G2803 | 836 | NAC (8-160) | P5326 (floral meristem-expressed AP1 prom.) | P7594 | 4589 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2803 | 836 | NAC (8-160) | P5284 (leaf-expressed RbcS3 prom.) | P7594 | 4589 | Inc. fruit weight |
| G2804 | 838 | NAC (38-130) | P5287 (epidermal tissue-expressed LTP1 prom.) | P8741 | 4760 | Inc. fruit weight |
| G2809 | 840 | HB (95-155) | P5326 (floral meristem-expressed AP1 prom.) | P8681 | 4742 | Inc. lycopene |
| G2818 | 842 | SWI/SNF (24-239, 456-539) | P5326 (floral meristem-expressed AP1 prom.) | P8585 | 4707 | Inc. fruit weight |
| G2826 | 844 | Z-C2H2 (75-95) | P5318 (shoot apical meristem-expressed STM prom.) | P7727 | 4597 | Inc. lycopene |
| G2826 | 844 | Z-C2H2 (75-95) | P5287 (epidermal tissue-expressed LTP1 prom.) | P7727 | 4597 | Inc. lycopene |
| G2826 | 844 | Z-C2H2 (75-95) | P5284 (leaf-expressed RbcS3 prom.) | P7727 | 4597 | Inc. lycopene |
| G2831 | 846 | Z-C2H2 (72-92, 148-168) | P5318 (shoot apical meristem-expressed STM prom.) | P8618 | 4719 | Inc. fruit weight |
| G2831 | 846 | Z-C2H2 (72-92, 148-168) | P5297 (fruit tissue-expressed PG prom.) | P8618 | 4719 | Inc. fruit weight |
| G2836 | 848 | Z-C2H2 (160-181) | P5326 (floral meristem-expressed AP1 prom.) | P7765 | 4608 | Inc. brix |
| G2837 | 850 | Z-C2H2 (140-160) | P5303 (fruit tissue-expressed PD prom.) | P8625 | 4722 | Inc. brix |
| G2837 | 850 | Z-C2H2 (140-160) | P5303 (fruit tissue-expressed PD prom.) | P8625 | 4722 | Inc. lycopene |
| G2837 | 850 | Z-C2H2 (140-160) | P5297 (fruit tissue-expressed PG prom.) | P8625 | 4722 | Inc. lycopene |
| G2838 | 852 | Z-C2H2 (57-77) | P5318 (shoot apical meristem-expressed STM prom.) | P8578 | 4705 | Inc. brix |
| G2838 | 852 | Z-C2H2 (57-77) | P6506 (constitutive CaMv 35S prom.) | P8578 | 4705 | Large flowers |
| G2840 | 854 | Z-C2H2 (246-266, 297-328, 335-356) | P5326 (floral meristem-expressed AP1 prom.) | P7741 | 4601 | Inc. brix |
| G2848 | 856 | HLH/MYC (29-83) | P5318 (shoot apical meristem-expressed STM prom.) | P7573 | 4585 | Inc. fruit weight |
| G2848 | 856 | HLH/MYC (29-83) | P5297 (fruit tissue-expressed PG prom.) | P7573 | 4585 | Inc. fruit weight |
| G2848 | 856 | HLH/MYC (29-83) | P5326 (floral meristem-expressed AP1 prom.) | P7573 | 4585 | Inc. fruit weight |
| G2848 | 856 | HLH/MYC (29-83) | P5287 (epidermal tissue-expressed LTP1 prom.) | P7573 | 4585 | Inc. fruit weight |
| G2849 | 858 | HLH/MYC (28-81) | P5297 (fruit tissue-expressed PG prom.) | P7784 | 4614 | Inc. brix |
| G2849 | 858 | HLH/MYC (28-81) | P5297 (fruit tissue-expressed PG prom.) | P7784 | 4614 | Inc. lycopene |
| G2855 | 862 | ACBF-like (105-285) | P5310 (root-expressed RSI1 prom.) | P8690 | 4745 | Inc. brix |
| G2855 | 862 | ACBF-like (105-285) | P5310 (root-expressed RSI1 prom.) | P8690 | 4745 | Inc. lycopene |
| G2855 | 862 | ACBF-like (105-285) | P5287 (epidermal tissue-expressed LTP1 prom.) | P8690 | 4745 | Inc. fruit weight |
| G2855 | 862 | ACBF-like (105-285) | P5284 (leaf-expressed RbcS3 prom.) | P8690 | 4745 | Inc. fruit weight |
| G2855 | 862 | ACBF-like (105-285) | P5318 (shoot apical meristem-expressed STM prom.) | P8690 | 4745 | Inc. fruit weight |
| G2855 | 862 | ACBF-like (105-285) | P5326 (floral meristem-expressed AP1 prom.) | P8690 | 4745 | Inc. fruit weight |
| G2856 | 864 | ACBF-like (25-335) | P5297 (fruit tissue-expressed PG prom.) | | | Inc. lycopene |
| G2856 | 864 | ACBF-like (25-335) | P5287 (epidermal tissue-expressed LTP1 prom.) | | | Inc. fruit weight |
| G2856 | 864 | ACBF-like (25-335) | P5318 (shoot apical meristem-expressed STM prom.) | | | Inc. fruit weight |
| G2876 | 868 | AKR (152-653) | P5297 (fruit tissue-expressed PG prom.) | | | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2885 | 872 | GARP (196-243) | P5287 (epidermal tissue-expressed LTP1 prom.) | P8143 | 4646 | Inc. brix |
| G2885 | 872 | GARP (196-243) | P5287 (epidermal tissue-expressed LTP1 prom.) | P8143 | 4646 | Inc. lycopene |
| G2887 | 874 | NAC (4-180) | P5326 (floral meristem-expressed AP1 prom.) | P8178 | 4656 | Inc. fruit weight |
| G2891 | 876 | AKR (92-594) | P5287 (epidermal tissue-expressed LTP1 prom.) | P9228 | 4813 | Inc. lycopene |
| G2891 | 876 | AKR (92-594) | P5284 (leaf-expressed RbcS3 prom.) | P9228 | 4813 | Inc. lycopene |
| G2891 | 876 | AKR (92-594) | P5310 (root-expressed RSI1 prom.) | P9228 | 4813 | Inc. lycopene |
| G2893 | 878 | MYB-(R1)R2R3 (19-120) | P5326 (floral meristem-expressed AP1 prom.) | P4729 | 4338 | Inc. lycopene |
| G2893 | 878 | MYB-(R1)R2R3 (19-120) | P5318 (shoot apical meristem-expressed STM prom.) | P4729 | 4338 | Inc. fruit weight |
| G2896 | 880 | HMG (30-102) | P5326 (floral meristem-expressed AP1 prom.) | P7588 | 4588 | Inc. lycopene |
| G2896 | 880 | HMG (30-102) | P5297 (fruit tissue-expressed PG prom.) | P7588 | 4588 | Inc. lycopene |
| G2898 | 882 | HMG (59-131) | P5326 (floral meristem-expressed AP1 prom.) | P8141 | 4645 | Inc. brix |
| G2898 | 882 | HMG (59-131) | P5284 (leaf-expressed RbcS3 prom.) | P8141 | 4645 | Inc. lycopene |
| G2898 | 882 | HMG (59-131) | P5297 (fruit tissue-expressed PG prom.) | P8141 | 4645 | Inc. lycopene |
| G2898 | 882 | HMG (59-131) | P5326 (floral meristem-expressed AP1 prom.) | P8141 | 4645 | Inc. lycopene |
| G2898 | 882 | HMG (59-131) | P5287 (epidermal tissue-expressed LTP1 prom.) | P8141 | 4645 | Inc. lycopene |
| G2902 | 888 | HMG (128-198, 242-311, 371-441) | P5284 (leaf-expressed RbcS3 prom.) | P8738 | 4759 | Inc. lycopene |
| G2902 | 888 | HMG (128-198, 242-311, 371-441) | P5318 (shoot apical meristem-expressed STM prom.) | P8738 | 4759 | Inc. lycopene |
| G2902 | 888 | HMG (128-198, 242-311, 371-441) | P5310 (root-expressed RSI1 prom.) | P8738 | 4759 | Inc. lycopene |
| G2906 | 890 | Z-C2H2 (119-140) | P5287 (epidermal tissue-expressed LTP1 prom.) | P7599 | 4591 | Inc. fruit weight |
| G2906 | 890 | Z-C2H2 (119-140) | P5324 (fruit vascular tissue-expressed Cru prom.) | P7599 | 4591 | Inc. fruit weight |
| G2906 | 890 | Z-C2H2 (119-140) | P5318 (shoot apical meristem-expressed STM prom.) | P7599 | 4591 | Inc. fruit weight |
| G2906 | 890 | Z-C2H2 (119-140) | P5284 (leaf-expressed RbcS3 prom.) | P7599 | 4591 | Inc. fruit weight |
| G2910 | 892 | PCGL (22-130, 778-847) | P5310 (root-expressed RSI1 prom.) | P8702 | 4749 | Inc. lycopene |
| G2918 | 894 | JUMONJI (108-143, 294-446) | P5326 (floral meristem-expressed AP1 prom.) | P8620 | 4720 | Inc. brix |
| G2918 | 894 | JUMONJI (108-143, 294-446) | P5284 (leaf-expressed RbcS3 prom.) | P8620 | 4720 | Inc. fruit weight |
| G2921 | 896 | JUMONJI (55-119, 267-419) | P5287 (epidermal tissue-expressed LTP1 prom.) | P8596 | 4712 | Inc. fruit weight |
| G2927 | 898 | HLH/MYC (341-398) | P5284 (leaf-expressed RbcS3 prom.) | P8564 | 4702 | Inc. fruit weight |
| G2929 | 900 | HLH/MYC (70-130) | P5284 (leaf-expressed RbcS3 prom.) | P8656 | 4732 | Inc. fruit weight |
| G2929 | 900 | HLH/MYC (70-130) | P5287 (epidermal tissue-expressed LTP1 prom.) | P8656 | 4732 | Inc. fruit weight |
| G2929 | 900 | HLH/MYC (70-130) | P5326 (floral meristem-expressed AP1 prom.) | P8656 | 4732 | Inc. fruit weight |
| G2930 | 902 | HLH/MYC (57-120) | P5297 (fruit tissue-expressed PG prom.) | P7565 | 4581 | Inc. brix |
| G2930 | 902 | HLH/MYC (57-120) | P6506 (constitutive CaMv 35S prom.) | P7565 | 4581 | Inc. brix |
| G2930 | 902 | HLH/MYC (57-120) | P5284 (leaf-expressed RbcS3 prom.) | P7565 | 4581 | Inc. brix |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G2931 | 904 | HLH/MYC (71-131) | P5287 (epidermal tissue-expressed LTP1 prom.) | P9179 | 4807 | Inc. fruit weight |
| G2931 | 904 | HLH/MYC (71-131) | P5284 (leaf-expressed RbcS3 prom.) | P9179 | 4807 | Inc. fruit weight |
| G2936 | 906 | HLH/MYC (82-142) | P5310 (root-expressed RSI1 prom.) | P9180 | 4808 | Inc. lycopene |
| G2936 | 906 | HLH/MYC (82-142) | P5318 (shoot apical meristem-expressed STM prom.) | P9180 | 4808 | Inc. fruit weight |
| G2936 | 906 | HLH/MYC (82-142) | P5284 (leaf-expressed RbcS3 prom.) | P9180 | 4808 | Inc. fruit weight |
| G2965 | 912 | Z-C2H2 (49-70) | P5284 (leaf-expressed RbcS3 prom.) | P7709 | 4594 | Inc. fruit weight |
| G2966 | 914 | Z-C2H2 (233-254) | P5326 (floral meristem-expressed AP1 prom.) | P8490 | 4685 | Inc. fruit weight |
| G2972 | 916 | Z-C2H2 (8-32, 129-149, 277-294) | P5284 (leaf-expressed RbcS3 prom.) | P7597 | 4590 | Inc. fruit weight |
| G2979 | 918 | E2F (192-211) | P5310 (root-expressed RSI1 prom.) | P8685 | 4743 | Inc. lycopene |
| G2980 | 920 | E2F (39-337) | P5318 (shoot apical meristem-expressed STM prom.) | P8686 | 4744 | Inc. fruit weight |
| G2982 | 922 | E2F (107-124) | P5326 (floral meristem-expressed AP1 prom.) | P8515 | 4692 | Inc. brix |
| G2982 | 922 | E2F (107-124) | P5297 (fruit tissue-expressed PG prom.) | P8515 | 4692 | Inc. brix |
| G2983 | 924 | HB (88-148) | P5297 (fruit tissue-expressed PG prom.) | P8539 | 4696 | Inc. brix |
| G2983 | 924 | HB (88-148) | P5310 (root-expressed RSI1 prom.) | P8539 | 4696 | Inc. lycopene |
| G2985 | 926 | OTHER (353-488) | P5287 (epidermal tissue-expressed LTP1 prom.) | P8221 | 4662 | Inc. fruit weight |
| G2985 | 926 | OTHER (353-488) | P5310 (root-expressed RSI1 prom.) | P8221 | 4662 | Inc. fruit weight |
| G2985 | 926 | OTHER (353-488) | P5318 (shoot apical meristem-expressed STM prom.) | P8221 | 4662 | Inc. fruit weight |
| G2989 | 928 | ZF-HB (50-105, 192-255) | P5284 (leaf-expressed RbcS3 prom.) | P7514 | 4569 | Inc. lycopene |
| G2989 | 928 | ZF-HB (50-105, 192-255) | P5284 (leaf-expressed RbcS3 prom.) | P7514 | 4569 | Inc. brix |
| G2990 | 930 | ZF-HB (54-109, 200-263) | P5287 (epidermal tissue-expressed LTP1 prom.) | P7515 | 4570 | Inc. fruit weight |
| G2992 | 932 | ZF-HB (29-84, 156-219) | P5326 (floral meristem-expressed AP1 prom.) | P8122 | 4641 | Inc. brix |
| G2992 | 932 | ZF-HB (29-84, 156-219) | P5318 (shoot apical meristem-expressed STM prom.) | P8122 | 4641 | Inc. brix |
| G2992 | 932 | ZF-HB (29-84, 156-219) | P5287 (epidermal tissue-expressed LTP1 prom.) | P8122 | 4641 | Inc. brix |
| G2992 | 932 | ZF-HB (29-84, 156-219) | P5297 (fruit tissue-expressed PG prom.) | P8122 | 4641 | Inc. brix |
| G2992 | 932 | ZF-HB (29-84, 156-219) | P5318 (shoot apical meristem-expressed STM prom.) | P8122 | 4641 | Inc. lycopene |
| G2992 | 932 | ZF-HB (29-84, 156-219) | P5326 (floral meristem-expressed AP1 prom.) | P8122 | 4641 | Inc. lycopene |
| G2993 | 934 | ZF-HB (85-138, 222-285) | P5297 (fruit tissue-expressed PG prom.) | P7787 | 4616 | Inc. brix |
| G2995 | 936 | ZF-HB (3-58, 115-178) | P5319 (emergent leaf primordia-expressed AS1 prom.) | P7516 | 4571 | Inc. fruit weight |
| G2996 | 938 | ZF-HB (73-126, 191-254) | P5297 (fruit tissue-expressed PG prom.) | P7513 | 4568 | Inc. fruit weight |
| G2998 | 940 | ZF-HB (74-127, 240-303) | P5284 (leaf-expressed RbcS3 prom.) | P7517 | 4572 | Inc. brix |
| G2999 | 942 | ZF-HB (80-133, 198-261) | P5310 (root-expressed RSI1 prom.) | P8587 | 4709 | Inc. brix |
| G2999 | 942 | ZF-HB (80-133, 198-261) | P5310 (root-expressed RSI1 prom.) | P8587 | 4709 | Inc. lycopene |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G3006 | 948 | HS (38-153) | P5284 (leaf-expressed RbcS3 prom.) | P9059 | 4772 | Inc. fruit weight |
| G3006 | 948 | HS (38-153) | P5318 (shoot apical meristem-expressed STM prom.) | P9059 | 4772 | Inc. fruit weight |
| G3006 | 948 | HS (38-153) | P5297 (fruit tissue-expressed PG prom.) | P9059 | 4772 | Inc. fruit weight |
| G3006 | 948 | HS (38-153) | P5326 (floral meristem-expressed AP1 prom.) | P9059 | 4772 | Inc. fruit weight |
| G3007 | 950 | TUBBY (21-137, 141-188) | P5326 (floral meristem-expressed AP1 prom.) | P8680 | 4741 | Inc. fruit weight |
| G3007 | 950 | TUBBY (21-137, 141-188) | P5284 (leaf-expressed RbcS3 prom.) | P8680 | 4741 | Inc. fruit weight |
| G3007 | 950 | TUBBY (21-137, 141-188) | P5318 (shoot apical meristem-expressed STM prom.) | P8680 | 4741 | Inc. fruit weight |
| G3007 | 950 | TUBBY (21-137, 141-188) | P5287 (epidermal tissue-expressed LTP1 prom.) | P8680 | 4741 | Inc. fruit weight |
| G3009 | 952 | SCR (228-293, 350-437, 441-515) | P5284 (leaf-expressed RbcS3 prom.) | P8491 | 4686 | Inc. lycopene |
| G3012 | 954 | HLH/MYC (257-314) | P5297 (fruit tissue-expressed PG prom.) | P7568 | 4583 | Inc. brix |
| G3012 | 954 | HLH/MYC (257-314) | P5287 (epidermal tissue-expressed LTP1 prom.) | P7568 | 4583 | Inc. lycopene |
| G3021 | 956 | HLH/MYC (91-148) | P5318 (shoot apical meristem-expressed STM prom.) | P7566 | 4582 | Inc. brix |
| G3021 | 956 | HLH/MYC (91-148) | P5287 (epidermal tissue-expressed LTP1 prom.) | P7566 | 4582 | Inc. lycopene |
| G3023 | 958 | HLH/MYC (8-68) | P5287 (epidermal tissue-expressed LTP1 prom.) | P7571 | 4584 | Inc. fruit weight |
| G3023 | 958 | HLH/MYC (8-68) | P5318 (shoot apical meristem-expressed STM prom.) | P7571 | 4584 | Inc. fruit weight |
| G3032 | 960 | GARP (285-333) | P5318 (shoot apical meristem-expressed STM prom.) | P8674 | 4739 | Inc. fruit weight |
| G3034 | 962 | GARP (218-266) | P5326 (floral meristem-expressed AP1 prom.) | P9194 | 4810 | Inc. fruit weight |
| G3037 | 964 | NAC (15-142) | P5318 (shoot apical meristem-expressed STM prom.) | P8621 | 4721 | Inc. fruit weight |
| G3037 | 964 | NAC (15-142) | P5287 (epidermal tissue-expressed LTP1 prom.) | P8621 | 4721 | Inc. fruit weight |
| G3037 | 964 | NAC (15-142) | P5326 (floral meristem-expressed AP1 prom.) | P8621 | 4721 | Inc. fruit weight |
| G3040 | 966 | NAC (4-144) | P5326 (floral meristem-expressed AP1 prom.) | P8666 | 4735 | Inc. brix |
| G3041 | 968 | NAC (8-136) | P5284 (leaf-expressed RbcS3 prom.) | P8220 | 4661 | Inc. fruit weight |
| G3041 | 968 | NAC (8-136) | P5318 (shoot apical meristem-expressed STM prom.) | P8220 | 4661 | Inc. fruit weight |
| G3054 | 970 | Z-C3H (77-96, 149-168) | P5319 (emergent leaf primordia-expressed AS1 prom.) | P7494 | 4561 | Inc. brix |
| G3054 | 970 | Z-C3H (77-96, 149-168) | P5297 (fruit tissue-expressed PG prom.) | P7494 | 4561 | Inc. brix |
| G3054 | 970 | Z-C3H (77-96, 149-168) | P5303 (fruit tissue-expressed PD prom.) | P7494 | 4561 | Inc. brix |
| G3054 | 970 | Z-C3H (77-96, 149-168) | P5284 (leaf-expressed RbcS3 prom.) | P7494 | 4561 | Inc. brix |
| G3055 | 972 | Z-C3H (97-115, 178-197, 266-287) | P5297 (fruit tissue-expressed PG prom.) | P7745 | 4602 | Inc. brix |
| G3055 | 972 | Z-C3H (97-115, 178-197, 266-287) | P5284 (leaf-expressed RbcS3 prom.) | P7745 | 4602 | Inc. lycopene |
| G3060 | 976 | Z-C3H (42-61, 219-237) | P5326 (floral meristem-expressed AP1 prom.) | P8177 | 4655 | Inc. lycopene |
| G3063 | 978 | Z-C2H2 (63-83, 139-159) | P5318 (shoot apical meristem-expressed STM prom.) | P8640 | 4727 | Inc. fruit weight |

TABLE 7-continued

Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|
| G3063 | 978 | Z-C2H2 (63-83, 139-159) | P5287 (epidermal tissue-expressed LTP1 prom.) | P8640 | 4727 | Inc. fruit weight |
| G3063 | 978 | Z-C2H2 (63-83, 139-159) | P5284 (leaf-expressed RbcS3 prom.) | P8640 | 4727 | Inc. fruit weight |
| G3064 | 980 | Z-C2H2 (154-175) | P5297 (fruit tissue-expressed PG prom.) | P8495 | 4689 | Inc. fruit weight |
| G3066 | 982 | Z-C2H2 (80-101, 284-306) | P5319 (emergent leaf primordia-expressed AS1 prom.) | P7702 | 4593 | Inc. fruit weight |
| G3066 | 982 | Z-C2H2 (80-101, 284-306) | P5287 (epidermal tissue-expressed LTP1 prom.) | P7702 | 4593 | Inc. fruit weight |
| G3066 | 982 | Z-C2H2 (80-101, 284-306) | P5297 (fruit tissue-expressed PG prom.) | P7702 | 4593 | Inc. fruit weight |
| G3067 | 984 | Z-C2H2 (198-219) | P5318 (shoot apical meristem-expressed STM prom.) | P7495 | 4562 | Inc. lycopene |
| G3074 | 986 | CAAT (3-86) | P5287 (epidermal tissue-expressed LTP1 prom.) | P8166 | 4652 | Inc. brix |
| G3074 | 986 | CAAT (3-86) | P5326 (floral meristem-expressed AP1 prom.) | P8166 | 4652 | Inc. brix |
| G3075 | 988 | CAAT (111-192) | P5287 (epidermal tissue-expressed LTP1 prom.) | P7738 | 4600 | Inc. lycopene |
| G3080 | 990 | bZIP-ZW2 (76-106, 210-237) | P5318 (shoot apical meristem-expressed STM prom.) | P7546 | 4579 | Inc. fruit weight |
| G3090 | 994 | PLATZ (12-147) | P5310 (root-expressed RSI1 prom.) | P8676 | 4740 | Inc. brix |
| G3090 | 994 | PLATZ (12-147) | P5326 (floral meristem-expressed AP1 prom.) | P8676 | 4740 | Inc. lycopene |
| G3090 | 994 | PLATZ (12-147) | P5310 (root-expressed RSI1 prom.) | P8676 | 4740 | Inc. lycopene |
| G3090 | 994 | PLATZ (12-147) | P5297 (fruit tissue-expressed PG prom.) | P8676 | 4740 | Inc. lycopene |
| G3101 | 996 | Z-C2H2 (14-78) | P5287 (epidermal tissue-expressed LTP1 prom.) | P8555 | 4699 | Inc. brix |
| G3101 | 996 | Z-C2H2 (14-78) | P5287 (epidermal tissue-expressed LTP1 prom.) | P8555 | 4699 | Inc. lycopene |
| G3102 | 998 | Z-C2H2 (397-440) | P5310 (root-expressed RSI1 prom.) | P8733 | 4756 | Inc. brix |
| G3102 | 998 | Z-C2H2 (397-440) | P5318 (shoot apical meristem-expressed STM prom.) | P8733 | 4756 | Inc. fruit weight |
| G3111 | 1000 | RING/C3H2C3 (111-152) | P5287 (epidermal tissue-expressed LTP1 prom.) | | | Inc. lycopene |

Abbreviations for Table 7:
inc. - increased or greater, relative to control plants
Cru - Cruciferin promoter
PG - Polygalacturonase promoter
PD - Phytoene desaturase promoter
ABI3/VP1 - Abscisic Acid Insensitive/maize VP1 like proteins
ACBF - AC-rich Binding Factors
AKR - Aldo-Keto Reductase family proteins
ARF - Auxin Response Factor family
BPF-1 Box P-binding factor Family proteins
CAAT - CCAAT-box binding family proteins
CPP - Cysteine-rich Polycomb-like Proteins
DBP - DNA-Binding Protein; miscellaneous proteins that bind to DNA
EIL - Ethylene Insensitive 3-Like proteins
ENBP - pea Early Nodulin gene-Binding Proteins
GF14 - G-Box Factor 14-3-3 Homolog family
GARP - Golgi-Associated Retrograde Protein complex proteins
HLH - Helix-Loop-Helix proteins
HMG - High Mobility Group family proteins
HS - Heat Shock transcription factor proteins
MADS - MCM1, AGAMOUS, DEFICIENS, and SRF, serum response factor family proteins
MYB - Myeloblastosis proto-oncogene product-like family of TFs
MYC - similar to myelocytomatosis viral oncogene (v-Myc) family proteins
PCF - PCF1- and PCF2-like proteins
Pcomb - Polycomb group (Pc-G) family proteins
PLATZ - Plant AT-rich sequence and Zinc-binding protein family proteins TABLE 7-continued Polypeptides of the invention, their conserved domains, families and the traits conferred by overexpressing the polypeptides in tomato plants

| Col. 1 GID | Col. 2 SEQ ID NO: | Col. 3 TF family (conserved domain amino acid coordinates) | Col. 4 First construct (expression system) | Col. 5 Second construct containing TF | Col. 6 SEQ ID NO: of second construct | Col. 7 Experimental observation (trait relative to controls) |
|---|---|---|---|---|---|---|

PMR - Putative Myb-Related family proteins
SCR - SCARECROW family proteins
SRS - Short Internodes or SHI transcription factor family proteins
SWI/SNF - switching mating type (SWI) and sucrose non-fermenting-like chromatin remodeling factors
TEO - Teosinte branched1 like proteins
TH - Triple Helix family proteins
ZF-HB - (also ZF-HD) zinc finger - homeodomain family proteins Example VIII Orthologs and Paralogs of the Sequences of the Invention Table 8 lists sequences discovered to be orthologous or paralogous to a number of transcription factors of the instant Sequence Listing. The columns headings include, from left to right: Column 1: the SEQ ID NO; Column 2: the corresponding *Arabidopsis* Gene identification (GID) numbers; Column 3: the sequence type (DNA or protein, PRT); Column 4: the species from which the sequence derives; and Column 5: the relationship to other sequences in this table and the Sequence Listing.

TABLE 8

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1 | G1004 | DNA | A. thaliana | Predicted polypeptide sequence is paralogous to G1419, G43, G46, G29; orthologous to G3849 |
| 2 | G1004 | PRT | A. thaliana | Paralogous to G1419, G43, G46, G29; Orthologous to G3849 |
| 3 | G1006 | DNA | A. thaliana | Predicted polypeptide sequence is paralogous to G22, G28; orthologous to G3430, G3659, G3660, G3661, G3717, G3718, G3841, G3843, G3844, G3845, G3846, G3848, G3852, G3856, G3857, G3858, G3864, G3865, G4626, G5171 |
| 4 | G1006 | PRT | A. thaliana | Paralogous to G22, G28; Orthologous to G3430, G3659, G3660, G3661, G3717, G3718, G3841, G3843, G3844, G3845, G3846, G3848, G3852, G3856, G3857, G3858, G3864, G3865, G4626, G5171 |
| 5 | G1007 | DNA | A. thaliana | Predicted polypeptide sequence is paralogous to G1846 |
| 6 | G1007 | PRT | A. thaliana | Paralogous to G1846 |
| 7 | G1008 | DNA | A. thaliana | Predicted polypeptide sequence is paralogous to G2130 |
| 8 | G1008 | PRT | A. thaliana | Paralogous to G2130 |
| 13 | G1021 | DNA | A. thaliana | Predicted polypeptide sequence is paralogous to G224, G1466, G223 |
| 14 | G1021 | PRT | A. thaliana | Paralogous to G224, G1466, G223 |
| 17 | G1033 | DNA | A. thaliana | Predicted polypeptide sequence is paralogous to G1029, G279 |
| 18 | G1033 | PRT | A. thaliana | Paralogous to G1029, G279 |
| 21 | G1053 | DNA | A. thaliana | Predicted polypeptide sequence is paralogous to G2629 |
| 22 | G1053 | PRT | A. thaliana | Paralogous to G2629 |
| 23 | G1057 | DNA | A. thaliana | Predicted polypeptide sequence is paralogous to G3027 |
| 24 | G1057 | PRT | A. thaliana | Paralogous to G3027 |
| 25 | G1062 | DNA | A. thaliana | Predicted polypeptide sequence is paralogous to G1664 |
| 26 | G1062 | PRT | A. thaliana | Paralogous to G1664 |
| 27 | G1065 | DNA | A. thaliana | Predicted polypeptide sequence is paralogous to G602 |
| 28 | G1065 | PRT | A. thaliana | Paralogous to G602 |
| 29 | G1067 | DNA | A. thaliana | Predicted polypeptide sequence is paralogous to G1073, G2156; orthologous to G3399, G3400 |
| 30 | G1067 | PRT | A. thaliana | Paralogous to G1073, G2156; Orthologous to G3399, G3400 |
| 33 | G1076 | DNA | A. thaliana | Predicted polypeptide sequence is paralogous to G1075; orthologous to G3406, G3407, G3458, G3459, G3460, G3461 |
| 34 | G1076 | PRT | A. thaliana | Paralogous to G1075; Orthologous to G3406, G3407, G3458, G3459, G3460, G3461 |
| 35 | G1078 | DNA | A. thaliana | Predicted polypeptide sequence is paralogous to G577 |
| 36 | G1078 | PRT | A. thaliana | Paralogous to G577 |
| 45 | G1091 | DNA | A. thaliana | Predicted polypeptide sequence is paralogous to G2588 |
| 46 | G1091 | PRT | A. thaliana | Paralogous to G2588 |
| 49 | G1113 | DNA | A. thaliana | Predicted polypeptide sequence is paralogous to G911 |
| 50 | G1113 | PRT | A. thaliana | Paralogous to G911 |
| 53 | G1131 | DNA | A. thaliana | Predicted polypeptide sequence is paralogous to G2767 |
| 54 | G1131 | PRT | A. thaliana | Paralogous to G2767 |
| 55 | G1133 | DNA | A. thaliana | Predicted polypeptide sequence is paralogous to G1137 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 56 | G1133 | PRT | A. thaliana | Paralogous to G1137 |
| 57 | G1134 | DNA | A. thaliana | Predicted polypeptide sequence is paralogous to G2555 |
| 58 | G1134 | PRT | A. thaliana | Paralogous to G2555 |
| 59 | G1136 | DNA | A. thaliana | Predicted polypeptide sequence is paralogous to G584 |
| 60 | G1136 | PRT | A. thaliana | Paralogous to G584 |
| 61 | G1137 | DNA | A. thaliana | Predicted polypeptide sequence is paralogous to G1133 |
| 62 | G1137 | PRT | A. thaliana | Paralogous to G1133 |
| 63 | G1140 | DNA | A. thaliana | Predicted polypeptide sequence is paralogous to G861; orthologous to G3984, G3985, G3986, G3987, G3988, G3989, G3990, G3991, G3992, G3998, G3999, G4060 |
| 64 | G1140 | PRT | A. thaliana | Paralogous to G861; Orthologous to G3984, G3985, G3986, G3987, G3988, G3989, G3990, G3991, G3992, G3998, G3999, G4060 |
| 65 | G1141 | DNA | A. thaliana | Predicted polypeptide sequence is paralogous to G38 |
| 66 | G1141 | PRT | A. thaliana | Paralogous to G38 |
| 67 | G1146 | DNA | A. thaliana | Predicted polypeptide sequence is paralogous to G1149, G1152 |
| 68 | G1146 | PRT | A. thaliana | Paralogous to G1149, G1152 |
| 73 | G1198 | DNA | A. thaliana | Predicted polypeptide sequence is paralogous to G1806, G554, G555, G556, G558, G578, G629 |
| 74 | G1198 | PRT | A. thaliana | Paralogous to G1806, G554, G555, G556, G558, G578, G629 |
| 75 | G1211 | DNA | A. thaliana | Predicted polypeptide sequence is paralogous to G291 |
| 76 | G1211 | PRT | A. thaliana | Paralogous to G291 |
| 77 | G1216 | DNA | A. thaliana | Predicted polypeptide sequence is paralogous to G2494 |
| 78 | G1216 | PRT | A. thaliana | Paralogous to G2494 |
| 81 | G1228 | DNA | A. thaliana | Predicted polypeptide sequence is paralogous to G1227 |
| 82 | G1228 | PRT | A. thaliana | Paralogous to G1227 |
| 85 | G1233 | DNA | A. thaliana | Predicted polypeptide sequence is paralogous to G1303 |
| 86 | G1233 | PRT | A. thaliana | Paralogous to G1303 |
| 87 | G1240 | DNA | A. thaliana | Predicted polypeptide sequence is paralogous to G1241 |
| 88 | G1240 | PRT | A. thaliana | Paralogous to G1241 |
| 89 | G1243 | DNA | A. thaliana | Predicted polypeptide sequence is paralogous to G1242 |
| 90 | G1243 | PRT | A. thaliana | Paralogous to G1242 |
| 93 | G1247 | DNA | A. thaliana | Predicted polypeptide sequence is paralogous to G1245 |
| 94 | G1247 | PRT | A. thaliana | Paralogous to G1245 |
| 97 | G1256 | DNA | A. thaliana | Predicted polypeptide sequence is paralogous to G2003 |
| 98 | G1256 | PRT | A. thaliana | Paralogous to G2003 |
| 99 | G1266 | DNA | A. thaliana | Predicted polypeptide sequence is orthologous to G5184, G5185, G5186, G5170 |
| 100 | G1266 | PRT | A. thaliana | Orthologous to G5184, G5185, G5186, G5170 |
| 105 | G1274 | DNA | A. thaliana | Predicted polypeptide sequence is paralogous to G1275; orthologous to G3722, G3723, G3724, G3731, G3732, G3803, G3719, G3720, G3721, G3725, G3726, G3727, G3728, G3729, G3730, G3733, G3795, G3797, G3802, G3804 |
| 106 | G1274 | PRT | A. thaliana | Paralogous to G1275; Orthologous to G3722, G3723, G3724, G3731, G3732, G3803, G3719, G3720, G3721, G3725, G3726, G3727, G3728, G3729, G3730, G3733, G3795, G3797, G3802, G3804 |
| 107 | G1275 | DNA | A. thaliana | Predicted polypeptide sequence is paralogous to G1274; orthologous to G3722, G3723, G3724, G3731, G3732, G3803, G3719, G3720, G3721, G3725, G3726, G3727, G3728, G3729, G3730, G3733, G3795, G3797, G3802, G3804 |
| 108 | G1275 | PRT | A. thaliana | Paralogous to G1274; Orthologous to G3722, G3723, G3724, G3731, G3732, G3803, G3719, G3720, G3721, G3725, G3726, G3727, G3728, G3729, G3730, G3733, G3795, G3797, G3802, G3804 |
| 111 | G1293 | DNA | A. thaliana | Predicted polypeptide sequence is paralogous to G2469 |
| 112 | G1293 | PRT | A. thaliana | Paralogous to G2469 |
| 115 | G1303 | DNA | A. thaliana | Predicted polypeptide sequence is paralogous to G1233 |
| 116 | G1303 | PRT | A. thaliana | Paralogous to G1233 |
| 121 | G1309 | DNA | A. thaliana | Predicted polypeptide sequence is paralogous to G237 |
| 122 | G1309 | PRT | A. thaliana | Paralogous to G237 |
| 123 | G1313 | DNA | A. thaliana | Predicted polypeptide sequence is paralogous to G1325 |
| 124 | G1313 | PRT | A. thaliana | Paralogous to G1325 |
| 127 | G1319 | DNA | A. thaliana | Predicted polypeptide sequence is paralogous to G670 |
| 128 | G1319 | PRT | A. thaliana | Paralogous to G670 |
| 129 | G1320 | DNA | A. thaliana | Predicted polypeptide sequence is paralogous to G1321 |
| 130 | G1320 | PRT | A. thaliana | Paralogous to G1321 |
| 131 | G1324 | DNA | A. thaliana | Predicted polypeptide sequence is paralogous to G2893 |
| 132 | G1324 | PRT | A. thaliana | Paralogous to G2893 |
| 135 | G1335 | DNA | A. thaliana | Predicted polypeptide sequence is paralogous to G652 |
| 136 | G1335 | PRT | A. thaliana | Paralogous to G652 |
| 139 | G1349 | DNA | A. thaliana | Predicted polypeptide sequence is paralogous to G1887, G896 |
| 140 | G1349 | PRT | A. thaliana | Paralogous to G1887, G896 |
| 143 | G1354 | DNA | A. thaliana | Predicted polypeptide sequence is paralogous to G1355, G1453, G1766, G2534, G522, G761 |
| 144 | G1354 | PRT | A. thaliana | Paralogous to G1355, G1453, G1766, G2534, G522, G761 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 145 | G1355 | DNA | A. thaliana | Predicted polypeptide sequence is paralogous to G1354, G1453, G1766, G2534, G522, G761 |
| 146 | G1355 | PRT | A. thaliana | Paralogous to G1354, G1453, G1766, G2534, G522, G761 |
| 149 | G1364 | DNA | A. thaliana | Predicted polypeptide sequence is paralogous to G2345, G481, G482, G485; orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 150 | G1364 | PRT | A. thaliana | Paralogous to G2345, G481, G482, G485; Orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 153 | G137 | DNA | A. thaliana | Predicted polypeptide sequence is paralogous to G139, G145 |
| 154 | G137 | PRT | A. thaliana | Paralogous to G139, G145 |
| 155 | G1379 | DNA | A. thaliana | Predicted polypeptide sequence is paralogous to G12, G1277, G24; orthologous to G3656 |
| 156 | G1379 | PRT | A. thaliana | Paralogous to G12, G1277, G24; Orthologous to G3656 |
| 161 | G1384 | DNA | A. thaliana | Predicted polypeptide sequence is paralogous to G1763 |
| 162 | G1384 | PRT | A. thaliana | Paralogous to G1763 |
| 165 | G139 | DNA | A. thaliana | Predicted polypeptide sequence is paralogous to G137, G145 |
| 166 | G139 | PRT | A. thaliana | Paralogous to G137, G145 |
| 167 | G1394 | DNA | A. thaliana | Predicted polypeptide sequence is paralogous to G1395, G1396 |
| 168 | G1394 | PRT | A. thaliana | Paralogous to G1395, G1396 |
| 169 | G1395 | DNA | A. thaliana | Predicted polypeptide sequence is paralogous to G1394, G1396 |
| 170 | G1395 | PRT | A. thaliana | Paralogous to G1394, G1396 |
| 171 | G140 | DNA | A. thaliana | Predicted polypeptide sequence is paralogous to G129, G136, G146 |
| 172 | G140 | PRT | A. thaliana | Paralogous to G129, G136, G146 |
| 177 | G1419 | DNA | A. thaliana | Predicted polypeptide sequence is paralogous to G43, G46, G1004, G29; orthologous to G3849 |
| 178 | G1419 | PRT | A. thaliana | Paralogous to G43, G46, G1004, G29; Orthologous to G3849 |
| 179 | G1421 | DNA | A. thaliana | Predicted polypeptide sequence is paralogous to G1750, G440, G864; orthologous to G4079, G4080, G4283, G4284, G4285, G4286, G4287, G4288, G4289, G4290, G4291, G4292, G4293 |
| 180 | G1421 | PRT | A. thaliana | Paralogous to G1750, G440, G864; Orthologous to G4079, G4080, G4283, G4284, G4285, G4286, G4287, G4288, G4289, G4290, G4291, G4292, G4293 |
| 181 | G1423 | DNA | A. thaliana | Predicted polypeptide sequence is paralogous to G1424, G2988 |
| 182 | G1423 | PRT | A. thaliana | Paralogous to G1424, G2988 |
| 183 | G1435 | DNA | A. thaliana | Predicted polypeptide sequence is paralogous to G2741; orthologous to G4240, G4241, G4243, G4244, G4245 |
| 184 | G1435 | PRT | A. thaliana | Paralogous to G2741; Orthologous to G4240, G4241, G4243, G4244, G4245 |
| 189 | G1439 | DNA | A. thaliana | Predicted polypeptide sequence is paralogous to G1868 |
| 190 | G1439 | PRT | A. thaliana | Paralogous to G1868 |
| 195 | G145 | DNA | A. thaliana | Predicted polypeptide sequence is paralogous to G137, G139 |
| 196 | G145 | PRT | A. thaliana | Paralogous to G137, G139 |
| 197 | G1451 | DNA | A. thaliana | Predicted polypeptide sequence is paralogous to G990 |
| 198 | G1451 | PRT | A. thaliana | Paralogous to G990 |
| 199 | G1456 | DNA | A. thaliana | Predicted polypeptide sequence is paralogous to G1927, G2184 |
| 200 | G1456 | PRT | A. thaliana | Paralogous to G1927, G2184 |
| 201 | G146 | DNA | A. thaliana | Predicted polypeptide sequence is paralogous to G129, G136, G140 |
| 202 | G146 | PRT | A. thaliana | Paralogous to G129, G136, G140 |
| 203 | G1460 | DNA | A. thaliana | Predicted polypeptide sequence is paralogous to G1458, G1459 |
| 204 | G1460 | PRT | A. thaliana | Paralogous to G1458, G1459 |
| 205 | G1462 | DNA | A. thaliana | Predicted polypeptide sequence is paralogous to G1461, G1463, G1464, G1465 |
| 206 | G1462 | PRT | A. thaliana | Paralogous to G1461, G1463, G1464, G1465 |
| 213 | G1478 | DNA | A. thaliana | Predicted polypeptide sequence is paralogous to G1929; orthologous to G4019 |
| 214 | G1478 | PRT | A. thaliana | Paralogous to G1929; Orthologous to G4019 |
| 215 | G148 | DNA | A. thaliana | Predicted polypeptide sequence is paralogous to G142 |
| 216 | G148 | PRT | A. thaliana | Paralogous to G142 |
| 217 | G1480 | DNA | A. thaliana | Predicted polypeptide sequence is paralogous to G897, G899 |
| 218 | G1480 | PRT | A. thaliana | Paralogous to G897, G899 |
| 219 | G1487 | DNA | A. thaliana | Predicted polypeptide sequence is paralogous to G1505 |
| 220 | G1487 | PRT | A. thaliana | Paralogous to G1505 |
| 221 | G1488 | DNA | A. thaliana | Predicted polypeptide sequence is paralogous to G1489 |
| 222 | G1488 | PRT | A. thaliana | Paralogous to G1489 |
| 223 | G1491 | DNA | A. thaliana | Predicted polypeptide sequence is paralogous to G2128 |
| 224 | G1491 | PRT | A. thaliana | Paralogous to G2128 |
| 225 | G1494 | DNA | A. thaliana | Predicted polypeptide sequence is paralogous to G789 |
| 226 | G1494 | PRT | A. thaliana | Paralogous to G789 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 231 | G1505 | DNA | A. thaliana | Predicted polypeptide sequence is paralogous to G1487 |
| 232 | G1505 | PRT | A. thaliana | Paralogous to G1487 |
| 233 | G1506 | DNA | A. thaliana | Predicted polypeptide sequence is paralogous to G1509 |
| 234 | G1506 | PRT | A. thaliana | Paralogous to G1509 |
| 235 | G1510 | DNA | A. thaliana | Predicted polypeptide sequence is paralogous to G1779 |
| 236 | G1510 | PRT | A. thaliana | Paralogous to G1779 |
| 239 | G1518 | DNA | A. thaliana | Predicted polypeptide sequence is orthologous to G4628, G4629, G4633, G4635 |
| 240 | G1518 | PRT | A. thaliana | Orthologous to G4628, G4629, G4633, G4635 |
| 249 | G1535 | DNA | A. thaliana | Predicted polypeptide sequence is paralogous to G389 |
| 250 | G1535 | PRT | A. thaliana | Paralogous to G389 |
| 251 | G1538 | DNA | A. thaliana | Predicted polypeptide sequence is paralogous to G1545, G412 |
| 252 | G1538 | PRT | A. thaliana | Paralogous to G1545, G412 |
| 253 | G154 | DNA | A. thaliana | Predicted polypeptide sequence is paralogous to G149, G627, G1011, G1797, G1798; orthologous to G4061, G4062, G4063, G4064, G4065, G4066, G4067 |
| 254 | G154 | PRT | A. thaliana | Paralogous to G149, G627, G1011, G1797, G1798; Orthologous to G4061, G4062, G4063, G4064, G4065, G4066, G4067 |
| 257 | G1543 | DNA | A. thaliana | Predicted polypeptide sequence is orthologous to G3510, G3490, G3524, G4369, G4370, G4371 |
| 258 | G1543 | PRT | A. thaliana | Orthologous to G3510, G3490, G3524, G4369, G4370, G4371 |
| 261 | G1550 | DNA | A. thaliana | Predicted polypeptide sequence is paralogous to G1592 |
| 262 | G1550 | PRT | A. thaliana | Paralogous to G1592 |
| 265 | G1553 | DNA | A. thaliana | Predicted polypeptide sequence is paralogous to G472, G716 |
| 266 | G1553 | PRT | A. thaliana | Paralogous to G472, G716 |
| 267 | G1559 | DNA | A. thaliana | Predicted polypeptide sequence is paralogous to G632 |
| 268 | G1559 | PRT | A. thaliana | Paralogous to G632 |
| 271 | G157 | DNA | A. thaliana | Predicted polypeptide sequence is paralogous to G1759, G1842, G1843, G1844, G859 |
| 272 | G157 | PRT | A. thaliana | Paralogous to G1759, G1842, G1843, G1844, G859 |
| 273 | G159 | DNA | A. thaliana | Predicted polypeptide sequence is paralogous to G165 |
| 274 | G159 | PRT | A. thaliana | Paralogous to G165 |
| 275 | G1592 | DNA | A. thaliana | Predicted polypeptide sequence is paralogous to G1550 |
| 276 | G1592 | PRT | A. thaliana | Paralogous to G1550 |
| 277 | G1634 | DNA | A. thaliana | Predicted polypeptide sequence is paralogous to G1638, G2452, G1641, G2701 |
| 278 | G1634 | PRT | A. thaliana | Paralogous to G1638, G2452, G1641, G2701 |
| 283 | G1638 | DNA | A. thaliana | Predicted polypeptide sequence is paralogous to G2452, G1641, G1634, G2701 |
| 284 | G1638 | PRT | A. thaliana | Paralogous to G2452, G1641, G1634, G2701 |
| 289 | G1646 | DNA | A. thaliana | Predicted polypeptide sequence is paralogous to G715; orthologous to G3883, G3884, G3885, G3886, G3889, G3543, G4259 |
| 290 | G1646 | PRT | A. thaliana | Paralogous to G715; Orthologous to G3883, G3884, G3885, G3886, G3889, G3543, G4259 |
| 291 | G165 | DNA | A. thaliana | Predicted polypeptide sequence is paralogous to G159 |
| 292 | G165 | PRT | A. thaliana | Paralogous to G159 |
| 299 | G166 | DNA | A. thaliana | Predicted polypeptide sequence is paralogous to G164 |
| 300 | G166 | PRT | A. thaliana | Paralogous to G164 |
| 313 | G168 | DNA | A. thaliana | Predicted polypeptide sequence is paralogous to G170, G2065 |
| 314 | G168 | PRT | A. thaliana | Paralogous to G170, G2065 |
| 319 | G1750 | DNA | A. thaliana | Predicted polypeptide sequence is paralogous to G1421, G440, G864; orthologous to G4079, G4080, G4283, G4284, G4285, G4286, G4287, G4288, G4289, G4290, G4291, G4292, G4293 |
| 320 | G1750 | PRT | A. thaliana | Paralogous to G1421, G440, G864; Orthologous to G4079, G4080, G4283, G4284, G4285, G4286, G4287, G4288, G4289, G4290, G4291, G4292, G4293 |
| 323 | G1752 | DNA | A. thaliana | Predicted polypeptide sequence is paralogous to G2512 |
| 324 | G1752 | PRT | A. thaliana | Paralogous to G2512 |
| 325 | G1755 | DNA | A. thaliana | Predicted polypeptide sequence is paralogous to G1754 |
| 326 | G1755 | PRT | A. thaliana | Paralogous to G1754 |
| 327 | G1757 | DNA | A. thaliana | Predicted polypeptide sequence is paralogous to G1847 |
| 328 | G1757 | PRT | A. thaliana | Paralogous to G1847 |
| 331 | G1759 | DNA | A. thaliana | Predicted polypeptide sequence is paralogous to G157, G1842, G1843, G1844, G859 |
| 332 | G1759 | PRT | A. thaliana | Paralogous to G157, G1842, G1843, G1844, G859 |
| 333 | G1760 | DNA | A. thaliana | Predicted polypeptide sequence is paralogous to G152, G153, G860; orthologous to G3479, G3480, G3481, G3482, G3483, G3484, G3485, G3487, G3488, G3489, G3980, G3981, G3982 |
| 334 | G1760 | PRT | A. thaliana | Paralogous to G152, G153, G860; Orthologous to G3479, G3480, G3481, G3482, G3483, G3484, G3485, G3487, G3488, G3489, G3980, G3981, G3982 |
| 335 | G1763 | DNA | A. thaliana | Predicted polypeptide sequence is paralogous to G1384 |
| 336 | G1763 | PRT | A. thaliana | Paralogous to G1384 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 353 | G1789 | DNA | A. thaliana | Predicted polypeptide sequence is paralogous to G1911, G2721, G997 |
| 354 | G1789 | PRT | A. thaliana | Paralogous to G1911, G2721, G997 |
| 357 | G1797 | DNA | A. thaliana | Predicted polypeptide sequence is paralogous to G149, G627, G1011, G154, G1798; orthologous to G4061, G4062, G4063, G4064, G4065, G4066, G4067 |
| 358 | G1797 | PRT | A. thaliana | Paralogous to G149, G627, G1011, G154, G1798; Orthologous to G4061, G4062, G4063, G4064, G4065, G4066, G4067 |
| 363 | G1806 | DNA | A. thaliana | Predicted polypeptide sequence is paralogous to G1198, G554, G555, G556, G558, G578, G629 |
| 364 | G1806 | PRT | A. thaliana | Paralogous to G1198, G554, G555, G556, G558, G578, G629 |
| 365 | G1807 | DNA | A. thaliana | Predicted polypeptide sequence is paralogous to G1050 |
| 366 | G1807 | PRT | A. thaliana | Paralogous to G1050 |
| 367 | G1808 | DNA | A. thaliana | Predicted polypeptide sequence is paralogous to G1047 |
| 368 | G1808 | PRT | A. thaliana | Paralogous to G1047 |
| 369 | G1809 | DNA | A. thaliana | Predicted polypeptide sequence is paralogous to G557; orthologous to G4627, G4630, G4631, G4632, G5158 |
| 370 | G1809 | PRT | A. thaliana | Paralogous to G557; Orthologous to G4627, G4630, G4631, G4632, G5158 |
| 377 | G1821 | DNA | A. thaliana | Predicted polypeptide sequence is paralogous to G620; orthologous to G3839, G3937, G3939 |
| 378 | G1821 | PRT | A. thaliana | Paralogous to G620; Orthologous to G3839, G3937, G3939 |
| 381 | G1836 | DNA | A. thaliana | Predicted polypeptide sequence is paralogous to G1818 |
| 382 | G1836 | PRT | A. thaliana | Paralogous to G1818 |
| 383 | G1838 | DNA | A. thaliana | Predicted polypeptide sequence is paralogous to G2572 |
| 384 | G1838 | PRT | A. thaliana | Paralogous to G2572 |
| 385 | G1839 | DNA | A. thaliana | Predicted polypeptide sequence is paralogous to G1749, G1840 |
| 386 | G1839 | PRT | A. thaliana | Paralogous to G1749, G1840 |
| 387 | G1842 | DNA | A. thaliana | Predicted polypeptide sequence is paralogous to G157, G1759, G1843, G1844, G859 |
| 388 | G1842 | PRT | A. thaliana | Paralogous to G157, G1759, G1843, G1844, G859 |
| 389 | G1843 | DNA | A. thaliana | Predicted polypeptide sequence is paralogous to G157, G1759, G1842, G1844, G859 |
| 390 | G1843 | PRT | A. thaliana | Paralogous to G157, G1759, G1842, G1844, G859 |
| 391 | G1844 | DNA | A. thaliana | Predicted polypeptide sequence is paralogous to G157, G1759, G1842, G1843, G859 |
| 392 | G1844 | PRT | A. thaliana | Paralogous to G157, G1759, G1842, G1843, G859 |
| 393 | G1847 | DNA | A. thaliana | Predicted polypeptide sequence is paralogous to G1757 |
| 394 | G1847 | PRT | A. thaliana | Paralogous to G1757 |
| 395 | G1850 | DNA | A. thaliana | Predicted polypeptide sequence is paralogous to G1181 |
| 396 | G1850 | PRT | A. thaliana | Paralogous to G1181 |
| 397 | G1855 | DNA | A. thaliana | Predicted polypeptide sequence is paralogous to G1186 |
| 398 | G1855 | PRT | A. thaliana | Paralogous to G1186 |
| 399 | G1863 | DNA | A. thaliana | Predicted polypeptide sequence is paralogous to G2334 |
| 400 | G1863 | PRT | A. thaliana | Paralogous to G2334 |
| 403 | G1881 | DNA | A. thaliana | Predicted polypeptide sequence is paralogous to G902 |
| 404 | G1881 | PRT | A. thaliana | Paralogous to G902 |
| 407 | G1888 | DNA | A. thaliana | Predicted polypeptide sequence is paralogous to G1482; orthologous to G5159 |
| 408 | G1888 | PRT | A. thaliana | Paralogous to G1482; Orthologous to G5159 |
| 415 | G19 | DNA | A. thaliana | Predicted polypeptide sequence is orthologous to G3851 |
| 416 | G19 | PRT | A. thaliana | Orthologous to G3851 |
| 419 | G1901 | DNA | A. thaliana | Predicted polypeptide sequence is paralogous to G1902 |
| 420 | G1901 | PRT | A. thaliana | Paralogous to G1902 |
| 421 | G1903 | DNA | A. thaliana | Predicted polypeptide sequence is paralogous to G1895 |
| 422 | G1903 | PRT | A. thaliana | Paralogous to G1895 |
| 425 | G1917 | DNA | A. thaliana | Predicted polypeptide sequence is paralogous to G383 |
| 426 | G1917 | PRT | A. thaliana | Paralogous to G383 |
| 439 | G1944 | DNA | A. thaliana | Predicted polypeptide sequence is paralogous to G605 |
| 440 | G1944 | PRT | A. thaliana | Paralogous to G605 |
| 447 | G1959 | DNA | A. thaliana | Predicted polypeptide sequence is paralogous to G1197 |
| 448 | G1959 | PRT | A. thaliana | Paralogous to G1197 |
| 449 | G1965 | DNA | A. thaliana | Predicted polypeptide sequence is paralogous to G1891 |
| 450 | G1965 | PRT | A. thaliana | Paralogous to G1891 |
| 457 | G1987 | DNA | A. thaliana | Predicted polypeptide sequence is paralogous to G1986 |
| 458 | G1987 | PRT | A. thaliana | Paralogous to G1986 |
| 461 | G1991 | DNA | A. thaliana | Predicted polypeptide sequence is paralogous to G2888 |
| 462 | G1991 | PRT | A. thaliana | Paralogous to G2888 |
| 463 | G2 | DNA | A. thaliana | Predicted polypeptide sequence is paralogous to G1416 |
| 464 | G2 | PRT | A. thaliana | Paralogous to G1416 |
| 469 | G2006 | DNA | A. thaliana | Predicted polypeptide sequence is paralogous to G208 |
| 470 | G2006 | PRT | A. thaliana | Paralogous to G208 |
| 471 | G2007 | DNA | A. thaliana | Predicted polypeptide sequence is paralogous to G231 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 472 | G2007 | PRT | A. thaliana | Paralogous to G231 |
| 475 | G2015 | DNA | A. thaliana | Predicted polypeptide sequence is paralogous to G2016, G2017 |
| 476 | G2015 | PRT | A. thaliana | Paralogous to G2016, G2017 |
| 477 | G2018 | DNA | A. thaliana | Predicted polypeptide sequence is paralogous to G2022 |
| 478 | G2018 | PRT | A. thaliana | Paralogous to G2022 |
| 479 | G2020 | DNA | A. thaliana | Predicted polypeptide sequence is paralogous to G2023, G2025 |
| 480 | G2020 | PRT | A. thaliana | Paralogous to G2023, G2025 |
| 481 | G204 | DNA | A. thaliana | Predicted polypeptide sequence is paralogous to G2717, G2709 |
| 482 | G204 | PRT | A. thaliana | Paralogous to G2717, G2709 |
| 483 | G2053 | DNA | A. thaliana | Predicted polypeptide sequence is paralogous to G515, G516, G517 |
| 484 | G2053 | PRT | A. thaliana | Paralogous to G515, G516, G517 |
| 485 | G2057 | DNA | A. thaliana | Predicted polypeptide sequence is paralogous to G618 |
| 486 | G2057 | PRT | A. thaliana | Paralogous to G618 |
| 489 | G206 | DNA | A. thaliana | Predicted polypeptide sequence is paralogous to G1307 |
| 490 | G206 | PRT | A. thaliana | Paralogous to G1307 |
| 493 | G2062 | DNA | A. thaliana | Predicted polypeptide sequence is paralogous to G2063, G2297, G2689 |
| 494 | G2062 | PRT | A. thaliana | Paralogous to G2063, G2297, G2689 |
| 495 | G2063 | DNA | A. thaliana | Predicted polypeptide sequence is paralogous to G2062, G2297, G2689 |
| 496 | G2063 | PRT | A. thaliana | Paralogous to G2062, G2297, G2689 |
| 499 | G2071 | DNA | A. thaliana | Predicted polypeptide sequence is paralogous to G1058 |
| 500 | G2071 | PRT | A. thaliana | Paralogous to G1058 |
| 513 | G2094 | DNA | A. thaliana | Predicted polypeptide sequence is paralogous to G1508 |
| 514 | G2094 | PRT | A. thaliana | Paralogous to G1508 |
| 515 | G21 | DNA | A. thaliana | Predicted polypeptide sequence is paralogous to G1381 |
| 516 | G21 | PRT | A. thaliana | Paralogous to G1381 |
| 517 | G210 | DNA | A. thaliana | Predicted polypeptide sequence is paralogous to G2426 |
| 518 | G210 | PRT | A. thaliana | Paralogous to G2426 |
| 521 | G2107 | DNA | A. thaliana | Predicted polypeptide sequence is paralogous to G40, G2513, G41, G42, G912; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 522 | G2107 | PRT | A. thaliana | Paralogous to G40, G2513, G41, G42, G912; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 537 | G2130 | DNA | A. thaliana | Predicted polypeptide sequence is paralogous to G1008 |
| 538 | G2130 | PRT | A. thaliana | Paralogous to G1008 |
| 547 | G2144 | DNA | A. thaliana | Predicted polypeptide sequence is paralogous to G1942 |
| 548 | G2144 | PRT | A. thaliana | Paralogous to G1942 |
| 549 | G2145 | DNA | A. thaliana | Predicted polypeptide sequence is paralogous to G2148 |
| 550 | G2145 | PRT | A. thaliana | Paralogous to G2148 |
| 553 | G2148 | DNA | A. thaliana | Predicted polypeptide sequence is paralogous to G2145 |
| 554 | G2148 | PRT | A. thaliana | Paralogous to G2145 |
| 559 | G2156 | DNA | A. thaliana | Predicted polypeptide sequence is paralogous to G1067, G1073; orthologous to G3399, G3400 |
| 560 | G2156 | PRT | A. thaliana | Paralogous to G1067, G1073; Orthologous to G3399, G3400 |
| 561 | G2157 | DNA | A. thaliana | Predicted polypeptide sequence is orthologous to G4570 |
| 562 | G2157 | PRT | A. thaliana | Orthologous to G4570 |
| 563 | G216 | DNA | A. thaliana | Predicted polypeptide sequence is paralogous to G2719 |
| 564 | G216 | PRT | A. thaliana | Paralogous to G2719 |
| 569 | G22 | DNA | A. thaliana | Predicted polypeptide sequence is paralogous to G1006, G28; orthologous to G3430, G3659, G3660, G3661, G3717, G3718, G3841, G3843, G3844, G3845, G3846, G3848, G3852, G3856, G3857, G3858, G3864, G3865, G4626, G5171 |
| 570 | G22 | PRT | A. thaliana | Paralogous to G1006, G28; Orthologous to G3430, G3659, G3660, G3661, G3717, G3718, G3841, G3843, G3844, G3845, G3846, G3848, G3852, G3856, G3857, G3858, G3864, G3865, G4626, G5171 |
| 573 | G2215 | DNA | A. thaliana | Predicted polypeptide sequence is paralogous to G2216 |
| 574 | G2215 | PRT | A. thaliana | Paralogous to G2216 |
| 587 | G225 | DNA | A. thaliana | Predicted polypeptide sequence is paralogous to G1816, G226, G2718, G682, G3930; orthologous to G3392, G3393, G3431, G3444, G3445, G3446, G3447, G3448, G3449, G3450 |
| 588 | G225 | PRT | A. thaliana | Paralogous to G1816, G226, G2718, G682, G3930; Orthologous to G3392, G3393, G3431, G3444, G3445, G3446, G3447, G3448, G3449, G3450 |
| 595 | G227 | DNA | A. thaliana | Predicted polypeptide sequence is paralogous to G207, G230, G242; orthologous to G4218, G4219, G4220, G4221, G4222, G4223, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G4224, G4225, G4226, G4227, G4228, G4229, G4230, G4231, G4232, G4234, G4235, G4236, G4237, G4238 |
| 596 | G227 | PRT | *A. thaliana* | Paralogous to G207, G230, G242; Orthologous to G4218, G4219, G4220, G4221, G4222, G4223, G4224, G4225, G4226, G4227, G4228, G4229, G4230, G4231, G4232, G4234, G4235, G4236, G4237, G4238 |
| 597 | G229 | DNA | *A. thaliana* | Predicted polypeptide sequence is paralogous to G678 |
| 598 | G229 | PRT | *A. thaliana* | Paralogous to G678 |
| 609 | G2299 | DNA | *A. thaliana* | Predicted polypeptide sequence is paralogous to G16 |
| 610 | G2299 | PRT | *A. thaliana* | Paralogous to G16 |
| 617 | G2316 | DNA | *A. thaliana* | Predicted polypeptide sequence is paralogous to G1817 |
| 618 | G2316 | PRT | *A. thaliana* | Paralogous to G1817 |
| 621 | G232 | DNA | *A. thaliana* | Predicted polypeptide sequence is paralogous to G234 |
| 622 | G232 | PRT | *A. thaliana* | Paralogous to G234 |
| 623 | G2334 | DNA | *A. thaliana* | Predicted polypeptide sequence is paralogous to G1863 |
| 624 | G2334 | PRT | *A. thaliana* | Paralogous to G1863 |
| 625 | G2342 | DNA | *A. thaliana* | Predicted polypeptide sequence is paralogous to G2427 |
| 626 | G2342 | PRT | *A. thaliana* | Paralogous to G2427 |
| 629 | G2344 | DNA | *A. thaliana* | Predicted polypeptide sequence is paralogous to G929; orthologous to G4267, G4268 |
| 630 | G2344 | PRT | *A. thaliana* | Paralogous to G929; Orthologous to G4267, G4268 |
| 631 | G236 | DNA | *A. thaliana* | Predicted polypeptide sequence is paralogous to G2715 |
| 632 | G236 | PRT | *A. thaliana* | Paralogous to G2715 |
| 633 | G237 | DNA | *A. thaliana* | Predicted polypeptide sequence is paralogous to G1309 |
| 634 | G237 | PRT | *A. thaliana* | Paralogous to G1309 |
| 635 | G2371 | DNA | *A. thaliana* | Predicted polypeptide sequence is paralogous to G925 |
| 636 | G2371 | PRT | *A. thaliana* | Paralogous to G925 |
| 641 | G2377 | DNA | *A. thaliana* | Predicted polypeptide sequence is paralogous to G2379 |
| 642 | G2377 | PRT | *A. thaliana* | Paralogous to G2379 |
| 645 | G2394 | DNA | *A. thaliana* | Predicted polypeptide sequence is paralogous to G1108 |
| 646 | G2394 | PRT | *A. thaliana* | Paralogous to G1108 |
| 649 | G241 | DNA | *A. thaliana* | Predicted polypeptide sequence is paralogous to G233; orthologous to G4306, G4307, G4308, G4309, G4310 |
| 650 | G241 | PRT | *A. thaliana* | Paralogous to G233; Orthologous to G4306, G4307, G4308, G4309, G4310 |
| 653 | G242 | DNA | *A. thaliana* | Predicted polypeptide sequence is paralogous to G207, G227, G230; orthologous to G4218, G4219, G4220, G4221, G4222, G4223, G4224, G4225, G4226, G4227, G4228, G4229, G4230, G4231, G4232, G4234, G4235, G4236, G4237, G4238 |
| 654 | G242 | PRT | *A. thaliana* | Paralogous to G207, G227, G230; Orthologous to G4218, G4219, G4220, G4221, G4222, G4223, G4224, G4225, G4226, G4227, G4228, G4229, G4230, G4231, G4232, G4234, G4235, G4236, G4237, G4238 |
| 655 | G2421 | DNA | *A. thaliana* | Predicted polypeptide sequence is paralogous to G1329, G2422, G663 |
| 656 | G2421 | PRT | *A. thaliana* | Paralogous to G1329, G2422, G663 |
| 657 | G2422 | DNA | *A. thaliana* | Predicted polypeptide sequence is paralogous to G1329, G2421, G663 |
| 658 | G2422 | PRT | *A. thaliana* | Paralogous to G1329, G2421, G663 |
| 661 | G2426 | DNA | *A. thaliana* | Predicted polypeptide sequence is paralogous to G210 |
| 662 | G2426 | PRT | *A. thaliana* | Paralogous to G210 |
| 663 | G2427 | DNA | *A. thaliana* | Predicted polypeptide sequence is paralogous to G2342 |
| 664 | G2427 | PRT | *A. thaliana* | Paralogous to G2342 |
| 665 | G243 | DNA | *A. thaliana* | Predicted polypeptide sequence is paralogous to G201, G202 |
| 666 | G243 | PRT | *A. thaliana* | Paralogous to G201, G202 |
| 667 | G2437 | DNA | *A. thaliana* | Predicted polypeptide sequence is paralogous to G1507 |
| 668 | G2437 | PRT | *A. thaliana* | Paralogous to G1507 |
| 671 | G2452 | DNA | *A. thaliana* | Predicted polypeptide sequence is paralogous to G1638, G1641, G1634, G2701 |
| 672 | G2452 | PRT | *A. thaliana* | Paralogous to G1638, G1641, G1634, G2701 |
| 673 | G2454 | DNA | *A. thaliana* | Predicted polypeptide sequence is paralogous to G2456 |
| 674 | G2454 | PRT | *A. thaliana* | Paralogous to G2456 |
| 675 | G2457 | DNA | *A. thaliana* | Predicted polypeptide sequence is paralogous to G2459 |
| 676 | G2457 | PRT | *A. thaliana* | Paralogous to G2459 |
| 681 | G2484 | DNA | *A. thaliana* | Predicted polypeptide sequence is paralogous to G1232 |
| 682 | G2484 | PRT | *A. thaliana* | Paralogous to G1232 |
| 685 | G2505 | DNA | *A. thaliana* | Predicted polypeptide sequence is paralogous to G2635 |
| 686 | G2505 | PRT | *A. thaliana* | Paralogous to G2635 |
| 691 | G2535 | DNA | *A. thaliana* | Predicted polypeptide sequence is paralogous to G957, G961 |
| 692 | G2535 | PRT | *A. thaliana* | Paralogous to G957, G961 |
| 693 | G2546 | DNA | *A. thaliana* | Predicted polypeptide sequence is paralogous to G2550 |
| 694 | G2546 | PRT | *A. thaliana* | Paralogous to G2550 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 695 | G255 | DNA | A. thaliana | Predicted polypeptide sequence is paralogous to G197, G664; orthologous to G3503, G3504, G3505, G3506, G3507, G3508, G3509, G3529, G3531, G3532, G3533, G3534, G3527, G3528, G4637, G4638, G4639, G4640 |
| 696 | G255 | PRT | A. thaliana | Paralogous to G197, G664; Orthologous to G3503, G3504, G3505, G3506, G3507, G3508, G3509, G3529, G3531, G3532, G3533, G3534, G3527, G3528, G4637, G4638, G4639, G4640 |
| 697 | G2550 | DNA | A. thaliana | Predicted polypeptide sequence is paralogous to G2546 |
| 698 | G2550 | PRT | A. thaliana | Paralogous to G2546 |
| 701 | G2553 | DNA | A. thaliana | Predicted polypeptide sequence is paralogous to G2556 |
| 702 | G2553 | PRT | A. thaliana | Paralogous to G2556 |
| 705 | G2555 | DNA | A. thaliana | Predicted polypeptide sequence is paralogous to G1134 |
| 706 | G2555 | PRT | A. thaliana | Paralogous to G1134 |
| 707 | G2556 | DNA | A. thaliana | Predicted polypeptide sequence is paralogous to G2553 |
| 708 | G2556 | PRT | A. thaliana | Paralogous to G2553 |
| 711 | G2574 | DNA | A. thaliana | Predicted polypeptide sequence is paralogous to G2110 |
| 712 | G2574 | PRT | A. thaliana | Paralogous to G2110 |
| 723 | G2586 | DNA | A. thaliana | Predicted polypeptide sequence is paralogous to G2587, G2686 |
| 724 | G2586 | PRT | A. thaliana | Paralogous to G2587, G2686 |
| 733 | G261 | DNA | A. thaliana | Predicted polypeptide sequence is paralogous to G265 |
| 734 | G261 | PRT | A. thaliana | Paralogous to G265 |
| 735 | G2616 | DNA | A. thaliana | Predicted polypeptide sequence is paralogous to G2809 |
| 736 | G2616 | PRT | A. thaliana | Paralogous to G2809 |
| 741 | G2632 | DNA | A. thaliana | Predicted polypeptide sequence is paralogous to G926; orthologous to G3924, G4261 |
| 742 | G2632 | PRT | A. thaliana | Paralogous to G926; Orthologous to G3924, G4261 |
| 743 | G2639 | DNA | A. thaliana | Predicted polypeptide sequence is paralogous to G2640, G2642 |
| 744 | G2639 | PRT | A. thaliana | Paralogous to G2640, G2642 |
| 747 | G2640 | DNA | A. thaliana | Predicted polypeptide sequence is paralogous to G2639, G2642 |
| 748 | G2640 | PRT | A. thaliana | Paralogous to G2639, G2642 |
| 749 | G265 | DNA | A. thaliana | Predicted polypeptide sequence is paralogous to G261 |
| 750 | G265 | PRT | A. thaliana | Paralogous to G261 |
| 751 | G2650 | DNA | A. thaliana | Predicted polypeptide sequence is paralogous to G617 |
| 752 | G2650 | PRT | A. thaliana | Paralogous to G617 |
| 753 | G2655 | DNA | A. thaliana | Predicted polypeptide sequence is paralogous to G1879 |
| 754 | G2655 | PRT | A. thaliana | Paralogous to G1879 |
| 761 | G268 | DNA | A. thaliana | Predicted polypeptide sequence is paralogous to G2876, G820 |
| 762 | G268 | PRT | A. thaliana | Paralogous to G2876, G820 |
| 765 | G2686 | DNA | A. thaliana | Predicted polypeptide sequence is paralogous to G2586, G2587 |
| 766 | G2686 | PRT | A. thaliana | Paralogous to G2586, G2587 |
| 769 | G2696 | DNA | A. thaliana | Predicted polypeptide sequence is paralogous to G2698 |
| 770 | G2696 | PRT | A. thaliana | Paralogous to G2698 |
| 771 | G2697 | DNA | A. thaliana | Predicted polypeptide sequence is paralogous to G1768, G2633, G313, G852; orthologous to G3815, G3825 |
| 772 | G2697 | PRT | A. thaliana | Paralogous to G1768, G2633, G313, G852; Orthologous to G3815, G3825 |
| 773 | G2699 | DNA | A. thaliana | Predicted polypeptide sequence is paralogous to G314 |
| 774 | G2699 | PRT | A. thaliana | Paralogous to G314 |
| 781 | G2715 | DNA | A. thaliana | Predicted polypeptide sequence is paralogous to G236 |
| 782 | G2715 | PRT | A. thaliana | Paralogous to G236 |
| 783 | G2719 | DNA | A. thaliana | Predicted polypeptide sequence is paralogous to G216 |
| 784 | G2719 | PRT | A. thaliana | Paralogous to G216 |
| 787 | G2721 | DNA | A. thaliana | Predicted polypeptide sequence is paralogous to G1789, G1911, G997 |
| 788 | G2721 | PRT | A. thaliana | Paralogous to G1789, G1911, G997 |
| 793 | G273 | DNA | A. thaliana | Predicted polypeptide sequence is paralogous to G819 |
| 794 | G273 | PRT | A. thaliana | Paralogous to G819 |
| 795 | G2739 | DNA | A. thaliana | Predicted polypeptide sequence is paralogous to G312 |
| 796 | G2739 | PRT | A. thaliana | Paralogous to G312 |
| 797 | G274 | DNA | A. thaliana | Predicted polypeptide sequence is paralogous to G833 |
| 798 | G274 | PRT | A. thaliana | Paralogous to G833 |
| 799 | G2742 | DNA | A. thaliana | Predicted polypeptide sequence is paralogous to G1492 |
| 800 | G2742 | PRT | A. thaliana | Paralogous to G1492 |
| 801 | G2747 | DNA | A. thaliana | Predicted polypeptide sequence is paralogous to G1010 |
| 802 | G2747 | PRT | A. thaliana | Paralogous to G1010 |
| 809 | G2766 | DNA | A. thaliana | Predicted polypeptide sequence is paralogous to G2149; orthologous to G3763, G3764, G3740, G3741, G3772 |
| 810 | G2766 | PRT | A. thaliana | Paralogous to G2149; Orthologous to G3763, G3764, G3740, G3741, G3772 |
| 815 | G2779 | DNA | A. thaliana | Predicted polypeptide sequence is paralogous to G2859 |
| 816 | G2779 | PRT | A. thaliana | Paralogous to G2859 |
| 817 | G2789 | DNA | A. thaliana | Predicted polypeptide sequence is paralogous to G596; orthologous to G3457 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 818 | G2789 | PRT | A. thaliana | Paralogous to G596; Orthologous to G3457 |
| 819 | G279 | DNA | A. thaliana | Predicted polypeptide sequence is paralogous to G1029, G1033 |
| 820 | G279 | PRT | A. thaliana | Paralogous to G1029, G1033 |
| 823 | G2791 | DNA | A. thaliana | Predicted polypeptide sequence is paralogous to G589, G1061; orthologous to G3748, G3749, G3774, G3760 |
| 824 | G2791 | PRT | A. thaliana | Paralogous to G589, G1061; Orthologous to G3748, G3749, G3774, G3760 |
| 827 | G28 | DNA | A. thaliana | Predicted polypeptide sequence is paralogous to G22, G1006; orthologous to G3430, G3659, G3660, G3661, G3717, G3718, G3841, G3843, G3844, G3845, G3846, G3848, G3852, G3856, G3857, G3858, G3864, G3865, G4626, G5171 |
| 828 | G28 | PRT | A. thaliana | Paralogous to G22, G1006; Orthologous to G3430, G3659, G3660, G3661, G3717, G3718, G3841, G3843, G3844, G3845, G3846, G3848, G3852, G3856, G3857, G3858, G3864, G3865, G4626, G5171 |
| 833 | G2802 | DNA | A. thaliana | Predicted polypeptide sequence is paralogous to G1672 |
| 834 | G2802 | PRT | A. thaliana | Paralogous to G1672 |
| 839 | G2809 | DNA | A. thaliana | Predicted polypeptide sequence is paralogous to G2616 |
| 840 | G2809 | PRT | A. thaliana | Paralogous to G2616 |
| 841 | G2818 | DNA | A. thaliana | Predicted polypeptide sequence is paralogous to G2817 |
| 842 | G2818 | PRT | A. thaliana | Paralogous to G2817 |
| 843 | G2826 | DNA | A. thaliana | Predicted polypeptide sequence is paralogous to G1995, G2838, G361, G362, G370 |
| 844 | G2826 | PRT | A. thaliana | Paralogous to G1995, G2838, G361, G362, G370 |
| 845 | G2831 | DNA | A. thaliana | Predicted polypeptide sequence is paralogous to G903 |
| 846 | G2831 | PRT | A. thaliana | Paralogous to G903 |
| 851 | G2838 | DNA | A. thaliana | Predicted polypeptide sequence is paralogous to G1995, G2826, G361, G362, G370 |
| 852 | G2838 | PRT | A. thaliana | Paralogous to G1995, G2826, G361, G362, G370 |
| 853 | G2840 | DNA | A. thaliana | Predicted polypeptide sequence is paralogous to G2834 |
| 854 | G2840 | PRT | A. thaliana | Paralogous to G2834 |
| 861 | G2855 | DNA | A. thaliana | Predicted polypeptide sequence is paralogous to G2158 |
| 862 | G2855 | PRT | A. thaliana | Paralogous to G2158 |
| 867 | G2876 | DNA | A. thaliana | Predicted polypeptide sequence is paralogous to G268, G820 |
| 868 | G2876 | PRT | A. thaliana | Paralogous to G268, G820 |
| 873 | G2887 | DNA | A. thaliana | Predicted polypeptide sequence is paralogous to G521 |
| 874 | G2887 | PRT | A. thaliana | Paralogous to G521 |
| 877 | G2893 | DNA | A. thaliana | Predicted polypeptide sequence is paralogous to G1324 |
| 878 | G2893 | PRT | A. thaliana | Paralogous to G1324 |
| 879 | G2896 | DNA | A. thaliana | Predicted polypeptide sequence is paralogous to G2895 |
| 880 | G2896 | PRT | A. thaliana | Paralogous to G2895 |
| 883 | G29 | DNA | A. thaliana | Predicted polypeptide sequence is paralogous to G1419, G43, G46, G1004; orthologous to G3849 |
| 884 | G29 | PRT | A. thaliana | Paralogous to G1419, G43, G46, G1004; Orthologous to G3849 |
| 885 | G290 | DNA | A. thaliana | Predicted polypeptide sequence is paralogous to G289 |
| 886 | G290 | PRT | A. thaliana | Paralogous to G289 |
| 887 | G2902 | DNA | A. thaliana | Predicted polypeptide sequence is paralogous to G2903 |
| 888 | G2902 | PRT | A. thaliana | Paralogous to G2903 |
| 911 | G2965 | DNA | A. thaliana | Predicted polypeptide sequence is paralogous to G3065 |
| 912 | G2965 | PRT | A. thaliana | Paralogous to G3065 |
| 913 | G2966 | DNA | A. thaliana | Predicted polypeptide sequence is paralogous to G3067 |
| 914 | G2966 | PRT | A. thaliana | Paralogous to G3067 |
| 917 | G2979 | DNA | A. thaliana | Predicted polypeptide sequence is paralogous to G2980 |
| 918 | G2979 | PRT | A. thaliana | Paralogous to G2980 |
| 919 | G2980 | DNA | A. thaliana | Predicted polypeptide sequence is paralogous to G2979 |
| 920 | G2980 | PRT | A. thaliana | Paralogous to G2979 |
| 921 | G2982 | DNA | A. thaliana | Predicted polypeptide sequence is paralogous to G2981 |
| 922 | G2982 | PRT | A. thaliana | Paralogous to G2981 |
| 927 | G2989 | DNA | A. thaliana | Predicted polypeptide sequence is paralogous to G2990; orthologous to G3680, G3681, G3691, G3859, G3860, G3861, G3934 |
| 928 | G2989 | PRT | A. thaliana | Paralogous to G2990; Orthologous to G3680, G3681, G3691, G3859, G3860, G3861, G3934 |
| 929 | G2990 | DNA | A. thaliana | Predicted polypeptide sequence is paralogous to G2989; orthologous to G3680, G3681, G3691, G3859, G3860, G3861, G3934 |
| 930 | G2990 | PRT | A. thaliana | Paralogous to G2989; Orthologous to G3680, G3681, G3691, G3859, G3860, G3861, G3934 |
| 933 | G2993 | DNA | A. thaliana | Predicted polypeptide sequence is paralogous to G2994 |
| 934 | G2993 | PRT | A. thaliana | Paralogous to G2994 |
| 939 | G2998 | DNA | A. thaliana | Predicted polypeptide sequence is paralogous to G2999; orthologous to G3663 |
| 940 | G2998 | PRT | A. thaliana | Paralogous to G2999; Orthologous to G3663 |
| 941 | G2999 | DNA | A. thaliana | Predicted polypeptide sequence is paralogous to G2998; orthologous to G3663 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 942 | G2999 | PRT | A. thaliana | Paralogous to G2998; Orthologous to G3663 |
| 943 | G3 | DNA | A. thaliana | Predicted polypeptide sequence is paralogous to G10 |
| 944 | G3 | PRT | A. thaliana | Paralogous to G10 |
| 945 | G30 | DNA | A. thaliana | Predicted polypeptide sequence is paralogous to G1791, G1792, G1795; orthologous to G3380, G3381, G3383, G3515, G3516, G3517, G3518, G3519, G3520, G3735, G3736, G3737, G3794, G3739, G3929, G4328, G4329, G4330 |
| 946 | G30 | PRT | A. thaliana | Paralogous to G1791, G1792, G1795; Orthologous to G3380, G3381, G3383, G3515, G3516, G3517, G3518, G3519, G3520, G3735, G3736, G3737, G3794, G3739, G3929, G4328, G4329, G4330 |
| 951 | G3009 | DNA | A. thaliana | Predicted polypeptide sequence is paralogous to G2738, G307, G308, G309; orthologous to G3816, G3817, G3818, G3819 |
| 952 | G3009 | PRT | A. thaliana | Paralogous to G2738, G307, G308, G309; Orthologous to G3816, G3817, G3818, G3819 |
| 961 | G3034 | DNA | A. thaliana | Predicted polypeptide sequence is paralogous to G1040, G729, G730 |
| 962 | G3034 | PRT | A. thaliana | Paralogous to G1040, G729, G730 |
| 967 | G3041 | DNA | A. thaliana | Predicted polypeptide sequence is paralogous to G760 |
| 968 | G3041 | PRT | A. thaliana | Paralogous to G760 |
| 973 | G306 | DNA | A. thaliana | Predicted polypeptide sequence is orthologous to G3821, G3822 |
| 974 | G306 | PRT | A. thaliana | Orthologous to G3821, G3822 |
| 983 | G3067 | DNA | A. thaliana | Predicted polypeptide sequence is paralogous to G2966 |
| 984 | G3067 | PRT | A. thaliana | Paralogous to G2966 |
| 985 | G3074 | DNA | A. thaliana | Predicted polypeptide sequence is orthologous to G4253, G4254, G4255 |
| 986 | G3074 | PRT | A. thaliana | Orthologous to G4253, G4254, G4255 |
| 989 | G3080 | DNA | A. thaliana | Predicted polypeptide sequence is paralogous to G3079 |
| 990 | G3080 | PRT | A. thaliana | Paralogous to G3079 |
| 991 | G309 | DNA | A. thaliana | Predicted polypeptide sequence is paralogous to G2738, G3009, G307, G308; orthologous to G3816, G3817, G3818, G3819 |
| 992 | G309 | PRT | A. thaliana | Paralogous to G2738, G3009, G307, G308; Orthologous to G3816, G3817, G3818, G3819 |
| 1009 | G326 | DNA | A. thaliana | Predicted polypeptide sequence is paralogous to G1337 |
| 1010 | G326 | PRT | A. thaliana | Paralogous to G1337 |
| 1011 | G328 | DNA | A. thaliana | Predicted polypeptide sequence is paralogous to G2436, G2443 |
| 1012 | G328 | PRT | A. thaliana | Paralogous to G2436, G2443 |
| 1021 | G35 | DNA | A. thaliana | Predicted polypeptide sequence is paralogous to G2138 |
| 1022 | G35 | PRT | A. thaliana | Paralogous to G2138 |
| 1023 | G350 | DNA | A. thaliana | Predicted polypeptide sequence is paralogous to G351, G545 |
| 1024 | G350 | PRT | A. thaliana | Paralogous to G351, G545 |
| 1025 | G351 | DNA | A. thaliana | Predicted polypeptide sequence is paralogous to G350, G545 |
| 1026 | G351 | PRT | A. thaliana | Paralogous to G350, G545 |
| 1027 | G352 | DNA | A. thaliana | Predicted polypeptide sequence is paralogous to G2827 |
| 1028 | G352 | PRT | A. thaliana | Paralogous to G2827 |
| 1029 | G354 | DNA | A. thaliana | Predicted polypeptide sequence is paralogous to G1889, G1974, G2839, G353 |
| 1030 | G354 | PRT | A. thaliana | Paralogous to G1889, G1974, G2839, G353 |
| 1033 | G36 | DNA | A. thaliana | Predicted polypeptide sequence is paralogous to G1748 |
| 1034 | G36 | PRT | A. thaliana | Paralogous to G1748 |
| 1035 | G362 | DNA | A. thaliana | Predicted polypeptide sequence is paralogous to G1995, G2826, G2838, G361, G370 |
| 1036 | G362 | PRT | A. thaliana | Paralogous to G1995, G2826, G2838, G361, G370 |
| 1045 | G383 | DNA | A. thaliana | Predicted polypeptide sequence is paralogous to G1917 |
| 1046 | G383 | PRT | A. thaliana | Paralogous to G1917 |
| 1047 | G385 | DNA | A. thaliana | Predicted polypeptide sequence is paralogous to G1588, G384 |
| 1048 | G385 | PRT | A. thaliana | Paralogous to G1588, G384 |
| 1049 | G392 | DNA | A. thaliana | Predicted polypeptide sequence is paralogous to G1548, G390, G391, G438 |
| 1050 | G392 | PRT | A. thaliana | Paralogous to G1548, G390, G391, G438 |
| 1051 | G399 | DNA | A. thaliana | Predicted polypeptide sequence is paralogous to G398, G964 |
| 1052 | G399 | PRT | A. thaliana | Paralogous to G398, G964 |
| 1053 | G4 | DNA | A. thaliana | Predicted polypeptide sequence is paralogous to G14; orthologous to G3957, G3974 |
| 1054 | G4 | PRT | A. thaliana | Paralogous to G14; Orthologous to G3957, G3974 |
| 1055 | G406 | DNA | A. thaliana | Predicted polypeptide sequence is paralogous to G699 |
| 1056 | G406 | PRT | A. thaliana | Paralogous to G699 |
| 1059 | G411 | DNA | A. thaliana | Predicted polypeptide sequence is paralogous to G2548 |
| 1060 | G411 | PRT | A. thaliana | Paralogous to G2548 |
| 1061 | G413 | DNA | A. thaliana | Predicted polypeptide sequence is paralogous to G713 |
| 1062 | G413 | PRT | A. thaliana | Paralogous to G713 |
| 1067 | G426 | DNA | A. thaliana | Predicted polypeptide sequence is paralogous to G2545, G425, G427 |
| 1068 | G426 | PRT | A. thaliana | Paralogous to G2545, G425, G427 |
| 1069 | G428 | DNA | A. thaliana | Predicted polypeptide sequence is paralogous to G1594 |
| 1070 | G428 | PRT | A. thaliana | Paralogous to G1594 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1071 | G43 | DNA | A. thaliana | Predicted polypeptide sequence is paralogous to G1419, G46, G1004, G29; orthologous to G3849 |
| 1072 | G43 | PRT | A. thaliana | Paralogous to G1419, G46, G1004, G29; Orthologous to G3849 |
| 1077 | G440 | DNA | A. thaliana | Predicted polypeptide sequence is paralogous to G1750, G1421, G864; orthologous to G4079, G4080, G4283, G4284, G4285, G4286, G4287, G4288, G4289, G4290, G4291, G4292, G4293 |
| 1078 | G440 | PRT | A. thaliana | Paralogous to G1750, G1421, G864; Orthologous to G4079, G4080, G4283, G4284, G4285, G4286, G4287, G4288, G4289, G4290, G4291, G4292, G4293 |
| 1079 | G443 | DNA | A. thaliana | Predicted polypeptide sequence is paralogous to G449, G451, G452 |
| 1080 | G443 | PRT | A. thaliana | Paralogous to G449, G451, G452 |
| 1081 | G449 | DNA | A. thaliana | Predicted polypeptide sequence is paralogous to G443, G451, G452 |
| 1082 | G449 | PRT | A. thaliana | Paralogous to G443, G451, G452 |
| 1083 | G450 | DNA | A. thaliana | Predicted polypeptide sequence is paralogous to G448, G455, G456 |
| 1084 | G450 | PRT | A. thaliana | Paralogous to G448, G455, G456 |
| 1085 | G451 | DNA | A. thaliana | Predicted polypeptide sequence is paralogous to G443, G449, G452 |
| 1086 | G451 | PRT | A. thaliana | Paralogous to G443, G449, G452 |
| 1087 | G452 | DNA | A. thaliana | Predicted polypeptide sequence is paralogous to G443, G449, G451 |
| 1088 | G452 | PRT | A. thaliana | Paralogous to G443, G449, G451 |
| 1089 | G463 | DNA | A. thaliana | Predicted polypeptide sequence is paralogous to G464 |
| 1090 | G463 | PRT | A. thaliana | Paralogous to G464 |
| 1091 | G467 | DNA | A. thaliana | Predicted polypeptide sequence is paralogous to G1390 |
| 1092 | G467 | PRT | A. thaliana | Paralogous to G1390 |
| 1093 | G468 | DNA | A. thaliana | Predicted polypeptide sequence is paralogous to G2866 |
| 1094 | G468 | PRT | A. thaliana | Paralogous to G2866 |
| 1095 | G47 | DNA | A. thaliana | Predicted polypeptide sequence is paralogous to G2133; orthologous to G3643, G3644, G3645, G3646, G3647, G3649, G3650, G3651 |
| 1096 | G47 | PRT | A. thaliana | Paralogous to G2133; Orthologous to G3643, G3644, G3645, G3646, G3647, G3649, G3650, G3651 |
| 1097 | G481 | DNA | A. thaliana | Predicted polypeptide sequence is paralogous to G1364, G2345, G482, G485; orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1098 | G481 | PRT | A. thaliana | Paralogous to G1364, G2345, G482, G485; Orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1099 | G482 | DNA | A. thaliana | Predicted polypeptide sequence is paralogous to G1364, G2345, G481, G485; orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1100 | G482 | PRT | A. thaliana | Paralogous to G1364, G2345, G481, G485; Orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1101 | G485 | DNA | A. thaliana | Predicted polypeptide sequence is paralogous to G1364, G2345, G481, G482; orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1102 | G485 | PRT | A. thaliana | Paralogous to G1364, G2345, G481, G482; Orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1103 | G489 | DNA | A. thaliana | Predicted polypeptide sequence is paralogous to G714; orthologous to G3542, G3544, G3545, G3547, G3549, G3550, G3551, G3552, G3553, G3554, G3555, G3867, G3892, G3893, G3894, G3896, G4257, G4256 |
| 1104 | G489 | PRT | A. thaliana | Paralogous to G714; Orthologous to G3542, G3544, G3545, G3547, G3549, G3550, G3551, G3552, G3553, G3554, G3555, G3867, G3892, G3893, G3894, G3896, G4257, G4256 |
| 1105 | G501 | DNA | A. thaliana | Predicted polypeptide sequence is paralogous to G502, G519, G767 |
| 1106 | G501 | PRT | A. thaliana | Paralogous to G502, G519, G767 |
| 1109 | G513 | DNA | A. thaliana | Predicted polypeptide sequence is paralogous to G1426, G1455, G960 |
| 1110 | G513 | PRT | A. thaliana | Paralogous to G1426, G1455, G960 |
| 1111 | G519 | DNA | A. thaliana | Predicted polypeptide sequence is paralogous to G501, G502, G767 |
| 1112 | G519 | PRT | A. thaliana | Paralogous to G501, G502, G767 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1113 | G522 | DNA | A. thaliana | Predicted polypeptide sequence is paralogous to G1354, G1355, G1453, G1766, G2534, G761 |
| 1114 | G522 | PRT | A. thaliana | Paralogous to G1354, G1355, G1453, G1766, G2534, G761 |
| 1115 | G525 | DNA | A. thaliana | Predicted polypeptide sequence is paralogous to G514, G523, G764 |
| 1116 | G525 | PRT | A. thaliana | Paralogous to G514, G523, G764 |
| 1119 | G529 | DNA | A. thaliana | Predicted polypeptide sequence is paralogous to G528, G530, G531, G532, G533, G534, G535, G536, G537 |
| 1120 | G529 | PRT | A. thaliana | Paralogous to G528, G530, G531, G532, G533, G534, G535, G536, G537 |
| 1121 | G530 | DNA | A. thaliana | Predicted polypeptide sequence is paralogous to G528, G529, G531, G532, G533, G534, G535, G536, G537 |
| 1122 | G530 | PRT | A. thaliana | Paralogous to G528, G529, G531, G532, G533, G534, G535, G536, G537 |
| 1123 | G531 | DNA | A. thaliana | Predicted polypeptide sequence is paralogous to G528, G529, G530, G532, G533, G534, G535, G536, G537 |
| 1124 | G531 | PRT | A. thaliana | Paralogous to G528, G529, G530, G532, G533, G534, G535, G536, G537 |
| 1125 | G532 | DNA | A. thaliana | Predicted polypeptide sequence is paralogous to G528, G529, G530, G531, G533, G534, G535, G536, G537 |
| 1126 | G532 | PRT | A. thaliana | Paralogous to G528, G529, G530, G531, G533, G534, G535, G536, G537 |
| 1127 | G547 | DNA | A. thaliana | Predicted polypeptide sequence is paralogous to G1832 |
| 1128 | G547 | PRT | A. thaliana | Paralogous to G1832 |
| 1131 | G556 | DNA | A. thaliana | Predicted polypeptide sequence is paralogous to G1198, G1806, G554, G555, G558, G578, G629 |
| 1132 | G556 | PRT | A. thaliana | Paralogous to G1198, G1806, G554, G555, G558, G578, G629 |
| 1133 | G558 | DNA | A. thaliana | Predicted polypeptide sequence is paralogous to G1198, G1806, G554, G555, G556, G578, G629 |
| 1134 | G558 | PRT | A. thaliana | Paralogous to G1198, G1806, G554, G555, G556, G578, G629 |
| 1135 | G559 | DNA | A. thaliana | Predicted polypeptide sequence is paralogous to G631 |
| 1136 | G559 | PRT | A. thaliana | Paralogous to G631 |
| 1137 | G562 | DNA | A. thaliana | Predicted polypeptide sequence is paralogous to G561 |
| 1138 | G562 | PRT | A. thaliana | Paralogous to G561 |
| 1143 | G568 | DNA | A. thaliana | Predicted polypeptide sequence is paralogous to G580 |
| 1144 | G568 | PRT | A. thaliana | Paralogous to G580 |
| 1145 | G577 | DNA | A. thaliana | Predicted polypeptide sequence is paralogous to G1078 |
| 1146 | G577 | PRT | A. thaliana | Paralogous to G1078 |
| 1149 | G580 | DNA | A. thaliana | Predicted polypeptide sequence is paralogous to G568 |
| 1150 | G580 | PRT | A. thaliana | Paralogous to G568 |
| 1153 | G591 | DNA | A. thaliana | Predicted polypeptide sequence is paralogous to G793; orthologous to G3752, G3753, G3751, G3750, G4311, G4312, G4313 |
| 1154 | G591 | PRT | A. thaliana | Paralogous to G793; Orthologous to G3752, G3753, G3751, G3750, G4311, G4312, G4313 |
| 1157 | G596 | DNA | A. thaliana | Predicted polypeptide sequence is paralogous to G2789; orthologous to G3457 |
| 1158 | G596 | PRT | A. thaliana | Paralogous to G2789; Orthologous to G3457 |
| 1161 | G599 | DNA | A. thaliana | Predicted polypeptide sequence is paralogous to G2159, G2781 |
| 1162 | G599 | PRT | A. thaliana | Paralogous to G2159, G2781 |
| 1169 | G631 | DNA | A. thaliana | Predicted polypeptide sequence is paralogous to G559 |
| 1170 | G631 | PRT | A. thaliana | Paralogous to G559 |
| 1183 | G653 | DNA | A. thaliana | Predicted polypeptide sequence is paralogous to G654 |
| 1184 | G653 | PRT | A. thaliana | Paralogous to G654 |
| 1189 | G659 | DNA | A. thaliana | Predicted polypeptide sequence is paralogous to G1323 |
| 1190 | G659 | PRT | A. thaliana | Paralogous to G1323 |
| 1191 | G663 | DNA | A. thaliana | Predicted polypeptide sequence is paralogous to G1329, G2421, G2422 |
| 1192 | G663 | PRT | A. thaliana | Paralogous to G1329, G2421, G2422 |
| 1193 | G664 | DNA | A. thaliana | Predicted polypeptide sequence is paralogous to G197, G255; orthologous to G3503, G3504, G3505, G3506, G3507, G3508, G3509, G3529, G3531, G3532, G3533, G3534, G3527, G3528, G4637, G4638, G4639, G4640 |
| 1194 | G664 | PRT | A. thaliana | Paralogous to G197, G255; Orthologous to G3503, G3504, G3505, G3506, G3507, G3508, G3509, G3529, G3531, G3532, G3533, G3534, G3527, G3528, G4637, G4638, G4639, G4640 |
| 1197 | G666 | DNA | A. thaliana | Predicted polypeptide sequence is paralogous to G256, G668, G932; orthologous to G3384, G3385, G3386, G3500, G3501, G3502, G3537, G3538, G3539, G3540, G3541 |
| 1198 | G666 | PRT | A. thaliana | Paralogous to G256, G668, G932; Orthologous to G3384, G3385, G3386, G3500, G3501, G3502, G3537, G3538, G3539, G3540, G3541 |
| 1205 | G682 | DNA | A. thaliana | Predicted polypeptide sequence is paralogous to G1816, G225, G226, G2718, G3930; orthologous to G3392, G3393, G3431, G3444, G3445, G3446, G3447, G3448, G3449, G3450 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1206 | G682 | PRT | A. thaliana | Paralogous to G1816, G225, G226, G2718, G3930; Orthologous to G3392, G3393, G3431, G3444, G3445, G3446, G3447, G3448, G3449, G3450 |
| 1207 | G699 | DNA | A. thaliana | Predicted polypeptide sequence is paralogous to G406 |
| 1208 | G699 | PRT | A. thaliana | Paralogous to G406 |
| 1211 | G707 | DNA | A. thaliana | Predicted polypeptide sequence is paralogous to G386 |
| 1212 | G707 | PRT | A. thaliana | Paralogous to G386 |
| 1213 | G714 | DNA | A. thaliana | Predicted polypeptide sequence is paralogous to G489; orthologous to G3542, G3544, G3545, G3547, G3549, G3550, G3551, G3552, G3553, G3554, G3555, G3867, G3892, G3893, G3894, G3896, G4257, G4256 |
| 1214 | G714 | PRT | A. thaliana | Paralogous to G489; Orthologous to G3542, G3544, G3545, G3547, G3549, G3550, G3551, G3552, G3553, G3554, G3555, G3867, G3892, G3893, G3894, G3896, G4257, G4256 |
| 1215 | G715 | DNA | A. thaliana | Predicted polypeptide sequence is paralogous to G1646; orthologous to G3883, G3884, G3885, G3886, G3889, G3543, G4259 |
| 1216 | G715 | PRT | A. thaliana | Paralogous to G1646; Orthologous to G3883, G3884, G3885, G3886, G3889, G3543, G4259 |
| 1219 | G721 | DNA | A. thaliana | Predicted polypeptide sequence is paralogous to G1041, G724 |
| 1220 | G721 | PRT | A. thaliana | Paralogous to G1041, G724 |
| 1221 | G722 | DNA | A. thaliana | Predicted polypeptide sequence is paralogous to G1037 |
| 1222 | G722 | PRT | A. thaliana | Paralogous to G1037 |
| 1223 | G724 | DNA | A. thaliana | Predicted polypeptide sequence is paralogous to G1041, G721 |
| 1224 | G724 | PRT | A. thaliana | Paralogous to G1041, G721 |
| 1225 | G727 | DNA | A. thaliana | Predicted polypeptide sequence is paralogous to G1493 |
| 1226 | G727 | PRT | A. thaliana | Paralogous to G1493 |
| 1227 | G730 | DNA | A. thaliana | Predicted polypeptide sequence is paralogous to G1040, G3034, G729 |
| 1228 | G730 | PRT | A. thaliana | Paralogous to G1040, G3034, G729 |
| 1229 | G732 | DNA | A. thaliana | Predicted polypeptide sequence is paralogous to G1035 |
| 1230 | G732 | PRT | A. thaliana | Paralogous to G1035 |
| 1231 | G748 | DNA | A. thaliana | Predicted polypeptide sequence is paralogous to G1900 |
| 1232 | G748 | PRT | A. thaliana | Paralogous to G1900 |
| 1239 | G763 | DNA | A. thaliana | Predicted polypeptide sequence is paralogous to G524 |
| 1240 | G763 | PRT | A. thaliana | Paralogous to G524 |
| 1241 | G764 | DNA | A. thaliana | Predicted polypeptide sequence is paralogous to G514, G523, G525 |
| 1242 | G764 | PRT | A. thaliana | Paralogous to G514, G523, G525 |
| 1247 | G789 | DNA | A. thaliana | Predicted polypeptide sequence is paralogous to G1494 |
| 1248 | G789 | PRT | A. thaliana | Paralogous to G1494 |
| 1249 | G790 | DNA | A. thaliana | Predicted polypeptide sequence is paralogous to G593 |
| 1250 | G790 | PRT | A. thaliana | Paralogous to G593 |
| 1251 | G792 | DNA | A. thaliana | Predicted polypeptide sequence is paralogous to G791 |
| 1252 | G792 | PRT | A. thaliana | Paralogous to G791 |
| 1253 | G793 | DNA | A. thaliana | Predicted polypeptide sequence is paralogous to G591; orthologous to G3752, G3753, G3751, G3750, G4311, G4312, G4313 |
| 1254 | G793 | PRT | A. thaliana | Paralogous to G591; Orthologous to G3752, G3753, G3751, G3750, G4311, G4312, G4313 |
| 1257 | G810 | DNA | A. thaliana | Predicted polypeptide sequence is paralogous to G807; orthologous to G3491, G3494, G3495, G3512 |
| 1258 | G810 | PRT | A. thaliana | Paralogous to G807; Orthologous to G3491, G3494, G3495, G3512 |
| 1261 | G812 | DNA | A. thaliana | Predicted polypeptide sequence is paralogous to G2467 |
| 1262 | G812 | PRT | A. thaliana | Paralogous to G2467 |
| 1263 | G819 | DNA | A. thaliana | Predicted polypeptide sequence is paralogous to G273 |
| 1264 | G819 | PRT | A. thaliana | Paralogous to G273 |
| 1273 | G881 | DNA | A. thaliana | Predicted polypeptide sequence is paralogous to G986 |
| 1274 | G881 | PRT | A. thaliana | Paralogous to G986 |
| 1277 | G896 | DNA | A. thaliana | Predicted polypeptide sequence is paralogous to G1349, G1887 |
| 1278 | G896 | PRT | A. thaliana | Paralogous to G1349, G1887 |
| 1279 | G897 | DNA | A. thaliana | Predicted polypeptide sequence is paralogous to G1480, G899 |
| 1280 | G897 | PRT | A. thaliana | Paralogous to G1480, G899 |
| 1281 | G902 | DNA | A. thaliana | Predicted polypeptide sequence is paralogous to G1881 |
| 1282 | G902 | PRT | A. thaliana | Paralogous to G1881 |
| 1293 | G927 | DNA | A. thaliana | Predicted polypeptide sequence is paralogous to G1334 |
| 1294 | G927 | PRT | A. thaliana | Paralogous to G1334 |
| 1295 | G929 | DNA | A. thaliana | Predicted polypeptide sequence is paralogous to G2344; orthologous to G4267, G4268 |
| 1296 | G929 | PRT | A. thaliana | Paralogous to G2344; Orthologous to G4267, G4268 |
| 1297 | G934 | DNA | A. thaliana | Predicted polypeptide sequence is paralogous to G2869, G2870, G2871, G2872, G2873 |
| 1298 | G934 | PRT | A. thaliana | Paralogous to G2869, G2870, G2871, G2872, G2873 |
| 1303 | G938 | DNA | A. thaliana | Predicted polypeptide sequence is paralogous to G940, G941 |
| 1304 | G938 | PRT | A. thaliana | Paralogous to G940, G941 |
| 1307 | G941 | DNA | A. thaliana | Predicted polypeptide sequence is paralogous to G938, G940 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1308 | G941 | PRT | A. thaliana | Paralogous to G938, G940 |
| 1309 | G961 | DNA | A. thaliana | Predicted polypeptide sequence is paralogous to G2535, G957 |
| 1310 | G961 | PRT | A. thaliana | Paralogous to G2535, G957 |
| 1315 | G975 | DNA | A. thaliana | Predicted polypeptide sequence is paralogous to G1387, G2583; orthologous to G4294 |
| 1316 | G975 | PRT | A. thaliana | Paralogous to G1387, G2583; Orthologous to G4294 |
| 1317 | G976 | DNA | A. thaliana | Predicted polypeptide sequence is paralogous to G913, G2514, G1753 |
| 1318 | G976 | PRT | A. thaliana | Paralogous to G913, G2514, G1753 |
| 1319 | G979 | DNA | A. thaliana | Predicted polypeptide sequence is paralogous to G2106, G2131 |
| 1320 | G979 | PRT | A. thaliana | Paralogous to G2106, G2131 |
| 1325 | G993 | DNA | A. thaliana | Predicted polypeptide sequence is paralogous to G1930, G867, G9; orthologous to G3388, G3389, G3390, G3391, G3432, G3433, G3451, G3452, G3453, G3454, G3455 |
| 1326 | G993 | PRT | A. thaliana | Paralogous to G1930, G867, G9; Orthologous to G3388, G3389, G3390, G3391, G3432, G3433, G3451, G3452, G3453, G3454, G3455 |
| 1327 | G997 | DNA | A. thaliana | Predicted polypeptide sequence is paralogous to G1789, G1911, G2721 |
| 1328 | G997 | PRT | A. thaliana | Paralogous to G1789, G1911, G2721 |
| 1331 | G10 | DNA | A. thaliana | Predicted polypeptide sequence is paralogous to G3 |
| 1332 | G10 | PRT | A. thaliana | Paralogous to G3 |
| 1333 | G1010 | DNA | A. thaliana | Predicted polypeptide sequence is paralogous to G2747 |
| 1334 | G1010 | PRT | A. thaliana | Paralogous to G2747 |
| 1335 | G1011 | DNA | A. thaliana | Predicted polypeptide sequence is paralogous to G149, G627, G154, G1797, G1798; orthologous to G4061, G4062, G4063, G4064, G4065, G4066, G4067 |
| 1336 | G1011 | PRT | A. thaliana | Paralogous to G149, G627, G154, G1797, G1798; Orthologous to G4061, G4062, G4063, G4064, G4065, G4066, G4067 |
| 1337 | G1029 | DNA | A. thaliana | Predicted polypeptide sequence is paralogous to G1033, G279 |
| 1338 | G1029 | PRT | A. thaliana | Paralogous to G1033, G279 |
| 1339 | G1035 | DNA | A. thaliana | Predicted polypeptide sequence is paralogous to G732 |
| 1340 | G1035 | PRT | A. thaliana | Paralogous to G732 |
| 1341 | G1037 | DNA | A. thaliana | Predicted polypeptide sequence is paralogous to G722 |
| 1342 | G1037 | PRT | A. thaliana | Paralogous to G722 |
| 1343 | G1040 | DNA | A. thaliana | Predicted polypeptide sequence is paralogous to G3034, G729, G730 |
| 1344 | G1040 | PRT | A. thaliana | Paralogous to G3034, G729, G730 |
| 1345 | G1041 | DNA | A. thaliana | Predicted polypeptide sequence is paralogous to G721, G724 |
| 1346 | G1041 | PRT | A. thaliana | Paralogous to G721, G724 |
| 1347 | G1047 | DNA | A. thaliana | Predicted polypeptide sequence is paralogous to G1808 |
| 1348 | G1047 | PRT | A. thaliana | Paralogous to G1808 |
| 1349 | G1050 | DNA | A. thaliana | Predicted polypeptide sequence is paralogous to G1807 |
| 1350 | G1050 | PRT | A. thaliana | Paralogous to G1807 |
| 1351 | G1058 | DNA | A. thaliana | Predicted polypeptide sequence is paralogous to G2071 |
| 1352 | G1058 | PRT | A. thaliana | Paralogous to G2071 |
| 1353 | G1061 | DNA | A. thaliana | Predicted polypeptide sequence is paralogous to G589, G2791; orthologous to G3748, G3749, G3774, G3760 |
| 1354 | G1061 | PRT | A. thaliana | Paralogous to G589, G2791; Orthologous to G3748, G3749, G3774, G3760 |
| 1355 | G1073 | DNA | A. thaliana | Predicted polypeptide sequence is paralogous to G1067, G2156; orthologous to G3399, G3400 |
| 1356 | G1073 | PRT | A. thaliana | Paralogous to G1067, G2156; Orthologous to G3399, G3400 |
| 1357 | G1075 | DNA | A. thaliana | Predicted polypeptide sequence is paralogous to G1076; orthologous to G3406, G3407, G3458, G3459, G3460, G3461 |
| 1358 | G1075 | PRT | A. thaliana | Paralogous to G1076; Orthologous to G3406, G3407, G3458, G3459, G3460, G3461 |
| 1359 | G1108 | DNA | A. thaliana | Predicted polypeptide sequence is paralogous to G2394 |
| 1360 | G1108 | PRT | A. thaliana | Paralogous to G2394 |
| 1361 | G1149 | DNA | A. thaliana | Predicted polypeptide sequence is paralogous to G1146, G1152 |
| 1362 | G1149 | PRT | A. thaliana | Paralogous to G1146, G1152 |
| 1363 | G1152 | DNA | A. thaliana | Predicted polypeptide sequence is paralogous to G1146, G1149 |
| 1364 | G1152 | PRT | A. thaliana | Paralogous to G1146, G1149 |
| 1365 | G1181 | DNA | A. thaliana | Predicted polypeptide sequence is paralogous to G1850 |
| 1366 | G1181 | PRT | A. thaliana | Paralogous to G1850 |
| 1367 | G1186 | DNA | A. thaliana | Predicted polypeptide sequence is paralogous to G1855 |
| 1368 | G1186 | PRT | A. thaliana | Paralogous to G1855 |
| 1369 | G1197 | DNA | A. thaliana | Predicted polypeptide sequence is paralogous to G1959 |
| 1370 | G1197 | PRT | A. thaliana | Paralogous to G1959 |
| 1371 | G12 | DNA | A. thaliana | Predicted polypeptide sequence is paralogous to G1277, G1379, G24; orthologous to G3656 |
| 1372 | G12 | PRT | A. thaliana | Paralogous to G1277, G1379, G24; Orthologous to G3656 |
| 1373 | G1227 | DNA | A. thaliana | Predicted polypeptide sequence is paralogous to G1228 |
| 1374 | G1227 | PRT | A. thaliana | Paralogous to G1228 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1375 | G1232 | DNA | A. thaliana | Predicted polypeptide sequence is paralogous to G2484 |
| 1376 | G1232 | PRT | A. thaliana | Paralogous to G2484 |
| 1377 | G1241 | DNA | A. thaliana | Predicted polypeptide sequence is paralogous to G1240 |
| 1378 | G1241 | PRT | A. thaliana | Paralogous to G1240 |
| 1379 | G1242 | DNA | A. thaliana | Predicted polypeptide sequence is paralogous to G1243 |
| 1380 | G1242 | PRT | A. thaliana | Paralogous to G1243 |
| 1381 | G1245 | DNA | A. thaliana | Predicted polypeptide sequence is paralogous to G1247 |
| 1382 | G1245 | PRT | A. thaliana | Paralogous to G1247 |
| 1383 | G1277 | DNA | A. thaliana | Predicted polypeptide sequence is paralogous to G12, G1379, G24; orthologous to G3656 |
| 1384 | G1277 | PRT | A. thaliana | Paralogous to G12, G1379, G24; Orthologous to G3656 |
| 1385 | G129 | DNA | A. thaliana | Predicted polypeptide sequence is paralogous to G136, G140, G146 |
| 1386 | G129 | PRT | A. thaliana | Paralogous to G136, G140, G146 |
| 1387 | G1307 | DNA | A. thaliana | Predicted polypeptide sequence is paralogous to G206 |
| 1388 | G1307 | PRT | A. thaliana | Paralogous to G206 |
| 1389 | G1321 | DNA | A. thaliana | Predicted polypeptide sequence is paralogous to G1320 |
| 1390 | G1321 | PRT | A. thaliana | Paralogous to G1320 |
| 1391 | G1323 | DNA | A. thaliana | Predicted polypeptide sequence is paralogous to G659 |
| 1392 | G1323 | PRT | A. thaliana | Paralogous to G659 |
| 1393 | G1325 | DNA | A. thaliana | Predicted polypeptide sequence is paralogous to G1313 |
| 1394 | G1325 | PRT | A. thaliana | Paralogous to G1313 |
| 1395 | G1329 | DNA | A. thaliana | Predicted polypeptide sequence is paralogous to G2421, G2422, G663 |
| 1396 | G1329 | PRT | A. thaliana | Paralogous to G2421, G2422, G663 |
| 1397 | G1334 | DNA | A. thaliana | Predicted polypeptide sequence is paralogous to G927 |
| 1398 | G1334 | PRT | A. thaliana | Paralogous to G927 |
| 1399 | G1337 | DNA | A. thaliana | Predicted polypeptide sequence is paralogous to G326 |
| 1400 | G1337 | PRT | A. thaliana | Paralogous to G326 |
| 1401 | G136 | DNA | A. thaliana | Predicted polypeptide sequence is paralogous to G129, G140, G146 |
| 1402 | G136 | PRT | A. thaliana | Paralogous to G129, G140, G146 |
| 1403 | G1381 | DNA | A. thaliana | Predicted polypeptide sequence is paralogous to G21 |
| 1404 | G1381 | PRT | A. thaliana | Paralogous to G21 |
| 1405 | G1387 | DNA | A. thaliana | Predicted polypeptide sequence is paralogous to G2583, G975; orthologous to G4294 |
| 1406 | G1387 | PRT | A. thaliana | Paralogous to G2583, G975; Orthologous to G4294 |
| 1407 | G1390 | DNA | A. thaliana | Predicted polypeptide sequence is paralogous to G467 |
| 1408 | G1390 | PRT | A. thaliana | Paralogous to G467 |
| 1409 | G1396 | DNA | A. thaliana | Predicted polypeptide sequence is paralogous to G1394, G1395 |
| 1410 | G1396 | PRT | A. thaliana | Paralogous to G1394, G1395 |
| 1411 | G14 | DNA | A. thaliana | Predicted polypeptide sequence is paralogous to G4; orthologous to G3957, G3974 |
| 1412 | G14 | PRT | A. thaliana | Paralogous to G4; Orthologous to G3957, G3974 |
| 1413 | G1416 | DNA | A. thaliana | Predicted polypeptide sequence is paralogous to G2 |
| 1414 | G1416 | PRT | A. thaliana | Paralogous to G2 |
| 1415 | G142 | DNA | A. thaliana | Predicted polypeptide sequence is paralogous to G148 |
| 1416 | G142 | PRT | A. thaliana | Paralogous to G148 |
| 1417 | G1424 | DNA | A. thaliana | Predicted polypeptide sequence is paralogous to G1423, G2988 |
| 1418 | G1424 | PRT | A. thaliana | Paralogous to G1423, G2988 |
| 1419 | G1426 | DNA | A. thaliana | Predicted polypeptide sequence is paralogous to G1455, G513, G960 |
| 1420 | G1426 | PRT | A. thaliana | Paralogous to G1455, G513, G960 |
| 1421 | G1453 | DNA | A. thaliana | Predicted polypeptide sequence is paralogous to G1354, G1355, G1766, G2534, G522, G761 |
| 1422 | G1453 | PRT | A. thaliana | Paralogous to G1354, G1355, G1766, G2534, G522, G761 |
| 1423 | G1455 | DNA | A. thaliana | Predicted polypeptide sequence is paralogous to G1426, G513, G960 |
| 1424 | G1455 | PRT | A. thaliana | Paralogous to G1426, G513, G960 |
| 1425 | G1458 | DNA | A. thaliana | Predicted polypeptide sequence is paralogous to G1459, G1460 |
| 1426 | G1458 | PRT | A. thaliana | Paralogous to G1459, G1460 |
| 1427 | G1459 | DNA | A. thaliana | Predicted polypeptide sequence is paralogous to G1458, G1460 |
| 1428 | G1459 | PRT | A. thaliana | Paralogous to G1458, G1460 |
| 1429 | G1461 | DNA | A. thaliana | Predicted polypeptide sequence is paralogous to G1462, G1463, G1464, G1465 |
| 1430 | G1461 | PRT | A. thaliana | Paralogous to G1462, G1463, G1464, G1465 |
| 1431 | G1463 | DNA | A. thaliana | Predicted polypeptide sequence is paralogous to G1461, G1462, G1464, G1465 |
| 1432 | G1463 | PRT | A. thaliana | Paralogous to G1461, G1462, G1464, G1465 |
| 1433 | G1464 | DNA | A. thaliana | Predicted polypeptide sequence is paralogous to G1461, G1462, G1463, G1465 |
| 1434 | G1464 | PRT | A. thaliana | Paralogous to G1461, G1462, G1463, G1465 |
| 1435 | G1465 | DNA | A. thaliana | Predicted polypeptide sequence is paralogous to G1461, G1462, G1463, G1464 |
| 1436 | G1465 | PRT | A. thaliana | Paralogous to G1461, G1462, G1463, G1464 |
| 1437 | G1466 | DNA | A. thaliana | Predicted polypeptide sequence is paralogous to G224, G1021, G223 |
| 1438 | G1466 | PRT | A. thaliana | Paralogous to G224, G1021, G223 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1439 | G1482 | DNA | A. thaliana | Predicted polypeptide sequence is paralogous to G1888; orthologous to G5159 |
| 1440 | G1482 | PRT | A. thaliana | Paralogous to G1888; Orthologous to G5159 |
| 1441 | G1489 | DNA | A. thaliana | Predicted polypeptide sequence is paralogous to G1488 |
| 1442 | G1489 | PRT | A. thaliana | Paralogous to G1488 |
| 1443 | G149 | DNA | A. thaliana | Predicted polypeptide sequence is paralogous to G627, G1011, G154, G1797, G1798; orthologous to G4061, G4062, G4063, G4064, G4065, G4066, G4067 |
| 1444 | G149 | PRT | A. thaliana | Paralogous to G627, G1011, G154, G1797, G1798; Orthologous to G4061, G4062, G4063, G4064, G4065, G4066, G4067 |
| 1445 | G1492 | DNA | A. thaliana | Predicted polypeptide sequence is paralogous to G2742 |
| 1446 | G1492 | PRT | A. thaliana | Paralogous to G2742 |
| 1447 | G1493 | DNA | A. thaliana | Predicted polypeptide sequence is paralogous to G727 |
| 1448 | G1493 | PRT | A. thaliana | Paralogous to G727 |
| 1449 | G1507 | DNA | A. thaliana | Predicted polypeptide sequence is paralogous to G2437 |
| 1450 | G1507 | PRT | A. thaliana | Paralogous to G2437 |
| 1451 | G1508 | DNA | A. thaliana | Predicted polypeptide sequence is paralogous to G2094 |
| 1452 | G1508 | PRT | A. thaliana | Paralogous to G2094 |
| 1453 | G1509 | DNA | A. thaliana | Predicted polypeptide sequence is paralogous to G1506 |
| 1454 | G1509 | PRT | A. thaliana | Paralogous to G1506 |
| 1455 | G152 | DNA | A. thaliana | Predicted polypeptide sequence is paralogous to G153, G1760, G860; orthologous to G3479, G3480, G3481, G3482, G3483, G3484, G3485, G3487, G3488, G3489, G3980, G3981, G3982 |
| 1456 | G152 | PRT | A. thaliana | Paralogous to G153, G1760, G860; Orthologous to G3479, G3480, G3481, G3482, G3483, G3484, G3485, G3487, G3488, G3489, G3980, G3981, G3982 |
| 1457 | G153 | DNA | A. thaliana | Predicted polypeptide sequence is paralogous to G152, G1760, G860; orthologous to G3479, G3480, G3481, G3482, G3483, G3484, G3485, G3487, G3488, G3489, G3980, G3981, G3982 |
| 1458 | G153 | PRT | A. thaliana | Paralogous to G152, G1760, G860; Orthologous to G3479, G3480, G3481, G3482, G3483, G3484, G3485, G3487, G3488, G3489, G3980, G3981, G3982 |
| 1459 | G1545 | DNA | A. thaliana | Predicted polypeptide sequence is paralogous to G1538, G412 |
| 1460 | G1545 | PRT | A. thaliana | Paralogous to G1538, G412 |
| 1461 | G1548 | DNA | A. thaliana | Predicted polypeptide sequence is paralogous to G390, G391, G392, G438 |
| 1462 | G1548 | PRT | A. thaliana | Paralogous to G390, G391, G392, G438 |
| 1463 | G1588 | DNA | A. thaliana | Predicted polypeptide sequence is paralogous to G384, G385 |
| 1464 | G1588 | PRT | A. thaliana | Paralogous to G384, G385 |
| 1465 | G1594 | DNA | A. thaliana | Predicted polypeptide sequence is paralogous to G428 |
| 1466 | G1594 | PRT | A. thaliana | Paralogous to G428 |
| 1467 | G16 | DNA | A. thaliana | Predicted polypeptide sequence is paralogous to G2299 |
| 1468 | G16 | PRT | A. thaliana | Paralogous to G2299 |
| 1469 | G164 | DNA | A. thaliana | Predicted polypeptide sequence is paralogous to G166 |
| 1470 | G164 | PRT | A. thaliana | Paralogous to G166 |
| 1471 | G1641 | DNA | A. thaliana | Predicted polypeptide sequence is paralogous to G1638, G2452, G1634, G2701 |
| 1472 | G1641 | PRT | A. thaliana | Paralogous to G1638, G2452, G1634, G2701 |
| 1473 | G1664 | DNA | A. thaliana | Predicted polypeptide sequence is paralogous to G1062 |
| 1474 | G1664 | PRT | A. thaliana | Paralogous to G1062 |
| 1475 | G1672 | DNA | A. thaliana | Predicted polypeptide sequence is paralogous to G2802 |
| 1476 | G1672 | PRT | A. thaliana | Paralogous to G2802 |
| 1477 | G170 | DNA | A. thaliana | Predicted polypeptide sequence is paralogous to G168, G2065 |
| 1478 | G170 | PRT | A. thaliana | Paralogous to G168, G2065 |
| 1479 | G1748 | DNA | A. thaliana | Predicted polypeptide sequence is paralogous to G36 |
| 1480 | G1748 | PRT | A. thaliana | Paralogous to G36 |
| 1481 | G1749 | DNA | A. thaliana | Predicted polypeptide sequence is paralogous to G1839, G1840 |
| 1482 | G1749 | PRT | A. thaliana | Paralogous to G1839, G1840 |
| 1483 | G1753 | DNA | A. thaliana | Predicted polypeptide sequence is paralogous to G913, G2514, G976 |
| 1484 | G1753 | PRT | A. thaliana | Paralogous to G913, G2514, G976 |
| 1485 | G1754 | DNA | A. thaliana | Predicted polypeptide sequence is paralogous to G1755 |
| 1486 | G1754 | PRT | A. thaliana | Paralogous to G1755 |
| 1487 | G1766 | DNA | A. thaliana | Predicted polypeptide sequence is paralogous to G1354, G1355, G1453, G2534, G522, G761 |
| 1488 | G1766 | PRT | A. thaliana | Paralogous to G1354, G1355, G1453, G2534, G522, G761 |
| 1489 | G1768 | DNA | A. thaliana | Predicted polypeptide sequence is paralogous to G2633, G2697, G313, G852; orthologous to G3815, G3825 |
| 1490 | G1768 | PRT | A. thaliana | Paralogous to G2633, G2697, G313, G852; Orthologous to G3815, G3825 |
| 1491 | G1779 | DNA | A. thaliana | Predicted polypeptide sequence is paralogous to G1510 |
| 1492 | G1779 | PRT | A. thaliana | Paralogous to G1510 |
| 1493 | G1791 | DNA | A. thaliana | Predicted polypeptide sequence is paralogous to G1792, G1795, G30; orthologous to G3380, G3381, G3383, G3515, G3516, G3517, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3518, G3519, G3520, G3735, G3736, G3737, G3794, G3739, G3929, G4328, G4329, G4330 |
| 1494 | G1791 | PRT | A. thaliana | Paralogous to G1792, G1795, G30; Orthologous to G3380, G3381, G3383, G3515, G3516, G3517, G3518, G3519, G3520, G3735, G3736, G3737, G3794, G3739, G3929, G4328, G4329, G4330 |
| 1495 | G1792 | DNA | A. thaliana | Predicted polypeptide sequence is paralogous to G1791, G1795, G30; orthologous to G3380, G3381, G3383, G3515, G3516, G3517, G3518, G3519, G3520, G3735, G3736, G3737, G3794, G3739, G3929, G4328, G4329, G4330 |
| 1496 | G1792 | PRT | A. thaliana | Paralogous to G1791, G1795, G30; Orthologous to G3380, G3381, G3383, G3515, G3516, G3517, G3518, G3519, G3520, G3735, G3736, G3737, G3794, G3739, G3929, G4328, G4329, G4330 |
| 1497 | G1795 | DNA | A. thaliana | Predicted polypeptide sequence is paralogous to G1791, G1792, G30; orthologous to G3380, G3381, G3383, G3515, G3516, G3517, G3518, G3519, G3520, G3735, G3736, G3737, G3794, G3739, G3929, G4328, G4329, G4330 |
| 1498 | G1795 | PRT | A. thaliana | Paralogous to G1791, G1792, G30; Orthologous to G3380, G3381, G3383, G3515, G3516, G3517, G3518, G3519, G3520, G3735, G3736, G3737, G3794, G3739, G3929, G4328, G4329, G4330 |
| 1499 | G1798 | DNA | A. thaliana | Predicted polypeptide sequence is paralogous to G149, G627, G1011, G154, G1797; orthologous to G4061, G4062, G4063, G4064, G4065, G4066, G4067 |
| 1500 | G1798 | PRT | A. thaliana | Paralogous to G149, G627, G1011, G154, G1797; Orthologous to G4061, G4062, G4063, G4064, G4065, G4066, G4067 |
| 1501 | G1816 | DNA | A. thaliana | Predicted polypeptide sequence is paralogous to G225, G226, G2718, G682, G3930; orthologous to G3392, G3393, G3431, G3444, G3445, G3446, G3447, G3448, G3449, G3450 |
| 1502 | G1816 | PRT | A. thaliana | Paralogous to G225, G226, G2718, G682, G3930; Orthologous to G3392, G3393, G3431, G3444, G3445, G3446, G3447, G3448, G3449, G3450 |
| 1503 | G1817 | DNA | A. thaliana | Predicted polypeptide sequence is paralogous to G2316 |
| 1504 | G1817 | PRT | A. thaliana | Paralogous to G2316 |
| 1505 | G1818 | DNA | A. thaliana | Predicted polypeptide sequence is paralogous to G1836 |
| 1506 | G1818 | PRT | A. thaliana | Paralogous to G1836 |
| 1507 | G1832 | DNA | A. thaliana | Predicted polypeptide sequence is paralogous to G547 |
| 1508 | G1832 | PRT | A. thaliana | Paralogous to G547 |
| 1509 | G1840 | DNA | A. thaliana | Predicted polypeptide sequence is paralogous to G1749, G1839 |
| 1510 | G1840 | PRT | A. thaliana | Paralogous to G1749, G1839 |
| 1511 | G1846 | DNA | A. thaliana | Predicted polypeptide sequence is paralogous to G1007 |
| 1512 | G1846 | PRT | A. thaliana | Paralogous to G1007 |
| 1513 | G1868 | DNA | A. thaliana | Predicted polypeptide sequence is paralogous to G1439 |
| 1514 | G1868 | PRT | A. thaliana | Paralogous to G1439 |
| 1515 | G1879 | DNA | A. thaliana | Predicted polypeptide sequence is paralogous to G2655 |
| 1516 | G1879 | PRT | A. thaliana | Paralogous to G2655 |
| 1517 | G1887 | DNA | A. thaliana | Predicted polypeptide sequence is paralogous to G1349, G896 |
| 1518 | G1887 | PRT | A. thaliana | Paralogous to G1349, G896 |
| 1519 | G1889 | DNA | A. thaliana | Predicted polypeptide sequence is paralogous to G1974, G2839, G353, G354 |
| 1520 | G1889 | PRT | A. thaliana | Paralogous to G1974, G2839, G353, G354 |
| 1521 | G1891 | DNA | A. thaliana | Predicted polypeptide sequence is paralogous to G1965 |
| 1522 | G1891 | PRT | A. thaliana | Paralogous to G1965 |
| 1523 | G1895 | DNA | A. thaliana | Predicted polypeptide sequence is paralogous to G1903 |
| 1524 | G1895 | PRT | A. thaliana | Paralogous to G1903 |
| 1525 | G1900 | DNA | A. thaliana | Predicted polypeptide sequence is paralogous to G748 |
| 1526 | G1900 | PRT | A. thaliana | Paralogous to G748 |
| 1527 | G1902 | DNA | A. thaliana | Predicted polypeptide sequence is paralogous to G1901 |
| 1528 | G1902 | PRT | A. thaliana | Paralogous to G1901 |
| 1529 | G1911 | DNA | A. thaliana | Predicted polypeptide sequence is paralogous to G1789, G2721, G997 |
| 1530 | G1911 | PRT | A. thaliana | Paralogous to G1789, G2721, G997 |
| 1531 | G1927 | DNA | A. thaliana | Predicted polypeptide sequence is paralogous to G1456, G2184 |
| 1532 | G1927 | PRT | A. thaliana | Paralogous to G1456, G2184 |
| 1533 | G1929 | DNA | A. thaliana | Predicted polypeptide sequence is paralogous to G1478; orthologous to G4019 |
| 1534 | G1929 | PRT | A. thaliana | Paralogous to G1478; Orthologous to G4019 |
| 1535 | G1930 | DNA | A. thaliana | Predicted polypeptide sequence is paralogous to G867, G9, G993; orthologous to G3388, G3389, G3390, G3391, G3432, G3433, G3451, G3452, G3453, G3454, G3455 |
| 1536 | G1930 | PRT | A. thaliana | Paralogous to G867, G9, G993; Orthologous to G3388, G3389, G3390, G3391, G3432, G3433, G3451, G3452, G3453, G3454, G3455 |
| 1537 | G1942 | DNA | A. thaliana | Predicted polypeptide sequence is paralogous to G2144 |
| 1538 | G1942 | PRT | A. thaliana | Paralogous to G2144 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1539 | G197 | DNA | A. thaliana | Predicted polypeptide sequence is paralogous to G255, G664; orthologous to G3503, G3504, G3505, G3506, G3507, G3508, G3509, G3529, G3531, G3532, G3533, G3534, G3527, G3528, G4637, G4638, G4639, G4640 |
| 1540 | G197 | PRT | A. thaliana | Paralogous to G255, G664; Orthologous to G3503, G3504, G3505, G3506, G3507, G3508, G3509, G3529, G3531, G3532, G3533, G3534, G3527, G3528, G4637, G4638, G4639, G4640 |
| 1541 | G1974 | DNA | A. thaliana | Predicted polypeptide sequence is paralogous to G1889, G2839, G353, G354 |
| 1542 | G1974 | PRT | A. thaliana | Paralogous to G1889, G2839, G353, G354 |
| 1543 | G1986 | DNA | A. thaliana | Predicted polypeptide sequence is paralogous to G1987 |
| 1544 | G1986 | PRT | A. thaliana | Paralogous to G1987 |
| 1545 | G1995 | DNA | A. thaliana | Predicted polypeptide sequence is paralogous to G2826, G2838, G361, G362, G370 |
| 1546 | G1995 | PRT | A. thaliana | Paralogous to G2826, G2838, G361, G362, G370 |
| 1547 | G2003 | DNA | A. thaliana | Predicted polypeptide sequence is paralogous to G1256 |
| 1548 | G2003 | PRT | A. thaliana | Paralogous to G1256 |
| 1549 | G201 | DNA | A. thaliana | Predicted polypeptide sequence is paralogous to G202, G243 |
| 1550 | G201 | PRT | A. thaliana | Paralogous to G202, G243 |
| 1551 | G2016 | DNA | A. thaliana | Predicted polypeptide sequence is paralogous to G2015, G2017 |
| 1552 | G2016 | PRT | A. thaliana | Paralogous to G2015, G2017 |
| 1553 | G2017 | DNA | A. thaliana | Predicted polypeptide sequence is paralogous to G2015, G2016 |
| 1554 | G2017 | PRT | A. thaliana | Paralogous to G2015, G2016 |
| 1555 | G202 | DNA | A. thaliana | Predicted polypeptide sequence is paralogous to G201, G243 |
| 1556 | G202 | PRT | A. thaliana | Paralogous to G201, G243 |
| 1557 | G2022 | DNA | A. thaliana | Predicted polypeptide sequence is paralogous to G2018 |
| 1558 | G2022 | PRT | A. thaliana | Paralogous to G2018 |
| 1559 | G2023 | DNA | A. thaliana | Predicted polypeptide sequence is paralogous to G2020, G2025 |
| 1560 | G2023 | PRT | A. thaliana | Paralogous to G2020, G2025 |
| 1561 | G2025 | DNA | A. thaliana | Predicted polypeptide sequence is paralogous to G2020, G2023 |
| 1562 | G2025 | PRT | A. thaliana | Paralogous to G2020, G2023 |
| 1563 | G2065 | DNA | A. thaliana | Predicted polypeptide sequence is paralogous to G168, G170 |
| 1564 | G2065 | PRT | A. thaliana | Paralogous to G168, G170 |
| 1565 | G207 | DNA | A. thaliana | Predicted polypeptide sequence is paralogous to G227, G230, G242; orthologous to G4218, G4219, G4220, G4221, G4222, G4223, G4224, G4225, G4226, G4227, G4228, G4229, G4230, G4231, G4232, G4234, G4235, G4236, G4237, G4238 |
| 1566 | G207 | PRT | A. thaliana | Paralogous to G227, G230, G242; Orthologous to G4218, G4219, G4220, G4221, G4222, G4223, G4224, G4225, G4226, G4227, G4228, G4229, G4230, G4231, G4232, G4234, G4235, G4236, G4237, G4238 |
| 1567 | G208 | DNA | A. thaliana | Predicted polypeptide sequence is paralogous to G2006 |
| 1568 | G208 | PRT | A. thaliana | Paralogous to G2006 |
| 1569 | G2106 | DNA | A. thaliana | Predicted polypeptide sequence is paralogous to G2131, G979 |
| 1570 | G2106 | PRT | A. thaliana | Paralogous to G2131, G979 |
| 1571 | G2110 | DNA | A. thaliana | Predicted polypeptide sequence is paralogous to G2574 |
| 1572 | G2110 | PRT | A. thaliana | Paralogous to G2574 |
| 1573 | G2128 | DNA | A. thaliana | Predicted polypeptide sequence is paralogous to G1491 |
| 1574 | G2128 | PRT | A. thaliana | Paralogous to G1491 |
| 1575 | G2131 | DNA | A. thaliana | Predicted polypeptide sequence is paralogous to G2106, G979 |
| 1576 | G2131 | PRT | A. thaliana | Paralogous to G2106, G979 |
| 1577 | G2133 | DNA | A. thaliana | Predicted polypeptide sequence is paralogous to G47; orthologous to G3643, G3644, G3645, G3646, G3647, G3649, G3650, G3651 |
| 1578 | G2133 | PRT | A. thaliana | Paralogous to G47; Orthologous to G3643, G3644, G3645, G3646, G3647, G3649, G3650, G3651 |
| 1579 | G2138 | DNA | A. thaliana | Predicted polypeptide sequence is paralogous to G35 |
| 1580 | G2138 | PRT | A. thaliana | Paralogous to G35 |
| 1581 | G2149 | DNA | A. thaliana | Predicted polypeptide sequence is paralogous to G2766; orthologous to G3763, G3764, G3740, G3741, G3772 |
| 1582 | G2149 | PRT | A. thaliana | Paralogous to G2766; Orthologous to G3763, G3764, G3740, G3741, G3772 |
| 1583 | G2158 | DNA | A. thaliana | Predicted polypeptide sequence is paralogous to G2855 |
| 1584 | G2158 | PRT | A. thaliana | Paralogous to G2855 |
| 1585 | G2159 | DNA | A. thaliana | Predicted polypeptide sequence is paralogous to G2781, G599 |
| 1586 | G2159 | PRT | A. thaliana | Paralogous to G2781, G599 |
| 1587 | G2184 | DNA | A. thaliana | Predicted polypeptide sequence is paralogous to G1456, G1927 |
| 1588 | G2184 | PRT | A. thaliana | Paralogous to G1456, G1927 |
| 1589 | G2216 | DNA | A. thaliana | Predicted polypeptide sequence is paralogous to G2215 |
| 1590 | G2216 | PRT | A. thaliana | Paralogous to G2215 |
| 1591 | G223 | DNA | A. thaliana | Predicted polypeptide sequence is paralogous to G224, G1021, G1466 |
| 1592 | G223 | PRT | A. thaliana | Paralogous to G224, G1021, G1466 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1593 | G224 | DNA | A. thaliana | Predicted polypeptide sequence is paralogous to G1021, G1466, G223 |
| 1594 | G224 | PRT | A. thaliana | Paralogous to G1021, G1466, G223 |
| 1595 | G226 | DNA | A. thaliana | Predicted polypeptide sequence is paralogous to G1816, G225, G2718, G682, G3930; orthologous to G3392, G3393, G3431, G3444, G3445, G3446, G3447, G3448, G3449, G3450 |
| 1596 | G226 | PRT | A. thaliana | Paralogous to G1816, G225, G2718, G682, G3930; Orthologous to G3392, G3393, G3431, G3444, G3445, G3446, G3447, G3448, G3449, G3450 |
| 1597 | G2297 | DNA | A. thaliana | Predicted polypeptide sequence is paralogous to G2062, G2063, G2689 |
| 1598 | G2297 | PRT | A. thaliana | Paralogous to G2062, G2063, G2689 |
| 1599 | G230 | DNA | A. thaliana | Predicted polypeptide sequence is paralogous to G207, G227, G242; orthologous to G4218, G4219, G4220, G4221, G4222, G4223, G4224, G4225, G4226, G4227, G4228, G4229, G4230, G4231, G4232, G4234, G4235, G4236, G4237, G4238 |
| 1600 | G230 | PRT | A. thaliana | Paralogous to G207, G227, G242; Orthologous to G4218, G4219, G4220, G4221, G4222, G4223, G4224, G4225, G4226, G4227, G4228, G4229, G4230, G4231, G4232, G4234, G4235, G4236, G4237, G4238 |
| 1601 | G231 | DNA | A. thaliana | Predicted polypeptide sequence is paralogous to G2007 |
| 1602 | G231 | PRT | A. thaliana | Paralogous to G2007 |
| 1603 | G233 | DNA | A. thaliana | Predicted polypeptide sequence is paralogous to G241; orthologous to G4306, G4307, G4308, G4309, G4310 |
| 1604 | G233 | PRT | A. thaliana | Paralogous to G241; Orthologous to G4306, G4307, G4308, G4309, G4310 |
| 1605 | G234 | DNA | A. thaliana | Predicted polypeptide sequence is paralogous to G232 |
| 1606 | G234 | PRT | A. thaliana | Paralogous to G232 |
| 1607 | G2345 | DNA | A. thaliana | Predicted polypeptide sequence is paralogous to G1364, G481, G482, G485; orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1608 | G2345 | PRT | A. thaliana | Paralogous to G1364, G481, G482, G485; Orthologous to G3394, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1609 | G2379 | DNA | A. thaliana | Predicted polypeptide sequence is paralogous to G2377 |
| 1610 | G2379 | PRT | A. thaliana | Paralogous to G2377 |
| 1611 | G24 | DNA | A. thaliana | Predicted polypeptide sequence is paralogous to G12, G1277, G1379; orthologous to G3656 |
| 1612 | G24 | PRT | A. thaliana | Paralogous to G12, G1277, G1379; Orthologous to G3656 |
| 1613 | G2436 | DNA | A. thaliana | Predicted polypeptide sequence is paralogous to G2443, G328 |
| 1614 | G2436 | PRT | A. thaliana | Paralogous to G2443, G328 |
| 1615 | G2443 | DNA | A. thaliana | Predicted polypeptide sequence is paralogous to G2436, G328 |
| 1616 | G2443 | PRT | A. thaliana | Paralogous to G2436, G328 |
| 1617 | G2456 | DNA | A. thaliana | Predicted polypeptide sequence is paralogous to G2454 |
| 1618 | G2456 | PRT | A. thaliana | Paralogous to G2454 |
| 1619 | G2459 | DNA | A. thaliana | Predicted polypeptide sequence is paralogous to G2457 |
| 1620 | G2459 | PRT | A. thaliana | Paralogous to G2457 |
| 1621 | G2467 | DNA | A. thaliana | Predicted polypeptide sequence is paralogous to G812 |
| 1622 | G2467 | PRT | A. thaliana | Paralogous to G812 |
| 1623 | G2469 | DNA | A. thaliana | Predicted polypeptide sequence is paralogous to G1293 |
| 1624 | G2469 | PRT | A. thaliana | Paralogous to G1293 |
| 1625 | G2494 | DNA | A. thaliana | Predicted polypeptide sequence is paralogous to G1216 |
| 1626 | G2494 | PRT | A. thaliana | Paralogous to G1216 |
| 1627 | G2512 | DNA | A. thaliana | Predicted polypeptide sequence is paralogous to G1752 |
| 1628 | G2512 | PRT | A. thaliana | Paralogous to G1752 |
| 1629 | G2513 | DNA | A. thaliana | Predicted polypeptide sequence is paralogous to G40, G2107, G41, G42, G912; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 1630 | G2513 | PRT | A. thaliana | Paralogous to G40, G2107, G41, G42, G912; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 1631 | G2514 | DNA | A. thaliana | Predicted polypeptide sequence is paralogous to G913, G976, G1753 |
| 1632 | G2514 | PRT | A. thaliana | Paralogous to G913, G976, G1753 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1633 | G2534 | DNA | A. thaliana | Predicted polypeptide sequence is paralogous to G1354, G1355, G1453, G1766, G522, G761 |
| 1634 | G2534 | PRT | A. thaliana | Paralogous to G1354, G1355, G1453, G1766, G522, G761 |
| 1635 | G2545 | DNA | A. thaliana | Predicted polypeptide sequence is paralogous to G425, G426, G427 |
| 1636 | G2545 | PRT | A. thaliana | Paralogous to G425, G426, G427 |
| 1637 | G2548 | DNA | A. thaliana | Predicted polypeptide sequence is paralogous to G411 |
| 1638 | G2548 | PRT | A. thaliana | Paralogous to G411 |
| 1639 | G256 | DNA | A. thaliana | Predicted polypeptide sequence is paralogous to G666, G668, G932; orthologous to G3384, G3385, G3386, G3500, G3501, G3502, G3537, G3538, G3539, G3540, G3541 |
| 1640 | G256 | PRT | A. thaliana | Paralogous to G666, G668, G932; Orthologous to G3384, G3385, G3386, G3500, G3501, G3502, G3537, G3538, G3539, G3540, G3541 |
| 1641 | G2572 | DNA | A. thaliana | Predicted polypeptide sequence is paralogous to G1838 |
| 1642 | G2572 | PRT | A. thaliana | Paralogous to G1838 |
| 1643 | G2583 | DNA | A. thaliana | Predicted polypeptide sequence is paralogous to G1387, G975; orthologous to G4294 |
| 1644 | G2583 | PRT | A. thaliana | Paralogous to G1387, G975; Orthologous to G4294 |
| 1645 | G2587 | DNA | A. thaliana | Predicted polypeptide sequence is paralogous to G2586, G2686 |
| 1646 | G2587 | PRT | A. thaliana | Paralogous to G2586, G2686 |
| 1647 | G2588 | DNA | A. thaliana | Predicted polypeptide sequence is paralogous to G1091 |
| 1648 | G2588 | PRT | A. thaliana | Paralogous to G1091 |
| 1649 | G2629 | DNA | A. thaliana | Predicted polypeptide sequence is paralogous to G1053 |
| 1650 | G2629 | PRT | A. thaliana | Paralogous to G1053 |
| 1651 | G2633 | DNA | A. thaliana | Predicted polypeptide sequence is paralogous to G1768, G2697, G313, G852; orthologous to G3815, G3825 |
| 1652 | G2633 | PRT | A. thaliana | Paralogous to G1768, G2697, G313, G852; Orthologous to G3815, G3825 |
| 1653 | G2635 | DNA | A. thaliana | Predicted polypeptide sequence is paralogous to G2505 |
| 1654 | G2635 | PRT | A. thaliana | Paralogous to G2505 |
| 1655 | G2642 | DNA | A. thaliana | Predicted polypeptide sequence is paralogous to G2639, G2640 |
| 1656 | G2642 | PRT | A. thaliana | Paralogous to G2639, G2640 |
| 1657 | G2689 | DNA | A. thaliana | Predicted polypeptide sequence is paralogous to G2062, G2063, G2297 |
| 1658 | G2689 | PRT | A. thaliana | Paralogous to G2062, G2063, G2297 |
| 1659 | G2698 | DNA | A. thaliana | Predicted polypeptide sequence is paralogous to G2696 |
| 1660 | G2698 | PRT | A. thaliana | Paralogous to G2696 |
| 1661 | G2701 | DNA | A. thaliana | Predicted polypeptide sequence is paralogous to G1638, G2452, G1641, G1634 |
| 1662 | G2701 | PRT | A. thaliana | Paralogous to G1638, G2452, G1641, G1634 |
| 1663 | G2709 | DNA | A. thaliana | Predicted polypeptide sequence is paralogous to G2717, G204 |
| 1664 | G2709 | PRT | A. thaliana | Paralogous to G2717, G204 |
| 1665 | G2717 | DNA | A. thaliana | Predicted polypeptide sequence is paralogous to G204, G2709 |
| 1666 | G2717 | PRT | A. thaliana | Paralogous to G204, G2709 |
| 1667 | G2718 | DNA | A. thaliana | Predicted polypeptide sequence is paralogous to G1816, G225, G226, G682, G3930; orthologous to G3392, G3393, G3431, G3444, G3445, G3446, G3447, G3448, G3449, G3450 |
| 1668 | G2718 | PRT | A. thaliana | Paralogous to G1816, G225, G226, G682, G3930; Orthologous to G3392, G3393, G3431, G3444, G3445, G3446, G3447, G3448, G3449, G3450 |
| 1669 | G2738 | DNA | A. thaliana | Predicted polypeptide sequence is paralogous to G3009, G307, G308, G309; orthologous to G3816, G3817, G3818, G3819 |
| 1670 | G2738 | PRT | A. thaliana | Paralogous to G3009, G307, G308, G309; Orthologous to G3816, G3817, G3818, G3819 |
| 1671 | G2741 | DNA | A. thaliana | Predicted polypeptide sequence is paralogous to G1435; orthologous to G4240, G4241, G4243, G4244, G4245 |
| 1672 | G2741 | PRT | A. thaliana | Paralogous to G1435; Orthologous to G4240, G4241, G4243, G4244, G4245 |
| 1673 | G2767 | DNA | A. thaliana | Predicted polypeptide sequence is paralogous to G1131 |
| 1674 | G2767 | PRT | A. thaliana | Paralogous to G1131 |
| 1675 | G2781 | DNA | A. thaliana | Predicted polypeptide sequence is paralogous to G2159, G599 |
| 1676 | G2781 | PRT | A. thaliana | Paralogous to G2159, G599 |
| 1677 | G2817 | DNA | A. thaliana | Predicted polypeptide sequence is paralogous to G2818 |
| 1678 | G2817 | PRT | A. thaliana | Paralogous to G2818 |
| 1679 | G2827 | DNA | A. thaliana | Predicted polypeptide sequence is paralogous to G352 |
| 1680 | G2827 | PRT | A. thaliana | Paralogous to G352 |
| 1681 | G2834 | DNA | A. thaliana | Predicted polypeptide sequence is paralogous to G2840 |
| 1682 | G2834 | PRT | A. thaliana | Paralogous to G2840 |
| 1683 | G2839 | DNA | A. thaliana | Predicted polypeptide sequence is paralogous to G1889, G1974, G353, G354 |
| 1684 | G2839 | PRT | A. thaliana | Paralogous to G1889, G1974, G353, G354 |
| 1687 | G2859 | DNA | A. thaliana | Predicted polypeptide sequence is paralogous to G2779 |
| 1688 | G2859 | PRT | A. thaliana | Paralogous to G2779 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1689 | G2866 | DNA | A. thaliana | Predicted polypeptide sequence is paralogous to G468 |
| 1690 | G2866 | PRT | A. thaliana | Paralogous to G468 |
| 1691 | G2869 | DNA | A. thaliana | Predicted polypeptide sequence is paralogous to G2870, G2871, G2872, G2873, G934 |
| 1692 | G2869 | PRT | A. thaliana | Paralogous to G2870, G2871, G2872, G2873, G934 |
| 1693 | G2870 | DNA | A. thaliana | Predicted polypeptide sequence is paralogous to G2869, G2871, G2872, G2873, G934 |
| 1694 | G2870 | PRT | A. thaliana | Paralogous to G2869, G2871, G2872, G2873, G934 |
| 1695 | G2871 | DNA | A. thaliana | Predicted polypeptide sequence is paralogous to G2869, G2870, G2872, G2873, G934 |
| 1696 | G2871 | PRT | A. thaliana | Paralogous to G2869, G2870, G2872, G2873, G934 |
| 1697 | G2872 | DNA | A. thaliana | Predicted polypeptide sequence is paralogous to G2869, G2870, G2871, G2873, G934 |
| 1698 | G2872 | PRT | A. thaliana | Paralogous to G2869, G2870, G2871, G2873, G934 |
| 1699 | G2873 | DNA | A. thaliana | Predicted polypeptide sequence is paralogous to G2869, G2870, G2871, G2872, G934 |
| 1700 | G2873 | PRT | A. thaliana | Paralogous to G2869, G2870, G2871, G2872, G934 |
| 1701 | G2888 | DNA | A. thaliana | Predicted polypeptide sequence is paralogous to G1991 |
| 1702 | G2888 | PRT | A. thaliana | Paralogous to G1991 |
| 1703 | G289 | DNA | A. thaliana | Predicted polypeptide sequence is paralogous to G290 |
| 1704 | G289 | PRT | A. thaliana | Paralogous to G290 |
| 1705 | G2895 | DNA | A. thaliana | Predicted polypeptide sequence is paralogous to G2896 |
| 1706 | G2895 | PRT | A. thaliana | Paralogous to G2896 |
| 1707 | G2903 | DNA | A. thaliana | Predicted polypeptide sequence is paralogous to G2902 |
| 1708 | G2903 | PRT | A. thaliana | Paralogous to G2902 |
| 1709 | G291 | DNA | A. thaliana | Predicted polypeptide sequence is paralogous to G1211 |
| 1710 | G291 | PRT | A. thaliana | Paralogous to G1211 |
| 1711 | G2981 | DNA | A. thaliana | Predicted polypeptide sequence is paralogous to G2982 |
| 1712 | G2981 | PRT | A. thaliana | Paralogous to G2982 |
| 1713 | G2988 | DNA | A. thaliana | Predicted polypeptide sequence is paralogous to G1423, G1424 |
| 1714 | G2988 | PRT | A. thaliana | Paralogous to G1423, G1424 |
| 1715 | G2994 | DNA | A. thaliana | Predicted polypeptide sequence is paralogous to G2993 |
| 1716 | G2994 | PRT | A. thaliana | Paralogous to G2993 |
| 1717 | G3027 | DNA | A. thaliana | Predicted polypeptide sequence is paralogous to G1057 |
| 1718 | G3027 | PRT | A. thaliana | Paralogous to G1057 |
| 1719 | G3065 | DNA | A. thaliana | Predicted polypeptide sequence is paralogous to G2965 |
| 1720 | G3065 | PRT | A. thaliana | Paralogous to G2965 |
| 1721 | G307 | DNA | A. thaliana | Predicted polypeptide sequence is paralogous to G2738, G3009, G308, G309; orthologous to G3816, G3817, G3818, G3819 |
| 1722 | G307 | PRT | A. thaliana | Paralogous to G2738, G3009, G308, G309; Orthologous to G3816, G3817, G3818, G3819 |
| 1723 | G3079 | DNA | A. thaliana | Predicted polypeptide sequence is paralogous to G3080 |
| 1724 | G3079 | PRT | A. thaliana | Paralogous to G3080 |
| 1725 | G308 | DNA | A. thaliana | Predicted polypeptide sequence is paralogous to G2738, G3009, G307, G309; orthologous to G3816, G3817, G3818, G3819 |
| 1726 | G308 | PRT | A. thaliana | Paralogous to G2738, G3009, G307, G309; Orthologous to G3816, G3817, G3818, G3819 |
| 1727 | G312 | DNA | A. thaliana | Predicted polypeptide sequence is paralogous to G2739 |
| 1728 | G312 | PRT | A. thaliana | Paralogous to G2739 |
| 1729 | G313 | DNA | A. thaliana | Predicted polypeptide sequence is paralogous to G1768, G2633, G2697, G852; orthologous to G3815, G3825 |
| 1730 | G313 | PRT | A. thaliana | Paralogous to G1768, G2633, G2697, G852; Orthologous to G3815, G3825 |
| 1731 | G314 | DNA | A. thaliana | Predicted polypeptide sequence is paralogous to G2699 |
| 1732 | G314 | PRT | A. thaliana | Paralogous to G2699 |
| 1733 | G3362 | DNA | M. truncatula | Predicted polypeptide sequence is paralogous to G3364, G3365, G3366, G3367, G3368, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1734 | G3362 | PRT | M. truncatula | Paralogous to G3364, G3365, G3366, G3367, G3368, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1735 | G3364 | DNA | M. truncatula | Predicted polypeptide sequence is paralogous to G3362, G3365, G3366, G3367, G3368, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1736 | G3364 | PRT | *M. truncatula* | Paralogous to G3362, G3365, G3366, G3367, G3368, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1737 | G3365 | DNA | *M. truncatula* | Predicted polypeptide sequence is paralogous to G3362, G3364, G3366, G3367, G3368, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1738 | G3365 | PRT | *M. truncatula* | Paralogous to G3362, G3364, G3366, G3367, G3368, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1739 | G3366 | DNA | *M. truncatula* | Predicted polypeptide sequence is paralogous to G3362, G3364, G3365, G3367, G3368, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1740 | G3366 | PRT | *M. truncatula* | Paralogous to G3362, G3364, G3365, G3367, G3368, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1741 | G3367 | DNA | *M. truncatula* | Predicted polypeptide sequence is paralogous to G3362, G3364, G3365, G3366, G3368, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1742 | G3367 | PRT | *M. truncatula* | Paralogous to G3362, G3364, G3365, G3366, G3368, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1743 | G3368 | DNA | *M. truncatula* | Predicted polypeptide sequence is paralogous to G3362, G3364, G3365, G3366, G3367, G3369; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1744 | G3368 | PRT | *M. truncatula* | Paralogous to G3362, G3364, G3365, G3366, G3367, G3369; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1745 | G3369 | DNA | *M. truncatula* | Predicted polypeptide sequence is paralogous to G3362, G3364, G3365, G3366, G3367, G3368; orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1746 | G3369 | PRT | *M. truncatula* | Paralogous to G3362, G3364, G3365, G3366, G3367, G3368; Orthologous to G40, G2107, G2513, G41, G42, G912, G3370, G3371, G3372, G3373, G3374, G3375, G3376, G3377, G3378, G3379, G3438, G3439, G3440, G3441, G3442, G3497, G3498, G3499, G3443, G3463, G3464, G3465, G3466, G3467, G3468, G3469 |
| 1747 | G3370 | DNA | *O. sativa* | Predicted polypeptide sequence is paralogous to G3371, G3374, G3376, G3378; orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1748 | G3370 | PRT | *O. sativa* | Paralogous to G3371, G3374, G3376, G3378; Orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1749 | G3371 | DNA | *O. sativa* | Predicted polypeptide sequence is paralogous to G3370, G3374, G3376, G3378; orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1750 | G3371 | PRT | *O. sativa* | Paralogous to G3370, G3374, G3376, G3378; Orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1751 | G3372 | DNA | *O. sativa* | Predicted polypeptide sequence is paralogous to G3373, G3375, G3377, G3379; orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1752 | G3372 | PRT | *O. sativa* | Paralogous to G3373, G3375, G3377, G3379; Orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1753 | G3373 | DNA | *O. sativa* | Predicted polypeptide sequence is paralogous to G3372, G3375, G3377, G3379; orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1754 | G3373 | PRT | *O. sativa* | Paralogous to G3372, G3375, G3377, G3379; Orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1755 | G3374 | DNA | *O. sativa* | Predicted polypeptide sequence is paralogous to G3370, G3371, G3376, G3378; orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1756 | G3374 | PRT | *O. sativa* | Paralogous to G3370, G3371, G3376, G3378; Orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1757 | G3375 | DNA | *O. sativa* | Predicted polypeptide sequence is paralogous to G3372, G3373, G3377, G3379; orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1758 | G3375 | PRT | *O. sativa* | Paralogous to G3372, G3373, G3377, G3379; Orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1759 | G3376 | DNA | *O. sativa* | Predicted polypeptide sequence is paralogous to G3370, G3371, G3374, G3378; orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1760 | G3376 | PRT | *O. sativa* | Paralogous to G3370, G3371, G3374, G3378; Orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1761 | G3377 | DNA | *O. sativa* | Predicted polypeptide sequence is paralogous to G3372, G3373, G3375, G3379; orthologous to G40, G2107, G2513, G41, G42, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1762 | G3377 | PRT | O. sativa | Paralogous to G3372, G3373, G3375, G3379; Orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1763 | G3378 | DNA | O. sativa | Predicted polypeptide sequence is paralogous to G3370, G3371, G3374, G3376; orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1764 | G3378 | PRT | O. sativa | Paralogous to G3370, G3371, G3374, G3376; Orthologous to G40, G2107, G2513, G41, G42, G912, G3362, G3364, G3365, G3366, G3367, G3368, G3372, G3373, G3375, G3377, G3379, G3438, G3439, G3440, G3441, G3442, G3369, G3497, G3498, G3499, G3443, G3463, G3464, G3465, G3466, G3467, G3468, G3469 |
| 1765 | G3379 | DNA | O. sativa | Predicted polypeptide sequence is paralogous to G3372, G3373, G3375, G3377; orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1766 | G3379 | PRT | O. sativa | Paralogous to G3372, G3373, G3375, G3377; Orthologous to G40, G2107, G2513, G41, G42, G912, G3362, G3364, G3365, G3366, G3367, G3368, G3370, G3371, G3374, G3376, G3378, G3438, G3439, G3440, G3441, G3442, G3369, G3497, G3498, G3499, G3443, G3463, G3464, G3465, G3466, G3467, G3468, G3469 |
| 1767 | G3380 | DNA | O. sativa | Predicted polypeptide sequence is paralogous to G3381, G3383, G3515, G3737; orthologous to G1791, G1792, G1795, G30, G3516, G3517, G3518, G3519, G3520, G3735, G3736, G3794, G3739, G3929, G4328, G4329, G4330 |
| 1768 | G3380 | PRT | O. sativa | Paralogous to G3381, G3383, G3515, G3737; Orthologous to G1791, G1792, G1795, G30, G3516, G3517, G3518, G3519, G3520, G3735, G3736, G3794, G3739, G3929, G4328, G4329, G4330 |
| 1769 | G3381 | DNA | O. sativa | Predicted polypeptide sequence is paralogous to G3380, G3383, G3515, G3737; orthologous to G1791, G1792, G1795, G30, G3516, G3517, G3518, G3519, G3520, G3735, G3736, G3794, G3739, G3929, G4328, G4329, G4330 |
| 1770 | G3381 | PRT | O. sativa | Paralogous to G3380, G3383, G3515, G3737; Orthologous to G1791, G1792, G1795, G30, G3516, G3517, G3518, G3519, G3520, G3735, G3736, G3794, G3739, G3929, G4328, G4329, G4330 |
| 1771 | G3383 | DNA | O. sativa | Predicted polypeptide sequence is paralogous to G3380, G3381, G3515, G3737; orthologous to G1791, G1792, G1795, G30, G3516, G3517, G3518, G3519, G3520, G3735, G3736, G3794, G3739, G3929, G4328, G4329, G4330 |
| 1772 | G3383 | PRT | O. sativa | Paralogous to G3380, G3381, G3515, G3737; Orthologous to G1791, G1792, G1795, G30, G3516, G3517, G3518, G3519, G3520, G3735, G3736, G3794, G3739, G3929, G4328, G4329, G4330 |
| 1773 | G3384 | DNA | O. sativa | Predicted polypeptide sequence is paralogous to G3385, G3386, G3502; orthologous to G256, G666, G668, G932, G3500, G3501, G3537, G3538, G3539, G3540, G3541 |
| 1774 | G3384 | PRT | O. sativa | Paralogous to G3385, G3386, G3502; Orthologous to G256, G666, G668, G932, G3500, G3501, G3537, G3538, G3539, G3540, G3541 |
| 1775 | G3385 | DNA | O. sativa | Predicted polypeptide sequence is paralogous to G3384, G3386, G3502; orthologous to G256, G666, G668, G932, G3500, G3501, G3537, G3538, G3539, G3540, G3541 |
| 1776 | G3385 | PRT | O. sativa | Paralogous to G3384, G3386, G3502; Orthologous to G256, G666, G668, G932, G3500, G3501, G3537, G3538, G3539, G3540, G3541 |
| 1777 | G3386 | DNA | O. sativa | Predicted polypeptide sequence is paralogous to G3384, G3385, G3502; orthologous to G256, G666, G668, G932, G3500, G3501, G3537, G3538, G3539, G3540, G3541 |
| 1778 | G3386 | PRT | O. sativa | Paralogous to G3384, G3385, G3502; Orthologous to G256, G666, G668, G932, G3500, G3501, G3537, G3538, G3539, G3540, G3541 |
| 1779 | G3388 | DNA | O. sativa | Predicted polypeptide sequence is paralogous to G3389, G3390, G3391; orthologous to G1930, G867, G9, G993, G3432, G3433, G3451, G3452, G3453, G3454, G3455 |
| 1780 | G3388 | PRT | O. sativa | Paralogous to G3389, G3390, G3391; Orthologous to G1930, G867, G9, G993, G3432, G3433, G3451, G3452, G3453, G3454, G3455 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1781 | G3389 | DNA | O. sativa | Predicted polypeptide sequence is paralogous to G3388, G3390, G3391; orthologous to G1930, G867, G9, G993, G3432, G3433, G3451, G3452, G3453, G3454, G3455 |
| 1782 | G3389 | PRT | O. sativa | Paralogous to G3388, G3390, G3391; Orthologous to G1930, G867, G9, G993, G3432, G3433, G3451, G3452, G3453, G3454, G3455 |
| 1783 | G3390 | DNA | O. sativa | Predicted polypeptide sequence is paralogous to G3388, G3389, G3391; orthologous to G1930, G867, G9, G993, G3432, G3433, G3451, G3452, G3453, G3454, G3455 |
| 1784 | G3390 | PRT | O. sativa | Paralogous to G3388, G3389, G3391; Orthologous to G1930, G867, G9, G993, G3432, G3433, G3451, G3452, G3453, G3454, G3455 |
| 1785 | G3391 | DNA | O. sativa | Predicted polypeptide sequence is paralogous to G3388, G3389, G3390; orthologous to G1930, G867, G9, G993, G3432, G3433, G3451, G3452, G3453, G3454, G3455 |
| 1786 | G3391 | PRT | O. sativa | Paralogous to G3388, G3389, G3390; Orthologous to G1930, G867, G9, G993, G3432, G3433, G3451, G3452, G3453, G3454, G3455 |
| 1787 | G3392 | DNA | O. sativa | Predicted polypeptide sequence is paralogous to G3393; orthologous to G1816, G225, G226, G2718, G682, G3431, G3444, G3445, G3446, G3447, G3448, G3449, G3450, G3930 |
| 1788 | G3392 | PRT | O. sativa | Paralogous to G3393; Orthologous to G1816, G225, G226, G2718, G682, G3431, G3444, G3445, G3446, G3447, G3448, G3449, G3450, G3930 |
| 1789 | G3393 | DNA | O. sativa | Predicted polypeptide sequence is paralogous to G3392; orthologous to G1816, G225, G226, G2718, G682, G3431, G3444, G3445, G3446, G3447, G3448, G3449, G3450, G3930 |
| 1790 | G3393 | PRT | O. sativa | Paralogous to G3392; Orthologous to G1816, G225, G226, G2718, G682, G3431, G3444, G3445, G3446, G3447, G3448, G3449, G3450, G3930 |
| 1791 | G3394 | DNA | O. sativa | Predicted polypeptide sequence is orthologous to G1364, G2345, G481, G482, G485, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1792 | G3394 | PRT | O. sativa | Orthologous to G1364, G2345, G481, G482, G485, G3395, G3396, G3397, G3398, G3429, G3434, G3435, G3436, G3437, G3470, G3471, G3472, G3473, G3474, G3475, G3476, G3478, G3866, G3868, G3870, G3873, G3874, G3875, G3876, G3938, G4272, G4276 |
| 1793 | G3395 | DNA | O. sativa | Predicted polypeptide sequence is paralogous to G3396, G3397, G3398, G3429, G3938; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1794 | G3395 | PRT | O. sativa | Paralogous to G3396, G3397, G3398, G3429, G3938; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1795 | G3396 | DNA | O. sativa | Predicted polypeptide sequence is paralogous to G3395, G3397, G3398, G3429, G3938; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1796 | G3396 | PRT | O. sativa | Paralogous to G3395, G3397, G3398, G3429, G3938; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1797 | G3397 | DNA | O. sativa | Predicted polypeptide sequence is paralogous to G3395, G3396, G3398, G3429, G3938; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1798 | G3397 | PRT | O. sativa | Paralogous to G3395, G3396, G3398, G3429, G3938; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1799 | G3398 | DNA | O. sativa | Predicted polypeptide sequence is paralogous to G3395, G3396, G3397, G3429, G3938; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1800 | G3398 | PRT | O. sativa | Paralogous to G3395, G3396, G3397, G3429, G3938; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1801 | G3399 | DNA | O. sativa | Predicted polypeptide sequence is paralogous to G3400; orthologous to G1067, G1073, G2156 |
| 1802 | G3399 | PRT | O. sativa | Paralogous to G3400; Orthologous to G1067, G1073, G2156 |
| 1803 | G3400 | DNA | O. sativa | Predicted polypeptide sequence is paralogous to G3399; orthologous to G1067, G1073, G2156 |
| 1804 | G3400 | PRT | O. sativa | Paralogous to G3399; Orthologous to G1067, G1073, G2156 |
| 1805 | G3406 | DNA | O. sativa | Predicted polypeptide sequence is paralogous to G3407; orthologous to G1075, G1076, G3458, G3459, G3460, G3461 |
| 1806 | G3406 | PRT | O. sativa | Paralogous to G3407; Orthologous to G1075, G1076, G3458, G3459, G3460, G3461 |
| 1807 | G3407 | DNA | O. sativa | Predicted polypeptide sequence is paralogous to G3406; orthologous to G1075, G1076, G3458, G3459, G3460, G3461 |
| 1808 | G3407 | PRT | O. sativa | Paralogous to G3406; Orthologous to G1075, G1076, G3458, G3459, G3460, G3461 |
| 1809 | G3429 | DNA | O. sativa | Predicted polypeptide sequence is paralogous to G3395, G3396, G3397, G3398, G3938; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1810 | G3429 | PRT | O. sativa | Paralogous to G3395, G3396, G3397, G3398, G3938; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 1811 | G3430 | DNA | O. sativa | Predicted polypeptide sequence is paralogous to G3848, G5171; orthologous to G22, G1006, G28, G3659, G3660, G3661, G3717, G3718, G3841, G3843, G3844, G3845, G3846, G3852, G3856, G3857, G3858, G3864, G3865, G4626 |
| 1812 | G3430 | PRT | O. sativa | Paralogous to G3848, G5171; Orthologous to G22, G1006, G28, G3659, G3660, G3661, G3717, G3718, G3841, G3843, G3844, G3845, G3846, G3852, G3856, G3857, G3858, G3864, G3865, G4626 |
| 1813 | G3431 | DNA | Z. mays | Predicted polypeptide sequence is paralogous to G3444; orthologous to G1816, G225, G226, G2718, G682, G3392, G3393, G3445, G3446, G3447, G3448, G3449, G3450, G3930 |
| 1814 | G3431 | PRT | Z. mays | Paralogous to G3444; Orthologous to G1816, G225, G226, G2718, G682, G3392, G3393, G3445, G3446, G3447, G3448, G3449, G3450, G3930 |
| 1815 | G3432 | DNA | Z. mays | Predicted polypeptide sequence is paralogous to G3433; orthologous to G1930, G867, G9, G993, G3388, G3389, G3390, G3391, G3451, G3452, G3453, G3454, G3455 |
| 1816 | G3432 | PRT | Z. mays | Paralogous to G3433; Orthologous to G1930, G867, G9, G993, G3388, G3389, G3390, G3391, G3451, G3452, G3453, G3454, G3455 |
| 1817 | G3433 | DNA | Z. mays | Predicted polypeptide sequence is paralogous to G3432; orthologous to G1930, G867, G9, G993, G3388, G3389, G3390, G3391, G3451, G3452, G3453, G3454, G3455 |
| 1818 | G3433 | PRT | Z. mays | Paralogous to G3432; Orthologous to G1930, G867, G9, G993, G3388, G3389, G3390, G3391, G3451, G3452, G3453, G3454, G3455 |
| 1819 | G3434 | DNA | Z. mays | Predicted polypeptide sequence is paralogous to G3435, G3436, G3437, G3866, G3876, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1820 | G3434 | PRT | Z. mays | Paralogous to G3435, G3436, G3437, G3866, G3876, G4272, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1821 | G3435 | DNA | Z. mays | Predicted polypeptide sequence is paralogous to G3434, G3436, G3437, G3866, G3876, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1822 | G3435 | PRT | Z. mays | Paralogous to G3434, G3436, G3437, G3866, G3876, G4272, G4276; Orthologous to G1364, G2345, G481, G482, G485, G3394, G3395, G3396, G3397, G3398, G3429, G3470, G3471, G3472, G3473, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3474, G3475, G3476, G3478, G3868, G3870, G3873, G3874, G3875, G3938 |
| 1823 | G3436 | DNA | Z. mays | Predicted polypeptide sequence is paralogous to G3434, G3435, G3437, G3866, G3876, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1824 | G3436 | PRT | Z. mays | Paralogous to G3434, G3435, G3437, G3866, G3876, G4272, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1825 | G3437 | DNA | Z. mays | Predicted polypeptide sequence is paralogous to G3434, G3435, G3436, G3866, G3876, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1826 | G3437 | PRT | Z. mays | Paralogous to G3434, G3435, G3436, G3866, G3876, G4272, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 1827 | G3438 | DNA | Z. mays | Predicted polypeptide sequence is paralogous to G3439, G3440, G3441, G3442, G3443; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1828 | G3438 | PRT | Z. mays | Paralogous to G3439, G3440, G3441, G3442, G3443; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1829 | G3439 | DNA | Z. mays | Predicted polypeptide sequence is paralogous to G3438, G3440, G3441, G3442, G3443; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1830 | G3439 | PRT | Z. mays | Paralogous to G3438, G3440, G3441, G3442, G3443; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1831 | G3440 | DNA | Z. mays | Predicted polypeptide sequence is paralogous to G3438, G3439, G3441, G3442, G3443; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1832 | G3440 | PRT | Z. mays | Paralogous to G3438, G3439, G3441, G3442, G3443; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1833 | G3441 | DNA | Z. mays | Predicted polypeptide sequence is paralogous to G3438, G3439, G3440, G3442, G3443; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1834 | G3441 | PRT | Z. mays | Paralogous to G3438, G3439, G3440, G3442, G3443; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1835 | G3442 | DNA | Z. mays | Predicted polypeptide sequence is paralogous to G3438, G3439, G3440, G3441, G3443; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1836 | G3442 | PRT | Z. mays | Paralogous to G3438, G3439, G3440, G3441, G3443; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1837 | G3443 | DNA | Z. mays | Predicted polypeptide sequence is paralogous to G3438, G3439, G3440, G3441, G3442; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1838 | G3443 | PRT | Z. mays | Paralogous to G3438, G3439, G3440, G3441, G3442; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3369, G3497, G3498, G3499, G3463, G3464, G3465, G3466, G3467, G3468, G3469 |
| 1839 | G3444 | DNA | Z. mays | Predicted polypeptide sequence is paralogous to G3431; orthologous to G1816, G225, G226, G2718, G682, G3392, G3393, G3445, G3446, G3447, G3448, G3449, G3450, G3930 |
| 1840 | G3444 | PRT | Z. mays | Paralogous to G3431; Orthologous to G1816, G225, G226, G2718, G682, G3392, G3393, G3445, G3446, G3447, G3448, G3449, G3450, G3930 |
| 1841 | G3445 | DNA | G. max | Predicted polypeptide sequence is paralogous to G3446, G3447, G3448, G3449, G3450; orthologous to G1816, G225, G226, G2718, G682, G3392, G3393, G3431, G3444, G3930 |
| 1842 | G3445 | PRT | G. max | Paralogous to G3446, G3447, G3448, G3449, G3450; Orthologous to G1816, G225, G226, G2718, G682, G3392, G3393, G3431, G3444, G3930 |
| 1843 | G3446 | DNA | G. max | Predicted polypeptide sequence is paralogous to G3445, G3447, G3448, G3449, G3450; orthologous to G1816, G225, G226, G2718, G682, G3392, G3393, G3431, G3444, G3930 |
| 1844 | G3446 | PRT | G. max | Paralogous to G3445, G3447, G3448, G3449, G3450; Orthologous to G1816, G225, G226, G2718, G682, G3392, G3393, G3431, G3444, G3930 |
| 1845 | G3447 | DNA | G. max | Predicted polypeptide sequence is paralogous to G3445, G3446, G3448, G3449, G3450; orthologous to G1816, G225, G226, G2718, G682, G3392, G3393, G3431, G3444, G3930 |
| 1846 | G3447 | PRT | G. max | Paralogous to G3445, G3446, G3448, G3449, G3450; Orthologous to G1816, G225, G226, G2718, G682, G3392, G3393, G3431, G3444, G3930 |
| 1847 | G3448 | DNA | G. max | Predicted polypeptide sequence is paralogous to G3445, G3446, G3447, G3449, G3450; orthologous to G1816, G225, G226, G2718, G682, G3392, G3393, G3431, G3444, G3930 |
| 1848 | G3448 | PRT | G. max | Paralogous to G3445, G3446, G3447, G3449, G3450; Orthologous to G1816, G225, G226, G2718, G682, G3392, G3393, G3431, G3444, G3930 |
| 1849 | G3449 | DNA | G. max | Predicted polypeptide sequence is paralogous to G3445, G3446, G3447, G3448, G3450; orthologous to G1816, G225, G226, G2718, G682, G3392, G3393, G3431, G3444, G3930 |
| 1850 | G3449 | PRT | G. max | Paralogous to G3445, G3446, G3447, G3448, G3450; Orthologous to G1816, G225, G226, G2718, G682, G3392, G3393, G3431, G3444, G3930 |
| 1851 | G3450 | DNA | G. max | Predicted polypeptide sequence is paralogous to G3445, G3446, G3447, G3448, G3449; orthologous to G1816, G225, G226, G2718, G682, G3392, G3393, G3431, G3444, G3930 |
| 1852 | G3450 | PRT | G. max | Paralogous to G3445, G3446, G3447, G3448, G3449; Orthologous to G1816, G225, G226, G2718, G682, G3392, G3393, G3431, G3444, G3930 |
| 1853 | G3451 | DNA | G. max | Predicted polypeptide sequence is paralogous to G3452, G3453, G3454, G3455; orthologous to G1930, G867, G9, G993, G3388, G3389, G3390, G3391, G3432, G3433 |
| 1854 | G3451 | PRT | G. max | Paralogous to G3452, G3453, G3454, G3455; Orthologous to G1930, G867, G9, G993, G3388, G3389, G3390, G3391, G3432, G3433 |
| 1855 | G3452 | DNA | G. max | Predicted polypeptide sequence is paralogous to G3451, G3453, G3454, G3455; orthologous to G1930, G867, G9, G993, G3388, G3389, G3390, G3391, G3432, G3433 |
| 1856 | G3452 | PRT | G. max | Paralogous to G3451, G3453, G3454, G3455; Orthologous to G1930, G867, G9, G993, G3388, G3389, G3390, G3391, G3432, G3433 |
| 1857 | G3453 | DNA | G. max | Predicted polypeptide sequence is paralogous to G3451, G3452, G3454, G3455; orthologous to G1930, G867, G9, G993, G3388, G3389, G3390, G3391, G3432, G3433 |
| 1858 | G3453 | PRT | G. max | Paralogous to G3451, G3452, G3454, G3455; Orthologous to G1930, G867, G9, G993, G3388, G3389, G3390, G3391, G3432, G3433 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1859 | G3454 | DNA | *G. max* | Predicted polypeptide sequence is paralogous to G3451, G3452, G3453, G3455; orthologous to G1930, G867, G9, G993, G3388, G3389, G3390, G3391, G3432, G3433 |
| 1860 | G3454 | PRT | *G. max* | Paralogous to G3451, G3452, G3453, G3455; Orthologous to G1930, G867, G9, G993, G3388, G3389, G3390, G3391, G3432, G3433 |
| 1861 | G3455 | DNA | *G. max* | Predicted polypeptide sequence is paralogous to G3451, G3452, G3453, G3454; orthologous to G1930, G867, G9, G993, G3388, G3389, G3390, G3391, G3432, G3433 |
| 1862 | G3455 | PRT | *G. max* | Paralogous to G3451, G3452, G3453, G3454; Orthologous to G1930, G867, G9, G993, G3388, G3389, G3390, G3391, G3432, G3433 |
| 1863 | G3457 | DNA | *G. max* | Predicted polypeptide sequence is orthologous to G2789, G596 |
| 1864 | G3457 | PRT | *G. max* | Orthologous to G2789, G596 |
| 1865 | G3458 | DNA | *G. max* | Predicted polypeptide sequence is paralogous to G3459, G3460, G3461; orthologous to G1075, G1076, G3406, G3407 |
| 1866 | G3458 | PRT | *G. max* | Paralogous to G3459, G3460, G3461; Orthologous to G1075, G1076, G3406, G3407 |
| 1867 | G3459 | DNA | *G. max* | Predicted polypeptide sequence is paralogous to G3458, G3460, G3461; orthologous to G1075, G1076, G3406, G3407 |
| 1868 | G3459 | PRT | *G. max* | Paralogous to G3458, G3460, G3461; Orthologous to G1075, G1076, G3406, G3407 |
| 1869 | G3460 | DNA | *G. max* | Predicted polypeptide sequence is paralogous to G3458, G3459, G3461; orthologous to G1075, G1076, G3406, G3407 |
| 1870 | G3460 | PRT | *G. max* | Paralogous to G3458, G3459, G3461; Orthologous to G1075, G1076, G3406, G3407 |
| 1871 | G3461 | DNA | *G. max* | Predicted polypeptide sequence is paralogous to G3458, G3459, G3460; orthologous to G1075, G1076, G3406, G3407 |
| 1872 | G3461 | PRT | *G. max* | Paralogous to G3458, G3459, G3460; Orthologous to G1075, G1076, G3406, G3407 |
| 1873 | G3463 | DNA | *G. max* | Predicted polypeptide sequence is paralogous to G3464, G3465, G3466, G3467, G3468, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1874 | G3463 | PRT | *G. max* | Paralogous to G3464, G3465, G3466, G3467, G3468, G3469; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1875 | G3464 | DNA | *G. max* | Predicted polypeptide sequence is paralogous to G3463, G3465, G3466, G3467, G3468, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1876 | G3464 | PRT | *G. max* | Paralogous to G3463, G3465, G3466, G3467, G3468, G3469; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1877 | G3465 | DNA | *G. max* | Predicted polypeptide sequence is paralogous to G3463, G3464, G3466, G3467, G3468, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1878 | G3465 | PRT | *G. max* | Paralogous to G3463, G3464, G3466, G3467, G3468, G3469; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1879 | G3466 | DNA | *G. max* | Predicted polypeptide sequence is paralogous to G3463, G3464, G3465, G3467, G3468, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1880 | G3466 | PRT | *G. max* | Paralogous to G3463, G3464, G3465, G3467, G3468, G3469; Orthologous to G40, G2107, G2513, G41, G42, G912, G3362, G3364, G3365, G3366, G3367, G3368, G3370, G3371, G3372, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3373, G3374, G3375, G3376, G3377, G3378, G3379, G3438, G3439, G3440, G3441, G3442, G3369, G3497, G3498, G3499, G3443 |
| 1881 | G3467 | DNA | *G. max* | Predicted polypeptide sequence is paralogous to G3463, G3464, G3465, G3466, G3468, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1882 | G3467 | PRT | *G. max* | Paralogous to G3463, G3464, G3465, G3466, G3468, G3469; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1883 | G3468 | DNA | *G. max* | Predicted polypeptide sequence is paralogous to G3463, G3464, G3465, G3466, G3467, G3469; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1884 | G3468 | PRT | *G. max* | Paralogous to G3463, G3464, G3465, G3466, G3467, G3469; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1885 | G3469 | DNA | *G. max* | Predicted polypeptide sequence is paralogous to G3463, G3464, G3465, G3466, G3467, G3468; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1886 | G3469 | PRT | *G. max* | Paralogous to G3463, G3464, G3465, G3466, G3467, G3468; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443 |
| 1887 | G3470 | DNA | *G. max* | Predicted polypeptide sequence is paralogous to G3471, G3472, G3473, G3474, G3475, G3476, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1888 | G3470 | PRT | *G. max* | Paralogous to G3471, G3472, G3473, G3474, G3475, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1889 | G3471 | DNA | *G. max* | Predicted polypeptide sequence is paralogous to G3470, G3472, G3473, G3474, G3475, G3476, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1890 | G3471 | PRT | *G. max* | Paralogous to G3470, G3472, G3473, G3474, G3475, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1891 | G3472 | DNA | *G. max* | Predicted polypeptide sequence is paralogous to G3470, G3471, G3473, G3474, G3475, G3476, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1892 | G3472 | PRT | *G. max* | Paralogous to G3470, G3471, G3473, G3474, G3475, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1893 | G3473 | DNA | *G. max* | Predicted polypeptide sequence is paralogous to G3470, G3471, G3472, G3474, G3475, G3476, G3478, G3873, G3874, G3875; orthologous to G1364, G2345, G481, G482, G485, G3394, G3395, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3396, G3397, G3398, G3429, G3434, G3435, G3436, G3437, G3866, G3868, G3870, G3876, G3938, G4272, G4276 |
| 1894 | G3473 | PRT | G. max | Paralogous to G3470, G3471, G3472, G3474, G3475, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1895 | G3474 | DNA | G. max | Predicted polypeptide sequence is paralogous to G3470, G3471, G3472, G3473, G3475, G3476, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1896 | G3474 | PRT | G. max | Paralogous to G3470, G3471, G3472, G3473, G3475, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1897 | G3475 | DNA | G. max | Predicted polypeptide sequence is paralogous to G3470, G3471, G3472, G3473, G3474, G3476, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1898 | G3475 | PRT | G. max | Paralogous to G3470, G3471, G3472, G3473, G3474, G3476, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1899 | G3476 | DNA | G. max | Predicted polypeptide sequence is paralogous to G3470, G3471, G3472, G3473, G3474, G3475, G3478, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1900 | G3476 | PRT | G. max | Paralogous to G3470, G3471, G3472, G3473, G3474, G3475, G3478, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1901 | G3478 | DNA | G. max | Predicted polypeptide sequence is paralogous to G3470, G3471, G3472, G3473, G3474, G3475, G3476, G3873, G3874, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1902 | G3478 | PRT | G. max | Paralogous to G3470, G3471, G3472, G3473, G3474, G3475, G3476, G3873, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 1903 | G3479 | DNA | O. sativa | Predicted polypeptide sequence is paralogous to G3480, G3481, G3482, G3483; orthologous to G152, G153, G1760, G860, G3484, G3485, G3487, G3488, G3489, G3980, G3981, G3982 |
| 1904 | G3479 | PRT | O. sativa | Paralogous to G3480, G3481, G3482, G3483; Orthologous to G152, G153, G1760, G860, G3484, G3485, G3487, G3488, G3489, G3980, G3981, G3982 |
| 1905 | G3480 | DNA | O. sativa | Predicted polypeptide sequence is paralogous to G3479, G3481, G3482, G3483; orthologous to G152, G153, G1760, G860, G3484, G3485, G3487, G3488, G3489, G3980, G3981, G3982 |
| 1906 | G3480 | PRT | O. sativa | Paralogous to G3479, G3481, G3482, G3483; Orthologous to G152, G153, G1760, G860, G3484, G3485, G3487, G3488, G3489, G3980, G3981, G3982 |
| 1907 | G3481 | DNA | O. sativa | Predicted polypeptide sequence is paralogous to G3479, G3480, G3482, G3483; orthologous to G152, G153, G1760, G860, G3484, G3485, G3487, G3488, G3489, G3980, G3981, G3982 |
| 1908 | G3481 | PRT | O. sativa | Paralogous to G3479, G3480, G3482, G3483; Orthologous to G152, G153, G1760, G860, G3484, G3485, G3487, G3488, G3489, G3980, G3981, G3982 |
| 1909 | G3482 | DNA | O. sativa | Predicted polypeptide sequence is paralogous to G3479, G3480, G3481, G3483; orthologous to G152, G153, G1760, G860, G3484, G3485, G3487, G3488, G3489, G3980, G3981, G3982 |
| 1910 | G3482 | PRT | O. sativa | Paralogous to G3479, G3480, G3481, G3483; Orthologous to G152, G153, G1760, G860, G3484, G3485, G3487, G3488, G3489, G3980, G3981, G3982 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1911 | G3483 | DNA | *O. sativa* | Predicted polypeptide sequence is paralogous to G3479, G3480, G3481, G3482; orthologous to G152, G153, G1760, G860, G3484, G3485, G3487, G3488, G3489, G3980, G3981, G3982 |
| 1912 | G3483 | PRT | *O. sativa* | Paralogous to G3479, G3480, G3481, G3482; Orthologous to G152, G153, G1760, G860, G3484, G3485, G3487, G3488, G3489, G3980, G3981, G3982 |
| 1913 | G3484 | DNA | *G. max* | Predicted polypeptide sequence is paralogous to G3485, G3980, G3981; orthologous to G152, G153, G1760, G860, G3479, G3480, G3481, G3482, G3483, G3487, G3488, G3489, G3982 |
| 1914 | G3484 | PRT | *G. max* | Paralogous to G3485, G3980, G3981; Orthologous to G152, G153, G1760, G860, G3479, G3480, G3481, G3482, G3483, G3487, G3488, G3489, G3982 |
| 1915 | G3485 | DNA | *G. max* | Predicted polypeptide sequence is paralogous to G3484, G3980, G3981; orthologous to G152, G153, G1760, G860, G3479, G3480, G3481, G3482, G3483, G3487, G3488, G3489, G3982 |
| 1916 | G3485 | PRT | *G. max* | Paralogous to G3484, G3980, G3981; Orthologous to G152, G153, G1760, G860, G3479, G3480, G3481, G3482, G3483, G3487, G3488, G3489, G3982 |
| 1917 | G3487 | DNA | *Z. mays* | Predicted polypeptide sequence is paralogous to G3488, G3489; orthologous to G152, G153, G1760, G860, G3479, G3480, G3481, G3482, G3483, G3484, G3485, G3980, G3981, G3982 |
| 1918 | G3487 | PRT | *Z. mays* | Paralogous to G3488, G3489; Orthologous to G152, G153, G1760, G860, G3479, G3480, G3481, G3482, G3483, G3484, G3485, G3980, G3981, G3982 |
| 1919 | G3488 | DNA | *Z. mays* | Predicted polypeptide sequence is paralogous to G3487, G3489; orthologous to G152, G153, G1760, G860, G3479, G3480, G3481, G3482, G3483, G3484, G3485, G3980, G3981, G3982 |
| 1920 | G3488 | PRT | *Z. mays* | Paralogous to G3487, G3489; Orthologous to G152, G153, G1760, G860, G3479, G3480, G3481, G3482, G3483, G3484, G3485, G3980, G3981, G3982 |
| 1921 | G3489 | DNA | *Z. mays* | Predicted polypeptide sequence is paralogous to G3487, G3488; orthologous to G152, G153, G1760, G860, G3479, G3480, G3481, G3482, G3483, G3484, G3485, G3980, G3981, G3982 |
| 1922 | G3489 | PRT | *Z. mays* | Paralogous to G3487, G3488; Orthologous to G152, G153, G1760, G860, G3479, G3480, G3481, G3482, G3483, G3484, G3485, G3980, G3981, G3982 |
| 1923 | G3490 | DNA | *Z. mays* | Predicted polypeptide sequence is paralogous to G4369, G4370; orthologous to G1543, G3510, G3524, G4371 |
| 1924 | G3490 | PRT | *Z. mays* | Paralogous to G4369, G4370; Orthologous to G1543, G3510, G3524, G4371 |
| 1925 | G3491 | DNA | *O. sativa* | Predicted polypeptide sequence is orthologous to G807, G810, G3494, G3495, G3512 |
| 1926 | G3491 | PRT | *O. sativa* | Orthologous to G807, G810, G3494, G3495, G3512 |
| 1927 | G3494 | DNA | *G. max* | Predicted polypeptide sequence is paralogous to G3495, G3512; orthologous to G807, G810, G3491 |
| 1928 | G3494 | PRT | *G. max* | Paralogous to G3495, G3512; Orthologous to G807, G810, G3491 |
| 1929 | G3495 | DNA | *G. max* | Predicted polypeptide sequence is paralogous to G3494, G3512; orthologous to G807, G810, G3491 |
| 1930 | G3495 | PRT | *G. max* | Paralogous to G3494, G3512; Orthologous to G807, G810, G3491 |
| 1931 | G3497 | DNA | *M. sativa* | Predicted polypeptide sequence is paralogous to G3498, G3499; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1932 | G3497 | PRT | *M. sativa* | Paralogous to G3498, G3499; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1933 | G3498 | DNA | *M. sativa* | Predicted polypeptide sequence is paralogous to G3497, G3499; orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1934 | G3498 | PRT | *M. sativa* | Paralogous to G3497, G3499; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1935 | G3499 | DNA | *M. sativa* | Predicted polypeptide sequence is paralogous to G3497, G3498; orthologous to G40, G2107, G2513, G41, G42, G912, G3362, G3364, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1936 | G3499 | PRT | *M. sativa* | Paralogous to G3497, G3498; Orthologous to G40, G2107, G2513, G41, G42, G912, G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3443, G3463, G3464, G3465, G3466, G3467, G3468, G3469 |
| 1937 | G3500 | DNA | *S. lycopersicum* | Predicted polypeptide sequence is paralogous to G3501; orthologous to G256, G666, G668, G932, G3384, G3385, G3386, G3502, G3537, G3538, G3539, G3540, G3541 |
| 1938 | G3500 | PRT | *S. lycopersicum* | Paralogous to G3501; Orthologous to G256, G666, G668, G932, G3384, G3385, G3386, G3502, G3537, G3538, G3539, G3540, G3541 |
| 1939 | G3501 | DNA | *S. lycopersicum* | Predicted polypeptide sequence is paralogous to G3500; orthologous to G256, G666, G668, G932, G3384, G3385, G3386, G3502, G3537, G3538, G3539, G3540, G3541 |
| 1940 | G3501 | PRT | *S. lycopersicum* | Paralogous to G3500; Orthologous to G256, G666, G668, G932, G3384, G3385, G3386, G3502, G3537, G3538, G3539, G3540, G3541 |
| 1941 | G3502 | DNA | *O. sativa* | Predicted polypeptide sequence is paralogous to G3384, G3385, G3386; orthologous to G256, G666, G668, G932, G3500, G3501, G3537, G3538, G3539, G3540, G3541 |
| 1942 | G3502 | PRT | *O. sativa* | Paralogous to G3384, G3385, G3386; Orthologous to G256, G666, G668, G932, G3500, G3501, G3537, G3538, G3539, G3540, G3541 |
| 1943 | G3503 | DNA | *O. sativa* | Predicted polypeptide sequence is paralogous to G3504, G3505, G3506, G3507, G3508; orthologous to G197, G255, G664, G3509, G3529, G3531, G3532, G3533, G3534, G3527, G3528, G4637, G4638, G4639, G4640 |
| 1944 | G3503 | PRT | *O. sativa* | Paralogous to G3504, G3505, G3506, G3507, G3508; Orthologous to G197, G255, G664, G3509, G3529, G3531, G3532, G3533, G3534, G3527, G3528, G4637, G4638, G4639, G4640 |
| 1945 | G3504 | DNA | *O. sativa* | Predicted polypeptide sequence is paralogous to G3503, G3505, G3506, G3507, G3508; orthologous to G197, G255, G664, G3509, G3529, G3531, G3532, G3533, G3534, G3527, G3528, G4637, G4638, G4639, G4640 |
| 1946 | G3504 | PRT | *O. sativa* | Paralogous to G3503, G3505, G3506, G3507, G3508; Orthologous to G197, G255, G664, G3509, G3529, G3531, G3532, G3533, G3534, G3527, G3528, G4637, G4638, G4639, G4640 |
| 1947 | G3505 | DNA | *O. sativa* | Predicted polypeptide sequence is paralogous to G3503, G3504, G3506, G3507, G3508; orthologous to G197, G255, G664, G3509, G3529, G3531, G3532, G3533, G3534, G3527, G3528, G4637, G4638, G4639, G4640 |
| 1948 | G3505 | PRT | *O. sativa* | Paralogous to G3503, G3504, G3506, G3507, G3508; Orthologous to G197, G255, G664, G3509, G3529, G3531, G3532, G3533, G3534, G3527, G3528, G4637, G4638, G4639, G4640 |
| 1949 | G3506 | DNA | *O. saliva* | Predicted polypeptide sequence is paralogous to G3503, G3504, G3505, G3507, G3508; orthologous to G197, G255, G664, G3509, G3529, G3531, G3532, G3533, G3534, G3527, G3528, G4637, G4638, G4639, G4640 |
| 1950 | G3506 | PRT | *O. salita* | Paralogous to G3503, G3504, G3505, G3507, G3508; Orthologous to G197, G255, G664, G3509, G3529, G3531, G3532, G3533, G3534, G3527, G3528, G4637, G4638, G4639, G4640 |
| 1951 | G3507 | DNA | *O. saliva* | Predicted polypeptide sequence is paralogous to G3503, G3504, G3505, G3506, G3508; orthologous to G197, G255, G664, G3509, G3529, G3531, G3532, G3533, G3534, G3527, G3528, G4637, G4638, G4639, G4640 |
| 1952 | G3507 | PRT | *O. saliva* | Paralogous to G3503, G3504, G3505, G3506, G3508; Orthologous to G197, G255, G664, G3509, G3529, G3531, G3532, G3533, G3534, G3527, G3528, G4637, G4638, G4639, G4640 |
| 1953 | G3508 | DNA | *O. saliva* | Predicted polypeptide sequence is paralogous to G3503, G3504, G3505, G3506. G3507; orthologous to G197, G255, G664, G3509, G3529, G3531, G3532, G3533, G3534, G3527, G3528, G4637, G4638, G4639, G4640 |
| 1954 | G3508 | PRT | *O. saliva* | Paralogous to G3503, G3504, G3505, G3506, G3507; Orthologous to G197, G255, G664, G3509, G3529, G3531, G3532, G3533, G3534, G3527, G3528, G4637, G4638, G4639, G4640 |
| 1955 | G3509 | DNA | *S. lycopersicum* | Predicted polypeptide sequence is orthologous to G197, G255, G664, G3503, G3504, G3505, G3506, G3507, G3508, G3529, G3531, G3532, G3533, G3534, G3527, G3528, G4637, G4638, G4639, G4640 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1956 | G3509 | PRT | S. lycopersicum | Orthologous to G197, G255, G664, G3503, G3504, G3505, G3506, G3507, G3508, G3529, G3531, G3532, G3533, G3534, G3527, G3528, G4637, G4638, G4639, G4640 |
| 1957 | G3510 | DNA | O. saliva | Predicted polypeptide sequence is orthologous to G1543, G3490, G3524, G4369, G4370, G4371 |
| 1958 | G3510 | PRT | O saliva | Orthologous to G1543, G3490, G3524, G4369, G4370, G4371 |
| 1959 | G3512 | DNA | G. max | Predicted polypeptide sequence is paralogous to G3494, G3495; orthologous to G807, G810, G3491 |
| 1960 | G3512 | PRT | Z. mays | Paralogous to G3494, G3495; Orthologous to G807, G810, G3491 |
| 1961 | G3515 | DNA | O. saliva | Predicted polypeptide sequence is paralogous to G3380, G3381, G3383, G3737; orthologous to G1791, G1792, G1795, G30, G3516, G3517, G3518, G3519, G3520, G3735, G3736, G3794, G3739, G3929, G4328, G4329, G4330 |
| 1962 | G3515 | PRT | O. saliva | Paralogous to G3380, G3381, G3383, G3737; Orthologous to G1791, G1792, G1795, G30, G3516, G3517, G3518, G3519, G3520, G3735, G3736, G3794, G3739, G3929, G4328, G4329, G4330 |
| 1963 | G3516 | DNA | Z. mays | Predicted polypeptide sequence is paralogous to G3517, G3794, G3739, G3929; orthologous to G1791, G1792, G1795, G30, G3380, G3381, G3383, G3515, G3518, G3519, G3520, G3735, G3736, G3737, G4328, G4329, G4330 |
| 1964 | G3516 | PRT | Z. mays | Paralogous to G3517, G3794, G3739, G3929; Orthologous to G1791, G1792, G1795, G30, G3380, G3381, G3383, G3515, G3518, G3519, G3520, G3735, G3736, G3737, G4328, G4329, G4330 |
| 1965 | G3517 | DNA | Z. mays | Predicted polypeptide sequence is paralogous to G3516, G3794, G3739, G3929; orthologous to G1791, G1792, G1795, G30, G3380, G3381, G3383, G3515, G3518, G3519, G3520, G3735, G3736, G3737, G4328, G4329, G4330 |
| 1966 | G3517 | PRT | Z. mays | Paralogous to G3516, G3794, G3739, G3929; Orthologous to G1791, G1792, G1795, G30, G3380, G3381, G3383, G3515, G3518, G3519, G3520, G3735, G3736, G3737, G4328, G4329, G4330 |
| 1967 | G3518 | DNA | G. max | Predicted polypeptide sequence is paralogous to G3519, G3520; orthologous to G1791, G1792, G1795, G30, G3380, G3381, G3383, G3515, G3516, G3517, G3735, G3736, G3737, G3794, G3739, G3929, G4328, G4329, G4330 |
| 1968 | G3518 | PRT | G. max | Paralogous to G3519, G3520; Orthologous to G1791, G1792, G1795, G30, G3380, G3381, G3383, G3515, G3516, G3517, G3735, G3736, G3737, G3794, G3739, G3929, G4328, G4329, G4330 |
| 1969 | G3519 | DNA | G. max | Predicted polypeptide sequence is paralogous to G3518, G3520; orthologous to G1791, G1792, G1795, G30, G3380, G3381, G3383, G3515, G3516, G3517, G3735, G3736, G3737, G3794, G3739, G3929, G4328, G4329, G4330 |
| 1970 | G3519 | PRT | G. max | Paralogous to G3518, G3520; Orthologous to G1791, G1792, G1795, G30, G3380, G3381, G3383, G3515, G3516, G3517, G3735, G3736, G3737, G3794, G3739, G3929, G4328, G4329, G4330 |
| 1971 | G3520 | DNA | G. max | Predicted polypeptide sequence is paralogous to G3518, G3519; orthologous to G1791, G1792, G1795, G30, G3380, G3381, G3383, G3515, G3516, G3517, G3735, G3736, G3737, G3794, G3739, G3929, G4328, G4329, G4330 |
| 1972 | G3520 | PRT | G. max | Paralogous to G3518, G3519; Orthologous to G1791, G1792, G1795, G30, G3380, G3381, G3383, G3515, G3516, G3517, G3735, G3736, G3737, G3794, G3739, G3929, G4328, G4329, G4330 |
| 1973 | G3524 | DNA | G. max | Predicted polypeptide sequence is paralogous to G4371; orthologous to G1543, G3510, G3490, G4369, G4370 |
| 1974 | G3524 | PRT | G. max | Paralogous to G4371; Orthologous to G1543, G3510, G3490, G4369, G4370 |
| 1975 | G3527 | DNA | G. max | Predicted polypeptide sequence is paralogous to G3529, G3528, G4639; orthologous to G197, G255, G664, G3503, G3504, G3505, G3506, G3507, G3508, G3509, G3531, G3532, G3533, G3534, G4637, G4638, G4640 |
| 1976 | G3527 | PRT | G. max | Paralogous to G3529, G3528, G4639; Orthologous to G197, G255, G664, G3503, G3504, G3505, G3506, G3507, G3508, G3509, G3531, G3532, G3533, G3534, G4637, G4638, G4640 |
| 1977 | G3528 | DNA | G. max | Predicted polypeptide sequence is paralogous to G3529, G3527, G4639; orthologous to G197, G255, G664, G3503, G3504, G3505, G3506, G3507, G3508, G3509, G3531, G3532, G3533, G3534, G4637, G4638, G4640 |
| 1978 | G3528 | PRT | G. max | Paralogous to G3529, G3527, G4639; Orthologous to G197, G255, G664, G3503, G3504, G3505, G3506, G3507, G3508, G3509, G3531, G3532, G3533, G3534, G4637, G4638, G4640 |
| 1979 | G3529 | DNA | G. max | Predicted polypeptide sequence is paralogous to G3527, G3528, G4639; orthologous to G197, G255, G664, G3503, G3504, G3505, G3506, G3507, G3508, G3509, G3531, G3532, G3533, G3534, G4637, G4638, G4640 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 1980 | G3529 | PRT | *G. max* | Paralogous to G3527, G3528, G4639; Orthologous to G197, G255, G664, G3503, G3504, G3505, G3506, G3507, G3508, G3509, G3531, G3532, G3533, G3534, G4637, G4638, G4640 |
| 1981 | G353 | DNA | *A. thaliana* | Predicted polypeptide sequence is paralogous to G1889, G1974, G2839, G354 |
| 1982 | G353 | PRT | *A. thaliana* | Paralogous to G1889, G1974, G2839, G354 |
| 1983 | G3531 | DNA | *Z. mays* | Predicted polypeptide sequence is paralogous to G3532, G3533, G3534, G4637, G4638, G4640; orthologous to G197, G255, G664, G3503, G3504, G3505, G3506, G3507, G3508, G3509, G3529, G3527, G3528, G4639 |
| 1984 | G3531 | PRT | *Z. mays* | Paralogous to G3532, G3533, G3534, G4637, G4638, G4640; Orthologous to G197, G255, G664, G3503, G3504, G3505, G3506, G3507, G3508, G3509, G3529, G3527, G3528, G4639 |
| 1985 | G3532 | DNA | *Z. mays* | Predicted polypeptide sequence is paralogous to G3531, G3533, G3534, G4637, G4638, G4640; orthologous to G197, G255, G664, G3503, G3504, G3505, G3506, G3507, G3508, G3509, G3529, G3527, G3528, G4639 |
| 1986 | G3532 | PRT | *Z. mays* | Paralogous to G3531, G3533, G3534, G4637, G4638, G4640; Orthologous to G197, G255, G664, G3503, G3504, G3505, G3506, G3507, G3508, G3509, G3529, G3527, G3528, G4639 |
| 1987 | G3533 | DNA | *Z. mays* | Predicted polypeptide sequence is paralogous to G3531, G3532, G3534, G4637, G4638, G4640; orthologous to G197, G255, G664, G3503, G3504, G3505, G3506, G3507, G3508, G3509, G3529, G3527, G3528, G4639 |
| 1988 | G3533 | PRT | *Z. mays* | Paralogous to G3531, G3532, G3534, G4637, G4638, G4640; Orthologous to G197, G255, G664, G3503, G3504, G3505, G3506, G3507, G3508, G3509, G3529, G3527, G3528, G4639 |
| 1989 | G3534 | DNA | *Z. mays* | Predicted polypeptide sequence is paralogous to G3531, G3532, G3533, G4637, G4638, G4640; orthologous to G197, G255, G664, G3503, G3504, G3505, G3506, G3507, G3508, G3509, G3529, G3527, G3528, G4639 |
| 1990 | G3534 | PRT | *Z. mays* | Paralogous to G3531, G3532, G3533, G4637, G4638, G4640; Orthologous to G197, G255, G664, G3503, G3504, G3505, G3506, G3507, G3508, G3509, G3529, G3527, G3528, G4639 |
| 1991 | G3537 | DNA | *G. max* | Predicted polypeptide sequence is paralogous to G3538, G3539; orthologous to G256, G666, G668, G932, G3384, G3385, G3386, G3500, G3501, G3502, G3540, G3541 |
| 1992 | G3537 | PRT | *G. max* | Paralogous to G3538, G3539; Orthologous to G256, G666, G668, G932, G3384, G3385, G3386, G3500, G3501, G3502, G3540, G3541 |
| 1993 | G3538 | DNA | *G. max* | Predicted polypeptide sequence is paralogous to G3537, G3539; orthologous to G256, G666, G668, G932, G3384, G3385, G3386, G3500, G3501, G3502, G3540, G3541 |
| 1994 | G3538 | PRT | *G. max* | Paralogous to G3537, G3539; Orthologous to G256, G666, G668, G932, G3384, G3385, G3386, G3500, G3501, G3502, G3540, G3541 |
| 1995 | G3539 | DNA | *G. max* | Predicted polypeptide sequence is paralogous to G3537, G3538; orthologous to G256, G666, G668, G932, G3384, G3385, G3386, G3500, G3501, G3502, G3540, G3541 |
| 1996 | G3539 | PRT | *G. max* | Paralogous to G3537, G3538; Orthologous to G256, G666, G668, G932, G3384, G3385, G3386, G3500, G3501, G3502, G3540, G3541 |
| 1997 | G3540 | DNA | *Z. mays* | Predicted polypeptide sequence is paralogous to G3541; orthologous to G256, G666, G668, G932, G3384, G3385, G3386, G3500, G3501, G3502, G3537, G3538, G3539 |
| 1998 | G3540 | PRT | *Z. mays* | Paralogous to G3541; Orthologous to G256, G666, G668, G932, G3384, G3385, G3386, G3500, G3501, G3502, G3537, G3538, G3539 |
| 1999 | G3541 | DNA | *Z. mays* | Predicted polypeptide sequence is paralogous to G3540; orthologous to G256, G666, G668, G932, G3384, G3385, G3386, G3500, G3501, G3502, G3537, G3538, G3539 |
| 2000 | G3541 | PRT | *Z. mays* | Paralogous to G3540; Orthologous to G256, G666, G668, G932, G3384, G3385, G3386, G3500, G3501, G3502, G3537, G3538, G3539 |
| 2001 | G3542 | DNA | *O. sativa* | Predicted polypeptide sequence is paralogous to G3544, G3545; orthologous to G489, G714, G3547, G3549, G3550, G3551, G3552, G3553, G3554, G3555, G3867, G3892, G3893, G3894, G3896, G4257, G4256 |
| 2002 | G3542 | PRT | *O. sativa* | Paralogous to G3544, G3545; Orthologous to G489, G714, G3547, G3549, G3550, G3551, G3552, G3553, G3554, G3555, G3867, G3892, G3893, G3894, G3896, G4257, G4256 |
| 2003 | G3543 | DNA | *O. sativa* | Predicted polypeptide sequence is orthologous to G1646, G715, G3883, G3884, G3885, G3886, G3889, G4259 |
| 2004 | G3543 | PRT | *O. sativa* | Orthologous to G1646, G715, G3883, G3884, G3885, G3886, G3889, G4259 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2005 | G3544 | DNA | O. sativa | Predicted polypeptide sequence is paralogous to G3542, G3545; orthologous to G489, G714, G3547, G3549, G3550, G3551, G3552, G3553, G3554, G3555, G3867, G3892, G3893, G3894, G3896, G4257, G4256 |
| 2006 | G3544 | PRT | O. sativa | Paralogous to G3542, G3545; Orthologous to G489, G714, G3547, G3549, G3550, G3551, G3552, G3553, G3554, G3555, G3867, G3892, G3893, G3894, G3896, G4257, G4256 |
| 2007 | G3545 | DNA | O. sativa | Predicted polypeptide sequence is paralogous to G3542, G3544; orthologous to G489, G714, G3547, G3549, G3550, G3551, G3552, G3553, G3554, G3555, G3867, G3892, G3893, G3894, G3896, G4257, G4256 |
| 2008 | G3545 | PRT | O. sativa | Paralogous to G3542, G3544; Orthologous to G489, G714, G3547, G3549, G3550, G3551, G3552, G3553, G3554, G3555, G3867, G3892, G3893, G3894, G3896, G4257, G4256 |
| 2009 | G3547 | DNA | G. max | Predicted polypeptide sequence is paralogous to G3549, G3550; orthologous to G489, G714, G3542, G3544, G3545, G3551, G3552, G3553, G3554, G3555, G3867, G3892, G3893, G3894, G3896, G4257, G4256 |
| 2010 | G3547 | PRT | G. max | Paralogous to G3549, G3550; Orthologous to G489, G714, G3542, G3544, G3545, G3551, G3552, G3553, G3554, G3555, G3867, G3892, G3893, G3894, G3896, G4257, G4256 |
| 2011 | G3549 | DNA | G. max | Predicted polypeptide sequence is paralogous to G3547, G3550; orthologous to G489, G714, G3542, G3544, G3545, G3551, G3552, G3553, G3554, G3555, G3867, G3892, G3893, G3894, G3896, G4257, G4256 |
| 2012 | G3549 | PRT | G. max | Paralogous to G3547, G3550; Orthologous to G489, G714, G3542, G3544, G3545, G3551, G3552, G3553, G3554, G3555, G3867, G3892, G3893, G3894, G3896, G4257, G4256 |
| 2013 | G3550 | DNA | G. max | Predicted polypeptide sequence is paralogous to G3547, G3549; orthologous to G489, G714, G3542, G3544, G3545, G3551, G3552, G3553, G3554, G3555, G3867, G3892, G3893, G3894, G3896, G4257, G4256 |
| 2014 | G3550 | PRT | G. max | Paralogous to G3547, G3549; Orthologous to G489, G714, G3542, G3544, G3545, G3551, G3552, G3553, G3554, G3555, G3867, G3892, G3893, G3894, G3896, G4257, G4256 |
| 2015 | G3551 | DNA | Z. mays | Predicted polypeptide sequence is paralogous to G3552, G4257, G4256; orthologous to G489, G714, G3542, G3544, G3545, G3547, G3549, G3550, G3553, G3554, G3555, G3867, G3892, G3893, G3894, G3896 |
| 2016 | G3551 | PRT | Z. mays | Paralogous to G3552, G4257, G4256; Orthologous to G489, G714, G3542, G3544, G3545, G3547, G3549, G3550, G3553, G3554, G3555, G3867, G3892, G3893, G3894, G3896 |
| 2017 | G3552 | DNA | Z. mays | Predicted polypeptide sequence is paralogous to G3551, G4257, G4256; orthologous to G489, G714, G3542, G3544, G3545, G3547, G3549, G3550, G3553, G3554, G3555, G3867, G3892, G3893, G3894, G3896 |
| 2018 | G3552 | PRT | Z. mays | Paralogous to G3551, G4257, G4256; Orthologous to G489, G714, G3542, G3544, G3545, G3547, G3549, G3550, G3553, G3554, G3555, G3867, G3892, G3893, G3894, G3896 |
| 2019 | G3553 | DNA | S. lycopersicum | Predicted polypeptide sequence is paralogous to G3554, G3555, G3894; orthologous to G489, G714, G3542, G3544, G3545, G3547, G3549, G3550, G3551, G3552, G3867, G3892, G3893, G3896, G4257, G4256 |
| 2020 | G3553 | PRT | S. lycopersicum | Paralogous to G3554, G3555, G3894; Orthologous to G489, G714, G3542, G3544, G3545, G3547, G3549, G3550, G3551, G3552, G3867, G3892, G3893, G3896, G4257, G4256 |
| 2021 | G3554 | DNA | S. lycopersicum | Predicted polypeptide sequence is paralogous to G3553, G3555, G3894; orthologous to G489, G714, G3542, G3544, G3545, G3547, G3549, G3550, G3551, G3552, G3867, G3892, G3893, G3896, G4257, G4256 |
| 2022 | G3554 | PRT | S. lycopersicum | Paralogous to G3553, G3555, G3894; Orthologous to G489, G714, G3542, G3544, G3545, G3547, G3549, G3550, G3551, G3552, G3867, G3892, G3893, G3896, G4257, G4256 |
| 2023 | G3555 | DNA | S. lycopersicum | Predicted polypeptide sequence is paralogous to G3553, G3554, G3894; orthologous to G489, G714, G3542, G3544, G3545, G3547, G3549, G3550, G3551, G3552, G3867, G3892, G3893, G3896, G4257, G4256 |
| 2024 | G3555 | PRT | S. lycopersicum | Paralogous to G3553, G3554, G3894; Orthologous to G489, G714, G3542, G3544, G3545, G3547, G3549, G3550, G3551, G3552, G3867, G3892, G3893, G3896, G4257, G4256 |
| 2025 | G361 | DNA | A. thaliana | Predicted polypeptide sequence is paralogous to G1995, G2826, G2838, G362, G370 |
| 2026 | G361 | PRT | A. thaliana | Paralogous to G1995, G2826, G2838, G362, G370 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2027 | G3643 | DNA | *G. max* | Predicted polypeptide sequence is orthologous to G2133, G47, G3644, G3645, G3646, G3647, G3649, G3650, G3651 |
| 2028 | G3643 | PRT | *G. max* | Orthologous to G2133, G47, G3644, G3645, G3646, G3647, G3649, G3650, G3651 |
| 2029 | G3644 | DNA | *O. sativa* | Predicted polypeptide sequence is paralogous to G3649, G3651; orthologous to G2133, G47, G3643, G3645, G3646, G3647, G3650 |
| 2030 | G3644 | PRT | *O. sativa* | Paralogous to G3649, G3651; Orthologous to G2133, G47, G3643, G3645, G3646, G3647, G3650 |
| 2031 | G3645 | DNA | *B. rapa* subsp. *Pekinensis* | Predicted polypeptide sequence is orthologous to G2133, G47, G3643, G3644, G3646, G3647, G3649, G3650, G3651 |
| 2032 | G3645 | PRT | *B. rapa* subsp. *Pekinensis* | Orthologous to G2133, G47, G3643, G3644, G3646, G3647, G3649, G3650, G3651 |
| 2033 | G3646 | DNA | *B. oleracea* | Predicted polypeptide sequence is orthologous to G2133, G47, G3643, G3644, G3645, G3647, G3649, G3650, G3651 |
| 2034 | G3646 | PRT | *B. oleracea* | Orthologous to G2133, G47, G3643, G3644, G3645, G3647, G3649, G3650, G3651 |
| 2035 | G3647 | DNA | *Z. elegans* | Predicted polypeptide sequence is orthologous to G2133, G47, G3643, G3644, G3645, G3646, G3649, G3650, G3651 |
| 2036 | G3647 | PRT | *Z. elegans* | Orthologous to G2133, G47, G3643, G3644, G3645, G3646, G3649, G3650, G3651 |
| 2037 | G3649 | DNA | *O. sativa* | Predicted polypeptide sequence is paralogous to G3644, G3651; orthologous to G2133, G47, G3643, G3645, G3646, G3647, G3650 |
| 2038 | G3649 | PRT | *O. sativa* | Paralogous to G3644, G3651; Orthologous to G2133, G47, G3643, G3645, G3646, G3647, G3650 |
| 2039 | G3650 | DNA | *Z. mays* | Predicted polypeptide sequence is orthologous to G2133, G47, G3643, G3644, G3645, G3646, G3647, G3649, G3651 |
| 2040 | G3650 | PRT | *Z. mays* | Orthologous to G2133, G47, G3643, G3644, G3645, G3646, G3647, G3649, G3651 |
| 2041 | G3651 | DNA | *O. sativa* | Predicted polypeptide sequence is paralogous to G3644, G3649; orthologous to G2133, G47, G3643, G3645, G3646, G3647, G3650 |
| 2042 | G3651 | PRT | *O. sativa* | Paralogous to G3644, G3649; Orthologous to G2133, G47, G3643, G3645, G3646, G3647, G3650 |
| 2043 | G3656 | DNA | *Z. mays* | Predicted polypeptide sequence is orthologous to G12, G1277, G1379, G24 |
| 2044 | G3656 | PRT | *Z. mays* | Orthologous to G12, G1277, G1379, G24 |
| 2045 | G3659 | DNA | *B. oleracea* | Predicted polypeptide sequence is paralogous to G3660; orthologous to G22, G1006, G28, G3430, G3661, G3717, G3718, G3841, G3843, G3844, G3845, G3846, G3848, G3852, G3856, G3857, G3858, G3864, G3865, G4626, G5171 |
| 2046 | G3659 | PRT | *B. oleracea* | Paralogous to G3660; Orthologous to G22, G1006, G28, G3430, G3661, G3717, G3718, G3841, G3843, G3844, G3845, G3846, G3848, G3852, G3856, G3857, G3858, G3864, G3865, G4626, G5171 |
| 2047 | G3660 | DNA | *B. oleracea* | Predicted polypeptide sequence is paralogous to G3659; orthologous to G22, G1006, G28, G3430, G3661, G3717, G3718, G3841, G3843, G3844, G3845, G3846, G3848, G3852, G3856, G3857, G3858, G3864, G3865, G4626, G5171 |
| 2048 | G3660 | PRT | *B. oleracea* | Paralogous to G3659; Orthologous to G22, G1006, G28, G3430, G3661, G3717, G3718, G3841, G3843, G3844, G3845, G3846, G3848, G3852, G3856, G3857, G3858, G3864, G3865, G4626, G5171 |
| 2049 | G3661 | DNA | *Z. mays* | Predicted polypeptide sequence is paralogous to G3856; orthologous to G22, G1006, G28, G3430, G3659, G3660, G3717, G3718, G3841, G3843, G3844, G3845, G3846, G3848, G3852, G3857, G3858, G3864, G3865, G4626, G5171 |
| 2050 | G3661 | PRT | *Z. mays* | Paralogous to G3856; Orthologous to G22, G1006, G28, G3430, G3659, G3660, G3717, G3718, G3841, G3843, G3844, G3845, G3846, G3848, G3852, G3857, G3858, G3864, G3865, G4626, G5171 |
| 2051 | G3663 | DNA | *L. corniculatus* var. *japonicus* | Predicted polypeptide sequence is orthologous to G2999, G2998 |
| 2052 | G3663 | PRT | *L. corniculatus* var. *japonicus* | Orthologous to G2999, G2998 |
| 2053 | G3680 | DNA | *Z. mays* | Predicted polypeptide sequence is paralogous to G3681; orthologous to G2989, G2990, G3691, G3859, G3860, G3861, G3934 |
| 2054 | G3680 | PRT | *Z. mays* | Paralogous to G3681; Orthologous to G2989, G2990, G3691, G3859, G3860, G3861, G3934 |
| 2055 | G3681 | DNA | *Z. mays* | Predicted polypeptide sequence is paralogous to G3680; orthologous to G2989, G2990, G3691, G3859, G3860, G3861, G3934 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2056 | G3681 | PRT | Z. mays | Paralogous to G3680; Orthologous to G2989, G2990, G3691, G3859, G3860, G3861, G3934 |
| 2057 | G3691 | DNA | O. sativa | Predicted polypeptide sequence is orthologous to G2989, G2990, G3680, G3681, G3859, G3860, G3861, G3934 |
| 2058 | G3691 | PRT | O. sativa | Orthologous to G2989, G2990, G3680, G3681, G3859, G3860, G3861, G3934 |
| 2059 | G370 | DNA | A. thaliana | Predicted polypeptide sequence is paralogous to G1995, G2826, G2838, G361, G362 |
| 2060 | G370 | PRT | A. thaliana | Paralogous to G1995, G2826, G2838, G361, G362 |
| 2061 | G3717 | DNA | G. max | Predicted polypeptide sequence is paralogous to G3718; orthologous to G22, G1006, G28, G3430, G3659, G3660, G3661, G3841, G3843, G3844, G3845, G3846, G3848, G3852, G3856, G3857, G3858, G3864, G3865, G4626, G5171 |
| 2062 | G3717 | PRT | G. max | Paralogous to G3718; Orthologous to G22, G1006, G28, G3430, G3659, G3660, G3661, G3841, G3843, G3844, G3845, G3846, G3848, G3852, G3856, G3857, G3858, G3864, G3865, G4626, G5171 |
| 2063 | G3718 | DNA | G. max | Predicted polypeptide sequence is paralogous to G3717; orthologous to G22, G1006, G28, G3430, G3659, G3660, G3661, G3841, G3843, G3844, G3845, G3846, G3848, G3852, G3856, G3857, G3858, G3864, G3865, G4626, G5171 |
| 2064 | G3718 | PRT | G. max | Paralogous to G3717; Orthologous to G22, G1006, G28, G3430, G3659, G3660, G3661, G3841, G3843, G3844, G3845, G3846, G3848, G3852, G3856, G3857, G3858, G3864, G3865, G4626, G5171 |
| 2065 | G3719 | DNA | Z. mays | Predicted polypeptide sequence is paralogous to G3722, G3720, G3727, G3728, G3804; orthologous to G1274, G3723, G3724, G3731, G3732, G3803, G1275, G3721, G3725, G3726, G3729, G3730, G3733, G3795, G3797, G3802 |
| 2066 | G3719 | PRT | Z. mays | Paralogous to G3722, G3720, G3727, G3728, G3804; Orthologous to G1274, G3723, G3724, G3731, G3732, G3803, G1275, G3721, G3725, G3726, G3729, G3730, G3733, G3795, G3797, G3802 |
| 2067 | G3720 | DNA | Z. mays | Predicted polypeptide sequence is paralogous to G3722, G3719, G3727, G3728, G3804; orthologous to G1274, G3723, G3724, G3731, G3732, G3803, G1275, G3721, G3725, G3726, G3729, G3730, G3733, G3795, G3797, G3802 |
| 2068 | G3720 | PRT | Z. mays | Paralogous to G3722, G3719, G3727, G3728, G3804; Orthologous to G1274, G3723, G3724, G3731, G3732, G3803, G1275, G3721, G3725, G3726, G3729, G3730, G3733, G3795, G3797, G3802 |
| 2069 | G3721 | DNA | O. sativa | Predicted polypeptide sequence is paralogous to G3725, G3726, G3729, G3730; orthologous to G1274, G3722, G3723, G3724, G3731, G3732, G3803, G1275, G3719, G3720, G3727, G3728, G3733, G3795, G3797, G3802, G3804 |
| 2070 | G3721 | PRT | O. sativa | Paralogous to G3725, G3726, G3729, G3730; Orthologous to G1274, G3722, G3723, G3724, G3731, G3732, G3803, G1275, G3719, G3720, G3727, G3728, G3733, G3795, G3797, G3802, G3804 |
| 2071 | G3722 | DNA | Z. mays | Predicted polypeptide sequence is paralogous to G3719, G3720, G3727, G3728, G3804; orthologous to G1274, G3723, G3724, G3731, G3732, G3803, G1275, G3721, G3725, G3726, G3729, G3730, G3733, G3795, G3797, G3802 |
| 2072 | G3722 | PRT | Z. mays | Paralogous to G3719, G3720, G3727, G3728, G3804; Orthologous to G1274, G3723, G3724, G3731, G3732, G3803, G1275, G3721, G3725, G3726, G3729, G3730, G3733, G3795, G3797, G3802 |
| 2073 | G3723 | DNA | G. max | Predicted polypeptide sequence is paralogous to G3724, G3803; orthologous to G1274, G3722, G3731, G3732, G1275, G3719, G3720, G3721, G3725, G3726, G3727, G3728, G3729, G3730, G3733, G3795, G3797, G3802, G3804 |
| 2074 | G3723 | PRT | G. max | Paralogous to G3724, G3803; Orthologous to G1274, G3722, G3731, G3732, G1275, G3719, G3720, G3721, G3725, G3726, G3727, G3728, G3729, G3730, G3733, G3795, G3797, G3802, G3804 |
| 2075 | G3724 | DNA | G. max | Predicted polypeptide sequence is paralogous to G3723, G3803; orthologous to G1274, G3722, G3731, G3732, G1275, G3719, G3720, G3721, G3725, G3726, G3727, G3728, G3729, G3730, G3733, G3795, G3797, G3802, G3804 |
| 2076 | G3724 | PRT | G. max | Paralogous to G3723, G3803; Orthologous to G1274, G3722, G3731, G3732, G1275, G3719, G3720, G3721, G3725, G3726, G3727, G3728, G3729, G3730, G3733, G3795, G3797, G3802, G3804 |
| 2077 | G3725 | DNA | O. sativa | Predicted polypeptide sequence is paralogous to G3721, G3726, G3729, G3730; orthologous to G1274, G3722, G3723, G3724, G3731, G3732, G3803, G1275, G3719, G3720, G3727, G3728, G3733, G3795, G3797, G3802, G3804 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2078 | G3725 | PRT | O. sativa | Paralogous to G3721, G3726, G3729, G3730; Orthologous to G1274, G3722, G3723, G3724, G3731, G3732, G3803, G1275, G3719, G3720, G3727, G3728, G3733, G3795, G3797, G3802, G3804 |
| 2079 | G3726 | DNA | O. sativa | Predicted polypeptide sequence is paralogous to G3721, G3725, G3729, G3730; orthologous to G1274, G3722, G3723, G3724, G3731, G3732, G3803, G1275, G3719, G3720, G3727, G3728, G3733, G3795, G3797, G3802, G3804 |
| 2080 | G3726 | PRT | O. sativa | Paralogous to G3721, G3725, G3729, G3730; Orthologous to G1274, G3722, G3723, G3724, G3731, G3732, G3803, G1275, G3719, G3720, G3727, G3728, G3733, G3795, G3797, G3802, G3804 |
| 2081 | G3727 | DNA | Z. mays | Predicted polypeptide sequence is paralogous to G3722, G3719, G3720, G3728, G3804; orthologous to G1274, G3723, G3724, G3731, G3732, G3803, G1275, G3721, G3725, G3726, G3729, G3730, G3733, G3795, G3797, G3802 |
| 2082 | G3727 | PRT | Z. mays | Paralogous to G3722, G3719, G3720, G3728, G3804; Orthologous to G1274, G3723, G3724, G3731, G3732, G3803, G1275, G3721, G3725, G3726, G3729, G3730, G3733, G3795, G3797, G3802 |
| 2083 | G3728 | DNA | Z. mays | Predicted polypeptide sequence is paralogous to G3722, G3719, G3720, G3727, G3804; orthologous to G1274, G3723, G3724, G3731, G3732, G3803, G1275, G3721, G3725, G3726, G3729, G3730, G3733, G3795, G3797, G3802 |
| 2084 | G3728 | PRT | Z. mays | Paralogous to G3722, G3719, G3720, G3727, G3804; Orthologous to G1274, G3723, G3724, G3731, G3732, G3803, G1275, G3721, G3725, G3726, G3729, G3730, G3733, G3795, G3797, G3802 |
| 2085 | G3729 | DNA | O. sativa | Predicted polypeptide sequence is paralogous to G3721, G3725, G3726, G3730; orthologous to G1274, G3722, G3723, G3724, G3731, G3732, G3803, G1275, G3719, G3720, G3727, G3728, G3733, G3795, G3797, G3802, G3804 |
| 2086 | G3729 | PRT | O. sativa | Paralogous to G3721, G3725, G3726, G3730; Orthologous to G1274, G3722, G3723, G3724, G3731, G3732, G3803, G1275, G3719, G3720, G3727, G3728, G3733, G3795, G3797, G3802, G3804 |
| 2087 | G3730 | DNA | O. sativa | Predicted polypeptide sequence is paralogous to G3721, G3725, G3726, G3729; orthologous to G1274, G3722, G3723, G3724, G3731, G3732, G3803, G1275, G3719, G3720, G3727, G3728, G3733, G3795, G3797, G3802, G3804 |
| 2088 | G3730 | PRT | O. sativa | Paralogous to G3721, G3725, G3726, G3729; Orthologous to G1274, G3722, G3723, G3724, G3731, G3732, G3803, G1275, G3719, G3720, G3727, G3728, G3733, G3795, G3797, G3802, G3804 |
| 2089 | G3731 | DNA | S. lycopersicum | Predicted polypeptide sequence is orthologous to G1274, G3722, G3723, G3724, G3732, G3803, G1275, G3719, G3720, G3721, G3725, G3726, G3727, G3728, G3729, G3730, G3733, G3795, G3797, G3802, G3804 |
| 2090 | G3731 | PRT | S. lycopersicum | Orthologous to G1274, G3722, G3723, G3724, G3732, G3803, G1275, G3719, G3720, G3721, G3725, G3726, G3727, G3728, G3729, G3730, G3733, G3795, G3797, G3802, G3804 |
| 2091 | G3732 | DNA | S. tuberosum | Predicted polypeptide sequence is orthologous to G1274, G3722, G3723, G3724, G3731, G3803, G1275, G3719, G3720, G3721, G3725, G3726, G3727, G3728, G3729, G3730, G3733, G3795, G3797, G3802, G3804 |
| 2092 | G3732 | PRT | S. tuberosum | Orthologous to G1274, G3722, G3723, G3724, G3731, G3803, G1275, G3719, G3720, G3721, G3725, G3726, G3727, G3728, G3729, G3730, G3733, G3795, G3797, G3802, G3804 |
| 2093 | G3733 | DNA | H. vulgare | Predicted polypeptide sequence is orthologous to G1274, G3722, G3723, G3724, G3731, G3732, G3803, G1275, G3719, G3720, G3721, G3725, G3726, G3727, G3728, G3729, G3730, G3795, G3797, G3802, G3804 |
| 2094 | G3733 | PRT | H. vulgare | Orthologous to G1274, G3722, G3723, G3724, G3731, G3732, G3803, G1275, G3719, G3720, G3721, G3725, G3726, G3727, G3728, G3729, G3730, G3795, G3797, G3802, G3804 |
| 2095 | G3735 | DNA | M. truncatula | Predicted polypeptide sequence is orthologous to G1791, G1792, G1795, G30, G3380, G3381, G3383, G3515, G3516, G3517, G3518, G3519, G3520, G3736, G3737, G3794, G3739, G3929, G4328, G4329, G4330 |
| 2096 | G3735 | PRT | M. truncatula | Orthologous to G1791, G1792, G1795, G30, G3380, G3381, G3383, G3515, G3516, G3517, G3518, G3519, G3520, G3736, G3737, G3794, G3739, G3929, G4328, G4329, G4330 |
| 2097 | G3736 | DNA | T. aestivum | Predicted polypeptide sequence is orthologous to G1791, G1792, G1795, G30, G3380, G3381, G3383, G3515, G3516, G3517, G3518, G3519, G3520, G3735, G3737, G3794, G3739, G3929, G4328, G4329, G4330 |
| 2098 | G3736 | PRT | T. aestivum | Orthologous to G1791, G1792, G1795, G30, G3380, G3381, G3383, G3515, G3516, G3517, G3518, G3519, G3520, G3735, G3737, G3794, G3739, G3929, G4328, G4329, G4330 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2099 | G3737 | DNA | *O. sativa* | Predicted polypeptide sequence is paralogous to G3380, G3381, G3383, G3515; orthologous to G1791, G1792, G1795, G30, G3516, G3517, G3518, G3519, G3520, G3735, G3736, G3794, G3739, G3929, G4328, G4329, G4330 |
| 2100 | G3737 | PRT | *O. sativa* | Paralogous to G3380, G3381, G3383, G3515; Orthologous to G1791, G1792, G1795, G30, G3516, G3517, G3518, G3519, G3520, G3735, G3736, G3794, G3739, G3929, G4328, G4329, G4330 |
| 2101 | G3739 | DNA | *Z. mays* | Predicted polypeptide sequence is paralogous to G3516, G3517, G3794, G3929; orthologous to G1791, G1792, G1795, G30, G3380, G3381, G3383, G3515, G3518, G3519, G3520, G3735, G3736, G3737, G4328, G4329, G4330 |
| 2102 | G3739 | PRT | *Z. mays* | Paralogous to G3516, G3517, G3794, G3929; Orthologous to G1791, G1792, G1795, G30, G3380, G3381, G3383, G3515, G3518, G3519, G3520, G3735, G3736, G3737, G4328, G4329, G4330 |
| 2103 | G3740 | DNA | *O. sativa* | Predicted polypeptide sequence is paralogous to G3741; orthologous to G3763, G3764, G2149, G2766, G3772 |
| 2104 | G3740 | PRT | *O. sativa* | Paralogous to G3741; Orthologous to G3763, G3764, G2149, G2766, G3772 |
| 2105 | G3741 | DNA | *O. sativa* | Predicted polypeptide sequence is paralogous to G3740; orthologous to G3763, G3764, G2149, G2766, G3772 |
| 2106 | G3741 | PRT | *O. sativa* | Paralogous to G3740; Orthologous to G3763, G3764, G2149, G2766, G3772 |
| 2107 | G3748 | DNA | *O. sativa* | Predicted polypeptide sequence is paralogous to G3749; orthologous to G589, G1061, G3774, G2791, G3760 |
| 2108 | G3748 | PRT | *O. sativa* | Paralogous to G3749; Orthologous to G589, G1061, G3774, G2791, G3760 |
| 2109 | G3749 | DNA | *O. sativa* | Predicted polypeptide sequence is paralogous to G3748; orthologous to G589, G1061, G3774, G2791, G3760 |
| 2110 | G3749 | PRT | *O. sativa* | Paralogous to G3748; Orthologous to G589, G1061, G3774, G2791, G3760 |
| 2111 | G3750 | DNA | *O. sativa* | Predicted polypeptide sequence is paralogous to G3752, G3751; orthologous to G3753, G793, G591, G4311, G4312, G4313 |
| 2112 | G3750 | PRT | *O. sativa* | Paralogous to G3752, G3751; Orthologous to G3753, G793, G591, G4311, G4312, G4313 |
| 2113 | G3751 | DNA | *O. sativa* | Predicted polypeptide sequence is paralogous to G3752, G3750; orthologous to G3753, G793, G591, G4311, G4312, G4313 |
| 2114 | G3751 | PRT | *O. sativa* | Paralogous to G3752, G3750; Orthologous to G3753, G793, G591, G4311, G4312, G4313 |
| 2115 | G3752 | DNA | *O. sativa* | Predicted polypeptide sequence is paralogous to G3751, G3750; orthologous to G3753, G793, G591, G4311, G4312, G4313 |
| 2116 | G3752 | PRT | *O. sativa* | Paralogous to G3751, G3750; Orthologous to G3753, G793, G591, G4311, G4312, G4313 |
| 2117 | G3753 | DNA | *Z. mays* | Predicted polypeptide sequence is paralogous to G4313; orthologous to G3752, G3751, G793, G591, G3750, G4311, G4312 |
| 2118 | G3753 | PRT | *Z. mays* | Paralogous to G4313; Orthologous to G3752, G3751, G793, G591, G3750, G4311, G4312 |
| 2119 | G3760 | DNA | *Z. mays* | Predicted polypeptide sequence is orthologous to G3748, G3749, G589, G1061, G3774, G2791 |
| 2120 | G3760 | PRT | *Z. mays* | Orthologous to G3748, G3749, G589, G1061, G3774, G2791 |
| 2121 | G3763 | DNA | *G. max* | Predicted polypeptide sequence is paralogous to G3764, G3772; orthologous to G2149, G2766, G3740, G3741 |
| 2122 | G3763 | PRT | *G. max* | Paralogous to G3764, G3772; Orthologous to G2149, G2766, G3740, G3741 |
| 2123 | G3764 | DNA | *G. max* | Predicted polypeptide sequence is paralogous to G3763, G3772; orthologous to G2149, G2766, G3740, G3741 |
| 2124 | G3764 | PRT | *G. max* | Paralogous to G3763, G3772; Orthologous to G2149, G2766, G3740, G3741 |
| 2125 | G3772 | DNA | *G. max* | Predicted polypeptide sequence is paralogous to G3763, G3764; orthologous to G2149, G2766, G3740, G3741 |
| 2126 | G3772 | PRT | *G. max* | Paralogous to G3763, G3764; Orthologous to G2149, G2766, G3740, G3741 |
| 2127 | G3774 | DNA | *G. max* | Predicted polypeptide sequence is orthologous to G3748, G3749, G589, G1061, G2791, G3760 |
| 2128 | G3774 | PRT | *G. max* | Orthologous to G3748, G3749, G589, G1061, G2791, G3760 |
| 2129 | G3794 | DNA | *Z. mays* | Predicted polypeptide sequence is paralogous to G3516, G3517, G3739, G3929; orthologous to G1791, G1792, G1795, G30, G3380, G3381, G3383, G3515, G3518, G3519, G3520, G3735, G3736, G3737, G4328, G4329, G4330 |
| 2130 | G3794 | PRT | *Z. mays* | Paralogous to G3516, G3517, G3739, G3929; Orthologous to G1791, G1792, G1795, G30, G3380, G3381, G3383, G3515, G3518, G3519, G3520, G3735, G3736, G3737, G4328, G4329, G4330 |
| 2131 | G3795 | DNA | *Capsicum annuum* | Predicted polypeptide sequence is orthologous to G1274, G3722, G3723, G3724, G3731, G3732, G3803, G1275, G3719, G3720, |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | G3721, G3725, G3726, G3727, G3728, G3729, G3730, G3733, G3797, G3802, G3804 |
| 2132 | G3795 | PRT | *Capsicum annuum* | Orthologous to G1274, G3722, G3723, G3724, G3731, G3732, G3803, G1275, G3719, G3720, G3721, G3725, G3726, G3727, G3728, G3729, G3730, G3733, G3797, G3802, G3804 |
| 2133 | G3797 | DNA | *Lactuca sativa* | Predicted polypeptide sequence is orthologous to G1274, G3722, G3723, G3724, G3731, G3732, G3803, G1275, G3719, G3720, G3721, G3725, G3726, G3727, G3728, G3729, G3730, G3733, G3795, G3802, G3804 |
| 2134 | G3797 | PRT | *Lactuca sativa* | Orthologous to G1274, G3722, G3723, G3724, G3731, G3732, G3803, G1275, G3719, G3720, G3721, G3725, G3726, G3727, G3728, G3729, G3730, G3733, G3795, G3802, G3804 |
| 2135 | G38 | DNA | *A. thaliana* | Predicted polypeptide sequence is paralogous to G1141 |
| 2136 | G38 | PRT | *A. thaliana* | Paralogous to G1141 |
| 2137 | G3802 | DNA | *Sorghum bicolor* | Predicted polypeptide sequence is orthologous to G1274, G3722, G3723, G3724, G3731, G3732, G3803, G1275, G3719, G3720, G3721, G3725, G3726, G3727, G3728, G3729, G3730, G3733, G3795, G3797, G3804 |
| 2138 | G3802 | PRT | *Sorghum bicolor* | Orthologous to G1274, G3722, G3723, G3724, G3731, G3732, G3803, G1275, G3719, G3720, G3721, G3725, G3726, G3727, G3728, G3729, G3730, G3733, G3795, G3797, G3804 |
| 2139 | G3803 | DNA | *G. max* | Predicted polypeptide sequence is paralogous to G3723, G3724; orthologous to G1274, G3722, G3731, G3732, G1275, G3719, G3720, G3721, G3725, G3726, G3727, G3728, G3729, G3730, G3733, G3795, G3797, G3802, G3804 |
| 2140 | G3803 | PRT | *G. max* | Paralogous to G3723, G3724; Orthologous to G1274, G3722, G3731, G3732, G1275, G3719, G3720, G3721, G3725, G3726, G3727, G3728, G3729, G3730, G3733, G3795, G3797, G3802, G3804 |
| 2141 | G3804 | DNA | *Z. mays* | Predicted polypeptide sequence is paralogous to G3722, G3719, G3720, G3727, G3728; orthologous to G1274, G3723, G3724, G3731, G3732, G3803, G1275, G3721, G3725, G3726, G3729, G3730, G3733, G3795, G3797, G3802 |
| 2142 | G3804 | PRT | *Z. mays* | Paralogous to G3722, G3719, G3720, G3727, G3728; Orthologous to G1274, G3723, G3724, G3731, G3732, G3803, G1275, G3721, G3725, G3726, G3729, G3730, G3733, G3795, G3797, G3802 |
| 2143 | G3815 | DNA | *O. sativa* | Predicted polypeptide sequence is orthologous to G1768, G2633, G2697, G313, G852, G3825 |
| 2144 | G3815 | PRT | *O. sativa* | Orthologous to G1768, G2633, G2697, G313, G852, G3825 |
| 2145 | G3816 | DNA | *T. aestivum* | Predicted polypeptide sequence is orthologous to G2738, G3009, G307, G308, G309, G3817, G3818, G3819 |
| 2146 | G3816 | PRT | *T. aestivum* | Orthologous to G2738, G3009, G307, G308, G309, G3817, G3818, G3819 |
| 2147 | G3817 | DNA | *O. sativa* | Predicted polypeptide sequence is paralogous to G3819; orthologous to G2738, G3009, G307, G308, G309, G3816, G3818 |
| 2148 | G3817 | PRT | *O. sativa* | Paralogous to G3819; Orthologous to G2738, G3009, G307, G308, G309, G3816, G3818 |
| 2149 | G3818 | DNA | *G. max* | Predicted polypeptide sequence is orthologous to G2738, G3009, G307, G308, G309, G3816, G3817, G3819 |
| 2150 | G3818 | PRT | *G. max* | Orthologous to G2738, G3009, G307, G308, G309, G3816, G3817, G3819 |
| 2151 | G3819 | DNA | *O. sativa* | Predicted polypeptide sequence is paralogous to G3817; orthologous to G2738, G3009, G307, G308, G309, G3816, G3818 |
| 2152 | G3819 | PRT | *O. sativa* | Paralogous to G3817; Orthologous to G2738, G3009, G307, G308, G309, G3816, G3818 |
| 2153 | G3821 | DNA | *Pisum sativum* | Predicted polypeptide sequence is orthologous to G306, G3822 |
| 2154 | G3821 | PRT | *Pisum sativum* | Orthologous to G306, G3822 |
| 2155 | G3822 | DNA | *Z. mays* | Predicted polypeptide sequence is orthologous to G306, G3821 |
| 2156 | G3822 | PRT | *Z. mays* | Orthologous to G306, G3821 |
| 2157 | G3825 | DNA | *S. lycopersicum* | Predicted polypeptide sequence is orthologous to G1768, G2633, G2697, G313, G852, G3815 |
| 2158 | G3825 | PRT | *S. lycopersicum* | Orthologous to G1768, G2633, G2697, G313, G852, G3815 |
| 2159 | G3839 | DNA | *Z. mays* | Predicted polypeptide sequence is paralogous to G3937; orthologous to G620, G1821, G3939 |
| 2160 | G3839 | PRT | *Z. mays* | Paralogous to G3937; Orthologous to G620, G1821, G3939 |
| 2161 | G384 | DNA | *A. thaliana* | Predicted polypeptide sequence is paralogous to G1588, G385 |
| 2162 | G384 | PRT | *A. thaliana* | Paralogous to G1588, G385 |
| 2163 | G3841 | DNA | *S. lycopersicum* | Predicted polypeptide sequence is paralogous to G3843, G3852, G4626; orthologous to G22, G1006, G28, G3430, G3659, G3660, G3661, G3717, G3718, G3844, G3845, G3846, G3848, G3856, G3857, G3858, G3864, G3865, G5171 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2164 | G3841 | PRT | S. lycopersicum | Paralogous to G3843, G3852, G4626; Orthologous to G22, G1006, G28, G3430, G3659, G3660, G3661, G3717, G3718, G3844, G3845, G3846, G3848, G3856, G3857, G3858, G3864, G3865, G5171 |
| 2165 | G3843 | DNA | S. lycopersicum | Predicted polypeptide sequence is paralogous to G3841, G3852, G4626; orthologous to G22, G1006, G28, G3430, G3659, G3660, G3661, G3717, G3718, G3844, G3845, G3846, G3848, G3856, G3857, G3858, G3864, G3865, G5171 |
| 2166 | G3843 | PRT | S. lycopersicum | Paralogous to G3841, G3852, G4626; Orthologous to G22, G1006, G28, G3430, G3659, G3660, G3661, G3717, G3718, G3844, G3845, G3846, G3848, G3856, G3857, G3858, G3864, G3865, G5171 |
| 2167 | G3844 | DNA | M. truncatula | Predicted polypeptide sequence is orthologous to G22, G1006, G28, G3430, G3659, G3660, G3661, G3717, G3718, G3841, G3843, G3845, G3846, G3848, G3852, G3856, G3857, G3858, G3864, G3865, G4626, G5171 |
| 2168 | G3844 | PRT | M. truncatula | Orthologous to G22, G1006, G28, G3430, G3659, G3660, G3661, G3717, G3718, G3841, G3843, G3845, G3846, G3848, G3852, G3856, G3857, G3858, G3864, G3865, G4626, G5171 |
| 2169 | G3845 | DNA | N. tabacum | Predicted polypeptide sequence is paralogous to G3846; orthologous to G22, G1006, G28, G3430, G3659, G3660, G3661, G3717, G3718, G3841, G3843, G3844, G3848, G3852, G3856, G3857, G3858, G3864, G3865, G4626, G5171 |
| 2170 | G3845 | PRT | N. tabacum | Paralogous to G3846; Orthologous to G22, G1006, G28, G3430, G3659, G3660, G3661, G3717, G3718, G3841, G3843, G3844, G3848, G3852, G3856, G3857, G3858, G3864, G3865, G4626, G5171 |
| 2171 | G3846 | DNA | N. tabacum | Predicted polypeptide sequence is paralogous to G3845; orthologous to G22, G1006, G28, G3430, G3659, G3660, G3661, G3717, G3718, G3841, G3843, G3844, G3848, G3852, G3856, G3857, G3858, G3864, G3865, G4626, G5171 |
| 2172 | G3846 | PRT | N. tabacum | Paralogous to G3845; Orthologous to G22, G1006, G28, G3430, G3659, G3660, G3661, G3717, G3718, G3841, G3843, G3844, G3848, G3852, G3856, G3857, G3858, G3864, G3865, G4626, G5171 |
| 2173 | G3848 | DNA | O. sativa | Predicted polypeptide sequence is paralogous to G3430, G5171; orthologous to G22, G1006, G28, G3659, G3660, G3661, G3717, G3718, G3841, G3843, G3844, G3845, G3846, G3852, G3856, G3857, G3858, G3864, G3865, G4626 |
| 2174 | G3848 | PRT | O. sativa | Paralogous to G3430, G5171; Orthologous to G22, G1006, G28, G3659, G3660, G3661, G3717, G3718, G3841, G3843, G3844, G3845, G3846, G3852, G3856, G3857, G3858, G3864, G3865, G4626 |
| 2175 | G3849 | DNA | S. lycopersicum | Predicted polypeptide sequence is orthologous to G1419, G43, G46, G1004, G29 |
| 2176 | G3849 | PRT | S. lycopersicum | Orthologous to G1419, G43, G46, G1004, G29 |
| 2177 | G3851 | DNA | S. lycopersicum | Predicted polypeptide sequence is orthologous to G19 |
| 2178 | G3851 | PRT | S. lycopersicum | Orthologous to G19 |
| 2179 | G3852 | DNA | S. lycopersicum | Predicted polypeptide sequence is paralogous to G3841, G3843, G4626; orthologous to G22, G1006, G28, G3430, G3659, G3660, G3661, G3717, G3718, G3844, G3845, G3846, G3848, G3856, G3857, G3858, G3864, G3865, G5171 |
| 2180 | G3852 | PRT | S. lycopersicum | Paralogous to G3841, G3843, G4626; Orthologous to G22, G1006, G28, G3430, G3659, G3660, G3661, G3717, G3718, G3844, G3845, G3846, G3848, G3856, G3857, G3858, G3864, G3865, G5171 |
| 2181 | G3856 | DNA | Z. mays | Predicted polypeptide sequence is paralogous to G3661; orthologous to G22, G1006, G28, G3430, G3659, G3660, G3717, G3718, G3841, G3843, G3844, G3845, G3846, G3848, G3852, G3857, G3858, G3864, G3865, G4626, G5171 |
| 2182 | G3856 | PRT | Z. mays | Paralogous to G3661; Orthologous to G22, G1006, G28, G3430, G3659, G3660, G3717, G3718, G3841, G3843, G3844, G3845, G3846, G3848, G3852, G3857, G3858, G3864, G3865, G4626, G5171 |
| 2183 | G3857 | DNA | S. tuberosum | Predicted polypeptide sequence is paralogous to G3858; orthologous to G22, G1006, G28, G3430, G3659, G3660, G3661, G3717, G3718, G3841, G3843, G3844, G3845, G3846, G3848, G3852, G3856, G3864, G3865, G4626, G5171 |
| 2184 | G3857 | PRT | S. tuberosum | Paralogous to G3858; Orthologous to G22, G1006, G28, G3430, G3659, G3660, G3661, G3717, G3718, G3841, G3843, G3844, G3845, G3846, G3848, G3852, G3856, G3864, G3865, G4626, G5171 |
| 2185 | G3858 | DNA | S. tuberosum | Predicted polypeptide sequence is paralogous to G3857; orthologous to G22, G1006, G28, G3430, G3659, G3660, G3661, G3717, G3718, G3841, G3843, G3844, G3845, G3846, G3848, G3852, G3856, G3864, G3865, G4626, G5171 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2186 | G3858 | PRT | *S. tuberosum* | Paralogous to G3857; Orthologous to G22, G1006, G28, G3430, G3659, G3660, G3661, G3717, G3718, G3841, G3843, G3844, G3845, G3846, G3848, G3852, G3856, G3864, G3865, G4626, G5171 |
| 2187 | G3859 | DNA | *Flaveria trinervia* | Predicted polypeptide sequence is orthologous to G2989, G2990, G3680, G3681, G3691, G3860, G3861, G3934 |
| 2188 | G3859 | PRT | *Flaveria trinervia* | Orthologous to G2989, G2990, G3680, G3681, G3691, G3860, G3861, G3934 |
| 2189 | G386 | DNA | *A. thaliana* | Predicted polypeptide sequence is paralogous to G707 |
| 2190 | G386 | PRT | *A. thaliana* | Paralogous to G707 |
| 2191 | G3860 | DNA | *Flaveria bidentis* | Predicted polypeptide sequence is paralogous to G3861; orthologous to G2989, G2990, G3680, G3681, G3691, G3859, G3934 |
| 2192 | G3860 | PRT | *Flaveria bidentis* | Paralogous to G3861; Orthologous to G2989, G2990, G3680, G3681, G3691, G3859, G3934 |
| 2193 | G3861 | DNA | *Flaveria bidentis* | Predicted polypeptide sequence is paralogous to G3860; orthologous to G2989, G2990, G3680, G3681, G3691, G3859, G3934 |
| 2194 | G3861 | PRT | *Flaveria bidentis* | Paralogous to G3860; Orthologous to G2989, G2990, G3680, G3681, G3691, G3859, G3934 |
| 2195 | G3864 | DNA | *T. aestivum* | Predicted polypeptide sequence is paralogous to G3865; orthologous to G22, G1006, G28, G3430, G3659, G3660, G3661, G3717, G3718, G3841, G3843, G3844, G3845, G3846, G3848, G3852, G3856, G3857, G3858, G4626, G5171 |
| 2196 | G3864 | PRT | *T. aestivum* | Paralogous to G3865; Orthologous to G22, G1006, G28, G3430, G3659, G3660, G3661, G3717, G3718, G3841, G3843, G3844, G3845, G3846, G3848, G3852, G3856, G3857, G3858, G4626, G5171 |
| 2197 | G3865 | DNA | *T. aestivum* | Predicted polypeptide sequence is paralogous to G3864; orthologous to G22, G1006, G28, G3430, G3659, G3660, G3661, G3717, G3718, G3841, G3843, G3844, G3845, G3846, G3848, G3852, G3856, G3857, G3858, G4626, G5171 |
| 2198 | G3865 | PRT | *T. aestivum* | Paralogous to G3864; Orthologous to G22, G1006, G28, G3430, G3659, G3660, G3661, G3717, G3718, G3841, G3843, G3844, G3845, G3846, G3848, G3852, G3856, G3857, G3858, G4626, G5171 |
| 2199 | G3866 | DNA | *Z. mays* | Predicted polypeptide sequence is paralogous to G3434, G3435, G3436, G3437, G3876, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2200 | G3866 | PRT | *Z. mays* | Paralogous to G3434, G3435, G3436, G3437, G3876, G4272, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2201 | G3867 | DNA | *P. patens* | Predicted polypeptide sequence is orthologous to G489, G714, G3542, G3544, G3545, G3547, G3549, G3550, G3551, G3552, G3553, G3554, G3555, G3892, G3893, G3894, G3896, G4257, G4256 |
| 2202 | G3867 | PRT | *P. patens* | Orthologous to G489, G714, G3542, G3544, G3545, G3547, G3549, G3550, G3551, G3552, G3553, G3554, G3555, G3892, G3893, G3894, G3896, G4257, G4256 |
| 2203 | G3868 | DNA | *P. patens* | Predicted polypeptide sequence is paralogous to G3870; orthologous to G1364, G2345, G481, G482, G485, G3394, G3395, G3396, G3397, G3398, G3429, G3434, G3435, G3436, G3437, G3470, G3471, G3472, G3473, G3474, G3475, G3476, G3478, G3866, G3873, G3874, G3875, G3876, G3938, G4272, G4276 |
| 2204 | G3868 | PRT | *P. patens* | Paralogous to G3870; Orthologous to G1364, G2345, G481, G482, G485, G3394, G3395, G3396, G3397, G3398, G3429, G3434, G3435, G3436, G3437, G3470, G3471, G3472, G3473, G3474, G3475, G3476, G3478, G3866, G3873, G3874, G3875, G3876, G3938, G4272, G4276 |
| 2205 | G3870 | DNA | *P. patens* | Predicted polypeptide sequence is paralogous to G3868; orthologous to G1364, G2345, G481, G482, G485, G3394, G3395, G3396, G3397, G3398, G3429, G3434, G3435, G3436, G3437, G3470, G3471, G3472, G3473, G3474, G3475, G3476, G3478, G3866, G3873, G3874, G3875, G3876, G3938, G4272, G4276 |
| 2206 | G3870 | PRT | *P. patens* | Paralogous to G3868; Orthologous to G1364, G2345, G481, G482, G485, G3394, G3395, G3396, G3397, G3398, G3429, G3434, G3435, G3436, G3437, G3470, G3471, G3472, G3473, G3474, G3475, G3476, G3478, G3866, G3873, G3874, G3875, G3876, G3938, G4272, G4276 |
| 2207 | G3873 | DNA | *G. max* | Predicted polypeptide sequence is paralogous to G3470, G3471, G3472, G3473, G3474, G3475, G3476, G3478, G3874, G3875; |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| | | | | orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2208 | G3873 | PRT | *G. max* | Paralogous to G3470, G3471, G3472, G3473, G3474, G3475, G3476, G3478, G3874, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2209 | G3874 | DNA | *G. max* | Predicted polypeptide sequence is paralogous to G3470, G3471, G3472, G3473, G3474, G3475, G3476, G3478, G3873, G3875; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2210 | G3874 | PRT | *G. max* | Paralogous to G3470, G3471, G3472, G3473, G3474, G3475, G3476, G3478, G3873, G3875; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2211 | G3875 | DNA | *G. max* | Predicted polypeptide sequence is paralogous to G3470, G3471, G3472, G3473, G3474, G3475, G3476, G3478, G3873, G3874; orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2212 | G3875 | PRT | *G. max* | Paralogous to G3470, G3471, G3472, G3473, G3474, G3475, G3476, G3478, G3873, G3874; Orthologous to G1364, G2345, G481, G482, G485, G3394, G3395, G3396, G3397, G3398, G3429, G3434, G3435, G3436, G3437, G3866, G3868, G3870, G3876, G3938, G4272, G4276 |
| 2213 | G3876 | DNA | *Z. mays* | Predicted polypeptide sequence is paralogous to G3434, G3435, G3436, G3437, G3866, G4272, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2214 | G3876 | PRT | *Z. mays* | Paralogous to G3434, G3435, G3436, G3437, G3866, G4272, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2215 | G3883 | DNA | *G. raimondii* | Predicted polypeptide sequence is orthologous to G1646, G715, G3884, G3885, G3886, G3889, G3543, G4259 |
| 2216 | G3883 | PRT | *G. raimondii* | Orthologous to G1646, G715, G3884, G3885, G3886, G3889, G3543, G4259 |
| 2217 | G3884 | DNA | *N. benthamiana* | Predicted polypeptide sequence is orthologous to G1646, G715, G3883, G3885, G3886, G3889, G3543, G4259 |
| 2218 | G3884 | PRT | *N. benthamiana* | Orthologous to G1646, G715, G3883, G3885, G3886, G3889, G3543, G4259 |
| 2219 | G3885 | DNA | *S. tuberosum* | Predicted polypeptide sequence is orthologous to G1646, G715, G3883, G3884, G3886, G3889, G3543, G4259 |
| 2220 | G3885 | PRT | *S. tuberosum* | Orthologous to G1646, G715, G3883, G3884, G3886, G3889, G3543, G4259 |
| 2221 | G3886 | DNA | *G. max* | Predicted polypeptide sequence is orthologous to G1646, G715, G3883, G3884, G3885, G3889, G3543, G4259 |
| 2222 | G3886 | PRT | *G. max* | Orthologous to G1646, G715, G3883, G3884, G3885, G3889, G3543, G4259 |
| 2223 | G3889 | DNA | *Z. mays* | Predicted polypeptide sequence is paralogous to G4259; orthologous to G1646, G715, G3883, G3884, G3885, G3886, G3543 |
| 2224 | G3889 | PRT | *Z. mays* | Paralogous to G4259; Orthologous to G1646, G715, G3883, G3884, G3885, G3886, G3543 |
| 2225 | G389 | DNA | *A. thaliana* | Predicted polypeptide sequence is paralogous to G1535 |
| 2226 | G389 | PRT | *A. thaliana* | Paralogous to G1535 |
| 2227 | G3892 | DNA | *S. tuberosum* | Predicted polypeptide sequence is paralogous to G3893; orthologous to G489, G714, G3542, G3544, G3545, G3547, G3549, G3550, G3551, G3552, G3553, G3554, G3555, G3867, G3894, G3896, G4257, G4256 |
| 2228 | G3892 | PRT | *S. tuberosum* | Paralogous to G3893; Orthologous to G489, G714, G3542, G3544, G3545, G3547, G3549, G3550, G3551, G3552, G3553, G3554, G3555, G3867, G3894, G3896, G4257, G4256 |
| 2229 | G3893 | DNA | *S. tuberosum* | Predicted polypeptide sequence is paralogous to G3892; orthologous to G489, G714, G3542, G3544, G3545, G3547, G3549, G3550, G3551, G3552, G3553, G3554, G3555, G3867, G3894, G3896, G4257, G4256 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2230 | G3893 | PRT | S. tuberosum | Paralogous to G3892; Orthologous to G489, G714, G3542, G3544, G3545, G3547, G3549, G3550, G3551, G3552, G3553, G3554, G3555, G3867, G3894, G3896, G4257, G4256 |
| 2231 | G3894 | DNA | S. lycopersicum | Predicted polypeptide sequence is paralogous to G3553, G3554, G3555; orthologous to G489, G714, G3542, G3544, G3545, G3547, G3549, G3550, G3551, G3552, G3867, G3892, G3893, G3896, G4257, G4256 |
| 2232 | G3894 | PRT | S. lycopersicum | Paralogous to G3553, G3554, G3555; Orthologous to G489, G714, G3542, G3544, G3545, G3547, G3549, G3550, G3551, G3552, G3867, G3892, G3893, G3896, G4257, G4256 |
| 2233 | G3896 | DNA | M. truncatula | Predicted polypeptide sequence is orthologous to G489, G714, G3542, G3544, G3545, G3547, G3549, G3550, G3551, G3552, G3553, G3554, G3555, G3867, G3892, G3893, G3894, G4257, G4256 |
| 2234 | G3896 | PRT | M. truncatula | Orthologous to G489, G714, G3542, G3544, G3545, G3547, G3549, G3550, G3551, G3552, G3553, G3554, G3555, G3867, G3892, G3893, G3894, G4257, G4256 |
| 2235 | G390 | DNA | A. thaliana | Predicted polypeptide sequence is paralogous to G1548, G391, G392, G438 |
| 2236 | G390 | PRT | A. thaliana | Paralogous to G1548, G391, G392, G438 |
| 2237 | G391 | DNA | A. thaliana | Predicted polypeptide sequence is paralogous to G1548, G390, G392, G438 |
| 2238 | G391 | PRT | A. thaliana | Paralogous to G1548, G390, G392, G438 |
| 2239 | G3924 | DNA | O. sativa | Predicted polypeptide sequence is orthologous to G926, G2632, G4261 |
| 2240 | G3924 | PRT | O. sativa | Orthologous to G926, G2632, G4261 |
| 2241 | G3929 | DNA | Z. mays | Predicted polypeptide sequence is paralogous to G3516, G3517, G3794, G3739; orthologous to G1791, G1792, G1795, G30, G3380, G3381, G3383, G3515, G3518, G3519, G3520, G3735, G3736, G3737, G4328, G4329, G4330 |
| 2242 | G3929 | PRT | Z. mays | Paralogous to G3516, G3517, G3794, G3739; Orthologous to G1791, G1792, G1795, G30, G3380, G3381, G3383, G3515, G3518, G3519, G3520, G3735, G3736, G3737, G4328, G4329, G4330 |
| 2243 | G3930 | DNA | A. thaliana | Predicted polypeptide sequence is paralogous to G1816, G225, G226, G2718, G682; orthologous to G3392, G3393, G3431, G3444, G3445, G3446, G3447, G3448, G3449, G3450 |
| 2244 | G3930 | PRT | A. thaliana | Paralogous to G1816, G225, G226, G2718, G682; Orthologous to G3392, G3393, G3431, G3444, G3445, G3446, G3447, G3448, G3449, G3450 |
| 2245 | G3934 | DNA | G. max | Predicted polypeptide sequence is orthologous to G2989, G2990, G3680, G3681, G3691, G3859, G3860, G3861 |
| 2246 | G3934 | PRT | G. max | Orthologous to G2989, G2990, G3680, G3681, G3691, G3859, G3860, G3861 |
| 2247 | G3937 | DNA | Z. mays | Predicted polypeptide sequence is paralogous to G3839; orthologous to G620, G1821, G3939 |
| 2248 | G3937 | PRT | Z. mays | Paralogous to G3839; Orthologous to G620, G1821, G3939 |
| 2249 | G3938 | DNA | O. sativa | Predicted polypeptide sequence is paralogous to G3395, G3396, G3397, G3398, G3429; orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 2250 | G3938 | PRT | O. sativa | Paralogous to G3395, G3396, G3397, G3398, G3429; Orthologous to G1364, G2345, G481, G482, G485, G3394, G3434, G3435, G3436, G3437, G3470, G3471, G3472, G3473, G3474, G3475, G3476, G3478, G3866, G3868, G3870, G3873, G3874, G3875, G3876, G4272, G4276 |
| 2251 | G3939 | DNA | O. sativa | Predicted polypeptide sequence is orthologous to G620, G1821, G3839, G3937 |
| 2252 | G3939 | PRT | O. sativa | Orthologous to G620, G1821, G3839, G3937 |
| 2253 | G3957 | DNA | Capsicum annuum | Predicted polypeptide sequence is orthologous to G14, G4, G3974 |
| 2254 | G3957 | PRT | Capsicum annuum | Orthologous to G14, G4, G3974 |
| 2255 | G3974 | DNA | S. lycopersicum | Predicted polypeptide sequence is orthologous to G14, G4, G3957 |
| 2256 | G3974 | PRT | S. lycopersicum | Orthologous to G14, G4, G3957 |
| 2257 | G398 | DNA | A. thaliana | Predicted polypeptide sequence is paralogous to G399, G964 |
| 2258 | G398 | PRT | A. thaliana | Paralogous to G399, G964 |
| 2259 | G3980 | DNA | G. max | Predicted polypeptide sequence is paralogous to G3484, G3485, G3981; orthologous to G152, G153, G1760, G860, G3479, G3480, G3481, G3482, G3483, G3487, G3488, G3489, G3982 |
| 2260 | G3980 | PRT | G. max | Paralogous to G3484, G3485, G3981; Orthologous to G152, G153, G1760, G860, G3479, G3480, G3481, G3482, G3483, G3487, G3488, G3489, G3982 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2261 | G3981 | DNA | *G. max* | Predicted polypeptide sequence is paralogous to G3484, G3485, G3980; orthologous to G152, G153, G1760, G860, G3479, G3480, G3481, G3482, G3483, G3487, G3488, G3489, G3982 |
| 2262 | G3981 | PRT | *G. max* | Paralogous to G3484, G3485, G3980; Orthologous to G152, G153, G1760, G860, G3479, G3480, G3481, G3482, G3483, G3487, G3488, G3489, G3982 |
| 2263 | G3982 | DNA | *A. majus* | Predicted polypeptide sequence is orthologous to G152, G153, G1760, G860, G3479, G3480, G3481, G3482, G3483, G3484, G3485, G3487, G3488, G3489, G3980, G3981 |
| 2264 | G3982 | PRT | *A. majus* | Orthologous to G152, G153, G1760, G860, G3479, G3480, G3481, G3482, G3483, G3487, G3488, G3489, G3980, G3981 |
| 2265 | G3984 | DNA | *S. lycopersicum* | Predicted polypeptide sequence is orthologous to G1140, G861, G3985, G3986, G3987, G3988, G3989, G3990, G3991, G3992, G3998, G3999, G4060 |
| 2266 | G3984 | PRT | *S. lycopersicum* | Orthologous to G1140, G861, G3985, G3986, G3987, G3988, G3989, G3990, G3991, G3992, G3998, G3999, G4060 |
| 2267 | G3985 | DNA | *Z. mays* | Predicted polypeptide sequence is paralogous to G3986, G3987, G3990; orthologous to G1140, G861, G3984, G3988, G3989, G3991, G3992, G3998, G3999, G4060 |
| 2268 | G3985 | PRT | *Z. mays* | Paralogous to G3986, G3987, G3990; Orthologous to G1140, G861, G3984, G3988, G3989, G3991, G3992, G3998, G3999, G4060 |
| 2269 | G3986 | DNA | *Z. mays* | Predicted polypeptide sequence is paralogous to G3985, G3987, G3990; orthologous to G1140, G861, G3984, G3988, G3989, G3991, G3992, G3998, G3999, G4060 |
| 2270 | G3986 | PRT | *Z. mays* | Paralogous to G3985, G3987, G3990; Orthologous to G1140, G861, G3984, G3988, G3989, G3991, G3992, G3998, G3999, G4060 |
| 2271 | G3987 | DNA | *Z. mays* | Predicted polypeptide sequence is paralogous to G3985, G3986, G3990; orthologous to G1140, G861, G3984, G3988, G3989, G3991, G3992, G3998, G3999, G4060 |
| 2272 | G3987 | PRT | *Z. mays* | Paralogous to G3985, G3986, G3990; Orthologous to G1140, G861, G3984, G3988, G3989, G3991, G3992, G3998, G3999, G4060 |
| 2273 | G3988 | DNA | *O. sativa* | Predicted polypeptide sequence is paralogous to G4060; orthologous to G1140, G861, G3984, G3985, G3986, G3987, G3989, G3990, G3991, G3992, G3998, G3999 |
| 2274 | G3988 | PRT | *O. sativa* | Paralogous to G4060; Orthologous to G1140, G861, G3984, G3985, G3986, G3987, G3989, G3990, G3991, G3992, G3998, G3999 |
| 2275 | G3989 | DNA | *G. max* | Predicted polypeptide sequence is paralogous to G3991, G3992; orthologous to G1140, G861, G3984, G3985, G3986, G3987, G3988, G3990, G3998, G3999, G4060 |
| 2276 | G3989 | PRT | *G. max* | Paralogous to G3991, G3992; Orthologous to G1140, G861, G3984, G3985, G3986, G3987, G3988, G3990, G3998, G3999, G4060 |
| 2277 | G3990 | DNA | *Z. mays* | Predicted polypeptide sequence is paralogous to G3985, G3986, G3987; orthologous to G1140, G861, G3984, G3988, G3989, G3991, G3992, G3998, G3999, G4060 |
| 2278 | G3990 | PRT | *Z. mays* | Paralogous to G3985, G3986, G3987; Orthologous to G1140, G861, G3984, G3988, G3989, G3991, G3992, G3998, G3999, G4060 |
| 2279 | G3991 | DNA | *G. max* | Predicted polypeptide sequence is paralogous to G3989, G3992; orthologous to G1140, G861, G3984, G3985, G3986, G3987, G3988, G3990, G3998, G3999, G4060 |
| 2280 | G3991 | PRT | *G. max* | Paralogous to G3989, G3992; Orthologous to G1140, G861, G3984, G3985, G3986, G3987, G3988, G3990, G3998, G3999, G4060 |
| 2281 | G3992 | DNA | *G. max* | Predicted polypeptide sequence is paralogous to G3989, G3991; orthologous to G1140, G861, G3984, G3985, G3986, G3987, G3988, G3990, G3998, G3999, G4060 |
| 2282 | G3992 | PRT | *G. max* | Paralogous to G3989, G3991; Orthologous to G1140, G861, G3984, G3985, G3986, G3987, G3988, G3990, G3998, G3999, G4060 |
| 2283 | G3998 | DNA | *B. rapa* | Predicted polypeptide sequence is orthologous to G1140, G861, G3984, G3985, G3986, G3987, G3988, G3989, G3990, G3991, G3992, G3999, G4060 |
| 2284 | G3998 | PRT | *B. rapa* | Orthologous to G1140, G861, G3984, G3985, G3986, G3987, G3988, G3989, G3990, G3991, G3992, G3999, G4060 |
| 2285 | G3999 | DNA | *E. occidentalis* | Predicted polypeptide sequence is orthologous to G1140, G861, G3984, G3985, G3986, G3987, G3988, G3989, G3990, G3991, G3992, G3998, G4060 |
| 2286 | G3999 | PRT | *E. occidentalis* | Orthologous to G1140, G861, G3984, G3985, G3986, G3987, G3988, G3989, G3990, G3991, G3992, G3998, G4060 |
| 2287 | G40 | DNA | *A. thaliana* | Predicted polypeptide sequence is paralogous to G2107, G2513, G41, G42, G912; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2288 | G40 | PRT | *A. thaliana* | Paralogous to G2107, G2513, G41, G42, G912; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2289 | G4019 | DNA | *G. max* | Predicted polypeptide sequence is orthologous to G1478, G1929 |
| 2290 | G4019 | PRT | *G. max* | Orthologous to G1478, G1929 |
| 2291 | G4060 | DNA | *O. sativa* | Predicted polypeptide sequence is paralogous to G3988; orthologous to G1140, G861, G3984, G3985, G3986, G3987, G3989, G3990, G3991, G3992, G3998, G3999 |
| 2292 | G4060 | PRT | *O. sativa* | Paralogous to G3988; Orthologous to G1140, G861, G3984, G3985, G3986, G3987, G3989, G3990, G3991, G3992, G3998, G3999 |
| 2293 | G4061 | DNA | *S. lycopersicum* | Predicted polypeptide sequence is orthologous to G149, G627, G1011, G154, G1797, G1798, G4062, G4063, G4064, G4065, G4066, G4067 |
| 2294 | G4061 | PRT | *S. lycopersicum* | Orthologous to G149, G627, G1011, G154, G1797, G1798, G4062, G4063, G4064, G4065, G4066, G4067 |
| 2295 | G4062 | DNA | *B. rapa* | Predicted polypeptide sequence is orthologous to G149, G627, G1011, G154, G1797, G1798, G4061, G4063, G4064, G4065, G4066, G4067 |
| 2296 | G4062 | PRT | *B. rapa* | Orthologous to G149, G627, G1011, G154, G1797, G1798, G4061, G4063, G4064, G4065, G4066, G4067 |
| 2297 | G4063 | DNA | *G. max* | Predicted polypeptide sequence is paralogous to G4064; orthologous to G149, G627, G1011, G154, G1797, G1798, G4061, G4062, G4065, G4066, G4067 |
| 2298 | G4063 | PRT | *G. max* | Paralogous to G4064; Orthologous to G149, G627, G1011, G154, G1797, G1798, G4061, G4062, G4065, G4066, G4067 |
| 2299 | G4064 | DNA | *G. max* | Predicted polypeptide sequence is paralogous to G4063; orthologous to G149, G627, G1011, G154, G1797, G1798, G4061, G4062, G4065, G4066, G4067 |
| 2300 | G4064 | PRT | *G. max* | Paralogous to G4063; Orthologous to G149, G627, G1011, G154, G1797, G1798, G4061, G4062, G4065, G4066, G4067 |
| 2301 | G4065 | DNA | *Z. mays* | Predicted polypeptide sequence is orthologous to G149, G627, G1011, G154, G1797, G1798, G4061, G4062, G4063, G4064, G4066, G4067 |
| 2302 | G4065 | PRT | *Z. mays* | Orthologous to G149, G627, G1011, G154, G1797, G1798, G4061, G4062, G4063, G4064, G4066, G4067 |
| 2303 | G4066 | DNA | *O. sativa* | Predicted polypeptide sequence is paralogous to G4067; orthologous to G149, G627, G1011, G154, G1797, G1798, G4061, G4062, G4063, G4064, G4065 |
| 2304 | G4066 | PRT | *O. sativa* | Paralogous to G4067; Orthologous to G149, G627, G1011, G154, G1797, G1798, G4061, G4062, G4063, G4064, G4065 |
| 2305 | G4067 | DNA | *O. sativa* | Predicted polypeptide sequence is paralogous to G4066; orthologous to G149, G627, G1011, G154, G1797, G1798, G4061, G4062, G4063, G4064, G4065 |
| 2306 | G4067 | PRT | *O. sativa* | Paralogous to G4066; Orthologous to G149, G627, G1011, G154, G1797, G1798, G4061, G4062, G4063, G4064, G4065 |
| 2307 | G4079 | DNA | *S. lycopersicum* | Predicted polypeptide sequence is orthologous to G1750, G1421, G4080, G440, G864, G4283, G4284, G4285, G4286, G4287, G4288, G4289, G4290, G4291, G4292, G4293 |
| 2308 | G4079 | PRT | *S. lycopersicum* | Orthologous to G1750, G1421, G4080, G440, G864, G4283, G4284, G4285, G4286, G4287, G4288, G4289, G4290, G4291, G4292, G4293 |
| 2309 | G4080 | DNA | *N. tabacum* | Predicted polypeptide sequence is orthologous to G1750, G1421, G4079, G440, G864, G4283, G4284, G4285, G4286, G4287, G4288, G4289, G4290, G4291, G4292, G4293 |
| 2310 | G4080 | PRT | *N. tabacum* | Orthologous to G1750, G1421, G4079, G440, G864, G4283, G4284, G4285, G4286, G4287, G4288, G4289, G4290, G4291, G4292, G4293 |
| 2311 | G41 | DNA | *A. thaliana* | Predicted polypeptide sequence is paralogous to G40, G2107, G2513, G42, G912; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2312 | G41 | PRT | *A. thaliana* | Paralogous to G40, G2107, G2513, G42, G912; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2313 | G412 | DNA | *A. thaliana* | Predicted polypeptide sequence is paralogous to G1538, G1545 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2314 | G412 | PRT | *A. thaliana* | Paralogous to G1538, G1545 |
| 2315 | G42 | DNA | *A. thaliana* | Predicted polypeptide sequence is paralogous to G40, G2107, G2513, G41, G912; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2316 | G42 | PRT | *A. thaliana* | Paralogous to G40, G2107, G2513, G41, G912; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2317 | G4218 | DNA | *G. max* | Predicted polypeptide sequence is paralogous to G4219, G4220, G4221, G4222, G4223, G4224, G4225; orthologous to G207, G227, G230, G242, G4226, G4227, G4228, G4229, G4230, G4231, G4232, G4234, G4235, G4236, G4237, G4238 |
| 2318 | G4218 | PRT | *G. max* | Paralogous to G4219, G4220, G4221, G4222, G4223, G4224, G4225; Orthologous to G207, G227, G230, G242, G4226, G4227, G4228, G4229, G4230, G4231, G4232, G4234, G4235, G4236, G4237, G4238 |
| 2319 | G4219 | DNA | *G. max* | Predicted polypeptide sequence is paralogous to G4218, G4220, G4221, G4222, G4223, G4224, G4225; orthologous to G207, G227, G230, G242, G4226, G4227, G4228, G4229, G4230, G4231, G4232, G4234, G4235, G4236, G4237, G4238 |
| 2320 | G4219 | PRT | *G. max* | Paralogous to G4218, G4220, G4221, G4222, G4223, G4224, G4225; Orthologous to G207, G227, G230, G242, G4226, G4227, G4228, G4229, G4230, G4231, G4232, G4234, G4235, G4236, G4237, G4238 |
| 2321 | G4220 | DNA | *G. max* | Predicted polypeptide sequence is paralogous to G4218, G4219, G4221, G4222, G4223, G4224, G4225; orthologous to G207, G227, G230, G242, G4226, G4227, G4228, G4229, G4230, G4231, G4232, G4234, G4235, G4236, G4237, G4238 |
| 2322 | G4220 | PRT | *G. max* | Paralogous to G4218, G4219, G4221, G4222, G4223, G4224, G4225; Orthologous to G207, G227, G230, G242, G4226, G4227, G4228, G4229, G4230, G4231, G4232, G4234, G4235, G4236, G4237, G4238 |
| 2323 | G4221 | DNA | *G. max* | Predicted polypeptide sequence is paralogous to G4218, G4219, G4220, G4222, G4223, G4224, G4225; orthologous to G207, G227, G230, G242, G4226, G4227, G4228, G4229, G4230, G4231, G4232, G4234, G4235, G4236, G4237, G4238 |
| 2324 | G4221 | PRT | *G. max* | Paralogous to G4218, G4219, G4220, G4222, G4223, G4224, G4225; Orthologous to G207, G227, G230, G242, G4226, G4227, G4228, G4229, G4230, G4231, G4232, G4234, G4235, G4236, G4237, G4238 |
| 2325 | G4222 | DNA | *G. max* | Predicted polypeptide sequence is paralogous to G4218, G4219, G4220, G4221, G4223, G4224, G4225; orthologous to G207, G227, G230, G242, G4226, G4227, G4228, G4229, G4230, G4231, G4232, G4234, G4235, G4236, G4237, G4238 |
| 2326 | G4222 | PRT | *G. max* | Paralogous to G4218, G4219, G4220, G4221, G4223, G4224, G4225; Orthologous to G207, G227, G230, G242, G4226, G4227, G4228, G4229, G4230, G4231, G4232, G4234, G4235, G4236, G4237, G4238 |
| 2327 | G4223 | DNA | *G. max* | Predicted polypeptide sequence is paralogous to G4218, G4219, G4220, G4221, G4222, G4224, G4225; orthologous to G207, G227, G230, G242, G4226, G4227, G4228, G4229, G4230, G4231, G4232, G4234, G4235, G4236, G4237, G4238 |
| 2328 | G4223 | PRT | *G. max* | Paralogous to G4218, G4219, G4220, G4221, G4222, G4224, G4225; Orthologous to G207, G227, G230, G242, G4226, G4227, G4228, G4229, G4230, G4231, G4232, G4234, G4235, G4236, G4237, G4238 |
| 2329 | G4224 | DNA | *G. max* | Predicted polypeptide sequence is paralogous to G4218, G4219, G4220, G4221, G4222, G4223, G4225; orthologous to G207, G227, G230, G242, G4226, G4227, G4228, G4229, G4230, G4231, G4232, G4234, G4235, G4236, G4237, G4238 |
| 2330 | G4224 | PRT | *G. max* | Paralogous to G4218, G4219, G4220, G4221, G4222, G4223, G4225; Orthologous to G207, G227, G230, G242, G4226, G4227, G4228, G4229, G4230, G4231, G4232, G4234, G4235, G4236, G4237, G4238 |
| 2331 | G4225 | DNA | *G. max* | Predicted polypeptide sequence is paralogous to G4218, G4219, G4220, G4221, G4222, G4223, G4224; orthologous to G207, G227, G230, G242, G4226, G4227, G4228, G4229, G4230, G4231, G4232, G4234, G4235, G4236, G4237, G4238 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2332 | G4225 | PRT | G. max | Paralogous to G4218, G4219, G4220, G4221, G4222, G4223, G4224; Orthologous to G207, G227, G230, G242, G4226, G4227, G4228, G4229, G4230, G4231, G4232, G4234, G4235, G4236, G4237, G4238 |
| 2333 | G4226 | DNA | Z. mays | Predicted polypeptide sequence is paralogous to G4227, G4228, G4229, G4230, G4231, G4232; orthologous to G207, G227, G230, G242, G4218, G4219, G4220, G4221, G4222, G4223, G4224, G4225, G4234, G4235, G4236, G4237, G4238 |
| 2334 | G4226 | PRT | Z. mays | Paralogous to G4227, G4228, G4229, G4230, G4231, G4232; Orthologous to G207, G227, G230, G242, G4218, G4219, G4220, G4221, G4222, G4223, G4224, G4225, G4234, G4235, G4236, G4237, G4238 |
| 2335 | G4227 | DNA | Z. mays | Predicted polypeptide sequence is paralogous to G4226, G4228, G4229, G4230, G4231, G4232; orthologous to G207, G227, G230, G242, G4218, G4219, G4220, G4221, G4222, G4223, G4224, G4225, G4234, G4235, G4236, G4237, G4238 |
| 2336 | G4227 | PRT | Z. mays | Paralogous to G4226, G4228, G4229, G4230, G4231, G4232; Orthologous to G207, G227, G230, G242, G4218, G4219, G4220, G4221, G4222, G4223, G4224, G4225, G4234, G4235, G4236, G4237, G4238 |
| 2337 | G4228 | DNA | Z. mays | Predicted polypeptide sequence is paralogous to G4226, G4227, G4229, G4230, G4231, G4232; orthologous to G207, G227, G230, G242, G4218, G4219, G4220, G4221, G4222, G4223, G4224, G4225, G4234, G4235, G4236, G4237, G4238 |
| 2338 | G4228 | PRT | Z. mays | Paralogous to G4226, G4227, G4229, G4230, G4231, G4232; Orthologous to G207, G227, G230, G242, G4218, G4219, G4220, G4221, G4222, G4223, G4224, G4225, G4234, G4235, G4236, G4237, G4238 |
| 2339 | G4229 | DNA | Z. mays | Predicted polypeptide sequence is paralogous to G4226, G4227, G4228, G4230, G4231, G4232; orthologous to G207, G227, G230, G242, G4218, G4219, G4220, G4221, G4222, G4223, G4224, G4225, G4234, G4235, G4236, G4237, G4238 |
| 2340 | G4229 | PRT | Z. mays | Paralogous to G4226, G4227, G4228, G4230, G4231, G4232; Orthologous to G207, G227, G230, G242, G4218, G4219, G4220, G4221, G4222, G4223, G4224, G4225, G4234, G4235, G4236, G4237, G4238 |
| 2341 | G4230 | DNA | Z. mays | Predicted polypeptide sequence is paralogous to G4226, G4227, G4228, G4229, G4231, G4232; orthologous to G207, G227, G230, G242, G4218, G4219, G4220, G4221, G4222, G4223, G4224, G4225, G4234, G4235, G4236, G4237, G4238 |
| 2342 | G4230 | PRT | Z. mays | Paralogous to G4226, G4227, G4228, G4229, G4231, G4232; Orthologous to G207, G227, G230, G242, G4218, G4219, G4220, G4221, G4222, G4223, G4224, G4225, G4234, G4235, G4236, G4237, G4238 |
| 2343 | G4231 | DNA | Z. mays | Predicted polypeptide sequence is paralogous to G4226, G4227, G4228, G4229, G4230, G4232; orthologous to G207, G227, G230, G242, G4218, G4219, G4220, G4221, G4222, G4223, G4224, G4225, G4234, G4235, G4236, G4237, G4238 |
| 2344 | G4231 | PRT | Z. mays | Paralogous to G4226, G4227, G4228, G4229, G4230, G4232; Orthologous to G207, G227, G230, G242, G4218, G4219, G4220, G4221, G4222, G4223, G4224, G4225, G4234, G4235, G4236, G4237, G4238 |
| 2345 | G4232 | DNA | Z. mays | Predicted polypeptide sequence is paralogous to G4226, G4227, G4228, G4229, G4230, G4231; orthologous to G207, G227, G230, G242, G4218, G4219, G4220, G4221, G4222, G4223, G4224, G4225, G4234, G4235, G4236, G4237, G4238 |
| 2346 | G4232 | PRT | Z. mays | Paralogous to G4226, G4227, G4228, G4229, G4230, G4231; Orthologous to G207, G227, G230, G242, G4218, G4219, G4220, G4221, G4222, G4223, G4224, G4225, G4234, G4235, G4236, G4237, G4238 |
| 2347 | G4234 | DNA | O. sativa | Predicted polypeptide sequence is paralogous to G4235, G4236, G4237, G4238; orthologous to G207, G227, G230, G242, G4218, G4219, G4220, G4221, G4222, G4223, G4224, G4225, G4226, G4227, G4228, G4229, G4230, G4231, G4232 |
| 2348 | G4234 | PRT | O. sativa | Paralogous to G4235, G4236, G4237, G4238; Orthologous to G207, G227, G230, G242, G4218, G4219, G4220, G4221, G4222, G4223, G4224, G4225, G4226, G4227, G4228, G4229, G4230, G4231, G4232 |
| 2349 | G4235 | DNA | O. sativa | Predicted polypeptide sequence is paralogous to G4234, G4236, G4237, G4238; orthologous to G207, G227, G230, G242, G4218, G4219, G4220, G4221, G4222, G4223, G4224, G4225, G4226, G4227, G4228, G4229, G4230, G4231, G4232 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2350 | G4235 | PRT | *O. sativa* | Paralogous to G4234, G4236, G4237, G4238; Orthologous to G207, G227, G230, G242, G4218, G4219, G4220, G4221, G4222, G4223, G4224, G4225, G4226, G4227, G4228, G4229, G4230, G4231, G4232 |
| 2351 | G4236 | DNA | *O. sativa* | Predicted polypeptide sequence is paralogous to G4234, G4235, G4237, G4238; orthologous to G207, G227, G230, G242, G4218, G4219, G4220, G4221, G4222, G4223, G4224, G4225, G4226, G4227, G4228, G4229, G4230, G4231, G4232 |
| 2352 | G4236 | PRT | *O. sativa* | Paralogous to G4234, G4235, G4237, G4238; Orthologous to G207, G227, G230, G242, G4218, G4219, G4220, G4221, G4222, G4223, G4224, G4225, G4226, G4227, G4228, G4229, G4230, G4231, G4232 |
| 2353 | G4237 | DNA | *O. sativa* | Predicted polypeptide sequence is paralogous to G4234, G4235, G4236, G4238; orthologous to G207, G227, G230, G242, G4218, G4219, G4220, G4221, G4222, G4223, G4224, G4225, G4226, G4227, G4228, G4229, G4230, G4231, G4232 |
| 2354 | G4237 | PRT | *O. sativa* | Paralogous to G4234, G4235, G4236, G4238; Orthologous to G207, G227, G230, G242, G4218, G4219, G4220, G4221, G4222, G4223, G4224, G4225, G4226, G4227, G4228, G4229, G4230, G4231, G4232 |
| 2355 | G4238 | DNA | *O. sativa* | Predicted polypeptide sequence is paralogous to G4234, G4235, G4236, G4237; orthologous to G207, G227, G230, G242, G4218, G4219, G4220, G4221, G4222, G4223, G4224, G4225, G4226, G4227, G4228, G4229, G4230, G4231, G4232 |
| 2356 | G4238 | PRT | *O. sativa* | Paralogous to G4234, G4235, G4236, G4237; Orthologous to G207, G227, G230, G242, G4218, G4219, G4220, G4221, G4222, G4223, G4224, G4225, G4226, G4227, G4228, G4229, G4230, G4231, G4232 |
| 2357 | G4240 | DNA | *Z. mays* | Predicted polypeptide sequence is orthologous to G1435, G2741, G4241, G4243, G4244, G4245 |
| 2358 | G4240 | PRT | *Z. mays* | Orthologous to G1435, G2741, G4241, G4243, G4244, G4245 |
| 2359 | G4241 | DNA | *O. sativa* | Predicted polypeptide sequence is orthologous to G1435, G2741, G4240, G4243, G4244, G4245 |
| 2360 | G4241 | PRT | *O. sativa* | Orthologous to G1435, G2741, G4240, G4243, G4244, G4245 |
| 2361 | G4243 | DNA | *G. max* | Predicted polypeptide sequence is paralogous to G4244; orthologous to G1435, G2741, G4240, G4241, G4245 |
| 2362 | G4243 | PRT | *G. max* | Paralogous to G4244; Orthologous to G1435, G2741, G4240, G4241, G4245 |
| 2363 | G4244 | DNA | *G. max* | Predicted polypeptide sequence is paralogous to G4243; orthologous to G1435, G2741, G4240, G4241, G4245 |
| 2364 | G4244 | PRT | *G. max* | Paralogous to G4243; Orthologous to G1435, G2741, G4240, G4241, G4245 |
| 2365 | G4245 | DNA | *S. lycopersicum* | Predicted polypeptide sequence is orthologous to G1435, G2741, G4240, G4241, G4243, G4244 |
| 2366 | G4245 | PRT | *S. lycopersicum* | Orthologous to G1435, G2741, G4240, G4241, G4243, G4244 |
| 2367 | G425 | DNA | *A. thaliana* | Predicted polypeptide sequence is paralogous to G2545, G426, G427 |
| 2368 | G425 | PRT | *A. thaliana* | Paralogous to G2545, G426, G427 |
| 2369 | G4253 | DNA | *Z. mays* | Predicted polypeptide sequence is paralogous to G4254, G4255; orthologous to G3074 |
| 2370 | G4253 | PRT | *Z. mays* | Paralogous to G4254, G4255; Orthologous to G3074 |
| 2371 | G4254 | DNA | *Z. mays* | Predicted polypeptide sequence is paralogous to G4253, G4255; orthologous to G3074 |
| 2372 | G4254 | PRT | *Z. mays* | Paralogous to G4253, G4255; Orthologous to G3074 |
| 2373 | G4255 | DNA | *Z. mays* | Predicted polypeptide sequence is paralogous to G4253, G4254; orthologous to G3074 |
| 2374 | G4255 | PRT | *Z. mays* | Paralogous to G4253, G4254; Orthologous to G3074 |
| 2375 | G4256 | DNA | *Z. mays* | Predicted polypeptide sequence is paralogous to G3551, G3552, G4257; orthologous to G489, G714, G3542, G3544, G3545, G3547, G3549, G3550, G3553, G3554, G3555, G3867, G3892, G3893, G3894, G3896 |
| 2376 | G4256 | PRT | *Z. mays* | Paralogous to G3551, G3552, G4257; Orthologous to G489, G714, G3542, G3544, G3545, G3547, G3549, G3550, G3553, G3554, G3555, G3867, G3892, G3893, G3894, G3896 |
| 2377 | G4257 | DNA | *Z. mays* | Predicted polypeptide sequence is paralogous to G3551, G3552, G4256; orthologous to G489, G714, G3542, G3544, G3545, G3547, G3549, G3550, G3553, G3554, G3555, G3867, G3892, G3893, G3894, G3896 |
| 2378 | G4257 | PRT | *Z. mays* | Paralogous to G3551, G3552, G4256; Orthologous to G489, G714, G3542, G3544, G3545, G3547, G3549, G3550, G3553, G3554, G3555, G3867, G3892, G3893, G3894, G3896 |
| 2379 | G4259 | DNA | *Z. mays* | Predicted polypeptide sequence is paralogous to G3889; orthologous to G1646, G715, G3883, G3884, G3885, G3886, G3543 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2380 | G4259 | PRT | Z. mays | Paralogous to G3889; Orthologous to G1646, G715, G3883, G3884, G3885, G3886, G3543 |
| 2381 | G4261 | DNA | Z. mays | Predicted polypeptide sequence is orthologous to G926, G2632, G3924 |
| 2382 | G4261 | PRT | Z. mays | Orthologous to G926, G2632, G3924 |
| 2383 | G4267 | DNA | Z. mays | Predicted polypeptide sequence is paralogous to G4268; orthologous to G2344, G929 |
| 2384 | G4267 | PRT | Z. mays | Paralogous to G4268; Orthologous to G2344, G929 |
| 2385 | G4268 | DNA | Z. mays | Predicted polypeptide sequence is paralogous to G4267; orthologous to G2344, G929 |
| 2386 | G4268 | PRT | Z. mays | Paralogous to G4267; Orthologous to G2344, G929 |
| 2387 | G427 | DNA | A. thaliana | Predicted polypeptide sequence is paralogous to G2545, G425, G426 |
| 2388 | G427 | PRT | A. thaliana | Paralogous to G2545, G425, G426 |
| 2389 | G4272 | DNA | Z. mays | Predicted polypeptide sequence is paralogous to G3434, G3435, G3436, G3437, G3866, G3876, G4276; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2390 | G4272 | PRT | Z. mays | Paralogous to G3434, G3435, G3436, G3437, G3866, G3876, G4276; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2391 | G4276 | DNA | Z. mays | Predicted polypeptide sequence is paralogous to G3434, G3435, G3436, G3437, G3866, G3876, G4272; orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2392 | G4276 | PRT | Z. mays | Paralogous to G3434, G3435, G3436, G3437, G3866, G3876, G4272; Orthologous to G1364, G2345, G481, G482, G485, G3394, G3395, G3396, G3397, G3398, G3429, G3470, G3471, G3472, G3473, G3474, G3475, G3476, G3478, G3868, G3870, G3873, G3874, G3875, G3938 |
| 2393 | G4283 | DNA | Z. mays | Predicted polypeptide sequence is paralogous to G4284; orthologous to G1750, G1421, G4079, G4080, G440, G864, G4285, G4286, G4287, G4288, G4289, G4290, G4291, G4292, G4293 |
| 2394 | G4283 | PRT | Z. mays | Paralogous to G4284; Orthologous to G1750, G1421, G4079, G4080, G440, G864, G4285, G4286, G4287, G4288, G4289, G4290, G4291, G4292, G4293 |
| 2395 | G4284 | DNA | Z. mays | Predicted polypeptide sequence is paralogous to G4283; orthologous to G1750, G1421, G4079, G4080, G440, G864, G4285, G4286, G4287, G4288, G4289, G4290, G4291, G4292, G4293 |
| 2396 | G4284 | PRT | Z. mays | Paralogous to G4283; Orthologous to G1750, G1421, G4079, G4080, G440, G864, G4285, G4286, G4287, G4288, G4289, G4290, G4291, G4292, G4293 |
| 2397 | G4285 | DNA | G. max | Predicted polypeptide sequence is paralogous to G4286, G4287; orthologous to G1750, G1421, G4079, G4080, G440, G864, G4283, G4284, G4288, G4289, G4290, G4291, G4292, G4293 |
| 2398 | G4285 | PRT | G. max | Paralogous to G4286, G4287; Orthologous to G1750, G1421, G4079, G4080, G440, G864, G4283, G4284, G4288, G4289, G4290, G4291, G4292, G4293 |
| 2399 | G4286 | DNA | G. max | Predicted polypeptide sequence is paralogous to G4285, G4287; orthologous to G1750, G1421, G4079, G4080, G440, G864, G4283, G4284, G4288, G4289, G4290, G4291, G4292, G4293 |
| 2400 | G4286 | PRT | G. max | Paralogous to G4285, G4287; Orthologous to G1750, G1421, G4079, G4080, G440, G864, G4283, G4284, G4288, G4289, G4290, G4291, G4292, G4293 |
| 2401 | G4287 | DNA | G. max | Predicted polypeptide sequence is paralogous to G4285, G4286; orthologous to G1750, G1421, G4079, G4080, G440, G864, G4283, G4284, G4288, G4289, G4290, G4291, G4292, G4293 |
| 2402 | G4287 | PRT | G. max | Paralogous to G4285, G4286; Orthologous to G1750, G1421, G4079, G4080, G440, G864, G4283, G4284, G4288, G4289, G4290, G4291, G4292, G4293 |
| 2403 | G4288 | DNA | O. sativa | Predicted polypeptide sequence is paralogous to G4289, G4290, G4291, G4292, G4293; orthologous to G1750, G1421, G4079, G4080, G440, G864, G4283, G4284, G4285, G4286, G4287 |
| 2404 | G4288 | PRT | O. sativa | Paralogous to G4289, G4290, G4291, G4292, G4293; Orthologous to G1750, G1421, G4079, G4080, G440, G864, G4283, G4284, G4285, G4286, G4287 |
| 2405 | G4289 | DNA | O. sativa | Predicted polypeptide sequence is paralogous to G4288, G4290, G4291, G4292, G4293; orthologous to G1750, G1421, G4079, G4080, G440, G864, G4283, G4284, G4285, G4286, G4287 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2406 | G4289 | PRT | O. sativa | Paralogous to G4288, G4290, G4291, G4292, G4293; Orthologous to G1750, G1421, G4079, G4080, G440, G864, G4283, G4284, G4285, G4286, G4287 |
| 2407 | G4290 | DNA | O. sativa | Predicted polypeptide sequence is paralogous to G4288, G4289, G4291, G4292, G4293; orthologous to G1750, G1421, G4079, G4080, G440, G864, G4283, G4284, G4285, G4286, G4287 |
| 2408 | G4290 | PRT | O. sativa | Paralogous to G4288, G4289, G4291, G4292, G4293; Orthologous to G1750, G1421, G4079, G4080, G440, G864, G4283, G4284, G4285, G4286, G4287 |
| 2409 | G4291 | DNA | O. sativa | Predicted polypeptide sequence is paralogous to G4288, G4289, G4290, G4292, G4293; orthologous to G1750, G1421, G4079, G4080, G440, G864, G4283, G4284, G4285, G4286, G4287 |
| 2410 | G4291 | PRT | O. sativa | Paralogous to G4288, G4289, G4290, G4292, G4293; Orthologous to G1750, G1421, G4079, G4080, G440, G864, G4283, G4284, G4285, G4286, G4287 |
| 2411 | G4292 | DNA | O. sativa | Predicted polypeptide sequence is paralogous to G4288, G4289, G4290, G4291, G4293; orthologous to G1750, G1421, G4079, G4080, G440, G864, G4283, G4284, G4285, G4286, G4287 |
| 2412 | G4292 | PRT | O. sativa | Paralogous to G4288, G4289, G4290, G4291, G4293; Orthologous to G1750, G1421, G4079, G4080, G440, G864, G4283, G4284, G4285, G4286, G4287 |
| 2413 | G4293 | DNA | O. sativa | Predicted polypeptide sequence is paralogous to G4288, G4289, G4290, G4291, G4292; orthologous to G1750, G1421, G4079, G4080, G440, G864, G4283, G4284, G4285, G4286, G4287 |
| 2414 | G4293 | PRT | O. sativa | Paralogous to G4288, G4289, G4290, G4291, G4292; Orthologous to G1750, G1421, G4079, G4080, G440, G864, G4283, G4284, G4285, G4286, G4287 |
| 2415 | G4294 | DNA | O. sativa | Predicted polypeptide sequence is orthologous to G1387, G2583, G975 |
| 2416 | G4294 | PRT | O. sativa | Orthologous to G1387, G2583, G975 |
| 2417 | G4306 | DNA | G. max | Predicted polypeptide sequence is orthologous to G233, G241, G4307, G4308, G4309, G4310 |
| 2418 | G4306 | PRT | G. max | Orthologous to G233, G241, G4307, G4308, G4309, G4310 |
| 2419 | G4307 | DNA | S. lycopersicum | Predicted polypeptide sequence is orthologous to G233, G241, G4306, G4308, G4309, G4310 |
| 2420 | G4307 | PRT | S. lycopersicum | Orthologous to G233, G241, G4306, G4308, G4309, G4310 |
| 2421 | G4308 | DNA | O. sativa | Predicted polypeptide sequence is orthologous to G233, G241, G4306, G4307, G4309, G4310 |
| 2422 | G4308 | PRT | O. sativa | Orthologous to G233, G241, G4306, G4307, G4309, G4310 |
| 2423 | G4309 | DNA | Z. mays | Predicted polypeptide sequence is paralogous to G4310; orthologous to G233, G241, G4306, G4307, G4308 |
| 2424 | G4309 | PRT | Z. mays | Paralogous to G4310; Orthologous to G233, G241, G4306, G4307, G4308 |
| 2425 | G4310 | DNA | Z. mays | Predicted polypeptide sequence is paralogous to G4309; orthologous to G233, G241, G4306, G4307, G4308 |
| 2426 | G4310 | PRT | Z. mays | Paralogous to G4309; Orthologous to G233, G241, G4306, G4307, G4308 |
| 2427 | G4311 | DNA | G. max | Predicted polypeptide sequence is paralogous to G4312; orthologous to G3752, G3753, G3751, G793, G591, G3750, G4313 |
| 2428 | G4311 | PRT | G. max | Paralogous to G4312; Orthologous to G3752, G3753, G3751, G793, G591, G3750, G4313 |
| 2429 | G4312 | DNA | G. max | Predicted polypeptide sequence is paralogous to G4311; orthologous to G3752, G3753, G3751, G793, G591, G3750, G4313 |
| 2430 | G4312 | PRT | G. max | Paralogous to G4311; Orthologous to G3752, G3753, G3751, G793, G591, G3750, G4313 |
| 2431 | G4313 | DNA | Z. mays | Predicted polypeptide sequence is paralogous to G3753; orthologous to G3752, G3751, G793, G591, G3750, G4311, G4312 |
| 2432 | G4313 | PRT | Z. mays | Paralogous to G3753; Orthologous to G3752, G3751, G793, G591, G3750, G4311, G4312 |
| 2433 | G4328 | DNA | S. tuberosum | Predicted polypeptide sequence is orthologous to G1791, G1792, G1795, G30, G3380, G3381, G3383, G3515, G3516, G3517, G3518, G3519, G3520, G3735, G3736, G3737, G3794, G3739, G3929, G4329, G4330 |
| 2434 | G4328 | PRT | S. tuberosum | Orthologous to G1791, G1792, G1795, G30, G3380, G3381, G3383, G3515, G3516, G3517, G3518, G3519, G3520, G3735, G3736, G3737, G3794, G3739, G3929, G4329, G4330 |
| 2435 | G4329 | DNA | Petunia x hybrida | Predicted polypeptide sequence is orthologous to G1791, G1792, G1795, G30, G3380, G3381, G3383, G3515, G3516, G3517, G3518, G3519, G3520, G3735, G3736, G3737, G3794, G3739, G3929, G4328, G4330 |
| 2436 | G4329 | PRT | Petunia x hybrida | Orthologous to G1791, G1792, G1795, G30, G3380, G3381, G3383, G3515, G3516, G3517, G3518, G3519, G3520, G3735, G3736, G3737, G3794, G3739, G3929, G4328, G4330 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2437 | G4330 | DNA | *Populus trichocarpa x Populus nigra* | Predicted polypeptide sequence is orthologous to G1791, G1792, G1795, G30, G3380, G3381, G3383, G3515, G3516, G3517, G3518, G3519, G3520, G3735, G3736, G3737, G3794, G3739, G3929, G4328, G4329 |
| 2438 | G4330 | PRT | *Populus trichocarpa x Populus nigra* | Orthologousto G1791, G1792, G1795, G30, G3380, G3381, G3383, G3515, G3516, G3517, G3518, G3519, G3520, G3735, G3736, G3737, G3794, G3739, G3929, G4328, G4329 |
| 2439 | G4369 | DNA | *Z. mays* | Predicted polypeptide sequence is paralogous to G3490, G4370; orthologous to G1543, G3510, G3524, G4371 |
| 2440 | G4369 | PRT | *Z. mays* | Paralogous to G3490, G4370; Orthologous to G1543, G3510, G3524, G4371 |
| 2441 | G4370 | DNA | *Z. mays* | Predicted polypeptide sequence is paralogous to G3490, G4369; orthologous to G1543, G3510, G3524, G4371 |
| 2442 | G4370 | PRT | *Z. mays* | Paralogous to G3490, G4369; Orthologous to G1543, G3510, G3524, G4371 |
| 2443 | G4371 | DNA | *G. max* | Predicted polypeptide sequence is paralogous to G3524; orthologous to G1543, G3510, G3490, G4369, G4370 |
| 2444 | G4371 | PRT | *G. max* | Paralogous to G3524; Orthologous to G1543, G3510, G3490, G4369, G4370 |
| 2445 | G438 | DNA | *A. thaliana* | Predicted polypeptide sequence is paralogous to G1548, G390, G391, G392 |
| 2446 | G438 | PRT | *A. thaliana* | Paralogous to G1548, G390, G391, G392 |
| 2447 | G448 | DNA | *A. thaliana* | Predicted polypeptide sequence is paralogous to G450, G455, G456 |
| 2448 | G448 | PRT | *A. thaliana* | Paralogous to G450, G455, G456 |
| 2449 | G455 | DNA | *A. thaliana* | Predicted polypeptide sequence is paralogous to G448, G450, G456 |
| 2450 | G455 | PRT | *A. thaliana* | Paralogous to G448, G450, G456 |
| 2451 | G456 | DNA | *A. thaliana* | Predicted polypeptide sequence is paralogous to G448, G450, G455 |
| 2452 | G456 | PRT | *A. thaliana* | Paralogous to G448, G450, G455 |
| 2453 | G4570 | DNA | *G. max* | Predicted polypeptide sequence is orthologous to G2157 |
| 2454 | G4570 | PRT | *G. max* | Orthologous to G2157 |
| 2455 | G46 | DNA | *A. thaliana* | Predicted polypeptide sequence is paralogous to G1419, G43, G1004, G29; orthologous to G3849 |
| 2456 | G46 | PRT | *A. thaliana* | Paralogous to G1419, G43, G1004, G29; Orthologous to G3849 |
| 2457 | G4626 | DNA | *S. lycopersicum* | Predicted polypeptide sequence is paralogous to G3841, G3843, G3852; orthologous to G22, G1006, G28, G3430, G3659, G3660, G3661, G3717, G3718, G3844, G3845, G3846, G3848, G3856, G3857, G3858, G3864, G3865, G5171 |
| 2458 | G4626 | PRT | *S. lycopersicum* | Paralogous to G3841, G3843, G3852; Orthologous to G22, G1006, G28, G3430, G3659, G3660, G3661, G3717, G3718, G3844, G3845, G3846, G3848, G3856, G3857, G3858, G3864, G3865, G5171 |
| 2459 | G4627 | DNA | *O. sativa* | Predicted polypeptide sequence is paralogous to G4630, G5158; orthologous to G1809, G557, G4631, G4632 |
| 2460 | G4627 | PRT | *O. sativa* | Paralogous to G4630, G5158; Orthologous to G1809, G557, G4631, G4632 |
| 2461 | G4628 | DNA | *O. sativa* | Predicted polypeptide sequence is orthologous to G1518, G4629, G4633, G4635 |
| 2462 | G4628 | PRT | *O. sativa* | Orthologous to G1518, G4629, G4633, G4635 |
| 2463 | G4629 | DNA | *Pisum sativum* | Predicted polypeptide sequence is orthologous to G1518, G4628, G4633, G4635 |
| 2464 | G4629 | PRT | *Pisum sativum* | Orthologous to G1518, G4628, G4633, G4635 |
| 2465 | G4630 | DNA | *O. sativa* | Predicted polypeptide sequence is paralogous to G4627, G5158; orthologous to G1809, G557, G4631, G4632 |
| 2466 | G4630 | PRT | *O. sativa* | Paralogous to G4627, G5158; Orthologous to G1809, G557, G4631, G4632 |
| 2467 | G4631 | DNA | *G. max* | Predicted polypeptide sequence is orthologous to G1809, G557, G4627, G4630, G4632, G5158 |
| 2468 | G4631 | PRT | *G. max* | Orthologous to G1809, G557, G4627, G4630, G4632, G5158 |
| 2469 | G4632 | DNA | *Z. mays* | Predicted polypeptide sequence is orthologous to G1809, G557, G4627, G4630, G4631, G5158 |
| 2470 | G4632 | PRT | *Z. mays* | Orthologous to G1809, G557, G4627, G4630, G4631, G5158 |
| 2471 | G4633 | DNA | *G. max* | Predicted polypeptide sequence is orthologous to G1518, G4628, G4629, G4635 |
| 2472 | G4633 | PRT | *G. max* | Orthologous to G1518, G4628, G4629, G4635 |
| 2473 | G4635 | DNA | *S. lycopersicum* | Predicted polypeptide sequence is orthologous to G1518, G4628, G4629, G4633 |
| 2474 | G4635 | PRT | *S. lycopersicum* | Orthologous to G1518, G4628, G4629, G4633 |
| 2475 | G4637 | DNA | *Z. mays* | Predicted polypeptide sequence is paralogous to G3531, G3532, G3533, G3534, G4638, G4640; orthologous to G197, G255, G664, G3503, G3504, G3505, G3506, G3507, G3508, G3509, G3529, G3527, G3528, G4639 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2476 | G4637 | PRT | Z. mays | Paralogous to G3531, G3532, G3533, G3534, G4638, G4640; Orthologous to G197, G255, G664, G3503, G3504, G3505, G3506, G3507, G3508, G3509, G3529, G3527, G3528, G4639 |
| 2477 | G4638 | DNA | Z. mays | Predicted polypeptide sequence is paralogous to G3531, G3532, G3533, G3534, G4637, G4640; orthologous to G197, G255, G664, G3503, G3504, G3505, G3506, G3507, G3508, G3509, G3529, G3527, G3528, G4639 |
| 2478 | G4638 | PRT | Z. mays | Paralogous to G3531, G3532, G3533, G3534, G4637, G4640; Orthologous to G197, G255, G664, G3503, G3504, G3505, G3506, G3507, G3508, G3509, G3529, G3527, G3528, G4639 |
| 2479 | G4639 | DNA | G. max | Predicted polypeptide sequence is paralogous to G3529, G3527, G3528; orthologous to G197, G255, G664, G3503, G3504, G3505, G3506, G3507, G3508, G3509, G3531, G3532, G3533, G3534, G4637, G4638, G4640 |
| 2480 | G4639 | PRT | G. max | Paralogous to G3529, G3527, G3528; Orthologous to G197, G255, G664, G3503, G3504, G3505, G3506, G3507, G3508, G3509, G3531, G3532, G3533, G3534, G4637, G4638, G4640 |
| 2481 | G464 | DNA | A. thaliana | Predicted polypeptide sequence is paralogous to G463 |
| 2482 | G464 | PRT | A. thaliana | Paralogous to G463 |
| 2483 | G4640 | DNA | Z. mays | Predicted polypeptide sequence is paralogous to G3531, G3532, G3533, G3534, G4637, G4638; orthologous to G197, G255, G664, G3503, G3504, G3505, G3506, G3507, G3508, G3509, G3529, G3527, G3528, G4639 |
| 2484 | G4640 | PRT | Z. mays | Paralogous to G3531, G3532, G3533, G3534, G4637, G4638; Orthologous to G197, G255, G664, G3503, G3504, G3505, G3506, G3507, G3508, G3509, G3529, G3527, G3528, G4639 |
| 2485 | G472 | DNA | A. thaliana | Predicted polypeptide sequence is paralogous to G1553, G716 |
| 2486 | G472 | PRT | A. thaliana | Paralogous to G1553, G716 |
| 2487 | G502 | DNA | A. thaliana | Predicted polypeptide sequence is paralogous to G501, G519, G767 |
| 2488 | G502 | PRT | A. thaliana | Paralogous to G501, G519, G767 |
| 2489 | G514 | DNA | A. thaliana | Predicted polypeptide sequence is paralogous to G523, G525, G764 |
| 2490 | G514 | PRT | A. thaliana | Paralogous to G523, G525, G764 |
| 2491 | G515 | DNA | A. thaliana | Predicted polypeptide sequence is paralogous to G2053, G516, G517 |
| 2492 | G515 | PRT | A. thaliana | Paralogous to G2053, G516, G517 |
| 2493 | G5158 | DNA | O. sativa | Predicted polypeptide sequence is paralogous to G4627, G4630; orthologous to G1809, G557, G4631, G4632 |
| 2494 | G5158 | PRT | O. sativa | Paralogous to G4627, G4630; Orthologous to G1809, G557, G4631, G4632 |
| 2495 | G5159 | DNA | O. sativa | Predicted polypeptide sequence is orthologous to G1482, G1888 |
| 2496 | G5159 | PRT | O. sativa | Orthologous to G1482, G1888 |
| 2497 | G516 | DNA | A. thaliana | Predicted polypeptide sequence is paralogous to G2053, G515, G517 |
| 2498 | G516 | PRT | A. thaliana | Paralogous to G2053, G515, G517 |
| 2499 | G517 | DNA | A. thaliana | Predicted polypeptide sequence is paralogous to G2053, G515, G516 |
| 2500 | G517 | PRT | A. thaliana | Paralogous to G2053, G515, G516 |
| 2501 | G5170 | DNA | S. lycopersicum | Predicted polypeptide sequence is orthologous to G1266, G5184, G5185, G5186 |
| 2502 | G5170 | PRT | S. lycopersicum | Orthologous to G1266, G5184, G5185, G5186 |
| 2503 | G5171 | DNA | O. sativa | Predicted polypeptide sequence is paralogous to G3430, G3848; orthologous to G22, G1006, G28, G3659, G3660, G3661, G3717, G3718, G3841, G3843, G3844, G3845, G3846, G3852, G3856, G3857, G3858, G3864, G3865, G4626 |
| 2504 | G5171 | PRT | O. sativa | Paralogous to G3430, G3848; Orthologous to G22, G1006, G28, G3659, G3660, G3661, G3717, G3718, G3841, G3843, G3844, G3845, G3846, G3852, G3856, G3857, G3858, G3864, G3865, G4626 |
| 2505 | G5184 | DNA | G. max | Predicted polypeptide sequence is paralogous to G5186; orthologous to G1266, G5185, G5170 |
| 2506 | G5184 | PRT | G. max | Paralogous to G5186; Orthologous to G1266, G5185, G5170 |
| 2507 | G5185 | DNA | Z. mays | Predicted polypeptide sequence is orthologous to G1266, G5184, G5186, G5170 |
| 2508 | G5185 | PRT | Z. mays | Orthologous to G1266, G5184, G5186, G5170 |
| 2509 | G5186 | DNA | G. max | Predicted polypeptide sequence is paralogous to G5184; orthologous to G1266, G5185, G5170 |
| 2510 | G5186 | PRT | G. max | Paralogous to G5184; Orthologous to G1266, G5185, G5170 |
| 2511 | G521 | DNA | A. thaliana | Predicted polypeptide sequence is paralogous to G2887 |
| 2512 | G521 | PRT | A. thaliana | Paralogous to G2887 |
| 2513 | G523 | DNA | A. thaliana | Predicted polypeptide sequence is paralogous to G514, G525, G764 |
| 2514 | G523 | PRT | A. thaliana | Paralogous to G514, G525, G764 |
| 2515 | G524 | DNA | A. thaliana | Predicted polypeptide sequence is paralogous to G763 |
| 2516 | G524 | PRT | A. thaliana | Paralogous to G763 |
| 2517 | G528 | DNA | A. thaliana | Predicted polypeptide sequence is paralogous to G529, G530, G531, G532, G533, G534, G535, G536, G537 |

237
238

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2518 | G528 | PRT | A. thaliana | Paralogous to G529, G530, G531, G532, G533, G534, G535, G536, G537 |
| 2519 | G533 | DNA | A. thaliana | Predicted polypeptide sequence is paralogous to G528, G529, G530, G531, G532, G534, G535, G536, G537 |
| 2520 | G533 | PRT | A. thaliana | Paralogous to G528, G529, G530, G531, G532, G534, G535, G536, G537 |
| 2521 | G534 | DNA | A. thaliana | Predicted polypeptide sequence is paralogous to G528, G529, G530, G531, G532, G533, G535, G536, G537 |
| 2522 | G534 | PRT | A. thaliana | Paralogous to G528, G529, G530, G531, G532, G533, G535, G536, G537 |
| 2523 | G535 | DNA | A. thaliana | Predicted polypeptide sequence is paralogous to G528, G529, G530, G531, G532, G533, G534, G536, G537 |
| 2524 | G535 | PRT | A. thaliana | Paralogous to G528, G529, G530, G531, G532, G533, G534, G536, G537 |
| 2525 | G536 | DNA | A. thaliana | Predicted polypeptide sequence is paralogous to G528, G529, G530, G531, G532, G533, G534, G535, G537 |
| 2526 | G536 | PRT | A. thaliana | Paralogous to G528, G529, G530, G531, G532, G533, G534, G535, G537 |
| 2527 | G537 | DNA | A. thaliana | Predicted polypeptide sequence is paralogous to G528, G529, G530, G531, G532, G533, G534, G535, G536 |
| 2528 | G537 | PRT | A. thaliana | Paralogous to G528, G529, G530, G531, G532, G533, G534, G535, G536 |
| 2529 | G545 | DNA | A. thaliana | Predicted polypeptide sequence is paralogous to G350, G351 |
| 2530 | G545 | PRT | A. thaliana | Paralogous to G350, G351 |
| 2531 | G554 | DNA | A. thaliana | Predicted polypeptide sequence is paralogous to G1198, G1806, G555, G556, G558, G578, G629 |
| 2532 | G554 | PRT | A. thaliana | Paralogous to G1198, G1806, G555, G556, G558, G578, G629 |
| 2533 | G555 | DNA | A. thaliana | Predicted polypeptide sequence is paralogous to G1198, G1806, G554, G556, G558, G578, G629 |
| 2534 | G555 | PRT | A. thaliana | Paralogous to G1198, G1806, G554, G556, G558, G578, G629 |
| 2535 | G557 | DNA | A. thaliana | Predicted polypeptide sequence is paralogous to G1809; orthologous to G4627, G4630, G4631, G4632, G5158 |
| 2536 | G557 | PRT | A. thaliana | Paralogous to G1809; Orthologous to G4627, G4630, G4631, G4632, G5158 |
| 2537 | G561 | DNA | A. thaliana | Predicted polypeptide sequence is paralogous to G562 |
| 2538 | G561 | PRT | A. thaliana | Paralogous to G562 |
| 2539 | G578 | DNA | A. thaliana | Predicted polypeptide sequence is paralogous to G1198, G1806, G554, G555, G556, G558, G629 |
| 2540 | G578 | PRT | A. thaliana | Paralogous to G1198, G1806, G554, G555, G556, G558, G629 |
| 2541 | G584 | DNA | A. thaliana | Predicted polypeptide sequence is paralogous to G1136 |
| 2542 | G584 | PRT | A. thaliana | Paralogous to G1136 |
| 2543 | G589 | DNA | A. thaliana | Predicted polypeptide sequence is paralogous to G1061, G2791; orthologous to G3748, G3749, G3774, G3760 |
| 2544 | G589 | PRT | A. thaliana | Paralogous to G1061, G2791; Orthologous to G3748, G3749, G3774, G3760 |
| 2545 | G593 | DNA | A. thaliana | Predicted polypeptide sequence is paralogous to G790 |
| 2546 | G593 | PRT | A. thaliana | Paralogous to G790 |
| 2547 | G602 | DNA | A. thaliana | Predicted polypeptide sequence is paralogous to G1065 |
| 2548 | G602 | PRT | A. thaliana | Paralogous to G1065 |
| 2549 | G605 | DNA | A. thaliana | Predicted polypeptide sequence is paralogous to G1944 |
| 2550 | G605 | PRT | A. thaliana | Paralogous to G1944 |
| 2551 | G617 | DNA | A. thaliana | Predicted polypeptide sequence is paralogous to G2650 |
| 2552 | G617 | PRT | A. thaliana | Paralogous to G2650 |
| 2553 | G618 | DNA | A. thaliana | Predicted polypeptide sequence is paralogous to G2057 |
| 2554 | G618 | PRT | A. thaliana | Paralogous to G2057 |
| 2555 | G620 | DNA | A. thaliana | Predicted polypeptide sequence is paralogous to G1821; orthologous to G3839, G3937, G3939 |
| 2556 | G620 | PRT | A. thaliana | Paralogous to G1821; Orthologous to G3839, G3937, G3939 |
| 2557 | G627 | DNA | A. thaliana | Predicted polypeptide sequence is paralogous to G149, G1011, G154, G1797, G1798; orthologous to G4061, G4062, G4063, G4064, G4065, G4066, G4067 |
| 2558 | G627 | PRT | A. thaliana | Paralogous to G149, G1011, G154, G1797, G1798; Orthologous to G4061, G4062, G4063, G4064, G4065, G4066, G4067 |
| 2559 | G629 | DNA | A. thaliana | Predicted polypeptide sequence is paralogous to G1198, G1806, G554, G555, G556, G558, G578 |
| 2560 | G629 | PRT | A. thaliana | Paralogous to G1198, G1806, G554, G555, G556, G558, G578 |
| 2561 | G632 | DNA | A. thaliana | Predicted polypeptide sequence is paralogous to G1559 |
| 2562 | G632 | PRT | A. thaliana | Paralogous to G1559 |
| 2563 | G652 | DNA | A. thaliana | Predicted polypeptide sequence is paralogous to G1335 |
| 2564 | G652 | PRT | A. thaliana | Paralogous to G1335 |
| 2565 | G654 | DNA | A. thaliana | Predicted polypeptide sequence is paralogous to G653 |
| 2566 | G654 | PRT | A. thaliana | Paralogous to G653 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2567 | G668 | DNA | A. thaliana | Predicted polypeptide sequence is paralogous to G256, G666, G932; orthologous to G3384, G3385, G3386, G3500, G3501, G3502, G3537, G3538, G3539, G3540, G3541 |
| 2568 | G668 | PRT | A. thaliana | Paralogous to G256, G666, G932; Orthologous to G3384, G3385, G3386, G3500, G3501, G3502, G3537, G3538, G3539, G3540, G3541 |
| 2569 | G670 | DNA | A. thaliana | Predicted polypeptide sequence is paralogous to G1319 |
| 2570 | G670 | PRT | A. thaliana | Paralogous to G1319 |
| 2571 | G678 | DNA | A. thaliana | Predicted polypeptide sequence is paralogous to G229 |
| 2572 | G678 | PRT | A. thaliana | Paralogous to G229 |
| 2573 | G713 | DNA | A. thaliana | Predicted polypeptide sequence is paralogous to G413 |
| 2574 | G713 | PRT | A. thaliana | Paralogous to G413 |
| 2575 | G716 | DNA | A. thaliana | Predicted polypeptide sequence is paralogous to G1553, G472 |
| 2576 | G716 | PRT | A. thaliana | Paralogous to G1553, G472 |
| 2577 | G729 | DNA | A. thaliana | Predicted polypeptide sequence is paralogous to G1040, G3034, G730 |
| 2578 | G729 | PRT | A. thaliana | Paralogous to G1040, G3034, G730 |
| 2579 | G760 | DNA | A. thaliana | Predicted polypeptide sequence is paralogous to G3041 |
| 2580 | G760 | PRT | A. thaliana | Paralogous to G3041 |
| 2581 | G761 | DNA | A. thaliana | Predicted polypeptide sequence is paralogous to G1354, G1355, G1453, G1766, G2534, G522 |
| 2582 | G761 | PRT | A. thaliana | Paralogous to G1354, G1355, G1453, G1766, G2534, G522 |
| 2583 | G767 | DNA | A. thaliana | Predicted polypeptide sequence is paralogous to G501, G502, G519 |
| 2584 | G767 | PRT | A. thaliana | Paralogous to G501, G502, G519 |
| 2585 | G791 | DNA | A. thaliana | Predicted polypeptide sequence is paralogous to G792 |
| 2586 | G791 | PRT | A. thaliana | Paralogous to G792 |
| 2587 | G807 | DNA | A. thaliana | Predicted polypeptide sequence is paralogous to G810; orthologous to G3491, G3494, G3495, G3512 |
| 2588 | G807 | PRT | A. thaliana | Paralogous to G810; Orthologous to G3491, G3494, G3495, G3512 |
| 2589 | G820 | DNA | A. thaliana | Predicted polypeptide sequence is paralogous to G268, G2876 |
| 2590 | G820 | PRT | A. thaliana | Paralogous to G268, G2876 |
| 2591 | G833 | DNA | A. thaliana | Predicted polypeptide sequence is paralogous to G274 |
| 2592 | G833 | PRT | A. thaliana | Paralogous to G274 |
| 2593 | G852 | DNA | A. thaliana | Predicted polypeptide sequence is paralogous to G1768, G2633, G2697, G313; orthologous to G3815, G3825 |
| 2594 | G852 | PRT | A. thaliana | Paralogous to G1768, G2633, G2697, G313; Orthologous to G3815, G3825 |
| 2595 | G859 | DNA | A. thaliana | Predicted polypeptide sequence is paralogous to G157, G1759, G1842, G1843, G1844 |
| 2596 | G859 | PRT | A. thaliana | Paralogous to G157, G1759, G1842, G1843, G1844 |
| 2597 | G860 | DNA | A. thaliana | Predicted polypeptide sequence is paralogous to G152, G153, G1760; orthologous to G3479, G3480, G3481, G3482, G3483, G3484, G3485, G3487, G3488, G3489, G3980, G3981, G3982 |
| 2598 | G860 | PRT | A. thaliana | Paralogous to G152, G153, G1760; Orthologous to G3479, G3480, G3481, G3482, G3483, G3484, G3485, G3487, G3488, G3489, G3980, G3981, G3982 |
| 2599 | G861 | DNA | A. thaliana | Predicted polypeptide sequence is paralogous to G1140; orthologous to G3984, G3985, G3986, G3987, G3988, G3989, G3990, G3991, G3992, G3998, G3999, G4060 |
| 2600 | G861 | PRT | A. thaliana | Paralogous to G1140; Orthologous to G3984, G3985, G3986, G3987, G3988, G3989, G3990, G3991, G3992, G3998, G3999, G4060 |
| 2601 | G864 | DNA | A. thaliana | Predicted polypeptide sequence is paralogous to G1750, G1421, G440; orthologous to G4079, G4080, G4283, G4284, G4285, G4286, G4287, G4288, G4289, G4290, G4291, G4292, G4293 |
| 2602 | G864 | PRT | A. thaliana | Paralogous to G1750, G1421, G440; Orthologous to G4079, G4080, G4283, G4284, G4285, G4286, G4287, G4288, G4289, G4290, G4291, G4292, G4293 |
| 2603 | G867 | DNA | A. thaliana | Predicted polypeptide sequence is paralogous to G1930, G9, G993; orthologous to G3388, G3389, G3390, G3391, G3432, G3433, G3451, G3452, G3453, G3454, G3455 |
| 2604 | G867 | PRT | A. thaliana | Paralogous to G1930, G9, G993; Orthologous to G3388, G3389, G3390, G3391, G3432, G3433, G3451, G3452, G3453, G3454, G3455 |
| 2605 | G899 | DNA | A. thaliana | Predicted polypeptide sequence is paralogous to G1480, G897 |
| 2606 | G899 | PRT | A. thaliana | Paralogous to G1480, G897 |
| 2607 | G9 | DNA | A. thaliana | Predicted polypeptide sequence is paralogous to G1930, G867, G993; orthologous to G3388, G3389, G3390, G3391, G3432, G3433, G3451, G3452, G3453, G3454, G3455 |
| 2608 | G9 | PRT | A. thaliana | Paralogous to G1930, G867, G993; Orthologous to G3388, G3389, G3390, G3391, G3432, G3433, G3451, G3452, G3453, G3454, G3455 |
| 2609 | G903 | DNA | A. thaliana | Predicted polypeptide sequence is paralogous to G2831 |
| 2610 | G903 | PRT | A. thaliana | Paralogous to G2831 |

TABLE 8-continued

Putative homologs of *Arabidopsis* transcription factor genes identified using BLAST analysis

| Col. 1 SEQ ID NO: | Col. 2 GID | Col. 3 DNA or PRT | Col. 4 Species | Col. 5 Relationship |
|---|---|---|---|---|
| 2611 | G911 | DNA | A. thaliana | Predicted polypeptide sequence is paralogous to G1113 |
| 2612 | G911 | PRT | A. thaliana | Paralogous to G1113 |
| 2613 | G912 | DNA | A. thaliana | Predicted polypeptide sequence is paralogous to G40, G2107, G2513, G41, G42; orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2614 | G912 | PRT | A. thaliana | Paralogous to G40, G2107, G2513, G41, G42; Orthologous to G3362, G3364, G3365, G3366, G3367, G3368, G3370, G3371, G3372, G3373, G3374, G3375, G3376, G3377, G3378, G3379, G3438, G3439, G3440, G3441, G3442, G3369, G3497, G3498, G3499, G3443, G3463, G3464, G3465, G3466, G3467, G3468, G3469 |
| 2615 | G913 | DNA | A. thaliana | Predicted polypeptide sequence is paralogous to G2514, G976, G1753 |
| 2616 | G913 | PRT | A. thaliana | Paralogous to G2514, G976, G1753 |
| 2617 | G925 | DNA | A. thaliana | Predicted polypeptide sequence is paralogous to G2371 |
| 2618 | G925 | PRT | A. thaliana | Paralogous to G2371 |
| 2619 | G926 | DNA | A. thaliana | Predicted polypeptide sequence is paralogous to G2632; orthologous to G3924, G4261 |
| 2620 | G926 | PRT | A. thaliana | Paralogous to G2632; Orthologous to G3924, G4261 |
| 2621 | G932 | DNA | A. thaliana | Predicted polypeptide sequence is paralogous to G256, G666, G668; orthologous to G3384, G3385, G3386, G3500, G3501, G3502, G3537, G3538, G3539, G3540, G3541 |
| 2622 | G932 | PRT | A. thaliana | Paralogous to G256, G666, G668; Orthologous to G3384, G3385, G3386, G3500, G3501, G3502, G3537, G3538, G3539, G3540, G3541 |
| 2623 | G940 | DNA | A. thaliana | Predicted polypeptide sequence is paralogous to G938, G941 |
| 2624 | G940 | PRT | A. thaliana | Paralogous to G938, G941 |
| 2625 | G957 | DNA | A. thaliana | Predicted polypeptide sequence is paralogous to G2535, G961 |
| 2626 | G957 | PRT | A. thaliana | Paralogous to G2535, G961 |
| 2627 | G960 | DNA | A. thaliana | Predicted polypeptide sequence is paralogous to G1426, G1455, G513 |
| 2628 | G960 | PRT | A. thaliana | Paralogous to G1426, G1455, G513 |
| 2629 | G964 | DNA | A. thaliana | Predicted polypeptide sequence is paralogous to G398, G399 |
| 2630 | G964 | PRT | A. thaliana | Paralogous to G398, G399 |
| 2631 | G986 | DNA | A. thaliana | Predicted polypeptide sequence is paralogous to G881 |
| 2632 | G986 | PRT | A. thaliana | Paralogous to G881 |
| 2633 | G990 | DNA | A. thaliana | Predicted polypeptide sequence is paralogous to G1451 |
| 2634 | G990 | PRT | A. thaliana | Paralogous to G1451 |

Example IX

Introduction of Polynucleotides into Dicotyledonous and Monocotyledonous Plants

Transcription factor sequences listed in the Sequence Listing recombined into expression vectors, such as pMEN20 or pMEN65, may be transformed into a plant for the purpose of modifying plant traits. It is now routine to produce transgenic plants using most dicot plants (see Weissbach and Weissbach, (1989); Gelvin et al. (1990); Herrera-Estrella et al. (1983); Bevan (1984); and Klee (1985)). Methods for analysis of traits are routine in the art and examples are disclosed above.

The cloning vectors of the invention may also be introduced into a variety of grasses (e.g., Switchgrass, *Miscanthus*, cane, or *Miscanthus*-cane hybrids), or cereal plants. Cereal plants such as, but not limited to, corn, wheat, rice, sorghum, or barley, may also be transformed with the present polynucleotide sequences in pMEN20 or pMEN65 expression vectors for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of monocots by means well known in the art such as, for example, direct DNA transfer or *Agrobacterium tumefaciens*-mediated transformation. It is now routine to produce transgenic plants of most cereal crops (Vasil (1994)) such as corn, wheat, rice, sorghum (Cassas et al. (1993)), and barley (Wan and Lemeaux (1994)). DNA transfer methods such as the microprojectile can be used for corn (Fromm et al. (1990); Gordon-Kamm et al. (1990); Ishida (1990)), wheat (Vasil et al. (1992); Vasil et al. (1993b); Weeks et al. (1993)), and rice (Christou (1991); Hiei et al. (1994); Aldemita and Hodges (1996); and Hiei et al. (1997)). For most cereal plants, embryogenic cells derived from immature scutellum tissues are the preferred cellular targets for transformation (Hiei et al. (1997); Vasil (1994)).

Vectors according to the present invention may be transformed into corn embryogenic cells derived from immature scutellar tissue by using microprojectile bombardment, with the A188XB73 genotype as the preferred genotype (Fromm et al. (1990); Gordon-Kamm et al. (1990)). After microprojectile bombardment the tissues are selected on phosphinothricin to identify the transgenic embryogenic cells (Gordon-Kamm et al. (1990)). Transgenic plants are regenerated by standard corn regeneration techniques (Fromm et al. (1990); Gordon-Kamm et al. (1990)).

The vectors prepared as described above can also be used to produce transgenic wheat and rice plants (Christou (1991); Hiei et al. (1994); Aldemita and Hodges (1996); and Hiei et al. (1997)) that coordinately express genes of interest by following standard transformation protocols known to those skilled in the art for rice and wheat (Vasil et al. (1992); Vasil et al. (1993); and Weeks et al. (1993)), where the bar gene is used as the selectable marker.

Example X

Genes that Confer Significant Improvements to Diverse Plant Species

The function of specific orthologs of the sequences of the invention may be further characterized and incorporated into crop plants. The ectopic overexpression of these orthologs may be regulated using constitutive, inducible, or tissue specific regulatory elements. Genes that have been examined and have been shown to modify plant traits (including increasing lycopene, soluble solids and disease tolerance) encode orthologs of the transcription factor polypeptides found in the Sequence Listing, Table 7 or Table 8. In addition to these sequences, it is expected that related polynucleotide sequences encoding polypeptides found in the Sequence Listing can also induce altered traits, including increasing lycopene, soluble solids and disease tolerance, when transformed into a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

Transgenic plants are subjected to assays to measure plant volume, lycopene, soluble solids, disease tolerance, and fruit set according to the methods disclosed in the above Examples.

These experiments demonstrate that a significant number the transcription factor polypeptide sequences of the invention can be identified and shown to increased volume, lycopene, soluble solids and disease tolerance. It is expected that the same methods may be applied to identify and eventually make use of other members of the clades of the present transcription factor polypeptides, with the transcription factor polypeptides deriving from a diverse range of species.

REFERENCES CITED

Aldemita and Hodges (11996) *Planta* 199:612-617
Ainley et al. (11993) *Plant Mol. Biol.* 22: 13-23
Altschul et al. (1990) *J. Mol. Biol.* 215: 403-410
Altschul (1993) *J. Mol. Evol.* 36: 290-300
Ammirato et al., eds. (1984) *Handbook of Plant Cell Culture—Crop Species*, Macmillan Publ. Co., NY
An et al. (11988) *Plant Physiol.* 88: 547-552
Anderson and Young (1985) "Quantitative Filter Hybridisation." In: Hames and Higgins, ed., *Nucleic Acid Hybridisation, A Practical Approach*. Oxford, TRL Press, 73-111
Angiosperm Phylogeny Group (1998) *Ann. Missouri Bot. Gard.* 84: 1-49
Aoyama et al. (11995) *Plant Cell* 7: 1773-1785
Ausubel et al. (11997) *Short Protocols in Molecular Biology*, John Wiley & Sons, New York, N.Y., unit 7.7
Ausubel et al., eds. (11998-2000) *Current Protocols in Molecular Biology*, Greene Publishing Associates, Inc. and John Wiley & Sons, Inc., (supplemented through 2000) ("Ausubel")
Baerson et al. (11993) *Plant Mol. Biol.* 22: 255-267
Baerson et al. (11994) *Plant Mol. Biol.* 26: 1947-1959
Bairoch et al. (11997) *Nucleic Acids Res.* 25: 217-221
Baumann et al., (1999) *Plant Cell* 11: 323-334
Beaucage et al. (11981) *Tetrahedron Letters* 22: 1859-1869
Berger and Kimmel (1987) *Guide to Molecular Cloning Techniques, Methods in Enzymology*, vol. 152 Academic Press, Inc., San Diego, Calif. ("Berger and Kimmel")
Bevan (11984) *Nucleic Acids Res.* 12: 8711-8721
Bhattacharjee et al. (2001) *Proc Natl. Acad. Sci.*, USA, 98: 13790-13795
Bird et al. (1988) *Plant Mol. Biol.* 11: 651-662
Borevitz et al. (2000) *Plant Cell* 12: 2383-2394
Boss and Thomas (2002) *Nature*, 416: 847-850
Breen and Crouch (11992) *Plant Mol. Biol.* 19:1049-1055
Bruce et al. (2000) *Plant Cell*, 12: 65-79
Buchel et al. (1999) *Plant Mol. Biol.* 40: 387-396
Bulyk et al. (11999) *Nature Biotechnol.* 17: 573-577
Brummelkamp et al. (2002) *Science* 296:550-553
Byrne et al (2000) *Nature* 408: 967-971
Cassas et al. (11993) *Proc. Natl. Acad. Sci.* 90: 11212-11216
Chase et al. (1993) *Ann. Missouri Bot. Gard.* 80: 528-580
Cheng et al. (1994) *Nature* 369: 684-685
Chien et al. (1991) *Proc. Natl. Acad. Sci.* 88: 9578-9582
Chrispeels et al. (2000) *Plant Mol. Biol.* 42: 279-290
Christou (1991) *Bio/Technology* 9: 957-962
Constans (2002) *The Scientist* 16: 36
Corona et al. (1996) *Plant J.* 9: 505-512
Coupland (1995) *Nature* 377: 482-483
Crowley et al. (1985) *Cell* 43: 633-641
Daly et al. (2001) *Plant Physiol* 127: 1328-1333
Doolittle, ed., (1996) *Methods Enzymol*, vol. 266, "Computer Methods for Macromolecular Sequence Analysis", Academic Press, Inc., San Diego, Calif., USA
Eddy (1996) *Curr. Opin. Str. Biol.* 6: 361-365
Eisen (1998) *Genome Res.* 8: 163-167
Eyal et al. (1992) *Plant Mol. Biol.* 19: 589-599
Feng and Doolittle (1987) *J. Mol. Evol.* 25: 351-360
Fire et al. (1998) *Nature* 391: 806-811
Fluhr et al (1986) *EMBO J.* 5: 2063-2071
Fowler and Thomashow (2002) *Plant Cell* 14: 1675-1690
Fraley et al. (1983) *Proc. Natl. Acad. Sci.* 80: 4803-4807
Fromm et al. (1985) *Proc. Natl. Acad. Sci.* 82: 5824-5828
Fromm et al. (1989) *Plant Cell* 1: 977-984
Fromm et al. (1990) *Bio/Technol* 8: 833-839
Fu et al. (2001) *Plant Cell* 13: 1791-1802
Gan and Amasino (1995) *Science* 270: 1986-1988)
Gatz (1997) *Annu. Rev. Plant Physiol. Plant Mol. Biol.* 48: 89-108
Gelvin et al. (1990) *Plant Molecular Biology Manual*, Kluwer Academic Publishers
Giniger and Ptashne (1987) *Nature* 330: 670-672
Gilmour et al. (1998) *Plant J.* 16: 433-442
Goodrich et al. (1993) *Cell* 75: 519-530
Gordon-Kamm (1990) *Plant Cell* 2: 603-618
Guevara-Garcia (1998) *Plant Mol Biol* 38: 743-753
Guyer et al. (1998) *Genetics* 149: 633-639
Hames and Higgins, eds. (1985) *Nucleic Acid Hybridisation: A Practical Approach*, IRL Press, Oxford, U. K.
Hammond et al. (2001) *Nature Rev Gen* 2: 110-119
Harlow and Lane (1988), *Antibodies: A Laboratory Manual*, Cold Spring Harbor Laboratory, New York
He et al. (2000) *Transgenic Res.* 9: 223-227

Hein (1990) *Methods Enzymol.* 183: 626-645
Hempel et al. (1997) *Development* 124: 3845-3853
Henikoff and Henikoff (1991) *Nucleic Acids Res.* 19: 6565-6572
Henikoff and Henikoff (1992) *Proc. Natl. Acad. Sci.* 89: 10915-10919
Herrera-Estrella et al. (1983) *Nature* 303: 209
Hiei et al. (1994) *Plant J.* 6:271-282
Hiei et al. (1997) *Plant Mol. Biol.* 35:205-218
Higgins and Sharp (1988) *Gene* 73: 237-244
Higgins et al. (1996) *Methods Enzymol* 266: 383-402
Hohn et al. (1982) *Molecular Biology of Plant Tumors Academic Press*, New York, N.Y., pp. 549-560
Horsch et al. (1984) *Science* 233: 496-498
Ichikawa et al. (1997) *Nature* 390 698-701
Isalan et al. (2001) *Nature Biotechnol.* 19: 656-660
Ishida (1990) *Nature Biotechnol* 14:745-750
Ishida et al. (1996) *Nature Biotechnol* 14: 745-750
Izant and Weintraub (1985) *Science* 229: 345-352
Jaglo et al. (2001) *Plant Physiol.* 127: 910-917
Jones et al. (1992) *Transgenic Res.* 1: 285-297
Kaiser et al. (1995) *Plant Mol. Biol.* 28: 231-243
Kakimoto et al. (1996) *Science* 274: 982-985
Karlin and Altschul (1993) *Proc. Natl. Acad. Sci.* 90: 5873-5787
Kashima et al. (1985) *Nature* 313:402-404
Kempin et al. (1997) *Nature* 389: 802-803
Kim and Wold (1985) *Cell* 42: 129-138
Kim et al. (2001) *Plant J.* 25: 247-259
Kimmel (1987) *Methods Enzymo.* 152: 507-511
Klee (1985) *Bio/Technology* 3: 637-642
Klein et al. (1987) *Nature* 327: 70-73
Koncz et al. (1992a) *Methods in Arabidopsis Research*, World Scientific, River Edge, N.J.
Koncz et al (1992b) *Plant Molec. Biol.* 20: 963-976
Kop et al. (1999) *Plant Mol Biol* 39: 979-990
Ku et al. (2000) *Proc. Natl. Acad. Sci.* 97: 9121-9126
Kuhlemeier et al. (1989) *Plant Cell* 1: 471-478
Kyozuka and Shimamoto (2002) *Plant Cell Physiol.* 43: 130-135
Lehming et al (1987) *EMBO J.* 6: 3145-3153
Lichtenstein and Nellen (1997) *Antisense Technology: A Practical Approach* IRL Press at Oxford University Press, Oxford, U.K
Lin et al. (1991) *Nature* 353: 569-571
Liu et al. (2001) *J. Biol. Chem.* 276: 11323-11334
Long and Barton (1998) *Development* 125: 3027-3035
Long and Barton (2000) *Dev. Biol.* 218: 341-353
Ma and Ptashne (1987) *Cell* 51: 113-119
Mandel et al. (1992a) *Nature* 360: 273-277
Mandel et al. (1992b) *Cell* 71: 133-143
Manners et al. (1998) *Plant Mol. Biol.* 38: 1071-1080
Matthes et al. (1984) *EMBO J.* 3: 801-805
Melton (1985) *Proc. Natl. Acad. Sci.* 82: 144-148
Meyers (1995) *Molecular Biology and Biotechnology*, Wiley VCH, New York, N.Y., p 856-853
Montgomery et al. (1993) *Plant Cell* 5: 1049-1062
Moore et al. (1988) in Schaad, ed., Laboratory Guide for the Identification of Plant Pathogenic Bacteria. APS Press, St. Paul, Minn.
Moore et al. (1998) *Proc. Natl. Acad. Sci.* 95: 376-381
Mount (2001) in *Bioinformatics: Sequence and Genome Analysis* Cold Spring Harbor Laboratory Press, Cold Spring Harbor, N.Y., page 543
Müller et al. (2001) *Plant J.* 28: 169-179
Mullis et al. (1990) *PCR Protocols A Guide to Methods and Applications* (Innis et al. eds) Academic Press Inc. San Diego, Calif.
Murashige and Skoog (1962) *Plant Physiol.* 15: 473-497
Nagel et al. (1990) *FEMS Microbiol. Letts.* 67: 325-328
Nandi et al. (2000) *Curr. Biol.* 10: 215-218
Needleman and Wunsch (1970) *J. Mol. Biol.* 48: 443-453
Nicholass et al. (1995) *Plant Mol. Biol.* 28: 423-435
Odell et al. (1985) *Nature* 313: 810-812
Odell et al. (1994) *Plant Physiol.* 106: 447-458
Ohl et al. (1990) *Plant Cell* 2: 837-848
Ori et al. (2000) *Development* 127: 5523-5532
Paddison, et al. (2002) *Genes & Dev.* 16: 948-958
Pearson and Lipman (1988) *Proc. Natl. Acad. Sci.* 85: 2444-2448
Peng et al. (1997) *Genes Development* 11:3194-3205
Peng et al. (1999) *Nature* 400: 256-261
Piazza et al. (2002) *Plant Physiol.* 128: 1077-1086
Preiss et al. (1985) *Nature* 313: 27-32
Ratcliffe et al. (2001) *Plant Physiol* 126: 122-132
Riechmann et al. (2000) *Science* 290: 2105-2110
Rieger et al. (1976) *Glossary of Genetics and Cytogenetics: Classical and Molecular*, 4th ed., Springer Verlag, Berlin
Ringli and Keller (1998) *Plant Mol Biol* 37: 977-988
Robson et al. (2001) *Plant J.* 28: 619-631
Rosenberg et al. (1985) *Nature* 313: 703-706
Sadowski et al. (1988) *Nature* 335: 563-564
Sambrook et al. (1989) *Molecular Cloning: A Laboratory Manual*, 2nd Ed., Vol. 1-3, Cold Spring Harbor Laboratory, Cold Spring Harbor, N.Y. ("Sambrook")
Schaffner and Sheen (1991) *Plant Cell* 3: 997-1012
Sharp (1999) *Genes and Development* 13: 139-141
Shi et al. (1998) *Plant Mol. Biol.* 38: 1053-1060
Shimamoto et al. (1989) *Nature* 338: 274-276
Shpaer (1997) *Methods Mol. Biol.* 70: 173-187
Siebertz et al. (1989) *Plant Cell* 1: 961-968
Sjodahl et al. (1995) *Planta* 197: 264-271
Smith and Waterman (1981) *Adv. Appl. Math.* 2: 482-489
Smith et al. (1988) *Nature,* 334: 724-726
Smith et al. (1990) *Plant Mol. Biol.* 14: 369-379
Smith et al. (1992) *Protein Engineering* 5: 35-51
Sonnhammer et al. (1997) *Proteins* 28: 405-420
Stemmer (1994a) *Nature* 370: 389-391
Stemmer (1994b) *Proc. Natl. Acad. Sci.* 91: 10747-10751
Suzuki et al. (2001) *Plant J.* 28: 409-418
Taylor and Scheuring (1994) *Mol. Gen. Genet.* 243: 148-157
Thoma et al. (1994) *Plant Physiol.* 105: 35-45
Thompson et al. (1994) *Nucleic Acids Res.* 22: 4673-4680
Timmons and Fire (1998) *Nature* 395: 854
Tudge (2000) in *The Variety of Life*, Oxford University Press, New York, N.Y., pp. 547-606
Vasil et al. (1990) *Bio/Technol.* 8: 429-434
Vasil et al. (1992) *Bio/Technol.* 10:667-674
Vasil (1993a) *Bio/Technology* 10: 667-674
Vasil et al. (1993b) *Bio/Technol.* 11:1553-1558
Vasil (1994) *Plant Mol. Biol.* 25: 925-937
Wahl and Berger (1987) *Methods Enzymol.* 152: 399-407
Wan and Lemeaux (1994) *Plant Physiol.* 104: 37-48
Wanner and Gruissem (1991) *Plant Cell* 3: 1289-1303
Weeks et al. (1993) *Plant Physiol* 102: 1077-1084
Weigel and Nilsson (1995) *Nature* 377: 482-500
Weissbach and Weissbach (1989) *Methods for Plant Molecular Biology*, Academic Press
Willmott et al. (1998) *Plant Molec. Biol.* 38: 817-825
Winans (1992) *Microbiol. Rev.* 56: 12-31
Wu, ed. (1993) *Methods Enzymol* (vol. 217, Academic Press, San Diego)

Xu et al. (2001) *Proc. Natl. Acad. Sci.*, USA, 98: 15089-15094

Zamore (2001) *Nature Struct. Biol.*, 8: 746-750

Zhang et al. (2000) *J. Biol. Chem.* 275: 33850-33860

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the claims. Modifications that become apparent from the foregoing description and accompanying figures fall within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07960612B2). An electronic copy of the "Sequence Listing" will also be available from the USPTO upon request and payment of the fee set forth in 37 CFR 1.19(b)(3).

What is claimed is:

1. A transformed plant transformed with an expression vector comprising a recombinant nucleic acid sequence encoding a polypeptide, wherein the polypeptide has at least 95% amino acid identity to SEQ ID NO: 1232, and wherein the transformed plant has greater yield as compared to a control plant that has not been transformed with said expression vector.

2. The transformed plant of claim 1, wherein the polypeptide has at least 98% amino acid identity to SEQ ID NO: 1232.

3. A recombinant plant host cell comprised within the transformed plant of claim 1.

4. A transgenic seed produced by the transformed plant of claim 1, wherein the transgenic seed comprises the expression vector.

5. The transformed plant of claim 1, wherein the transformed plant is a dicot.

6. The transformed plant of claim 1, wherein the polypeptide is SEQ ID NO: 1232.

7. A transformed tomato plant transformed with an expression vector comprising a recombinant nucleic acid sequence encoding a polypeptide, wherein the polypeptide has at least 95% amino acid identity to SEQ ID NO: 1232, and wherein the transformed tomato plant has greater yield, increased lycopene levels, or greater fruit weight as compared to a control plant that has not been transformed with said expression vector.

8. The transformed tomato plant of claim 7, wherein the transformed tomato plant has greater yield as compared to a control plant not transformed with said expression vector.

9. The transformed tomato plant of claim 7, wherein the transformed tomato plant has increased lycopene levels as compared to a control plant not transformed with said expression vector.

10. The transformed tomato plant of claim 7, wherein the transformed tomato plant has greater fruit weight as compared to a control plant not transformed with said expression vector.

11. The transformed tomato plant of claim 7, wherein the polypeptide has at least 98% amino acid identity to SEQ ID NO: 1232.

12. The transformed tomato plant of claim 7, wherein the polypeptide is SEQ ID NO: 1232.

* * * * *